US007589206B2

(12) United States Patent
Eatherton et al.

(10) Patent No.: US 7,589,206 B2
(45) Date of Patent: Sep. 15, 2009

(54) PYRROLOPYRIDINE DERIVATIVES

(75) Inventors: Andrew John Eatherton, Harlow (GB); Gerard Martin Paul Giblin, Harlow (GB); Matthew Russell Johnson, Harlow (GB); William Leonard Mitchell, Harlow (GB); Brian Peter Slingsby, Harlow (GB); Alcide Perboni, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 74 days.

(21) Appl. No.: 11/570,099

(22) PCT Filed: Jun. 7, 2005

(86) PCT No.: PCT/EP2005/006182

§ 371 (c)(1),
(2), (4) Date: Dec. 6, 2006

(87) PCT Pub. No.: WO2005/121140

PCT Pub. Date: Dec. 22, 2005

(65) Prior Publication Data

US 2007/0219229 A1    Sep. 20, 2007

(30) Foreign Application Priority Data

Jun. 9, 2004 (GB) ................... 0412908.6
Nov. 11, 2004 (GB) ................... 0424950.4

(51) Int. Cl.
*C07D 471/02* (2006.01)
(52) U.S. Cl. ..................................... 546/113
(58) Field of Classification Search ................. 546/113
See application file for complete search history.

(56) References Cited

U.S. PATENT DOCUMENTS

| 4,758,558 | A | * | 7/1988 | Kanno et al. ................. 514/207 |
| 5,112,820 | A | | 5/1992 | Ward et al. |
| 5,624,941 | A | | 4/1997 | Barth et al. |
| 6,232,320 | B1 | | 5/2001 | Stewart et al. |
| 6,579,882 | B2 | | 6/2003 | Stewart et al. |
| 2001/0020030 | A1 | | 9/2001 | Stewart et al. |
| 2001/0030030 | A1 | | 10/2001 | Kemper et al. |
| 2002/0147189 | A1 | | 10/2002 | Cai et al. |
| 2003/0069240 | A1 | | 4/2003 | Breitenbucher et al. |
| 2003/0069421 | A1 | | 4/2003 | Tang et al. |
| 2003/0220365 | A1 | | 11/2003 | Stewart et al. |
| 2004/0063744 | A1 | | 4/2004 | Wang et al. |
| 2004/0167030 | A1 | | 8/2004 | Bernotas et al. |

FOREIGN PATENT DOCUMENTS

| CA | 390948 A1 | 12/2000 |
| DE | 4129603 | 3/1993 |
| EP | 436333 | 7/1991 |
| EP | 511791 | 11/1992 |
| EP | 0531883 | 3/1993 |
| EP | 0576357 | 12/1993 |
| EP | 436361 | 9/1994 |
| EP | 716855 | 6/1996 |
| EP | 1181296 A1 | 12/2000 |
| EP | 668279 | 6/2001 |
| EP | 1132389 | 9/2001 |
| FR | 2845388 | 4/2004 |
| JP | 09020779 | 1/1997 |
| JP | 2004509059 | 3/2004 |
| WO | 9307140 A1 | 4/1993 |
| WO | 9522545 A1 | 8/1995 |
| WO | 9611929 A1 | 4/1996 |
| WO | 9744319 A1 | 11/1997 |
| WO | 9806703 A1 | 2/1998 |
| WO | 9843956 A1 | 10/1998 |
| WO | 9850356 A1 | 11/1998 |
| WO | 200012084 A1 | 3/2000 |
| WO | 200053178 A1 | 9/2000 |
| WO | 200053179 A1 | 9/2000 |
| WO | 200053180 A1 | 9/2000 |
| WO | 200053181 A1 | 9/2000 |
| WO | 200053185 A1 | 9/2000 |
| WO | 200053602 A1 | 9/2000 |
| WO | 200055159 A2 | 9/2000 |
| WO | 0075145 A1 | 12/2000 |
| WO | 200162255 A1 | 8/2001 |
| WO | 2001058869 A2 | 8/2001 |
| WO | 200182909 A2 | 11/2001 |
| WO | 200183472 A1 | 11/2001 |
| WO | 200220013 A2 | 3/2002 |

(Continued)

OTHER PUBLICATIONS

Barth F.; "Cannabinoid receptor agonists and antagonists"; Expert Opinion on Therapeutic Patents; Mar. 1998; 8/3: 301-313.

Goya P et al.; "Recent advances in cannabinoid receptor agonists and antagonists."; Expert Opinion on Therapeutic Patents; 2000; 10/10; 1529-1538.

Palmer S.L. et al.; "Cannabinergic ligands."; Chemistry and Physics of Lipids. Limerick, IR: 2002: 121: 3-9.

Pertwee G.R.; "Cannabinold receptor ligands: clinical and neuropharmacological considerations relevant to future drug discovery and development."; Current Opinion in Investigational Drugs: 2000: 9/7; 1553-1571.

(Continued)

*Primary Examiner*—D. Margaret Seaman
*Assistant Examiner*—Nizal S Chandrakumar
(74) *Attorney, Agent, or Firm*—J. Scott Young

(57) ABSTRACT

The present invention relates to novel pyrrolopyridine derivatives, pharmaceutical compositions containing these compounds and their use in the treatment of diseases, particularly pain, which diseases are caused directly or indirectly by an increase or decrease in activity of the cannabinoid receptor.

13 Claims, No Drawings

FOREIGN PATENT DOCUMENTS

| | | | |
|---|---|---|---|
| WO | 200228831 | A1 | 4/2002 |
| WO | 200257246 | A2 | 7/2002 |
| WO | 200262423 | A1 | 8/2002 |
| WO | 2002072549 | A1 | 9/2002 |
| WO | 200281443 | A1 | 10/2002 |
| WO | 200292090 | A1 | 11/2002 |
| WO | 2003000254 | | 1/2003 |
| WO | 2003009852 | A1 | 2/2003 |
| WO | 2003020731 | A1 | 3/2003 |
| WO | 2003022214 | A2 | 3/2003 |
| WO | 2003033496 | A1 | 4/2003 |
| WO | 2003037861 | A1 | 5/2003 |
| WO | 2003053970 | A1 | 7/2003 |
| WO | 2003068221 | A1 | 8/2003 |
| WO | 200372549 | A1 | 9/2003 |
| WO | 2003080608 | A2 | 10/2003 |
| WO | 2003087087 | A2 | 10/2003 |
| WO | 2003101990 | A1 | 12/2003 |
| WO | 2004000210 | A2 | 12/2003 |
| WO | 2004009600 | A1 | 1/2004 |
| WO | 2004013141 | A1 | 2/2004 |
| WO | 2004014380 | A1 | 2/2004 |
| WO | 2004/018434 | A1 | 3/2004 |
| WO | 2004/029026 | A1 | 4/2004 |
| WO | 2004028481 | A2 | 4/2004 |
| WO | 2004/094421 | A1 | 11/2004 |
| WO | 2005/121140 | A1 | 12/2005 |
| WO | 200214317 | A2 | 2/2006 |

OTHER PUBLICATIONS

Barth F.; "Cannabinoid receptor agonists and antagonists."; Expert Opinion on Therapeutic Patents: Mar. 1998; 8/3:301-313;.

Goya P. et al.; 'Recent advances in cannabinoid receptor agonists and antagonists; Expert Opinion on Therapeutic Patents; 2000: 10/10;1529-1538:.

Palmer S.L. et a.l; "Cannabinergic ligands."; Chemistry and Physics of Lipids. Limerick, IR: 2002; 121;3-9:.

Pertwee G.R.; "Cannabinold receptor ligands; clinical and neuropharmacological considerations relevant to future drug discovery and development."; Current Opinion in Investigational Drugs; 2000;9/7;1553-1571;.

* cited by examiner

PYRROLOPYRIDINE DERIVATIVES

CROSS-REFERENCE TO RELATED APPLICATIQNS

This application is filed pursuant to 35 USC 371 as a United States National Phase Application of International Patent Application Serial No. PCT/EP2005/006182 filed on Jun. 7, 2005, which claims priority from 0412908.6 filed on Jun. 9,2004 and 0424950.4 filed on Nov. 11, 2004 in the United Kingdom.

FIELD OF THE INVENTION

The present invention relates to novel pyrrolopyridine derivatives, pharmaceutical compositions containing these compounds and their use in the treatment of diseases, particularly pain, which diseases are caused directly or indirectly by an increase or decrease in activity of the cannabinoid receptor.

BACKGROUND OF THE INVENTION

Cannabinoids are a specific class of psychoactive compounds present in Indian cannabis (*Cannabis sativa*), including about sixty different molecules, the most representative being cannabinol, cannabidiol and several isomers of tetrahydrocannabinol. Knowledge of the therapeutic activity of cannabis dates back to the ancient dynasties of China, where, 5,000 years ago, cannabis was used for the treatment of asthma, migraine and some gynaecological disorders. These uses later became so established that, around 1850, cannabis extracts were included in the US Pharmacopaeia and remained there until 1947.

Cannabinoids are known to cause different effects on various systems and/or organs, the most important being on the central nervous system and on the cardiovascular system. These effects include alterations in memory and cognition, euphoria, and sedation. Cannabinoids also increase heart rate and vary systemic arterial pressure. Peripheral effects related to bronchial constriction, immunomodulation, and inflammation have also been observed. The capability of cannabinoids to reduce intraocular pressure and to affect respiratory and endocrine systems is also well documented. See e.g. L. E. Hollister, Health Aspects of Cannabis, *Pharmacological Reviews*, Vol. 38, pp. 1-20, (1986). More recently, it was found that cannabinoids suppress the cellular and humoral immune responses and exhibit antiinflammatory properties. Wirth et al., Antiinflammatory Properties of Cannabichrome, *Life Science*, Vol. 26, pp. 1991-1995, (1980).

In spite of the foregoing benefits, the therapeutic use of cannabis is controversial, both due to its relevant psychoactive effects (causing dependence and addiction), and due to manifold side effects that have not yet been completely clarified. Although work in this field has been ongoing since the 1940's, evidence indicating that the peripheral effects of cannabinoids are directly mediated, and not secondary to a CNS effect, has been limited by the lack of receptor characterization, the lack of information concerning an endogenous cannabinoid ligand and, until recently, the lack of receptor subtype selective compounds.

The first cannabinoid receptor was found to be mainly located in the brain, in neural cell lines, and, only to a lesser extent, at the peripheral level. In view of its location, it was called the central receptor ("CB1"). See Matsuda et al., "Structure of a Cannabinoid Receptor and Functional Expression of the Cloned cDNA," *Nature*, Vol. 346, pp. 561-564 (1990). The second cannabinoid receptor ("CB2") was identified in the spleen, and was assumed to modulate the non psychoactive effects of the cannabinoids. See Munro et al., "Molecular Characterization of a Peripheral Receptor for Cannabinoids," *Nature*, Vol. 365, pp. 61-65 (1993).

Recently, some compounds have been prepared which are capable of acting as agonists on both the cannabinoid receptors. For example, use of derivatives of dihydroxypyrrole-(1,2,3-d,e)-1,4-benzoxazine in the treatment of glaucoma and the use of derivatives of 1,5-diphenyl-pyrazole as immunomodulators or psychotropic agents in the treatment of various neuropathologies, migraine, epilepsy, glaucoma, etc are known. See U.S. Pat. No. 5,112,820 and EP 576357, respectively. However, because these compounds are active on both the CB1 and CB2 receptor, they can lead to serious psychoactive effects.

The foregoing indications and the preferential localization of the CB2 receptor in the immune system confirms a specific role of CB2 in modulating the immune and antiinflammatory response to stimuli of different sources.

The total size of the patient population suffering from pain is vast (almost 300 million), dominated by those suffering from back pain, osteo-arthritic pain and post-operative pain. Neuropathic pain (associated with neuronal lesions such as those induced by diabetes, HIV, herpes infection, or stroke) occurs with lower, but still substantial prevalence, as does cancer pain.

The pathogenic mechanisms that give rise to pain symptoms can be grouped into two main categories:
- those that are components of inflammatory tissue responses (Inflammatory Pain);
- those that result from a neuronal lesion of some form (Neuropathic Pain).

Chronic inflammatory pain consists predominantly of osteoarthritis, chronic low back pain and rheumatoid arthritis. The pain results from acute and on-going injury and/or inflammation. There may be both spontaneous and provoked pain.

There is an underlying pathological hypersensitivity as a result of physiological hyperexcitability and the release of inflammatory mediators which further potentiate this hyperexcitability. CB2 receptors are expressed on inflammatory cells (T cells, B cells, macrophages, mast cells) and mediate immune suppression through inhibition of cellular interaction/inflammatory mediator release. CB2 receptors may also be expressed on sensory nerve terminals and therefore directly inhibit hyperalgesia.

More recently, data suggests a role for CB2 receptor activation in the CNS. Until recently the CB2 receptor was thought to be restricted to the periphery, however emerging data suggests inflammatory pain-mediated induction of CB2 receptor expression in rat spinal cord which coincides with the appearance of activated microglia (Zhang et. al., 2003). Furthermore CB2 receptor agonists have been shown to reduce mechanically evoked responses and wind-up of wide dynamic range neurones in spinal cord dorsal horn in animal models of inflammatory pain (Zhang et. al., 2003, Eur J. Neurosci. 17: 2750-2754, Nackley et. al., 2004, J. Neurophys. 92: 3562-3574, Elmes et. al., 2004, Eur. J. Neurosci. 20: 2311-2320.)

The role of CB2 in immunomodulation, inflammation, osteoporosis, cardiovascular, renal and other disease conditions is now being examined.

Based on the foregoing, there is a need for compounds which have activity against the CB2 receptor. Thus, CB2 modulators are believed to offer an unique approach toward the pharmacotherapy of immune disorders, inflammation, osteoporosis, renal ischemia and other pathophysiological conditions.

SUMMARY OF THE INVENTION

The present invention provides novel pyrrolopyridine derivatives of formula (I) and pharmaceutically acceptable derivatives thereof, pharmaceutical compositions containing these compounds or derivatives, and their use as CB2 receptor modulators, which are useful in the treatment of a variety of disorders.

The present invention further comprises a method for treating disease mediated by CB2 receptors in an animal, including humans, which comprises administering to an animal in need thereof an effective amount of a compound of formula (I) or a pharmaceutically acceptable derivative thereof.

In light of the fact that cannabinoids act on receptors capable of modulating different functional effects, and in view of the low homology between CB2 and CB1, a class of drugs selective for the specific receptor sub-type is desirable. The natural or synthetic cannabinoids currently available do not fulfill this function because they are active on both receptors.

In one embodiment of the present invention includes compounds which are capable of selectively modulating the receptors for cannabinoids and therefore the pathologies associated with such receptors.

The invention provides compounds of formula (I):

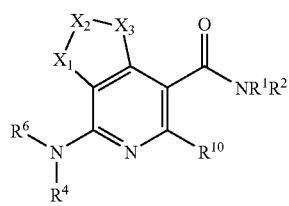

(I)

wherein:
$X_1$ is $NR^{12}$ and $X_2$ and $X_3$ together form a $—CR^{13}=CR^{11}—$ group or $X_3$ is $NR^{12}$ and $X_2$ and $X_1$ together form a $—CR^{13}=CR^{11}—$ group;

$R^1$ is selected from hydrogen, $C_{1-6}$ alkyl, $C_{3-6}$ cycloalkyl and halosubstituted $C_{1-6}$ alkyl;

$R^2$ is hydrogen or $(CH_2)_mR^3$ where m is 0 or 1;

or $R^1$ and $R^2$ together with N to which they are attached form an optionally substituted 4- to 8- membered non-aromatic heterocyclyl ring;

$R^3$ is a 4- to 8- membered non-aromatic heterocyclyl group, a $C_{3-8}$ cycloalkyl group, a straight or branched $C_{1-10}$ alkyl, a $C_{2-10}$ alkenyl, a $C_{3-8}$ cycloalkenyl, a $C_{2-10}$ alkynyl, a $C_{3-8}$ cycloalkynyl or phenyl group, any of which can be unsubstituted or substituted, or $R^5$;

$R^4$ is selected from hydrogen, $C_{1-6}$ alkyl, $C_{3-6}$ cycloalkyl, halosubstituted $C_{1-6}$ alkyl, $COCH_3$, and $SO_2Me$;

$R^5$ is

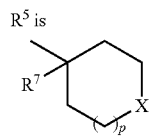

wherein p is 0, 1 or 2, and X is $CH_2$, O, S, or $SO_2$;

$R^6$ is unsubstituted or substituted phenyl, unsubstituted or substituted $C_{3-6}$ cycloalkyl or an unsubstituted or substituted 4- to 8- membered non-aromatic heterocyclyl ring;

or $R^4$ and $R^6$ together with N to which they are attached form an optionally substituted 4- to 8- membered non-aromatic heterocyclyl ring;

$R^7$ is OH, $C_{1-6}$ alkoxy, $NR^{8a}R^{8b}$, $NHCOR^9$, $NHSO_2R^9$ or $SOqR^9$;

$R^{8a}$ is H or $C_{1-6}$ alkyl;
$R^{8b}$ is H or $C_{1-6}$ alkyl;
$R^9$ is $C_{1-6}$ alkyl;
$R^{10}$ is hydrogen, substituted or unsubstituted $(C_{1-6})$alkyl or chloro;
$R^{11}$ is hydrogen or $C_{1-6}$ alkyl;
$R^{12}$ is hydrogen or $C_{1-6}$ alkyl;
$R^{13}$ is hydrogen or $C_{1-6}$ alkyl;
q is 0, 1 or 2;

and pharmaceutically acceptable derivatives thereof wherein the compound is not 3-methyl-7-morpholin-4-yl-1H-pyrrolo[2,3-c]pyridine-4-carboxylic acid (tetrahydro-pyran-4-yl)-amide or 3-methyl-7-morpholin-4-yl-1H-pyrrolo[2,3-c]pyridine-4-carboxylic acid (tetrahydro-pyran-4-ylmethyl)-amide.

Compounds 3-methyl-7-morpholin-4-yl-1H-pyrrolo[2,3-c]pyridine-4-carboxylic acid (tetrahydro-pyran-4-yl)-amide or 3-methyl-7-morpholin-4-yl-1H-pyrrolo[2,3-c]pyridine-4-carboxylic acid (tetrahydro-pyran-4-ylmethyl)-amide, (Examples 22 and 23) did not appear to have CB2 activity in the assay used.

In one embodiment compounds of formula (I) are compounds of formula (Ia) or (Ib):

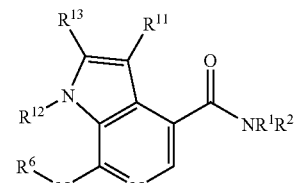

(Ia)

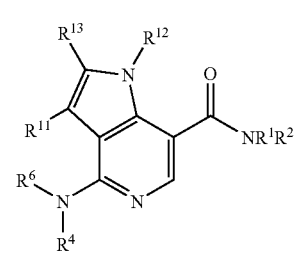

(Ib)

wherein $R^1$, $R^2$, $R^4$, $R^6$, $R^{11}$, $R^{12}$ and $R^{13}$ are as defined for compounds of formula (I).

In one embodiment $R^1$ is hydrogen.
In one embodiment $R^{13}$ is hydrogen.
In one embodiment $R^2$ is $(CH_2)_mR^3$ where m is 0 or 1.
When $R^3$ or $R^6$ are independently selected from a non-aromatic heterocyclyl group, the ring may contain 1, 2, 3, or 4 hetero atoms. In one embodiment the hetero atoms are selected from oxygen, nitrogen or sulphur. Examples of 4- membered groups are 2- or 3- azetidinyl, oxetanyl, thioxetanyl, thioxetanyl-s-oxide and thioxetanyl-s,s-dioxide. Examples of 5- membered heterocyclyl groups in this instance include dioxolanyl, pyrrolidinyl, tetrahydrofuranyl, tetrahydrothiophenyl and tetrahydrothiophenyl-s,s-dioxide. An additional example is tetrahydrothiophenyl-s-oxide. Examples of 6- membered heterocyclyl groups are morpholinyl, piperidinyl, piperazinyl, tetrahydropyranyl, tetrahydrothiopyranyl, tetrahydrothiopyranyl-s,s-dioxide, thiomorpholinyl, thiomorpholinyl-s,s-dioxide, tetrahydropyridinyl, dioxanyl, and tetrahydrothiopyran-1,1-dioxide. An additional example is tetrahydrothiopyran-1-oxide. Examples of a 7- membered heterocyclyl ring are azapine or oxapine. Examples of 8- membered groups are azacyclooctanyl, azaoxacyclooctanyl or azathiacyclooctanyl, oxacylcooctanyl, or thiacyclooctanyl. Additional examples of 8- membered groups are azathiacyclooctanyl-s-oxide, azathiacyclooctanyl-s,s-dioxide, thiacyclooctanyl-s,s-dioxide, and thiacyclooctanyl-s-oxide.

In one embodiment $R^3$ is a 4- to 8- membered non-aromatic heterocyclyl group, a $C_{3-8}$ cycloalkyl group, a straight or branched $C_{1-10}$ alkyl, a $C_{2-10}$alkenyl, a $C_{3-8}$cycloalkenyl, a $C_{2-10}$alkynyl, or a $C_{3-8}$cycloalkynyl, any of which can be unsubstituted or substituted or $R^5$.

In one embodiment $R^3$ is an unsubstituted or substituted 4- to 8- membered non-aromatic heterocyclyl group, an unsubstituted or substituted $C_{3-8}$ cycloalkyl group or an unsubstituted or substituted $C_{1-6}$alkyl.

In one embodiment $R^3$ is an unsubstituted or substituted 4- to 8- membered non-aromatic heterocyclyl group, or an unsubstituted or substituted $C_{3-8}$ cycloalkyl group.

In one embodiment when $R^3$ is an unsubstituted or substituted 4- to 8- membered non-aromatic heterocyclyl group, said group is selected from tetrahydrofuranyl, tetrahydropyranyl, piperidinyl or morpholinyl.

In one embodiment $R^3$ is a selected from tetrahydropyranyl, tetrahydrofuranyl, a $C_{3-6}$ cycloalkyl group, a straight or branched $C_{1-6}$ alkyl, or phenyl group, any of which can be unsubstituted or substituted;

In one embodiment $R^3$ is tetrahydrofuranyl, tetrahydropyranyl, or $C_{3-6}$cycloalkyl for example cyclobutyl or cyclopropyl.

In one embodiment $R^3$ is tetrahydrofuranyl, or $C_{3-6}$cycloalkyl for example cyclobutyl or cyclopropyl.

In one embodiment $R^4$ is $C_{1-6}$ alkyl or hydrogen, for example methyl or hydrogen.

In one embodiment $R^4$ is hydrogen.

When $R^1$ and $R^2$ taken together with the N to which they are attached form an optionally substituted non-aromatic heterocyclyl ring, or when $R^4$ and $R^6$ taken together with the N to which they are attached form an optionally substituted non-aromatic heterocyclyl ring the ring may optionally contain 1, 2, 3 or 4 further hetero atoms. The ring may be saturated or unsaturated. In one embodiment the further hetero atoms are selected from oxygen, nitrogen or sulphur. An example of a 4-membered heterocyclyl ring is azetidinyl. Examples of a 5-membered heterocyclyl ring are pyrrolidinyl and pyrazolidinyl. Examples of 6-membered heterocyclyl rings are morpholinyl, piperazinyl or piperidinyl. Additional examples are tetrahydropyridinyl, thiomorpholine-s,s-dioxide Further examples are thiomorpholinyl and thiomorpholinyl-s-oxide. Examples of a 7- membered heterocyclyl ring are azapine or oxapine. Examples of 8-membered heterocyclyl rings are azacyclooctanyl, azaoxacyclooctanyl or azathiacyclooctanyl.

In one embodiment when $R^1$ and $R^2$ together with the nitrogen to which they are attached form a morpholinyl, pyrrolidinyl, piperidinyl, azetidinyl, azapine, or thiomorpholinyl-s,s-dioxide ring.

In one embodiment when $R^1$ and $R^2$ together with the nitrogen to which they are attached form a morpholinyl, pyrrolidinyl, piperidinyl, azetidinyl or azapine ring.

In one embodiment when $R^1$ and $R^2$ together with the nitrogen to which they are attached form a morpholinyl, pyrrolidinyl or piperidinyl ring.

In one embodiment $R^6$ is phenyl, $C_{3-6}$cycloalkyl, tetrahydropyranyl, any of which can be unsubstituted or substituted.

In one embodiment $R^6$ is a substituted phenyl, cyclohexyl or tetrahydropyranyl.

In one embodiment $R^6$ is a substituted phenyl.

In one embodiment when $R^4$ and $R^6$ together with the nitrogen to which they are attached form a morpholinyl, pyrrolidinyl or piperidinyl ring.

In one embodiment $R^7$ is OH.

In one embodiment $R^{10}$ is hydrogen.

In one embodiment $R^{11}$ is methyl or hydrogen.

In one embodiment $R^{12}$ is methyl or hydrogen.

In one embodiment $R^{13}$ is methyl or hydrogen.

In one embodiment X is $CH_2$.

When $R^6$ is substituted, it may be substituted by 1, 2 or 3 substituents, the substituent or substituents may be selected from: $C_{1-6}$ alkyl, halosubstituted$C_{1-6}$ alkyl e.g. trifluoromethyl, $C_{1-6}$ alkoxy, a hydroxy group, a cyano group, halo, a $C_{1-6}$alkyl sulfonyl group, —$CONH_2$, —$NHCOCH_3$, —COOH, halosubstituted $C_{1-6}$ alkoxy e.g. trifluoromethoxy and $SO_2NR^{8a}R^{8b}$ wherein $R^{8a}$ and $R^{8b}$ are as defined above.

In one embodiment $R^6$ is substituted by 1 or 2 substituents.

In one embodiment $R^6$ is substituted by halo, cyano, methyl, trifluoromethyl, methoxy or trifluoromethoxy.

When $R^1$ and $R^2$ or $R^4$ and $R^6$ together with N to which they are attached form a 4- to 8- membered non-aromatic heterocyclyl ring which is substituted, or when $R^3$ is substituted, the substituent or substituents may be selected from: $C_{1-6}$ alkyl, $C_{1-6}$ alkoxy, a hydroxy group, halosubstituted $C_{1-6}$alkyl e.g. trifluoromethyl, halosubstituted $C_{1-6}$alkoxy e.g. trifluoromethoxy, a cyano group, halo or a sulfonyl group, methylsulfonyl, $NR^{8a}R^{8b}$, $CONH_2$, $NHCOCH_3$, (=O), COOH, $CONHCH_3$, $CON(CH_3)_2$ and $NHSO_2CH_3$ wherein $R^{8a}$ and $R^{8b}$ are as described above.

When $R^1$ and $R^2$ or $R^4$ and $R^6$ together with N to which they are attached form a 4- to 8- membered non-aromatic heterocyclyl ring which is substituted, or when $R^3$ is substituted there can be 1, 2 or 3 substituents.

When $R^{10}$ is substituted, the substituents may be selected from halogen.

In one embodiment the invention is compounds of formula (Ic) or (Id);

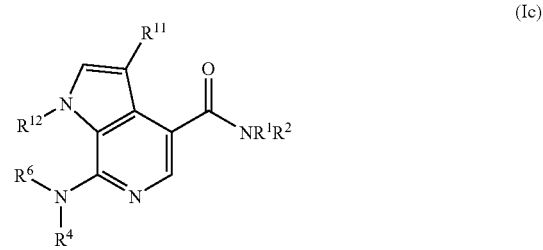

(Ic)

-continued

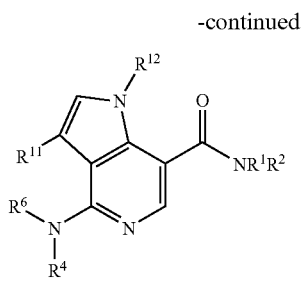

(Id)

wherein
R¹ is hydrogen;
R² is (CH₂)ₘR³ where m is 0 or 1;
or R¹ and R² together with N to which they are attached form a morpholinyl, pyrrolidinyl, piperidinyl, thiomorpholine-s,s-dioxide, azetidinyl or azapine ring any of which may be unsubstituted or substituted;
R³ is a selected from tetrahydropyranyl, tetrahydrofuranyl, a C₃₋₆ cycloalkyl group, a straight or branched C₁₋₆ alkyl and phenyl group, any of which can be unsubstituted or substituted;
R⁴ is hydrogen or methyl,
R⁶ is phenyl, C₃₋₆cycloalkyl or tetrahydropyranyl, any of which can be unsubstituted or substituted;
R¹¹ is hydrogen or methyl;
R¹² is hydrogen or methyl;

and pharmaceutically acceptable derivatives thereof.

In one embodiment the compound is selected from:
1-[7-(3-Chloro-phenylamino)-3-methyl-1H-pyrrolo[2,3-c]pyridin-4-yl]-1-morpholin-4-yl-methanone;
1-[4-(3-Chloro-phenylamino)-1-methyl-1H-pyrrolo[3,2-c]pyridin-7-yl]-1-piperidin-1-yl-methanone;
1-[4-(3-Chloro-phenylamino)-1-methyl-1H-pyrrolo[3,2-c]pyridin-7-yl]-1-morpholin-4-yl-methanone;
1-[4-(3-Chloro-phenylamino)-1-methyl-1H-pyrrolo[3,2-c]pyridin-7-yl]-1-pyrrolidin-1-yl-methanone;
N-(3-Bromophenyl)-1-methyl-7-(4-morpholinylcarbonyl)-1H-pyrrolo[3,2-c]pyridine-4-amine hydrochloride;
N-(3,4-Dichlorophenyl)-1-methyl-7-(4-morpholinylcarbonyl)-1H-pyrrolo[3,2-c]pyridin-4-amine;
1-Methyl-7-(4-morpholinylcarbonyl)-N-{3-[(trifluoromethyl)oxy]phenyl}-1H-pyrrolo[3,2-c]pyridin-4-amine;
N-(3-Fluorophenyl)-1-methyl-7-(4-morpholinylcarbonyl)-1H-pyrrolo[3,2-c]pyridin-4-amine;
N-(4-Bromo-3-chlorophenyl)-1-methyl-7-(4-morpholinylcarbonyl)-1H-pyrrolo[3,2-c]pyridin-4-amine;
N-(3-Chloro-4-fluorophenyl)-1-methyl-7-(1-piperidinylcarbonyl)-1H-pyrrolo[3,2-c]pyridin-4-amine;
1-Methyl-7-(1-piperidinylcarbonyl)-N-{3-[(trifluoromethyl)oxy]phenyl}-1H-pyrrolo[3,2-c]pyridin-4-amine;
N-(3-Chlorophenyl)-1-ethyl-7-(4-morpholinylcarbonyl)-11H-pyrrolo[3,2-c]pyridin-4-amine;
N-(3,5-Difluorophenyl)-1-methyl-7-(4-morpholinylcarbonyl)-1H-pyrrolo[3,2-c]pyridin-4-amine and pharmaceutically acceptable derivatives thereof.

In certain embodiments compounds of formula (I) show selectivity for CB2 over CB1.

In one embodiment compounds of formula (I) have an EC50 value at the cloned human cannabinoid CB2 receptor of at least 50 times the EC50 values at the cloned human cannabinoid CB1 receptor and/or have less than 10% efficacy at the CB1 receptor.

Compounds of formula (I) may be more potent and/or more soluble and/or more bioavailable and/or produce a more linear increase in exposure when the compounds are orally administered to a mammal than earlier published compounds which are agonists of CB2.

DETAILED DESCRIPTION

The invention is described using the following definitions unless otherwise indicated.

The term "pharmaceutically acceptable derivative" means any pharmaceutically acceptable salt, ester, salt of such ester or solvate of the compounds of formula (I), or any other compound which upon administration to the recipient is capable of providing (directly or indirectly) a compound of formula (I) or an active metabolite or residue thereof. In one embodiment the pharmaceutically acceptable derivative is a salt or solvate of compound of formula (I).

It will be appreciated by those skilled in the art that compounds of formula (I) may be modified to provide pharmaceutically acceptable derivatives thereof at any of the functional groups in the compounds, and that the compounds of formula (I) may be derivatised at more than one position.

It will be appreciated that, for pharmaceutical use, the salts referred to above will be physiologically acceptable salts, but other salts may find use, for example in the preparation of compounds of formula (I) and the physiological acceptable salts thereof. Pharmaceutically acceptable salts include those described by Berge, Bighley and Monkhouse, J. Pharm. Sci., 1977, 66, 1-19. The term "pharmaceutically acceptable salts" includes salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, trishydroxylmethyl amino methane, tripropyl anine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Examples of pharmaceutically acceptable salts include the ammonium, calcium, magnesium, potassium, and sodium salts, and those formed from maleic, fumaric, benzoic, ascorbic, pamoic, succinic, hydrochloric, sulfuric, bismethylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitric acids.

The terms 'halogen or halo' are used to represent fluorine, chlorine, bromine or iodine.

The term 'alkyl' as a group or part of a group means a straight or branched chain alkyl group or combinations thereof, for example a methyl, ethyl, n-propyl, i-propyl, n-butyl, s-butyl, t-butyl, i-butyl, pentyl, hexyl, 1,1-dimethylethyl, heptyl, octyl, nonyl, decyl or combinations thereof.

The term 'alkoxy' as a group or as part of a group means a straight, branched or cyclic chain alkyl group having an oxygen atom attached to the chain, for example a methoxy, ethoxy, n-propoxy, i-propoxy, n-butoxy, s-butoxy, t-butoxy group, i-butoxy, pentoxy, hexyloxy group, cyclopentoxy or cyclohexyloxy group.

The term 'cycloalkyl' means a closed saturated ring, for example cyclopropyl, cyclobutyl, cyclopentyl, cyclohexyl or cycloheptyl, or cyclooctyl.

The term 'alkenyl' means as a group or part of a group means a straight or branched chain carbon chain or combinations thereof containing 1 or more double bonds, for example butenyl, pentenyl, hexenyl or heptenyl, or octenyl.

The term 'cycloalkenyl' means a closed non-aromatic carbon ring containing 1 or more double bonds, for example cyclobutenyl, cyclopentenyl, cyclohexenyl or cycloheptenyl, or cyclooctenyl.

The term 'alkynyl' as a group or part of a group means a straight or branched chain carbon chain or combinations containing 1 or more triple carbon bonds for example ethynyl, propynyl, butynyl, pentynyl, hexynyl or combinations thereof.

The term 'cycloalkynyl' means a closed non-aromatic carbon ring containing 1 or more triple carbon bonds for example cyclopropynyl, cyclobutynyl, cyclopentynyl, cyclohexynyl or combinations thereof.

The term 'aryl' means a 5- or 6- membered aromatic ring, for example phenyl, or a 7- to 12- membered bicyclic ring system where at least one of the rings is aromatic, for example naphthyl.

Compounds of formula (I) wherein $X_1$ is $NR^{12}$ can be prepared as set forth in scheme 1:

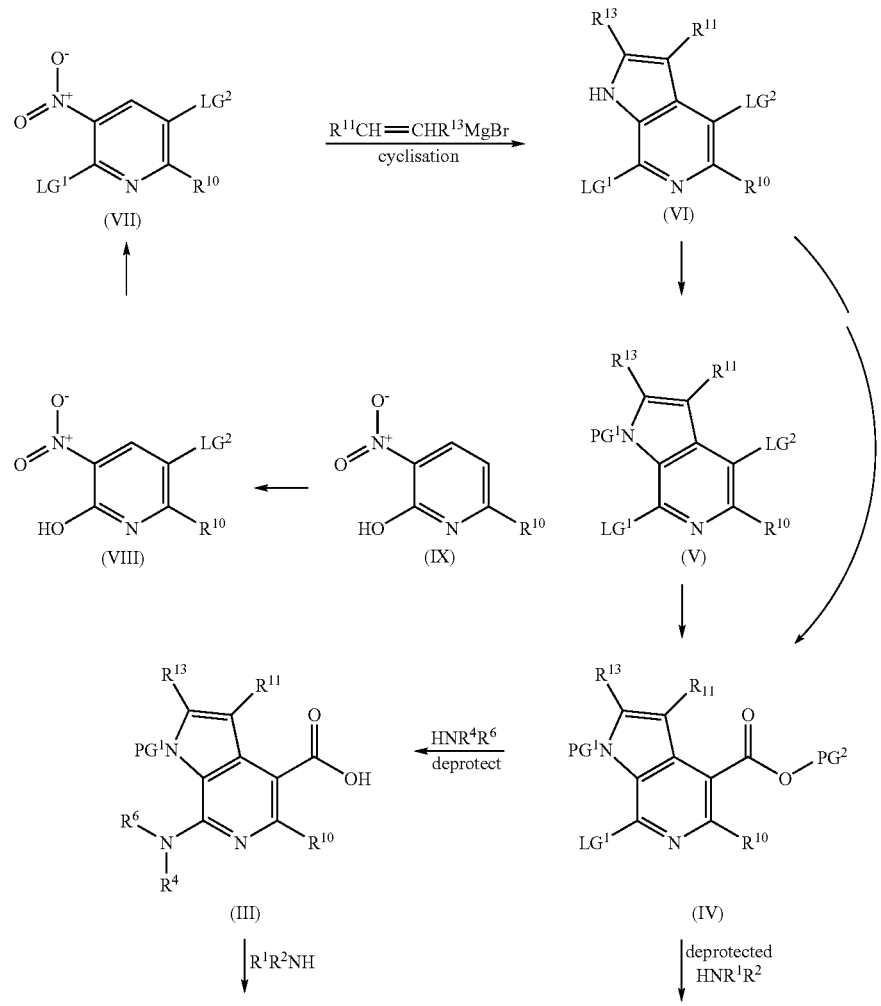

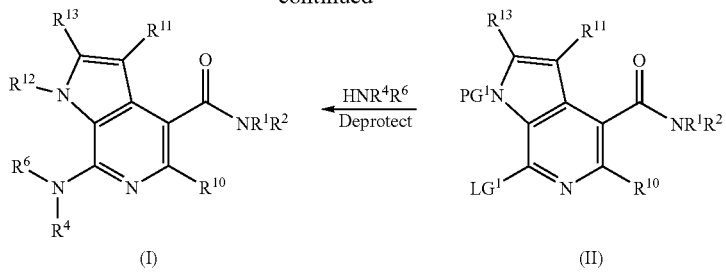

wherein LG¹ is a leaving group, for example halo e.g. chloro, LG² is a leaving group, for example halo, e.g. chloro, bromo or iodo PG¹ is a protecting group such as t-butyldimethylsilanyl or t-butyl ester or $R^{12}$, PG² is a protecting group such as ethyl, and $R^1$, $R^2$, $R^4$, $R^6$, $R^{10}$, $R^{11}$ $R^{12}$ and $R^{13}$ are as defined for compounds of formula (I).

Compounds of formula (I) wherein $X_3$ is $NR^{12}$ can be prepared as set forth in scheme 2:

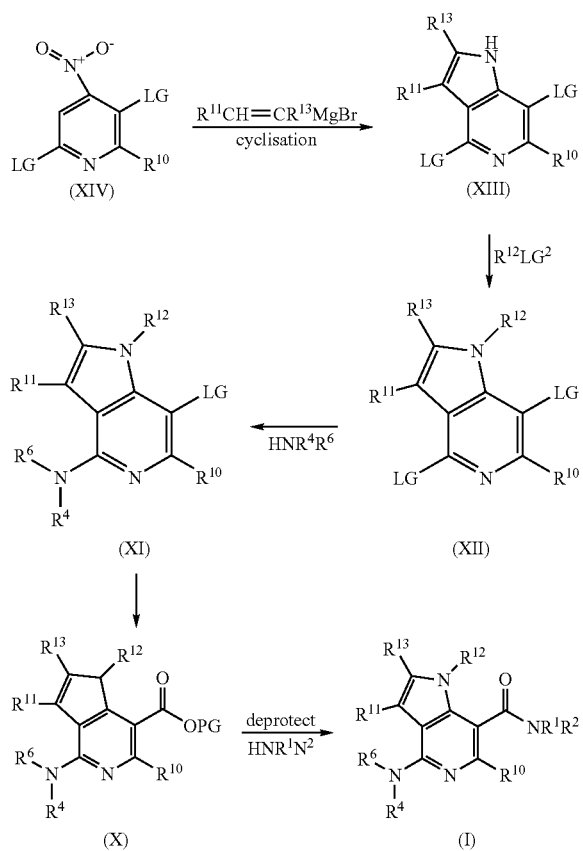

wherein LG is a leaving group, for example halo, LG² is a leaving group, for example halo or $OSO_2W$ where W can be trifluoromethyl, methyl or phenyl, PG is a hydrogen or ethyl and $R^1$, $R^2$, $R^4$, $R^6$, $R^{10}$, $R^{11}$, $R^{12}$ and $R^{13}$ are as defined for compounds of formula (I).

Compounds of formula (I) wherein $X_3$ is $NR^{12}$ can be prepared as set forth in scheme 3:

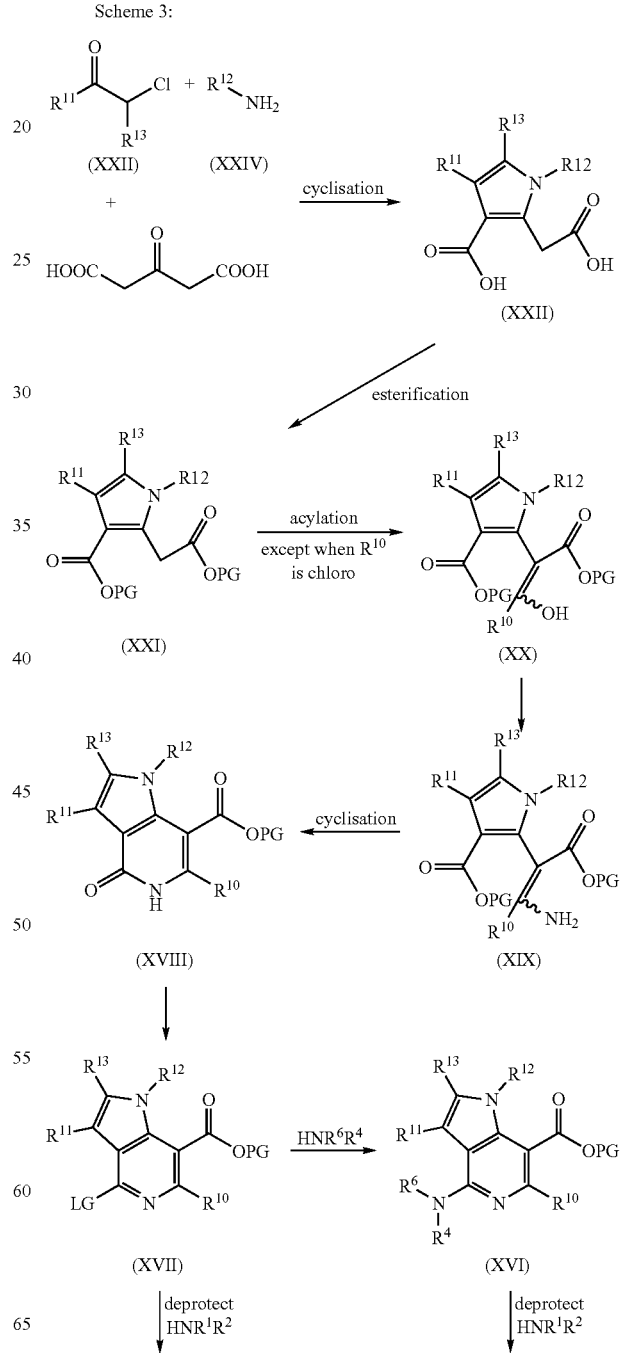

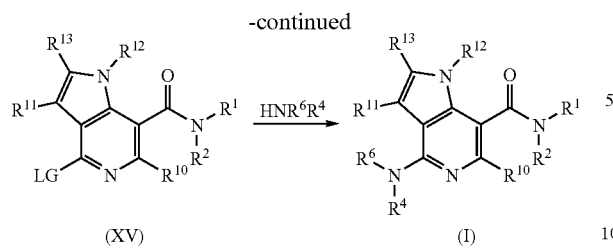

wherein LG is a leaving group, for example halo, PG is a hydrogen or $C_{1-6}$alkyl for example methyl and $R^1$, $R^2$, $R^4$, $R^6$, $R^{10}$, $R^{11}$, $R^{12}$ and $R^{13}$ are as defined for compounds of formula (I). In the above scheme when $R^{12}$ is methyl, methylamine and 2-chloropropionaldehyde could be used instead of $R^{12}$—$NH_2$.

Alternatively compounds of formula (I) wherein $X^3$ is $NR^{12}$ can be prepared as set forth in scheme 4:

Scheme 4.

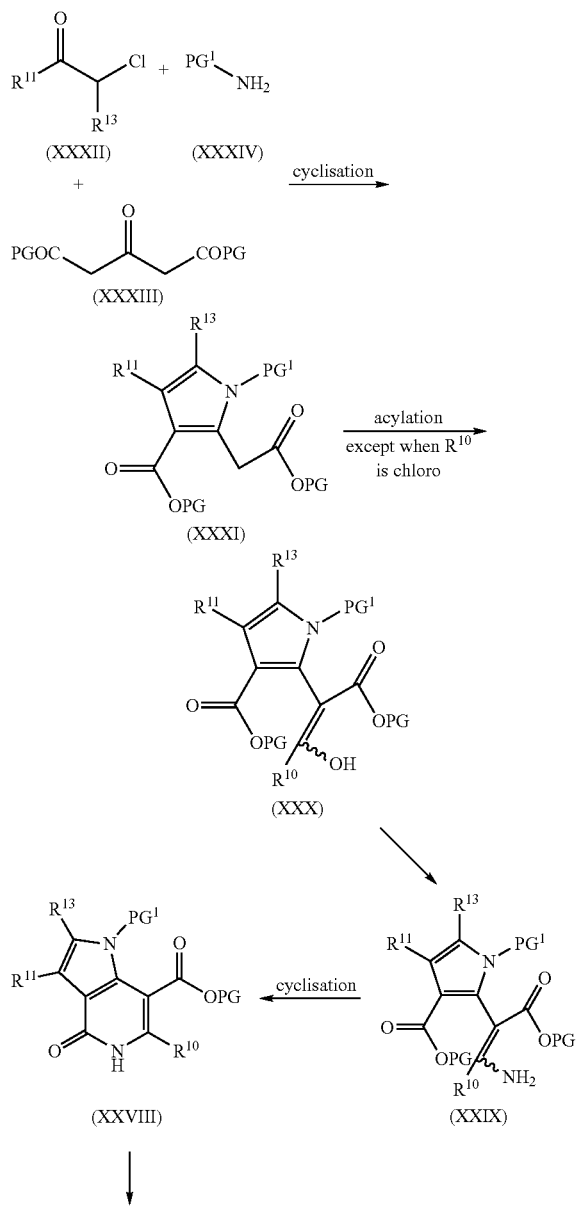

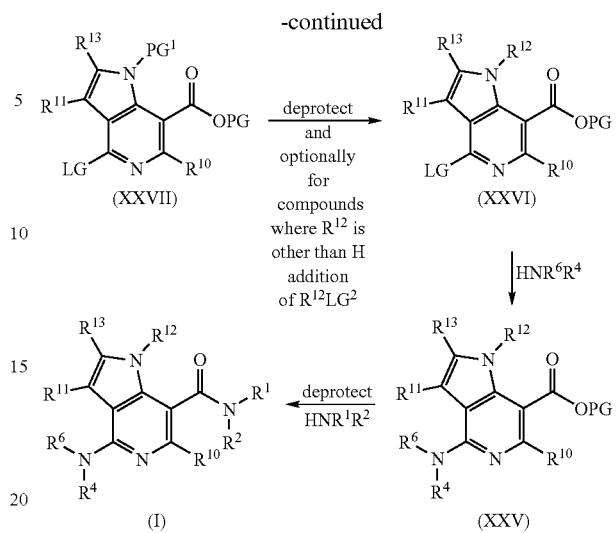

wherein PG is $C_{1-6}$alkyl, for example methyl or ethyl, $PG^1$ is paramethoxy benzyl, and $R^1$, $R^2$, $R^4$, $R^6$, $R^{10}$, $R^{11}$, $R^{12}$ and $R^{13}$ are as defined for compounds of formula (I).

It is to be understood that the present invention encompasses all isomers of compounds of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The subject invention also includes isotopically-labeled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^8F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula (I) and following of this invention can generally be prepared by carrying out the procedures disclosed in the Schemes and/or in the Examples below, by substituting a readily available isotopically labeled reagent for a non-isotopically labeled reagent.

Compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

In view of their ability to bind to the CB2 receptor, it is believed that compounds of the invention will be useful in the treatment of the disorders that follow. Thus, compounds of formula (I) may be useful as analgesics. For example they may be useful in the treatment of chronic inflammatory pain (e.g. pain associated with rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

Compounds of the invention may also have disease modification or joint structure preservation properties in multiple sclerosis, rheumatoid arthritis, osteo-arthritis, rheumatoid spondylitis, gouty arthritis and juvenile arthritis.

Compounds of the invention may be particularly useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Compounds of formula (I) may also be useful in the treatment of fever.

Compounds of formula (I) may also be useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, chronic obstructive pulmonary disease, (COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastroesophageal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, tendinitis, bursitis, and Sjogren's syndrome.

Compounds of formula (I) may also be useful in the treatment of bladder hyperrelexia following bladder inflammation.

Compounds of formula (I) may also be useful in the treatment of immunological diseases such as autoimmune diseases, immunological deficiency diseases or organ transplantation. The compounds of formula (I) may also be effective in increasing the latency of HIV infection.

Compounds of formula (I) may also be useful in the treatment of diseases of abnormal platelet function (e.g. occlusive vascular diseases).

Compounds of formula (I) may also be useful in the treatment of neuritis, heart burn, dysphagia, pelvic hypersensitivity, urinary incontinence, cystitis or pruritus.

Compounds of formula (I) may also be useful for the preparation of a drug with diuretic action.

Compounds of formula (I) may also be useful in the treatment of impotence or erectile dysfunction.

Compounds of formula (I) may also be useful for attenuating the hemodynamic side effects of non-steroidal anti-inflammatory drugs (NSAID's) and cyclooxygenase-2 (COX-2) inhibitors.

Compounds of formula (I) may also be useful in the treatment of neurodegenerative diseases and neurodegeneration such as dementia, particularly degenerative dementia (including senile dementia, Alzheimer's disease, Pick's disease, Huntingdon's chorea, Parkinson's disease and Creutzfeldt-Jakob disease, motor neuron disease); vascular dementia (including multi-infarct dementia); as well as dementia associated with intracranial space occupying lesions; trauma; infections and related conditions (including HIV infection); dementia in Parkinson's disease; metabolism; toxins; anoxia and vitamin deficiency; and mild cognitive impairment associated with ageing, particularly Age Associated Memory Impairment. The compounds may also be useful for the treatment of amyotrophic lateral sclerosis (ALS) and neuroinflamation.

Compounds of formula (D may also be useful in neuroprotection and in the treatment of neurodegeneration following stroke, cardiac arrest, pulmonary bypass, traumatic brain injury, spinal cord injury or the like.

Compounds of formula (I) may also be useful in the treatment of tinnitus.

Compounds of formula (I) may also be useful in the treatment of psychiatric disease for example schizophrenia, depression (which term is used herein to include bipolar depression, unipolar depression, single or recurrent major depressive episodes with or without psychotic features, catatonic features, melancholic features, atypical features or post-partum onset, seasonal affective disorder, dysthymic disorders with early or late onset and with or without atypical features, neurotic depression and social phobia, depression accompanying dementia for example of the Alzheimer's type, schizoaffective disorder or the depressed type, and depressive disorders resulting from general medical conditions including, but not limited to, myocardial infarction, diabetes, miscarriage or abortion, etc), anxiety disorders (including generalised anxiety disorder and social anxiety disorder), panic disorder, agoraphobia, social phobia, obsessive compulsive disorder and post-traumatic stress disorder, memory disorders, including dementia, amnesic disorders and age-associated memory impairment, disorders of eating behaviours, including anorexia nervosa and bulimia nervosa, sexual dysfunction, sleep disorders (including disturbances of circadian rhythm, dyssomnia, insomnia, sleep apnea and narcolepsy), withdrawal from abuse of drugs such as of cocaine, ethanol, nicotine, benzodiazepines, alcohol, caffeine, phencyclidine (phencyclidine-like compounds), opiates (e.g. heroin, morphine), amphetamine or amphetamine-related drugs (e.g. dextroamphetamine, methylamphetamine) or a combination thereof.

Compounds of formula (I) may also be useful in preventing or reducing dependence on, or preventing or reducing tolerance or reverse tolerance to, a dependence-inducing agent. Examples of dependence inducing agents include opioids (e.g. morphine), CNS depressants (e.g. ethanol), psychostimulants (e.g. cocaine) and nicotine.

Compounds of formula (I) may also be useful in the treatment of kidney dysfunction (nephritis, particularly mesangial proliferative glomerulonephritis, nephritic syndrome), liver dysfunction (hepatitis, cirrhosis), gastrointestinal dysfunction (diarrhoea) and colon cancer.

Compounds of the invention may bind selectively to the CB2 receptor; such compounds may be particularly useful in treating CB2 receptor mediated diseases.

The term "treatment" or "treating" as used herein includes the treatment of established disorders and also includes the prophylaxis thereof. The term "prophylaxis" is used herein to mean preventing symptoms in an already afflicted subject or preventing recurrence of symptoms in an afflicted subject and is not limited to complete prevention of an affliction.

According to a further aspect of the invention, we provide a compound of formula (I) or a pharmaceutically acceptable derivative thereof for use in human or veterinary medicine.

According to another aspect of the invention, we provide a compound of formula (I) or a pharmaceutically acceptable derivative thereof for use in the treatment of a condition which is mediated by the activity of cannabinoid 2 receptors.

According to a further aspect of the invention, we provide a method of treating a mammal, for example a human suffering from a condition which is mediated by the activity of cannabinoid 2 receptors which comprises administering to said subject a therapeutically effective amount of a compound of formula (I) or a pharmaceutically acceptable derivative thereof.

According to a further aspect of the invention we provide a method of treating a mammal, for example a human suffering from an immune disorder, an inflammatory disorder, pain, rheumatoid arthritis, multiple sclerosis, osteoarthritis or osteoporosis which method comprises administering to said subject an effective amount of a compound of formula (I) or a pharmaceutically acceptable derivative thereof.

In one embodiment the pain is selected from inflammatory pain, visceral pain, cancer pain, neuropathic pain, lower back pain, muscular skeletal, post operative pain, acute pain and migraine. For example, the inflammatory pain is pain associated with rheumatoid arthritis or osteoarthritis.

According to another aspect of the invention is provided the use of a compound of formula (I) or a pharmaceutically acceptable derivative thereof for the manufacture of a therapeutic agent for the treatment or prevention of a condition such as an immune disorder, an inflammatory disorder, pain, rheumatoid arthritis, multiple sclerosis, osteoarthritis or osteoporosis.

In order to use a compound of formula (I) or a pharmaceutically acceptable derivative thereof for the treatment of humans and other mammals it is normally formulated in accordance with standard pharmaceutical practice as a pharmaceutical composition. Therefore in another aspect of the invention is provided a pharmaceutical composition comprising a compound of formula (I) or a pharmaceutically acceptable derivative thereof adapted for use in human or veterinary medicine.

As used herein, "modulator" means both antagonist, partial or full agonist and inverse agonist. In one embodiment the present modulators are agonists.

Compounds of formula (I) and their pharmaceutically acceptable derivatives may be administered in a standard manner for the treatment of the indicated diseases, for example orally, parenterally, sub-lingually, dermally, intranasally, transdermally, rectally, via inhalation or via buccal administration.

Compounds of formula (I) and their pharmaceutically acceptable derivatives which are active when given orally can be formulated as liquids, tablets, capsules and lozenges. A liquid formulation will generally consist of a suspension or solution of the compound or salt in a liquid carrier for example, ethanol, olive oil, glycerine, glucose (syrup) or water with a flavouring, suspending, or colouring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers or a semi solid e.g. mono di-glycerides of capric acid, Gelucire™ and Labrasol™, or a hard capsule shell e.g gelatin. Where the composition is in the form of a soft shell capsule e.g. gelatin, any pharmaceutical carrier routinely used for preparing dispersions or suspensions may be considered, for example aqueous gums or oils, and are incorporated in a soft capsule shell.

Typical parenteral compositions consist of a solution or suspension of a compound or derivative in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of formula (I) or a pharmaceutically acceptable derivative thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

In one embodiment the composition is in unit dosage form, for example a tablet, capsule or metered aerosol dose, so that the patient may administer a single dose.

Each dosage unit for oral administration contains suitably from 0.001 mg to 500 mg, for example 0.01 mg to 500 mg such as from 0.01 mg to 100 mg, and each dosage unit for parenteral administration contains suitably from 0.001 mg to 100 mg, of a compound of formula (I) or a pharmaceutically acceptable derivative thereof calculated as the free acid. Each dosage unit for suppository administration contains suitably from 0.001 mg to 500 mg, for example 0.01 mg to 500 mg such as from 0.01 mg to 100 mg. Each dosage unit for intranasal administration contains suitably 1400 mg and suitably 10 to 200 mg per person. A topical formulation contains suitably 0.01 to 5.0% of a compound of formula (I).

The daily dosage regimen for oral administration is suitably about 0.01 mg/Kg to 1000 mg/Kg, of a compound of formula (I) or a pharmaceutically acceptable derivative thereof calculated as the free acid. The daily dosage regimen for parenteral administration is suitably about 0.001 mg/Kg to 200 mg/Kg, of a compound of formula (I) or a pharmaceutically acceptable derivative thereof calculated as the free acid. The daily dosage regimen for suppository administration is suitably about 0.01 mg/Kg to 1000 mg/Kg, of a compound of formula (I) or a pharmaceutically acceptable derivative thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

It may be advantageous to prepare the compounds of the present invention as nanoparticles.

This may improve the oral bioavailability of the compounds. For the purposes of the present invention "nanoparticulate" is defined as solid particles with 50% of the particles having a particle size of less than 1 μm, for example less than 0.75 μm.

The particle size of the solid particles of compound (I) may be determined by laser diffraction. A suitable machine for determining particle size by laser diffraction is a Lecotrac laser particle size analyser, using an HELOS optical bench fitted with a QUIXEL dispersion unit.

Numerous processes for the synthesis of solid particles in nanoparticulate form are known. Typically these processes involve a milling process, for example a wet milling process in the presence of a surface modifying agent that inhibits aggregation and/or crystal growth of the nanoparticles once created. Alternatively these processes may involve a precipitation process, for example, a process of precipitation in an aqueous medium from a solution of the drug in a non-aqueous solvent.

Accordingly, in a further aspect, the present invention provides a process for preparing compound (I) in nanoparticulate form as hereinbefore defined, which process comprises milling or precipitation.

Representative processes for the preparation of solid particles in nanoparticulate form are described in the patents and publications listed below.

U.S. Pat. No. 4,826,689 to Violanto & Fischer, U.S. Pat. No. 5,145,684 to Liversidge et al U.S. Pat. No. 5,298,262 to Na & Rajagopalan, U.S. Pat. No. 5,302,401 Liversidge et al U.S. Pat. No. 5,336,507 to Na & Rajagopalan, U.S. Pat. No. 5,340,564 to Illig & Sarpotdar U.S. Pat. No. 5,346,702 to Na Rajagopalan, U.S. Pat. No. 5,352,459 to Hollister et al U.S. Pat. No. 5,354,560 to Lovrecich, U.S. Pat. No. 5,384,124 to Courteille et al, U.S. Pat. No. 5,429,824 to June, U.S. Pat. No. 5,503,723 to Ruddy et al, U.S. Pat. No. 5,510,118 to Bosch et al, U.S. Pat. No. 5,518 to Bruno et al, U.S. Pat. No. 5,518,738 to Eickhoff et al, U.S. Pat. No. 5,534,270 to De Castro, U.S. Pat. No. 5,536,508 to Canal et al, U.S. Pat. No. 5,552,160 to Liversidge et al, U.S. Pat. No. 5,560,931 to Eickhoff et al, U.S. Pat. No. 5,560,932 to Bagchi et al, U.S. Pat. No. 5,565,188 to Wong et al, U.S. Pat. No. 5,571,536 to Eickhoff et al, U.S. Pat. No. 5,573,783 to Desieno & Stetsko, U.S. Pat. No. 5,580,579 to Ruddy et al, U.S. Pat. No. 5,585,108 to Ruddy et al, U.S. Pat. No. 5,587,143 to Wong, U.S. Pat. No. 5,591,456 to Franson et al, U.S. Pat. No. 5,622,938 to Wong, U.S. Pat. No. 5,662,883 to Bagchi et al, U.S. Pat. No. 5,665,331 to Bagchi et al, U.S. Pat. No. 5,718,919 to Ruddy et al, U.S. Pat. No. 5,747,001 to Wiedmann et al, WO93/25190, WO96/24336, WO 97/14407, WO 98/35666, WO 99/65469, WO 00/18374, WO 00/27369, WO 00/30615 and WO 01/41760.

Such processes may be readily adapted for the preparation of compound (I) in nanoparticulate form. Such processes form a further aspect of the invention.

The process of the present invention may use a wet milling step carried out in a mill such as a dispersion mill in order to produce a nanoparticulate form of the compound. The present invention may be put into practice using a conventional wet milling technique, such as that described in Lachman et al., The Theory and Practice of Industrial Pharmacy, Chapter 2, "Milling" p. 45 (1986).

In a further refinement, WO02/00196 (SmithKline Beecham plc) describes a wet milling procedure using a mill in which at least some of the surfaces are made of nylon (polyamide) comprising one or more internal lubricants, for use in the preparation of solid particles of a drug substance in nanoparticulate form.

In another aspect the present invention provides a process for preparing compounds of the invention in nanoparticulate form comprising wet milling a suspension of compound in a mill having at least one chamber and agitation means, said chamber(s) and/or said agitation means comprising a lubricated nylon, as described in WO02/00196.

The suspension of a compound of the invention for use in the wet milling is typically a liquid suspension of the coarse compound in a liquid medium. By "suspension" is meant that the compound is essentially insoluble in the liquid medium. Representative liquid media include an aqueous medium. Using the process of the present invention the average particle size of coarse compound of the invention may be up to 1 mm in diameter. This advantageously avoids the need to pre-process the compound.

In a further aspect of the invention the aqueous medium to be subjected to the milling comprises compound (I) present in from about 1% to about 40% w/w, suitably from about 10% to about 30% W/W, for example about 20% w/w.

The aqueous medium may further comprise one or more pharmaceutically acceptable water-soluble carriers which are suitable for steric stabilisation and the subsequent processing of compound (I) after milling to a pharmaceutical composition, e.g. by spray drying. Pharmaceutically acceptable excipients most suitable for steric stabilisation and spray-drying are surfactants such as poloxamers, sodium lauryl sulphate and polysorbates etc; stabilisers such as celluloses e.g. hydroxypropylmethyl cellulose; and carriers such as carbohydrates e.g. mannitol.

In a further aspect of the invention the aqueous medium to be subjected to the milling may further comprise hydroxypropylmethyl cellulose (HPMC) present from about 0.1 to about 10% w/w.

The process of the present invention may comprise the subsequent step of drying compound of the invention to yield a powder.

Accordingly, in a further aspect, the present invention provides a process for preparing a pharmaceutical composition contain a compound of the present invention which process comprises producing compound of formula (I) in nanoparticulate form optionally followed by drying to yield a powder.

A further aspect of the invention is a pharmaceutical composition comprising a compound of formula (I) or a pharmaceutically acceptable deriviate thereof in which the compound of formula (I) or a pharmaceutically acceptable deriviate thereof is present in solid particles in nanoparticulate form, in admixture with one or more pharmaceutically acceptable carriers or excipients.

By "drying" is meant the removal of any water or other liquid vehicle used during the process to keep compound of formula (I) in liquid suspension or solution. This drying step may be any process for drying known in the art, including freeze drying, spray granulation or spray drying. Of these methods spray drying is particularly preferred. All of these techniques are well known in the art. Spray drying/fluid bed granulation of milled compositions is carried out most suitably using a spray dryer such as a Mobile Minor Spray Dryer [Niro, Denmark], or a fluid bed drier, such as those manufactured by Glatt, Germany.

In a further aspect the invention provides a pharmaceutical composition as hereinbefore defined, in the form of a dried powder, obtainable by wet milling solid particles of compound of formula (I) followed by spray-drying the resultant suspension.

In one embodiment, the pharmaceutical composition as hereinbefore defined, further comprises HPMC present in less than 15% w/w, for example, in the range 0.1 to 10% w/w.

The CB2 receptor compounds for use in the instant invention may be used in combination with other therapeutic agents, for example COX-2 inhibitors, such as celecoxib, deracoxib, rofecoxib, valdecoxib, parecoxib or COX-189; 5-lipoxygenase inhibitors; NSAID's, such as aspirin, diclofenac, indomethacin, nabumetone or ibuprofen; leukotriene receptor antagonists; DMARD's such as methotrexate; adenosine A1 receptor agonists; sodium channel blockers, such as lamotrigine; NMDA receptor modulators, such as glycine receptor antagonists; gabapentin and related compounds; tricyclic antidepressants such as amitriptyline; neurone stabilising antiepileptic drugs; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; $EP_1$ receptor ligands, $EP_4$ receptor ligands; $EP_2$ receptor ligands; $EP_3$ receptor ligands; $EP_4$ antagonists; $EP_2$ antagonists and $EP_3$ antagonists; bradykinin receptor ligands and vanilloid receptor ligand, antirheumatoid arthritis drugs, for example anti TNF drugs e.g. enbrel, remicade, anti-IL-1 drugs, DMARDS e.g. leflunamide or $5HT_6$ compounds. When the compounds are used in combination with other therapeutic agents, the compounds may be administered either sequentially or simultaneously by any convenient route.

Additional COX-2 inhibitors are disclosed in U.S. Pat. No. 5,474,995 U.S. Pat. No. 5,633,272; U.S. Pat. No. 5,466,823, U.S. Pat. No. 6,310,099 and U.S. Pat. No. 6,291,523; and in WO 96/25405, WO 97/38986, WO 98/03484, WO 97/14691, WO99/12930, WO00/26216, WO0/52008, WO00/38311, WO01/58881 and WO02/18374.

Suitable 5HT6 compounds for a combination suitable for the treatment of e.g Alzhemiers disease or cognitive enhancement, may be selected from SGS518 (Saegis), BGC20 761 (BTG disclosed in WO00/34242), WAY466 (Wyeth), PO4368554 (Hoffman le Roche), BVT5182 (Biovitron) and LY483518 (Lily), SB742457 (GSK) and/or compounds disclosed as Example 1 to 50 in WO03/080580.

The compound of the present invention may be administered in combination with other active substances such as 5HT3 antagonists, NK-1 antagonists, serotonin agonists, selective serotonin reuptake inhibitors (SSRI), noradrenaline re-uptake inhibitors (SNRI), tricyclic antidepressants and/or dopaminergic antidepressants.

Suitable 5HT3 antagonists which may be used in combination of the compound of the inventions include for example ondansetron, granisetron, metoclopramide.

Suitable serotonin agonists which may be used in combination with the compound of the invention include sumatriptan, rauwolscine, yohimbine, metoclopramide.

Suitable SSRIs which may be used in combination with the compound of the invention include fluoxetine, citalopram, femoxetine, fluvoxamine, paroxetine, indalpine, sertraline, zimeldine.

Suitable SNRIs which may be used in combination with the compound of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

Compounds of the present invention may used in combination with PDE4 inhibitors. The PDE4 inhibitor useful in this invention may be any compound that is known to inhibit the PDE4 enzyme or which is discovered to act in as PDE4 inhibitor, and which is only or essentially only a PDE4 inhibitor, not compounds which inhibit to a degree of exhibiting a therapeutic effect other members of the PDE family as well as PDE4. Generally it is preferred to use a PDE4 antagonist which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. Compounds of the present invention or combinations with PDE4 can be used in treating inflammation and as bronchodilators.

There are at least two binding forms on human monocyte recombinant PDE 4 (hPDE 4) at which inhibitors bind. One explanation for these observations is that hPDE 4 exists in two distinct forms. One binds the likes of rolipram and denbufylline with a high affinity while the other binds these compounds with a low affinity. The preferred PDE4 inhibitors of for use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE 4 catalytic form which binds rolipram with a high affinity divided by the $IC_{50}$ for the form which binds rolipram with a low affinity.

Reference is made to U.S. Pat. No. 5,998,428, which describes these methods in more detail. It is incorporated herein in full as though set forth herein.

Suitably the PDE4 inhibitors are those PDE4 inhibitors which have an $IC_{50}$ ratio of greater than 0.5, and particularly those compounds having a ratio of greater than 1.0.

A further aspect of the invention is an CB2 modulator in combination with a PDE4 inhibitor and pharmaceutical compositions comprising said combination.

A further aspect of the invention is a method of treating lung disorders for example asthma, bronchitis, emphysema, allergic rhinitis, respiratory distress syndrome, pigeon fancier's disease, farmer's lung, chronic obstructive pulmonary disease, (COPD) and cough or a disorder which can be treated with a bronchodilator which comprises administering to a mammal including man, an effective amount of a CB modulator or a pharmaceutically acceptable derivative therefore and an effective amount of a PDE4 inhibitor or a pharmaceutically acceptable derivative thereof.

An additional aspect of the invention is the use of an effective amount of a CB2 modulator or a pharmaceutically acceptable derivative therefore and an effective amount of a PDE4 inhibitor or a pharmaceutically acceptable derivative thereof in the manufacture of a medicament in the treatment of lung disorders for example asthma, bronchitis, emphysema, allergic rhinitis, respiratory distress syndrome, pigeon fancier's disease, farmer's lung, chronic obstructive pulmonary disease, (COPD) and cough or for the manufacture of a bronchodilator.

When used herein cough can have a number of forms and includes productive, non-productive, hyper-reactive, asthma and COPD associated.

A further aspect of the invention is a patient pack comprising an effective amount of a CB 2 modulator or a pharmaceutically acceptable derivative therefore and an effective amount of a PDE4 inhibitor or a pharmaceutically acceptable derivative Possible PDE4 compounds are cis[cyano-4-(3-cyclopentyloxy-4-methoxyphenyl)cyclohexan-1-carboxylate] also known as cilomilast or Ariflo®, 2-carbomethoxy-4-cyano-4-(3-cyclopropylmethoxy-4-difluoromethoxyphenyl)cyclohexan-1-one, and cis[4-cyano-4-(3-cyclopropylmethoxy-4-difluoromethoxyphenyl)cyclohexan-1-ol]. They can be made by the processed described in U.S. Pat. Nos. 5,449,686 and 5,552,438. Other PDE4 inhibitors, specific inhibitors, which can be used in this invention are AWD-12-281 from ASTA MEDICA (Hofgen, N. et al. 15th EFMC Int Symp Med Chem (September 6-10, Edinburgh) 1998, Abst P.98); a 9-benzyladenine derivative nominated NCS-613 (INSERM); D-4418 from Chiroscience and Schering-Plough; a benzodiazepine PDE4 inhibitor identified as CI-1018 (PD-168787; Parke-Davis/Warner-Lambert); a benzodioxole derivative Kyowa Hakko disclosed in WO 9916766; V-11294A from Napp (Landells, L. J. et al. Eur Resp J [Annu Cong Eur Resp Soc (September 19-23, Geneva) 1998] 1998, 12(Suppl. 28): Abst P2393); roflumilast (CAS reference No 162401-32-3) and a pthalazinone (WO 99/47505) from Byk-Gulden (now Altana); or a compound identified as T-440 (Tanabe Seiyaku; Fuji, K. et al. *J Pharmacol Exp Ther,* 1998, 284(1): 162).

Additional PDE4 inhibitors are disclosed on pages 2 to 15 of WO 01/13953. Specifically selected are arofylline, atizoram, BAY-19-8004, benafentrine, BYK-33043, CC-3052, CDP-840, cipamfylline, CP-220629, CP-293121, D-22888, D-4396, denbufylline, filaminast, GW-3600, ibudilast, KF-17625, KS-506-G, laprafylline, NA-0226A, NA-23063A, ORG-20241, ORG-30029, PDB-093, pentoxifylline, piclamilast, rolipram, RPR-117658, RPR-122818, RPR-132294, RPR-132703, RS-17597, RS-25344-000, SB-207499, SB210667, SB211572, SB-211600, SB212066, SB212179, SDZ-ISQ-844, SDZ-MNS-949, SKF-107806, SQ-20006, T-2585, tibenelast, tolafentrine, UCB-29646, V-11294A, YM-58997, YM-976 and zardaverine.

In one embodiment the PDE4 inhibitor is selected from cilomilast, AWD-12-281, NCS-613, D-4418, CI-1018, V-11294A, roflumilast or T-440.

Compounds of the present invention may also be of use in treating atherosclerosis in combination with an anti-hyperlipidaemic, anti-atherosclerotic, anti-diabetic, anti-anginal, anti-hypertension agent or an agent for lowering Lp(a). Examples of the above include cholesterol synthesis inhibitors such as statins, anti-oxidants such as probucol, insulin sensitisers, calcium channel antagonists. Examples of agents for lowering Lp(a) include the aminophosphonates described in WO 97/02037, WO 98/28310, WO 98/28311 and WO 98/28312 (Symphar SA and SmithKline Beecham). Examples of antihyerpertension agents are angiotensin-converting enzyme inhibitors, angiotensin-II receptor antagonists, ACE/NEP inhibitors, -blockers, calcium channel blockers, PDE inhibitors, aldosterone blockers A preferred combination therapy will be the use of a compound of the present invention and a statin. The statins are a well known class of cholesterol lowering agents and include atorvastatin, simvarstatin, pravastatin, cerivastatin, fluvastatin, lovastatin and ZD 4522 (also referred to as S4522, Astra Zeneca). The two agents may be administered at substantially the same time or at different times, according to the discretion of the physician.

A further preferred combination therapy will be the use of a compound of the present invention and an anti-diabetic agent or an insulin sensitiser. Within this class, preferred compounds for use with a compound of the present invention include the PPARgamma activators, for instance G1262570 (Glaxo Wellcome) and also the glitazone class of compounds such as rosiglitazone (Avandia, SmithKline Beecham), troglitazone and pioglitazone.

It will be appreciated that the compounds of any of the above combinations or compositions may be administered simultaneously (either in the same or different pharmaceutical formulations), separately or sequentially.

The invention thus provides, in a further aspect, a combination comprising a compound of formula (I) or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

Determination of Cannabinoid CB1 Receptor Agonist Activity

The cannabinoid CB1 receptor agonist activity of compounds of formula (I) was determined in accordance with the following experimental method.

Experimental Method

Yeast (*Saccharomyces cerevisiae*) cells expressing the human cannabinoid CB1 receptor were generated by integration of an expression cassette into the ura3 chromosomal locus of yeast strain MMY23. This cassette consisted of DNA sequence encoding the human CB1 receptor flanked by the yeast GPD promoter to the 5' end of CB1 and a yeast transcriptional terminator sequence to the 3' end of CB1. MMY23 expresses a yeast/mammalian chimeric G-protein alpha subunit in which the C-terminal 5 amino acids of Gpa1 are replaced with the C-terminal 5 amino acids of human G$\alpha$i3 (as described in Brown et al. (2000), *Yeast* 16:11-22). Cells were grown at 30° C. in liquid Synthetic Complete (SC) yeast media (Guthrie and Fink (1991), Methods in Enzymology, Vol. 194) lacking uracil, tryptophan, adenine and leucine to late logarithmic phase (approximately 6 $OD_{600}$/ml).

Agonists were prepared as 10 mM stocks in DMSO. $EC_{50}$ values (the concentration required to produce 50% maximal response) were estimated using dilutions of between 3- and 5-fold (BiomekFX, Beckman) into DMSO. Agonist solutions in DMSO (1% final assay volume) were transferred into black, clear bottom, microtitre plates from NUNC (96- or 384-well). Cells were suspended at a density of 0.2 $OD_{600}$/ml in SC media lacking histidine, uracil, tryptophan, adenine and leucine and supplemented with 10 mM 3-aminotriazole, 0.1M sodium phosphate pH 7.0, and 20 μM fluorescein di-β-D-glucopyranoside (FDGlu). This mixture (50 ul per well for 384-well plates, 200 ul per well for 96-well plates) was added to agonist in the assay plates (Multidrop 384, Labsystems). After incubation at 30° C. for 24 hours, fluorescence resulting from degradation of FDGlu to fluorescein due to exoglucanase, an endogenous yeast enzyme produced during agonist-stimulated cell growth, was determined using a Spectrofluor microtitre plate reader (Tecan; excitation wavelength: 485 nm; emission wavelength: 535 nm). Fluorescence was plotted against compound concentration and iteratively curve fitted using a four parameter fit to generate a concentration effect value. Efficacy ($E_{max}$) was calculated from the equation $$E_{max} = Max_{[compound\ X]} - Min_{[compound\ X]}/Max_{[HU210]} - Min_{[HU210]} \times 100\%$$

where $Max_{[compound\ X]}$ and $Min_{[compound\ X]}$ are the fitted maximum and minimum respectively from the concentration effect curve for compound X, and $Max_{[HU210]}$ and $Min_{[HU210]}$ are the fitted maximum and minimum respectively from the concentration effect curve for (6aR,10aR)-3-(1,1'-Dimethylheptyl)-6a,7,10,10a-tetrahydro-1-hydroxy-6,6-dimethyl-6H-dibenzo[b,d]pyran-9-methanol (HU210; available from Tocris). Equieffective molar ratio (EMR) values were calculated from the equation $$EMR = EC_{50\ [compound\ X]}/EC_{50\ [HU210]}$$

Where $EC_{50\ [compound\ X]}$ is the $EC_{50}$ of compound X and $EC_{50\ [HU210]}$ is the $EC_{50}$ of HU210.

Compounds of the Examples tested according to this method had $EC_{50}$ values >1,000 nM and/or an efficacy of <30% at the cloned human cannabinoid CB1 receptor, except for Example 124 (508 nM, 75%), Example 130 (897 nM, 30%), Example 237 (738 nM, 92%) and Example 162 (801 nM, 33%)

Determination of Cannabinoid CB2 Receptor Agonist Activity

The cannabinoid CB2 receptor agonist activity of compounds of formula (I) was determined in accordance with the following experimental method.

Experimental Method

Yeast (*Saccharomyces cerevisiae*) cells expressing the human cannabinoid CB2 receptor were generated by integration of an expression cassette into the ura3 chromosomal locus of yeast strain MMY23. This cassette consisted of DNA sequence encoding the human CB2 receptor flanked by the yeast GPD promoter to the 5' end of CB2 and a yeast transcriptional terminator sequence to the 3' end of CB2. MMY23 expresses a yeast/mammalian chimeric G-protein alpha subunit in which the C-terminal 5 amino acids of Gpa1 are replaced with the C-terminal 5 amino acids of human Gαi3 (as described in Brown et al. (2000), *Yeast* 16:11-22). Cells were grown at 30° C. in liquid Synthetic Complete (SC) yeast media (Guthrie and Fink (1991), Methods in Enzymology, Vol. 194) lacking uracil, tryptophan, adenine and leucine to late logarithmic phase (approximately 6 $OD_{600}$/m).

Agonists were prepared as 10 mM solutions in DMSO. $EC_{50}$ values (the concentration required to produce 50% maximal response) were estimated using dilutions of between 3- and 5-fold (BiomekFX, Beckman) into DMSO. Agonist solutions in DMSO (1% final assay volume) were transferred into black microtitre plates from NUNC (96- or 384-well). Cells were suspended at a density of 0.2 $OD_{600}$/ml in SC media lacking histidine, uracil, tryptophan, adenine and leucine and supplemented with 10 mM 3-aminotriazole, 0.1M sodium phosphate pH 7.0, and 20μM fluorescein di-β-D-glucopyranoside(FDGlu). This mixture (50 ul per well) was added to agonist in the assay plates (Multidrop 384, Labsystems). After incubation at 30° C. for 24 hours, fluorescence resulting from degradation of FDGlu to fluorescein due to exoglucanase, an endogenous yeast enzyme produced during agonist-stimulated cell growth, was determined using a fluorescence microtitre plate reader (Tecan Spectrofluor or LJL Analyst excitation wavelength: 485 nm; emission wavelength: 535 nm). Fluorescence was plotted against compound concentration and iteratively curve fitted using a four parameter fit to generate a concentration effect value. Efficacy ($E_{max}$) was calculated from the equation $$E_{max} = Max_{[compound\ X]} - Min_{[compound\ X]}/Max_{[HU210]} - Min_{[HU210]} \times 100\%$$

where $Max_{[compound\ X]}$ and $Min_{[compound\ X]}$ are the fitted maximum and minimum respectively from the concentration effect curve for compound X, and $Max_{[HU210]}$ and $Min_{[HU210]}$ are the fitted maximum and minimum respectively from the concentration effect curve for (6aR,10aR)-3-(1,1'-Dimethylheptyl)-6a,7,10,10a-tetrahydro-1-hydroxy-6,6-dimethyl-6H-dibenzo[b,d]pyran-9-methanol (HU210; available from Tocris). Equieffective molar ratio (EMR) values were calculated from the equation $$EMR = EC_{50\ [compound\ X]}/EC_{50\ [HU210]}$$

Where $EC_{50\ [compound\ X]}$ is the $EC_{50}$ of compound X and $EC_{50\ [HU210]}$ is the $EC_{50}$ of HU210.

The compounds of Examples 1 to 6, 24 to 36, and 51 to 62, 64 to 66, 73 to 87, 101 to 182, 188 to 205 and 222 to 246 tested according to this method had an $EC_{50}$ values of <300 nM and efficacy value of >50% at the cloned human cannabinoid CB2 receptor.

The compounds of Example 7 to 9, 37 to 40, 67 and 72, 88 to 92, 183, 184, 206 to 214 tested according to this method had an $EC_{50}$ values between 300 nM and 1000 nM and efficacy value of >50% at the cloned human cannabinoid CB2 receptor.

The compounds of Examples 10 to 21, 41 to 50, 63, 68 to 71, 93 to 100, 185 to 187, 215 to 221 tested according to this method had an $EC_{50}$ values >1000 nM and/or efficacy value <50% at the cloned human cannabinoid CB2 receptor.

The compounds of Examples 22 and 23 were inactive at the cloned human cannabinoid CB2 receptor.

Experimental Method

Measurement of CB2 Agonist Effects in a Reporter Gene Assay

CB2 agonist effects were determined using a reporter gene assay. These studies were performed using a CHO-K1 cell line expressing human recombinant CB2 receptors (CHO-K1 CB2 CRE-LUC cells). These cells additionally express a "CRE-LUC" reporter gene construct comprising the gene for luciferase under the control of multiple cAMP response element binding protein promoters. In these cells, increases in intracellular cAMP levels leads to transcription of the luciferase gene and the subsequent production of luciferase. The expression of luciferase is measured by addition to the cells of a proprietary mixture containing luciferin, the substrate for luciferase (Luclite, Perkin Elmer, Cat No 6016919). The resultant reaction leads to the generation of light which is measured in a TopCount scintillation counter. In the CHO-K1 CB2 CRE-LUC cells, forskolin produces a marked increase in luciferase expression and CB2 agonists inhibit this response. The CHO-K1 CB2 CRE-LUC cells routinely express a high level of constitutive CB2 receptor activity. This was overcome in these experiments by pre-treating the cells with the inverse agonist, SR144528, for 30-60 mins before use. This treatment has been shown to eliminate constitutive CB2 receptor activity (Bouaboula et al., 1999).

Methods

CHO-K1 CB2 CRE-LUC cells were grown in DMEM/F12 plus glutamax I medium (Gibco Cat. No. 31331-028), supplemented with 9% FBS (Gibco, Cat. No. 16000-040) and 0.5 mg·ml$^{-1}$ G418 (Gibco, Cat. No. 10131-027) and 0.5 mg·ml$^{-1}$ Hygromycin (Invitrogen, Cat. No. 10687-010). Cells were grown as a monolayer culture in 162 cm$^2$ vented Nunclon flasks (NUNC, Cat. No. 178883) in 27.5 ml of media in a humidified 95% air and 5% $CO_2$ atmosphere at 37° C. When confluent, the growth media was replaced with DMEM/F12 medium (Gibco, Cat. No. 31331-028) containing 100 nM of the CB2 inverse agonist, SR144528, and the cells were incubated at 37° C. for 30-60 mins. Flasks were rinsed twice with 25 ml Dulbecco's phosphate buffered saline (PBS, Gibco Cat. No. 14190-094) and then harvested by incubation for 10 mins in 10 ml of Versene (Gibco, Cat. No. 15040-033). Cells were detached by a sharp blow to the flask and the cell suspension made up to 50 ml with PBS and centrifuged at 250×g for 5 mins. The cell pellet was re-suspended in 24 mls of phenol-red free DMEM/F12 assay buffer (Gibco, Cat. No. 11039-021) and 50 μl of cell suspension (approximately 50,000 cells) added to 96 well plates (Costar, Cat. No. 3904—clear bottomed black well plates) containing 50 μl of test agonist in 20 μm forskolin (final assay concentration of 1 μM FSK). Test agonists were prepared as 10 mM solutions in DMSO and diluted into phenol-red free DMEM/F12 assay buffer containing 2 μM forskolin to produce a 20 μM solution of test agonist. Subsequent serial dilutions of test agonist were prepared in the assay buffer containing forskolin and each test agonist was routinely examined over a final assay concentration range of 10 μM to 10 nM (or lower if required). The plates were mixed on a plate shaker for 5 mins (800-1000 rpm) and then centrifuged briefly (5-10 s) at 250×g, placed in a Bio-plate without their lids, and incubated for 4-5 hr in a humidified 95% air and 5% $CO_2$ atmosphere at 37° C. The 96 well plates were removed from the incubator and placed at RT for 10-15 mins before addition of 25 μl of Luclite solution, prepared according to the manufacturer's instructions. The plates were sealed with Topseal A (Perkin Elmer, Cat. No. 6005185), mixed on a plate shaker for 5 mins (800-1000 rpm) and then centrifuged briefly (5-10 s) at 250×g. Finally, luminescence was measured using a Packard TopCount scintillation counter.

Data Analysis

For each compound maximal inhibition of the forskolin response and the EC50 for this effect was determined. In each experiment the reference agonist HU210 was included and the maximal effect of each test agonist was expressed relative to the maximal effect produced by HU210 to provide an estimate of intrinsic activity. In addition the EC50 of each compound was divided by the EC50 for HU210 to calculate the equipotent molar ratio (EMR) for the test compound.

The compounds of Examples 1 and 24 tested according to this method had mean $pEC_{50}$ values of >7.4. Other compounds of the Examples which were tested were found to be active except compounds of Examples 22 and 23.

Reference

Bouaboula M. Dussossoy D. Casellas P. Regulation of peripheral cannabinoid receptor CB2 phosphorylation by the inverse agonist SR 144528. Implications for receptor biological responses. *Journal of Biological Chemistry.* 274 (29):20397-405, 1999

The following examples are illustrative, but not limiting of the embodiments of the present invention.

Abbreviations:

AcOH (acetic acid), Bn (benzyl), Bu, Pr, Me, Et (butyl, propyl, methyl ethyl), DMSO (dimethyl sulfoxide), DCM (dichloromethane), DME (1,2-dimethoxyethane), DMF (N,N-dimethylformamide), EDC (1-(3-dimethylaminopropyl)-3-ethylcarbodiimide), EtOAc (ethyl acetate), EtOH (ethanol), HPLC (High pressure liquid chromatography), LC/MS (Liquid chromatography/Mass spectroscopy), MDAP (Mass Directed AutoPurification), MeCN (acetonitrile), MeOH (methanol), NMR (Nuclear Magnetic Resonance (spectrum)), NMP (N-methylpyrrolidone), SPE (Solid Phase Extraction), TFA (Trifluoroacetic acid), THF (tetrahydrofuran), s, d, t, q, m, br (singlet, doublet, triplet, quartet, multiplet, broad.)

Conditions, Hardware, and Software Used for Mass-Directed Autopurification Used for Examples 1 to 24 Route 1

Hardware

Waters 600 gradient pump, Waters 2700 sample manager, Waters Reagent Manager, Micromass ZMD mass spectrometer, Gilson 202—fraction collector, Gilson Aspec—waste collector.

Software

Micromass Masslynx version 3.5

Column

The column used is typically a Supelco ABZ+ column whose dimensions are 10 mm internal diameter by 100 mm in length. The stationary phase particle size is 5 μm.

Solvents

A. Aqueous solvent=Water+0.1% Formic Acid
B. Organic solvent=MeCN:Water 95:5+0.05% Formic Acid
Make up solvent=MeOH:Water 80:20+50 mMol Ammonium Acetate
Needle rinse solvent=MeOH:Water:DMSO 80:10:10

Methods

Five methods are used depending on the analytical retention time of the compound of interest. They all have a flow rate of 20 ml/min and a 15-minute runtime, which comprises of a 10-minute gradient followed by a 5-minute column flush and re-equilibration step.

Method 1 MDP 1.5-2.2=0-30% B
Method 2 MDP 2.0-2.8=5-30% B
Method 3 MDP 2.5-3.0=15-55% B
Method 4 MDP 2.8-4.0=30-80% B
Method 5 MDP 3.8-5.5=50-90% B Conditions Used for Analytical LCMS Systems Hardware
Agilent 1100 gradient pump
Agilent 1100 Autosampler
Agilent 1100 PDA Detector
Agilent 1100 Degasser
Micromass ZQ mass spectrometer

PL-ELS 1000

Software

Micromass Masslynx versions 3.5/4.0

Column

The column used is a Supelcosil ABZ+PLUS, the dimensions of which are 4.6 mm×33 mm. The stationary phase particle size is 3 mm.

Solvents

A: Aqueous solvent=10 mMol Ammonium Acetate+0.1% Formic Acid

B: Organic solvent=95% Acetonitrile+0.05% Formic Acid

Method

The generic method used has 5.5 minute runtime, which comprises of a 4.7-minute gradient (0-100% B) followed by a 0.6 minute column flush and 0.2 minute re-equilibration step.

Flow Rate

The above method has a flow rate of 3 ml/mins

Conditions Used for NMR

Hardware

Bruker 400 MHz Ultrashield
Bruker B-ACS60 Autosampler
Bruker Advance 400 Console Software User interface—NMR Kiosk
Controlling software—XWin NMR version 3.0

Conditions Used for the Biotage Horizon.

Column: Biotage C18HS 25+S
Fraction volume: 9 ml UV Threshold: 0.03 AU
Solvent A=Water, B=Acetonitrile
Gradient:

| Volume(ml) | A | B |
|---|---|---|
| 0 | 70% | 30% |
| 240 | 0% | 100% |

Conditions Used for the Microwave

Hardware

Personal Chemistry Creator or Personal Chemistry Optimiser instruments were used.

Specifications

Heating temperature up to 250° C.
Microwave radiation 50-300 W at 2.45 GHz

EXAMPLE 1 AND 1a

1-[7-(3-Chloro-phenylamino)-3-methyl-1H-pyrrolo[2,3-c]pyridin-4-yl]-1-morpholin-4-yl-methanone and its hydrochloride salt

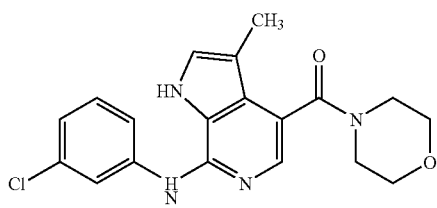

Method 1.

(a) 5-Bromo-2-chloro-3-nitro-pyridine

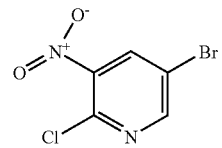

A suspension of 5-bromo-2-hydroxy-3-nitro-pyridine (10 g; ex. Maybridge) in phosphorus oxychloride (10 ml) was heated at 130° C. to give a red solution. The solution was heated at 130° C. for 2.5. The reaction mixture was poured onto iced water and then neutralised by the portionwise addition of solid sodium bicarbonate. The aqueous was extracted twice with ethyl acetate and the combined organics were dried (MgSO$_4$), filtered and evaporated to give the title compound as a yellow solid (10.28 g).

NMR (d$^6$-DMSO) δ 8.93 (2H, s).

LC/MS t=2.6 min, [MH$^+$]+acetonitrile 279 consistent with molecular formula $C_5H_2{}^{81}Br^{35}ClN_2O_2$ (b) 4-Bromo-7-chloro-3-methyl-1H-pyrrolo[2,3-c]pyridine

To a solution of 5-bromo-2-chloro-3-nitro-pyridine, (10.28 g) in dry tetrahydrofuran (450 ml) at −78° C. under an atmosphere of nitrogen was added dropwise, a solution of 1-propenylmagnesium bromide (0.5M in tetrahydrofuran; 305 ml), keeping the internal temperature below −70° C. The solution was allowed to warm to −40° C. over 1 h then quenched with saturated ammonium chloride (350 ml). The aqueous was extracted twice with ethyl acetate (2×200 ml) and the combined organics were dried (MgSO$_4$), filtered and evaporated to give a brown oil. The mixture was dissolved in ether, a solid filtered off then evaporated. The residue was dissolved in ether, loaded onto four Biotage silica samplets and purified by Biotage chromatography over silica gel (4×100 g), eluting with 10% ethyl acetate/isohexane (1 L) followed by 15% ethyl acetate/isohexane (1 L). The fractions containing product from the four columns were combined and evaporated to afford an orange solid. The orange solid was triturated with isohexane, filtered and washed with isohexane and dried to give the title compound as an off white solid. (1.07 g).

NMR (d$^6$-DMSO) δ 2.45 (3H, s), 7.58 (1H, d), 7.97 (1H, s), 12.10 (1H, s).

LC/MS t=3.1 min, [MH$^+$] 247 consistent with molecular formula $C_8H_6{}^{81}Br^{35}Cl\,N_2$

(c) 4-Bromo-1-(tert-butyl-dimethyl-silanyl)-7-chloro-3-methyl-1H-pyrrolo[2,3-c]pyridine

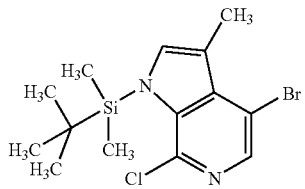

To a solution of 4-bromo-7-chloro-3-methyl-1H-pyrrolo[2,3-c]pyridine (1.07 g) in dry tetrahydrofuran (50 ml) at 0° C. under an atmosphere of nitrogen was added portionwise sodium hydride (60% dispersed in mineral oil, 384 mg). After addition, the solution was stirred at room temperature for 30 minutes. The solution was then recooled to 0° C. and a solution of tert-butyldimethylsilyl trifluoromethanesulphonate (2 ml) in dry tetrahydrofuran (10 ml) was added dropwise. The solution was stored at 5° C. overnight. The solution was partitioned between ethyl acetate and water and washed with water twice. The organic layer was dried (MgSO$_4$) and evaporated to give a brown oil (2 g). The residue was used in the next step (d) without further purification.

(d) 7-Chloro-3-methyl-1H-pyrrolo[2,3-c]pyridine-4-carboxylic acid ethyl ester

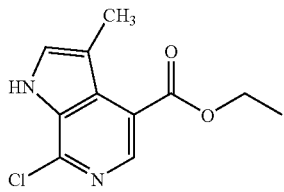

Carbon monoxide gas was bubbled through a mixture of crude 4-bromo-1-(tert-butyl-dimethyl-silanyl)-7-chloro-3-methyl-1H-pyrrolo[2,3-c]pyridine (2 g) and dichlorobis(triphenylphosphine)-palladium (II) (155 mg) in ethanol (20 ml) and triethylamine (7.5 ml) for 15 minutes. A reflux condenser fitted with a balloon of carbon monoxide gas was attached and the mixture stirred at 80° C. overnight. A further 160 mg of catalyst was added and resaturated in carbon monoxide gas and stirred at 80 C overnight. The mixture was evaporated to dryness and then redissolved in ethyl acetate and the solution absorbed onto silica gel. The residue was purified by Biotage chromatography over silica gel (10 g), eluting with 10% ethyl acetate/isohexane (2 L) followed by 15% ethyl acetate/isohexane. Pure fractions were evaporated and dried to give the title compound as a pale yellow solid. (185 mg).

NMR (d$^6$-DMSO) δ 1.35 (3H, t) 2.35 (3H, s), 4.38 (2H, q), 7.65 (1H, d), 8.32 (1H, s), 12.10 (1H, s).

LC/MS t=2.7 min, [MH$^+$] 239 consistent with molecular formula C$_{11}$H$_{11}$$^{35}$ClN$_2$O$_2$

(e) 7-(3-Chloro-phenylamino)-3-methyl-1H-pyrrolo[2,3-c]pyridine-4-carboxylic acid

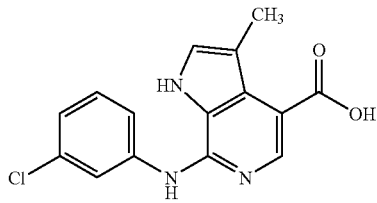

A mixture of 7-chloro-3-methyl-1H-pyrrolo[2,3-c]pyridine-4-carboxylic acid ethyl ester (180 mg), 3-chloroaniline (160 µl), and methanesulfonic acid (98 µl) in 1,4-dioxane (5 ml) was heated under microwave conditions at 180° C. for 30 minutes. The solid mass obtained was suspended in ethanol (6 ml) and treated with a solution of potassium hydroxide (170 mg) in ethanol (2 ml) and then refluxed overnight. The ethanol was evaporated and replaced with methanol (8 ml) and potassium hydroxide (56 mg) added and then the mixture was refluxed overnight. The mixture was evaporated to dryness and the residue dissolved in water which washed twice with diethyl ether. The aqueous was then acidified with concentrated hydrochloric acid to afford a precipitate. The precipitate was filtered off and washed with water. The solid was then sucked dry and dried to afford the title compound (178 mg).

NMR (d$^6$-DMSO) δ 2.40 (3H, s), 7.32 (1H, d), 7.50-7.57 (3H, m), 7.74 (1H, s), 7.83 (1H, s), 8.00 (1H, s), 11.00 (1H, s), 12.55 (1H, s).

LC/MS t=2.6 min, [MH$^+$] 302 consistent with molecular formula C$_{15}$H$_{12}$$^{35}$ClN$_3$O$_2$

(f) 1-[7-(3-Chloro-phenylamino)-3-methyl-1H-pyrrolo[2,3-c]pyridin-4-yl]-1-morpholin-4-yl-methanone To a solution of 7-(3-chloro-phenylamino)-3-methyl-1H-pyrrolo[2,3-c]pyridine-4-carboxylic acid (34 mg) in dimethylformamide (2 ml) was added 4-ethylmorpholine (57 µl), morpholine (19 µl), 1-hydroxybenzotriazole hydrate (24 mg) and 1-(3-dimethylaminopropyl)-3-ethylcarbodiimide hydrochloride (26 mg) and the solution stirred at room temperature overnight. The dimethylformamide was evaporated and the residue triturated with 5% sodium bicarbonate to give an off white solid. The solid was filtered, washed thoroughly with water, and dried over sodium hydroxide at 50° C. to afford 1-[7-(3-chloro-phenylamino)-3-methyl-1H-pyrrolo[2,3-c]pyridin-4-yl]-1-morpholin-4-yl-methanone (22 mg).

NMR (d$^6$-DMSO) δ 2.14 (3H, s), 3.25-3.67 (8H, brm), 6.96 (1H, dd), 7.32 (1H, t), 7.39 (1H, s), 7.58 (1H, dd), 7.64 (1H, s), 8.23 (1H, t), 8.99 (1H, s), 11.15 (1H, s).

LC/MS t=2.3 min, [MH$^+$] 371 consistent with molecular formula C$_{19}$H$_{15}$$^{35}$ClN$_4$O$_2$ Method 2: 1-[7-(3-Chloro-phenylamino)-3-methyl-1H-pyrrolo[2,3-c]pyridin-4-yl]-1-morpholin-4-yl-methanone hydrochloride salt (a) 5-Iodo-3-nitro-pyridin-2-ol

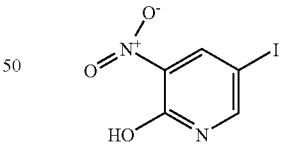

A suspension of 2-hydroxy-3-nitro pyridine (can be purchased form Aldrich) (51.4 g) in acetic acid (230 ml), water (50 ml), concentrated sulfuric acid (7 ml) and periodic acid (17.6 g) was stirred at 90° C. for 15 minutes whereby a solution was obtained. Iodine crystals (38.25 g) were added portionwise and after 20 minutes a dense yellow precipitate had formed. The mixture was cooled and saturated sodium thiosulphate (250 ml) added. The solid was filtered and washed with saturated sodium thiosulphate (250 ml) followed by water. The solid was sucked dry then dried over sodium hydroxide at 50° C. under vacuum to afford the title compound (91.4 g).

NMR (d$^6$-DMSO) δ 8.14 (1H, d), 8.53 (1H, d), 13.10 (1H, s).

LC/MS t=1.6 min, [MH⁺] 267 consistent with molecular formula $C_5H_3{}^{127}IN_2O_3$ (b) 2-Chloro-5-iodo-3-nitro-pyridine

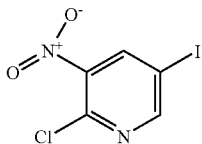

A suspension of 5-iodo-3-nitro-pyridin-2-ol (20 g) in phenyl dichlorophosphate (60 ml) was heated at 180° C. for 30 minutes whereby a brown solution was obtained. The solution was allowed to cool then poured onto ice/water, neutralised by a portionwise addition of solid sodium hydrogen carbonate and extracted with ethyl acetate (300 ml) which was then washed twice with 5% sodium hydrogen carbonate solution (250 ml). The organic layer was dried (MgSO₄), and evaporated to give a pale brown solid. The solid was stirred in isohexane for 2 h, filtered off, washed with isohexane and dried to afford the title compound (18.4 g).

NMR(CDCl₃) δ 8.49 (1H, d), 8.81 (1H, d).

LC/MS t=2.8 min, [M-I⁻] 158 consistent with molecular formula $C_5H_2{}^{35}Cl^{127}IN_2O_2$ (c)
7-Chloro-4-iodo-3-methyl-1H-pyrrolo[2,3-c]pyridine

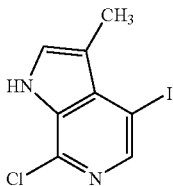

To a solution of 1-propenylmagnesium bromide (0.5M solution in tetrahydrofuran, 264 ml) at 0° C. under nitrogen was added a solution of 2-chloro-5-iodo-3-nitro-pyridine (11 g) in dry tetrahydrofuran (225 ml), dropwise over 45 minutes. After 10 minutes at 0° C. the reaction was quenched with saturated ammonium chloride (300 ml). The mixture was then extracted with ethyl acetate (300 ml) which was dried over magnesium sulphate, filtered and evaporated to give a red oily solid. The residue was triturated with diethyl ether and refrigerated over night. The solid was then filtered onto a sinter, sucked dry then dried at 60° C. under vacuum to afford the title compound (3.27 g). The filtrate was evaporated, dissolved in the minimum of diethyl ether and seeded with the above, refrigerated overnight, filtered and dried under vacuum at 60° C. to afford a further crop (345 mg).

NMR (d⁶-DMSO) δ 2.44 (3H, s), 7.58 (1H, d), 8.12 (1H, s), 12.00 (1H, s).

LC/MS t=3.4 min, [MH⁺] 293 consistent with molecular formula $C_8H_6{}^{35}ClIN_2$ (d) 7-Chloro-3-methyl-1H-pyrrolo[2,3-c]pyridine-4-carboxylic acid ethyl ester

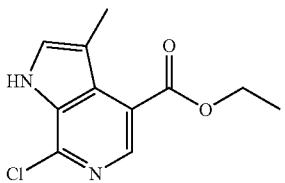

Carbon monoxide gas was bubbled through a mixture of 7-chloro-4-iodo-3-methyl-1H-pyrrolo[2,3-c]pyridine (1 g) and dichlorobis(triphenylphosphine)-palladium (II) (250 mg) in ethanol (40 ml) and triethylamine (15 ml) for 20 minutes. A reflux condenser fitted with a balloon of carbon monoxide gas was attached and the mixture stirred at 80° C. overnight. The mixture was evaporated to dryness and then redissolved in ethyl acetate and the solution absorbed onto silica gel. The residue was purified by Biotage chromatography over silica gel (100 g), eluting with 10% ethyl acetate/isohexane (2 L) followed by 15% ethyl acetate/isohexane to give the title compound as a off white solid. (158 mg).

NMR (d⁶-DMSO) δ 1.35 (3H, t) 2.35 (3H, s), 4.38 (2H, q), 7.65 (1H, d), 8.32 (1H, s), 12.10 (1H, s).

LC/MS t=2.9 min, [MH⁺] 239 consistent with molecular formula $C_{11}H_{11}{}^{35}ClN_2O_2$ (e) 7-(3-Chloro-phenylamino)-3-methyl-1H-pyrrolo[2,3c]pyridine-4-carboxylic acid

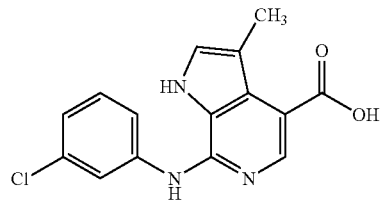

A mixture of 7-chloro-3-methyl-1H-pyrrolo[2,3-c]pyridine-4-carboxylic acid ethyl ester (150 mg), 3-chloroaniline (133 μl), and methanesulfonic acid (81 μl) in 1,4-dioxane was heated under microwave conditions at 180° C. for 30 minutes. The solid mass obtained was dissolved in methanol (6 ml) and treated with a solution of potassium hydroxide (212 mg) in methanol (2 ml) and then refluxed overnight. A solution of potassium hydroxide (106 mg) in methanol (1 ml) was added. A further solution of potassium hydroxide (212 mg) in methanol (2 ml) was added and then refluxed overnight. The mixture was evaporated to dryness and the residue dissolved in water which washed twice with diethyl ether. The aqueous was then acidified to pH1 with concentrated hydrochloric acid to afford a precipitate. The precipitate was filtered and washed with water. The solid was then sucked dry and dried over sodium hydroxide at 50° C. to afford the title compound (154 mg).

NMR (d⁶-DMSO) δ 2.40 (3H, s), 7.32 (1H, d), 7.50-7.57 (3H, m), 7.74 (1H, s), 7.83 (1H, s), 8.00 (1H, s), 11.00 (1H, s), 12.55 (1H, s).

LC/MS t=2.6 min, [MH⁺] 302 consistent with molecular formula $C_{15}H_{12}{}^{35}ClN_3O_2$ (f) 1-[7-(3-Chloro-phenylamino)-3-methyl-1H-pyrrolo[2,3-c]pyridin-4-yl]-1-morpholin-4-yl-methanone hydrochloride salt To a solution of 7-(3-chloro-phenylamino)-3-methyl-1H-pyrrolo[2,3-c]pyridine-4-carboxylic acid (150 mg) in dimethylformamide (4 ml) was added 4-ethylmorpholine (253 μl), morpholine (88 μl), 1-hydroxybenzotriazole hydrate (105 mg) and 1-(3-dimethylaminopropyl)-3-ethylcarbodiimide hydrochloride (115 mg) and the solution stirred at room temperature overnight. The dimethylformamide was evaporated and the residue dissolved in ethyl acetate (40 ml). The organic layer was then washed with 5% sodium hydrogen carbonate solution (25 ml) and twice with water (2×25 ml). The organic layer was dried (MgSO₄) and evaporated to give an orange oil. The residue was purified by Biotage chromatography over silica gel (50 g), eluting with 2% methanol/dichloromethane and then triturated with diethyl ether to give a white solid which was then filtered off, sucked dry then dried to afford the free base (107 mg). A sample of the free base (50 mg) was dissolved in warm ethyl acetate (10 ml) and treated with a solution of 1M hydrochloric acid in diethyl ether (10) drops. The resultant solid precipitate was then filtered onto a sinter, sucked dry then dried to afford the title compound (42 mg).

NMR (d⁶-DMSO) δ 2.16 (3H, s), 3.30 (4H, brs), 3.69 (4H, brs), 7.34 (1H, d), 7.49 (3H, m), 7.74 (2H, s), 11.00 (1H, brs), 12.55 (1H, brs).

LC/MS t=2.8 min, [MH⁺] 371 consistent with molecular formula $C_{19}H_{19}{}^{35}ClN_4O_2$

EXAMPLE 2

1-[7-(3-Chloro-phenylamino)-3-methyl-1H-pyrrolo[2,3-c]pyridin-4-yl]-1-pyrrolidin-1-yl-methanone

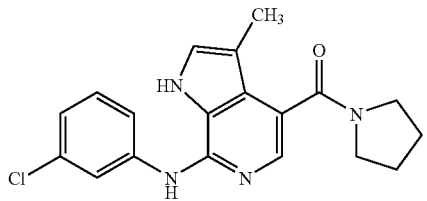

Prepared in a similar manner to Example 1 Method 1(f) using pyrrolidine (18 µl) instead of morpholine. The title compound was further purified using the Biotage Horizon to afford an off white solid (20 mg).

NMR (d⁶-DMSO) δ 1.79 (2H, m), 1.88 (2H,m), 2.10 (3H, s), 3.12 (2H, t), 3.50 (2H, t), 6.96 (1H, dd), 7.32 (1H, t), 7.37 (1H, s), 7.59 (1H, dd), 7.66 (1H, s), 8.21 (1H, t), 8.96 (1H, s), 11.10 (1H, s).

LC/MS t=2.5 min, [MH⁺] 355 consistent with molecular formula $C_{19}H_{19}{}^{35}ClN_4O$

EXAMPLE 3a AND 3b 7-(3-Chloro-phenylamino)-3-methyl-1H-pyrrolo[2,3-c]pyridine-4-carboxylic acid cyclopropylmethylamide and the hydrochloride salt

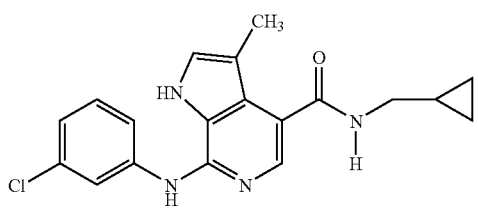

a) Prepared in a similar manner to Example 1 Method 1(f) using cyclopropylmethylamine (19 µl) instead of morpholine. The title compound was further purified using the Biotage Horizon to afford an off white solid NMR (d⁶-DMSO) δ 0.25 (2H, m), 0.43 (2H,m), 1.05 (1H, m), 2.24 (3H, s), 3.33 (2H, t), 6.96 (1H, dd), 7.32 (1H, t), 7.37 (1H, d), 7.58 (1H, dd), 7.84 (1H, s), 8.24 (1H, t), 8.34 (1H, t), 8.99 (1H, s), 11.10 (1H, s).

LC/MS t=2.7 min, [MH⁺] 355 consistent with molecular formula $C_{19}H_{19}{}^{35}ClN_4O$ b) Furthermore a hydrochloride salt of Example 3a was prepared by treating a solution of the compound of Example 3a (12 mg) in ethanol (2 ml) with two drops of concentrated hydrochloric acid giving a white precipitate. The solution was evaporated to dryness to afford 7-(3-chloro-phenylamino)-3-methyl-1H-pyrrolo[2,3-c]pyridine-4-carboxylic acid cyclopropylmethylamide hydrochloride salt. (12 mg).

NMR (d⁶-DMSO) δ 0.25 (2H, m), 0.43 (2H,m), 1.03 (1H, m), 2.25 (3H, s), 3.16 (2H, t), 7.34 (1H, brs), 7.50 (3H, m), 7.73 (2H, brs), 8.64 (1H, s), 11.10 (1H, s), 12.40 (1H, s).

LC/MS t=2.9 min, [MH⁺] 355 consistent with molecular formula $C_{19}H_{19}{}^{35}ClN_4O$

EXAMPLE 4

1-[7-(3-Bromo-phenylamino)-3-methyl-1-pyrrolo[2,3-c]pyridin-4-yl]-1-morpholin-4-yl-methanone hydrochloride salt

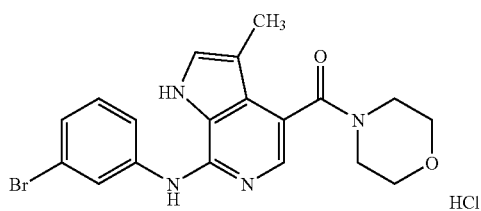

(a) 7-Chloro-4-iodo-3-methyl-pyrrolo[2,3-c]pyridine-1-carboxylic acid tert-butyl ester

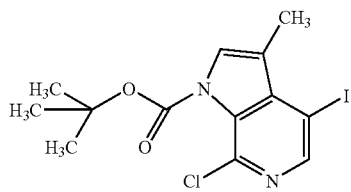

To a solution of 7-chloro-4-iodo-3-methyl-1H-pyrrolo[2,3-c]pyridine (2 g) in dry tetrahydrofuran (100 ml) at 0° C. under an atmosphere of nitrogen was added portionwise sodium hydride (60% dispersion in mineral oil, 600 mg). After addition, the solution was stirred at room temperature for 30 minutes. The solution was then recooled to 0° C. and a solution of di-tert-butyl dicarbonate (1.8 g) in dry tetrahydrofuran (20 ml) was added dropwise. The solution was stirred for 1 h allowing to warm to room temperature whereby a further portion of di-tert-butyl dicarbonate (375 mg) in dry tetrahydrofuran (4 ml) was added dropwise. The solution was stirred for 1 h allowing to warm to room temperature and then partitioned between ethyl acetate and water and washed with water until the pH of the aqueous was neutral. The organic layer was dried (MgSO₄) and evaporated to give a brown oil which solidified. The solid was triturated with isohexane, filtered off, sucked dry then dried at 40° C. under vacuum to afford the title compound (1.27 g). The filtrate was evaporated, and purified by Biotage chromatography over silica gel (100 g), eluting with isohexane followed by 5% ethyl acetate/isohexane to give more of the title compound as a pale yellow solid. (890 mg).

NMR (d⁶-DMSO) δ 1.60 (9H, s), 2.50 (3H, t), 7.91 (1H, d), 8.44 (1H, s).
LC/MS t=4.1 min, [M-$^t$Bu] 337 consistent with molecular formula $C_{13}H_{14}{}^{35}ClN_2O_2$ (b) 7-Chloro-3-methyl-pyrrolo[2,3-c]pyridine-1,4-dicarboxylic acid 1-tert-butyl ester

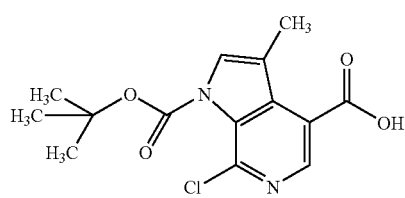

To a solution of 7-chloro-4-iodo-3-methyl-pyrrolo[2,3-c]pyridine-1-carboxylic acid tert-butyl ester (200 mg) in dry tetrahydrofuran (4 ml) at −40° C. under an atmosphere of nitrogen, was added dropwise, a solution of isopropylmagnesium chloride (2M in tetrahydrofuran, 600 ul) and the solution stirred at −40° C. for 15 minutes. The solution was saturated with a stream of carbon dioxide gas and then diluted with ethyl acetate. The organic was extracted with saturated ammonium chloride followed by 1N sodium hydroxide solution. The combined aqueous was then acidified to pH1 with concentrated hydrochloric acid to afford a precipitate. The precipitate was filtered and washed with water until neutral. The solid was then sucked dry and dried over sodium hydroxide at 50° C. to afford the title compound (86 mg).
NMR (d⁶-DMSO) δ 1.61 (9H, s), 2.50 (3H, t), 7.92 (1H, d), 8.50 (1H, s), 13.60 (1H, s).
LC/MS t=2.9 min, [M-$^t$Bu] 255 consistent with molecular formula $C_{14}H_{15}{}^{35}ClN_2O_4$ (c) 7-Chloro-3-methyl-4-(1-morpholin-4-yl-methanoyl)-pyrrolo[2,3-c]pyridine-1-carboxylic acid tert-butyl ester

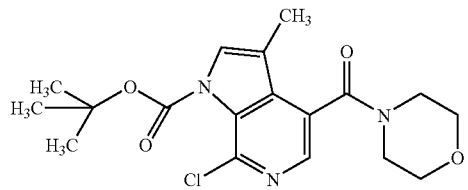

To a solution of 7-chloro-3-methyl-pyrrolo[2,3-c]pyridine-1,4-dicarboxylic acid 1-tert-butyl ester (80 mg) in dimethylformamide (2 ml) was added 4-ethylmorpholine (131 μl), morpholine (46 μl), 1-hydroxybenzotriazole hydrate (54 mg) and 1-(3-dimethylaminopropyl)-3-ethylcarbodiimide hydrochloride (60 mg) and the solution stirred at room temperature overnight. The dimethylformamide was evaporated and the residue dissolved in ethyl acetate (20 ml). The organic layer was then washed with 5% sodium hydrogen carbonate solution (2×4 ml) and water (2×10 ml). The organic layer was dried (MgSO₄) and evaporated to give a yellow oil (107 mg) which was used without further purification.
LC/MS t=2.8 min, [MH⁺] 380 consistent with molecular formula $C_{18}H_{19}{}^{35}ClN_3O_4$ (d) 1-[7-(3-Bromo-phenylamino)-3-methyl-1H-pyrrolo[2,3-c]pyridin-4-yl]-1-morpholin-4-yl-methanone hydrochloride salt A mixture of 7-chloro-3-methyl-4-(1-morpholin-4-yl-methanoyl)-pyrrolo[2,3-c]pyridine-1-carboxylic acid tert-butyl ester, 3-bromoaniline (56 μl), and methanesulfonic acid (33 μl) in 1,4-dioxane (2 ml) was heated under microwave conditions at 180° C. for 30 minutes. The solid mass obtained was dissolved in methanol, transferred to a round bottom flask and evaporated. The residue was dissolved in ethyl acetate and washed with 5% sodium hydrogen carbonate solution and water. The organic layer was dried (MgSO₄) and evaporated to give an off-white solid. The solid was triturated with diethyl ether, filtered off and sucked dry. The solid was then dissolved in warm ethyl acetate (10 ml) and treated with a solution of 1M hydrochloric acid in diethyl ether (10 drops). The resultant solid precipitate was then filtered off, sucked dry then dried at 40° C. under vacuum to afford the title compound (58 mg).
NMR (d⁶-DMSO) δ 2.16 (3H, s), 3.30-3.69 (8H, b), 7.42-7.55 (4H, m), 7.73 (1H, s), 7.86 (1H, s), δ 11.00 (1H, brs), 12.55 (1H, brs).
LC/MS t=2.8 min, [MH⁺] 417 consistent with molecular formula $C_{19}H_{19}{}^{81}BrN_4O_2$

EXAMPLE 5

7-(3-Bromo-phenylamino)-3-methyl-1H-pyrrolo[2,3-c]pyridine-4-carboxylic acid (tetrahydro-pyran-4-ylmethyl)-amide hydrochloride salt

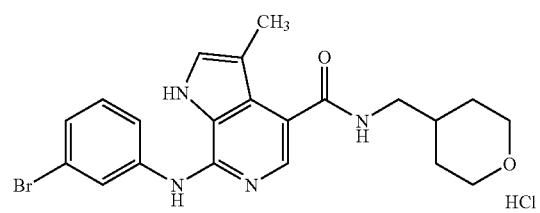

Prepared in a similar manner to Example 4 (d) from 7-chloro-3-methyl-4-[(tetrahydro-pyran-4-ylmethyl)-carbamoyl)]-pyrrolo[2,3-c]pyridine-1-carboxylic acid tert-butyl ester (Example 8a) and 3-bromoaniline to afford the title compound as a white solid (43 mg).
NMR (d⁶-DMSO) δ 1.20 (2H, m), 1.62 (2H, d), 1.79 (1H, m), 2.22 (3H, s), 3.17 (2H, t), 3.27 (2H, t), 3.85 (2H, dd), 7.46-7.55 (4H, brm), 7.73-7.83 (2H, d), 8.59 (1H, s), 11.10 (1H, brs), 12.55 (1H, brs).
LC/MS t=2.9 min, [MH⁺] 445 consistent with molecular formula $C_{21}H_{23}{}^{81}BrN_4O_2$

EXAMPLE 6

7-(3-Bromo-phenylamino)-3-methyl-1H-pyrrolo[2,3-c]pyridine-4-carboxylic acid cyclopropylmethyl-amide hydrochloride salt

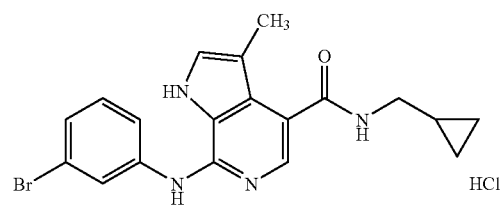

Prepared in a similar manner to Example 4 (d) using compound of Example 17(a) and 3-bromoaniline. The crude solid mass was dissolved in the minimum of methanol and absorbed onto silica gel. The residue was purified by Biotage chromatography over silica gel (50 g), eluting with 2% methanol/dichloromethane followed by 5% methanol/dichloromethane. The residue was dissolved in warm ethyl acetate and treated with a solution of 1M hydrochloric acid in diethyl ether (10) drops. The solution was evaporated and triturated with diethyl ether and the resultant solid was then filtered off, sucked dry then dried at 40° C. under vacuum to afford the title compound (30 mg).

NMR (d$^6$-DMSO) δ 0.25 (2H, m), 0.43 (2H,m), 1.05 (1H, m), 2.24 (3H, s), 3.16 (2H, t), 7.48 (4H, m), 7.76 (2H, d), 8.68 (1H, t), 11.10 (1H, s), 12.70 (2H, brs).

LC/MS t=3.3 min, [MH$^+$] 401 consistent with molecular formula $C_{19}H_{19}{}^{81}BrN_4O$

EXAMPLE 7

7-(3-Chloro-phenylamino)-3-methyl-1H-pyrrolo[2,3-c]pyridine-4-carboxylic acid cyclopropylamide

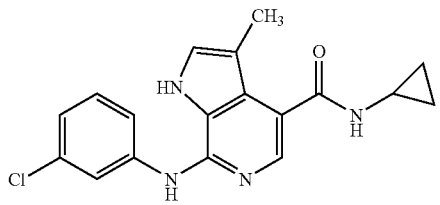

Prepared in a similar manner to Example 1 Method 1(f) using cyclopropylamine (16 μl) instead of morpholine. The title compound was further purified using the Biotage Horizon to afford an off white solid (18 mg).

NMR (d$^6$-DMSO) δ 0.55 (2H, m), 0.68 (2H,m), 2.22 (3H, s), 2.85 (1H,m), 6.96 (1H, dd), 7.32 (1H, t), 7.37 (1H, d), 7.55 (1H, dd), 7.80 (1H, s), 8.24 (1H, t), 8.28 (1H, d), 8.98 (1H, s), 11.10 (1H, s).

LC/MS t=2.4 min, [MH$^+$] 341 consistent with molecular formula $C_{18}H_{17}{}^{35}ClN_4O$

EXAMPLE 8

7-(3-Chloro-phenylamino)-3-methyl-1H-pyrrolo[2,3-c]pyridine-4-carboxylic acid (tetrahydro-pyran-4-ylmethyl)-amide hydrochloride salt

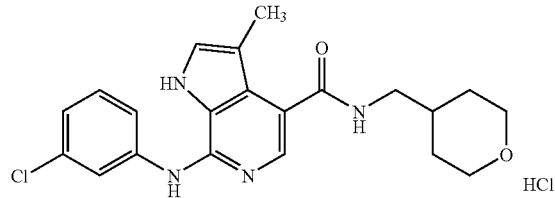

(a) 7-Chloro-3-methyl-4-[(tetrahydro-pyran-4-ylmethyl)-carbamoyl)]-pyrrolo[2,3-c]pyridine-1-carboxylic acid tert-butyl ester

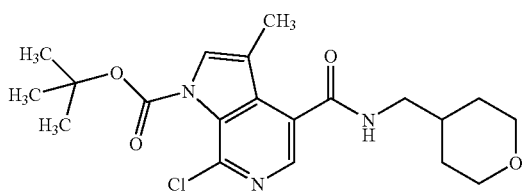

Prepared in a similar manner to Example 11 (b) using tetrahydro-pyran-4-ylmethylamine (222 mg) instead of morpholine to give the title compound as an off-white foam (413 mg).

NMR (d$^6$-DMSO) δ 1.20 (2H, m), 1.60 (9H, s), 1.65 (2H, s), 1.79 (1H,m), 2.16 (3H, s), 3.19 (2H, t), 3.27 (2H, t), 3.85 (2H, dd), 7.84 (1H, s), 8.16 (1H, s), 8.71 (1H, t).

LC/MS t=2.9 min, [MH$^+$] 408 consistent with molecular formula $C_{20}H_{26}{}^{35}ClN_3O_4$ (b) 7-(3-Chloro-phenylamino)-3-methyl-1H-pyrrolo[2,3-c]pyridine-4-carboxylic acid (tetrahydro-pyran-4-ylmethyl)-amide hydrochloride salt Prepared in a similar manner to Example 11(c) from 7-chloro-3-methyl-4-[(tetrahydro-pyran-4-ylmethyl)-carbamoyl)]-pyrrolo[2,3-c]pyridine-1-carboxylic acid tert-butyl ester and using 3-chloroaniline (42 ul) instead of morpholine and isolated as described in Example 14 (b) to give the title compound (57 mg).

NMR (d$^6$-DMSO) δ 1.20 (2H, m), 1.62 (2H, d), 1.79 (1H, m), 2.22 (3H, s), 3.16 (2H, t), 3.27 (2H, t), 3.85 (2H, dd), 7.33 (1H, brs), 7.49-7.54 (3H, bd), 7.73 (2H, s), 8.61 (1H, s), 11.50 (1H, brs), 12.85 (1H, brs).

LC/MS t=2.7 min, [MH$^+$] 399 consistent with molecular formula $C_{21}H_{23}{}^{35}ClN_4O_2$

EXAMPLE 9

1-[7-(3-Chloro-phenylamino)-1H-pyrrolo[2,3-c]pyridin-4-yl]-1-morpholin-4-yl-methanone

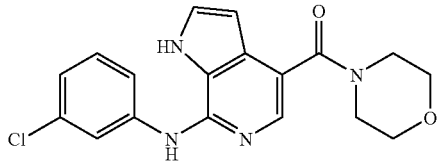

(a) 1-(7-Chloro-1H-pyrrolo[2,3-c]pyridin-4-yl)-1-morpholin-4-yl-methanone

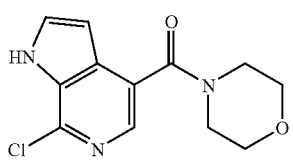

Prepared from 7-chloro-1H-pyrrolo[2,3-c]pyridine-4-carboxylic acid in a similar manner to Example 19 (e) using morpholine instead of tetrahydro-pyran-4-ylmethylamine to give the title compound (32 mg).

NMR (d$^6$-DMSO) δ 3.33-3.67 (8H, b), 6.62 (1H, d), 7.78 (1H, d), 7.94 (1H, s), 12.35 (1H, s).

LC/MS t=1.7 min, [MH$^+$] 266 consistent with molecular formula $C_{12}H_{12}{}^{35}ClN_3O_2$ (b) 1-[7-(3-Chloro-phenylamino)-1H-pyrrolo[2,3-c]pyridin-4-yl]-1-morpholin-4-yl-methanone Prepared in a similar manner to Example 19 (f) except that purification was by MDAP to give the title compound (17 mg).

NMR (d$^6$-DMSO) δ 3.51 (4H, brs), 3.61 (4H, brs), 6.55 (1H, s), 7.10 (1H, s), 7.40 (1H, t), 7.65 (1H, d), 7.75 (2H, d), 8.13 (1H, s), 9.80 (1H, brs), 11.85 (1H, brs).

LC/MS t=2.6 min, [MH⁺] 357 consistent with molecular formula $C_{18}H_{17}^{35}ClN_4O_2$

EXAMPLE 10

7-(3-Chloro-phenylamino)-3-methyl-1H-pyrrolo[2,3-c]pyridine-4-carboxylic acid dimethylamide

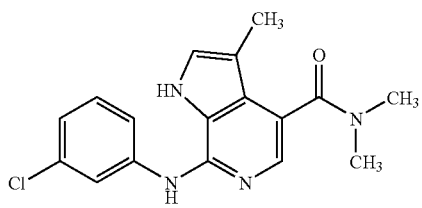

Prepared in a similar manner to Example 1 Method 1(f) using dimethylamine hydrochloride (18 mg) instead of morpholine. The title compound was further purified using the Biotage Horizon to afford an off white solid (18 mg).

NMR (d⁶-DMSO) δ 2.08 (3H, s), 2.81 (3H, s), 3.04 (3H, s), 6.97 (1H, dd), 7.32 (1H, t), 7.38 (1H, s), 7.59 (1H, s), 7.60 (1H, s), 8.21 (1H, t), 8.97 (1H, s), 11.10 (1H, s).

LC/MS t=2.32 min, [MH⁺] 329 consistent with molecular formula $C_{17}H_{17}^{35}ClN_4O$

EXAMPLE 11

1-(3-Methyl-7-morpholin-4-yl-1H-pyrrolo[2,3-c]pyridin-4-yl)-1-morpholin-4-yl-methanone hydrochloride salt

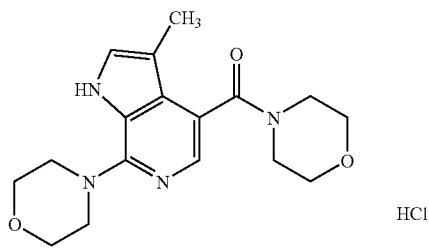

(a) 7-Chloro-3-methyl-pyrrolo[2,3-c]pyridine-1,4-dicarboxylic acid 1-tert-butyl ester

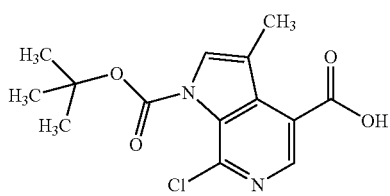

To a solution of 7-chloro-4-iodo-3-methyl-pyrrolo[2,3-c]pyridine-1-carboxylic acid tert-butyl ester (2 g) in dry tetrahydrofuran (40 ml) was added 4 A molecular sieves. The solution was stirred at room temperature for 15 minutes then cooled to 40° C. Under an atmosphere of nitrogen was added dropwise, a solution of isopropylmagnesium chloride (2M in tetrahydrofuran, 5.4 ml) and the solution stirred at −40° C. for 10 minutes. The solution was saturated with a stream of carbon dioxide gas which had been passed through a column of Drierite and then diluted with ethyl acetate. The organic was extracted with 1N sodium hydroxide solution until complete extraction and the combined aqueous was then acidified to pH1 with concentrated hydrochloric acid. The acidified aqueous was extracted twice with ethyl acetate which was combined and washed with water until neutral. The ethyl acetate layer was then dried (MgSO₄) and evaporated to give a solid. The solid was triturated with isohexane, filtered off and washed with isohexane. The solid was sucked dry then dried at 50° C. under vacuum to afford the title compound (1.22 g).

NMR (d⁶-DMSO) δ 1.61 (9H, s), 2.50 (3H, t), 7.92 (1H, d), 8.50 (1H, s), 13.60 (1H, s).

LC/MS t=3.0 min, [M-ᵗBu] 255 consistent with molecular formula $C_{14}H_{15}^{35}ClN_2O_4$ (b) 7-Chloro-3-methyl-4-(1-morpholin-4-yl-methanoyl)-pyrrolo[2,3-c]pyridine-1-carboxylic acid tert-butyl ester

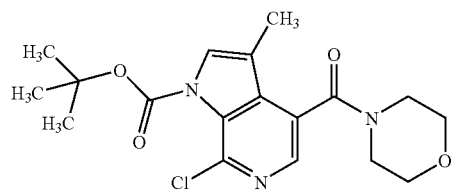

To a solution of 7-chloro-3-methyl-pyrrolo[2,3-c]pyridine-1,4-dicarboxylic acid 1-tert-butyl ester (300 mg) in dimethylformamide (4 ml) was added 4-ethylmorpholine (492 ul), morpholine (172 ul), 1-hydroxybenzotriazole hydrate (204 mg) and 1-(3-dimethylaminopropyl)-3-ethylcarbodiimide hydrochloride (223 mg) and the solution stirred at room temperature overnight. The solution was diluted with ethyl acetate (50 ml). The organic layer was then washed with 5% sodium hydrogen carbonate solution (2×10 ml) and water (2×20 ml). The organic layer was dried (MgSO₄) and evaporated to give an off-white foam (107 mg) which was used without further purification.

LC/MS t=2.8 nm in, [MH⁺] 380 consistent with molecular formula $C_{18}H_{19}^{35}ClN_3O_4$ (c) 1-(3-Methyl-7-morpholin-4-yl-1H-pyrrolo[2,3-c]pyridin-4-yl)-1-morpholin-4-yl-methanone hydrochloride salt

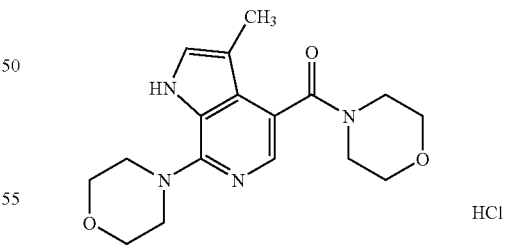

A mixture of 7-chloro-3-methyl-4-(1-morpholin-4-yl-methanoyl)-pyrrolo[2,3-c]pyridine-1-carboxylic acid tert-butyl ester (70 mg), morpholine (64 μl), and methanesulfonic acid (48 μl) in 1,4-dioxane (1 ml) was heated under microwave conditions at 180° C. for 30 minutes. The solid mass obtained was dissolved in methanol, transferred to a round bottom flask and evaporated. The residue was dissolved in dichloromethane (40 ml) and washed with 5% sodium hydrogen carbonate solution (4 ml). The organic layer was dried (MgSO$_4$) and evaporated to give a pale brown foam. The residue was purified by Biotage chromatography over silica gel (50 g), eluting with 2% methanol/dichloromethane followed by 5% methanol/dichloromethane. The residue was dissolved in dichloromethane and treated with a solution of 1M hydrochloric acid in diethyl ether (10 drops). The solution was evaporated and triturated with diethyl ether and the resultant solid was then filtered off, sucked dry then dried at 40° C. under vacuum to afford the title compound (36 mg).

NMR (d$^6$-DMSO) δ 2.15 (3H, s), 3.23-3.83 (16H, b), 7.62 (1H, s), 7.70 (1H, s), 12.30 (1H, brs), 13.40 (1H, brs).

LC/MS t=1.5 min, [MH$^+$] 331 consistent with molecular formula C$_{17}$H$_{22}$N$_4$O$_3$

EXAMPLE 12

1-(7-Cyclohexylamino-3-methyl-1H-pyrrolo[2,3-c]pyridin-4-yl)-1-morpholin-4-yl-methanone hydrochloride salt

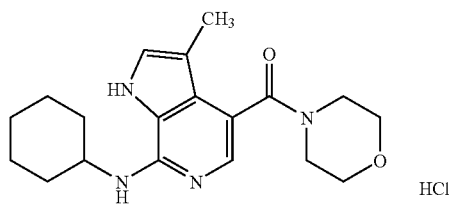

A mixture of 7-chloro-3-methyl-4-(1-morpholin-4-yl-methanoyl)-pyrrolo[2,3-c]pyridine-1-carboxylic acid tert-butyl ester (66 mg), cyclohexylamine (80 ul), and methanesulfonic acid (45 ul) in 1,4-dioxane (1 ml) was heated under microwave conditions at 180° C. for 30 minutes. Cyclohexylamine (600 ul in total) was added and the mixture heated under microwave conditions at 180° C. for 2.5 h. The solid mass obtained was purified as described in Example 11(c) to afford the title compound (31 mg).

NMR (d$^6$-DMSO) δ 1.23-1.39 (5H, m), 1.65 (1H, d), 1.77 (2H, m), 2.00 (2H, m), 2.10 (3H, s), 3.39-3.92 (9H, b), 7.40 (1H, s), 7.45 (1H, s), 12.00 (1H, brs), 12.65 (1H, brs).

LC/MS t=1.8 min, [MH$^+$] 343 consistent with molecular formula C$_{19}$H$_{26}$N$_4$O$_2$

EXAMPLE 13

1-[3-Methyl-7-(tetrahydro-pyran-4-ylamino)-1H-pyrrolo[2,3-c]pyridin-4-yl]-1-morpholin-4-yl-methanone hydrochloride salt

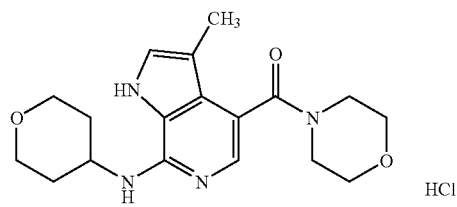

Prepared in a similar manner to Example 12 using tetrahydro-pyran-4-ylamine (270 mg) instead of cyclohexylamine to afford the title compound as a white solid (8 mg).

LC/MS t=1.5 min, [MH$^+$] 345 consistent with molecular formula C$_{18}$H$_{24}$N$_4$O$_3$

EXAMPLE 14

7-(3-Chloro-phenylamino)-3-methyl-1H-pyrrolo[2,3-c]pyridine-4-carboxylic acid (tetrahydro-pyran-4-yl)-amide hydrochloride salt

(a) 7-Chloro-3-methyl-4-(tetrahydro-pyran-4-ylcarbamoyl)-pyrrolo[2,3-c]pyridine-1-carboxylic acid tert-butyl ester

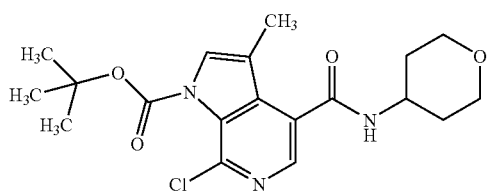

Prepared in a similar manner to Example 11 (b) from 7-chloro-3-methyl-pyrrolo[2,3-c]pyridine-1,4-dicarboxylic acid 1-tert-butyl ester and using tetrahydro-pyran-4-ylamine (195 mg) instead of morpholine. The title compound was further purified by trituration with ether/isohexane to give an off-white solid (324 mg).

NMR (d$^6$-DMSO) δ 1.49-1.56 (2H, m), 1.60 (9H, s), 1.84 (2H, d), 2.18 (3H, s), 3.41 (2H, t), 3.86 (2H, d), 4.03 (1H, m), 7.84 (1H, s), 8.14 (1H, s), 8.66 (1H, d).

LC/MS t=2.8 min, [MH$^+$] 394 consistent with molecular formula C$_{19}$H$_{24}$$^{35}$ClN$_3$O$_4$ (b) 7-(3-Chloro-phenylamino)-3-methyl-1H-pyrrolo[2,3-c]pyridine-4-carboxylic acid (tetrahydro-pyran-4-yl)-amide hydrochloride salt Prepared in a similar manner to Example 11 (c) using 3-chloroaniline (43 μl) instead of morpholine, except that the title compound remained as a solid at the interface when partitioned between 5% sodium hydrogen carbonate solution and dichloromethane. The solid was filtered off and the hydrochloride salt was formed by dissolving the solid above in methanol, treatment with 1N HCl (few drops), evaporation and trituration with diethyl ether to afford the title compound (37 mg).

NMR (d$^6$-DMSO) δ 1.49-1.58 (2H, m), 1.83 (2H, d), 2.23 (3H, s), 3.41 (2H, t), 3.87 (2H, d), 4.01 (1H, m), 7.35-7.74 (6H, b), 8.55 (1H, d), 11.10 (1H, brs), 12.60 (1H, brs).

LC/MS t=2.71 min, [MH⁺] 385 consistent with molecular formula $C_{20}H_{21}{}^{35}ClN_4O_2$

EXAMPLE 15

7-Cyclohexylamino-3-methyl-1H-pyrrolo[2,3-c]pyridine-4-carboxylic acid (tetrahydro-pyran-4-yl)-amide hydrochloride salt

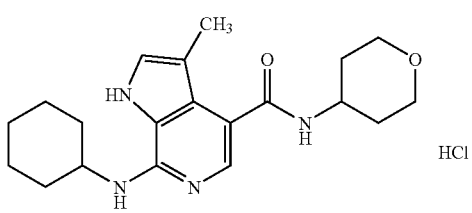

Prepared in a similar manner to Example 12, from 7-chloro-3-methyl-4-(tetrahydro-pyran-4-ylcarbamoyl)-pyrrolo[2,3-c]pyridine-1-carboxylic acid tert-butyl ester except that the methanesulfonic acid was omitted. Cyclohexylamine (900 ul) was used and the reaction time was 15 h. Ethyl acetate was used instead of dichloromethane as solvent in the work up, no chromatography was required, and ethyl acetate was used instead of dichloromethane in the salt formation, to give the title compound (13 mg).

NMR (d⁶-DMSO) δ 1.23-1.45 (5H, m), 1.45-1.70 (3H, m), 1.79 (4H, m), 2.00 (2H, m), 2.17 (3H, s), 3.39 (2H, t), 3.85-3.88 (4H, m), 7.48 (2H, s), 8.35 (1H, s), 12.70 (1H, s).

LC/MS t=1.9 min, [MH⁺] 357 consistent with molecular formula $C_{20}H_{28}N_4O_2$

EXAMPLE 16

7-Cyclohexylamino-3-methyl-1H-pyrrolo[2,3-c]pyridine-4-carboxylic acid (tetrahydro-pyran-4-ylmethyl)-amide hydrochloride salt

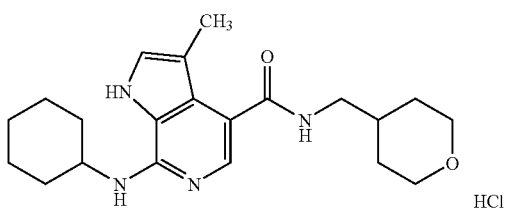

Prepared in a similar manner to Example 12, from 7-chloro-3-methyl-4-[(tetrahydro-pyran-4-ylmethyl)-carbamoyl)]-pyrrolo[2,3-c]pyridine-1-carboxylic acid tert-butyl ester except that the methanesulfonic acid was omitted. Cyclohexylamine (1.5 ml) was used and the reaction time was 10 h.

The solid mass was dissolved in the minimum of methanol and absorbed onto silica gel. The residue was purified as described in Example 6 to afford the title compound (28 mg).

NMR (d⁶-DMSO) δ 1.17-1.30 (3H, m), 1.33-150 (4H, m), 1.60-1.70 (3H, m), 1.8 (3H, m), 2.00 (2H, s), 2.17 (3H, s), 3.16 (2H, t), 3.24 (2H, t), 3.84-3.87 (3H, m), 7.40 (1H, s), 7.61 (1H, s), 8.58 (1H, t), 9.00 (1H, s), 12.70 (2H, d).

LC/MS t=1.9 min, [MH⁺] 371 consistent with molecular formula $C_{21}H_{30}N_4O_2$

EXAMPLE 17

7-Cyclohexylamino-3-methyl-1H-pyrrolo[2,3-c]pyridine-4-carboxylic acid cyclopropylmethyl-amide hydrochloride salt

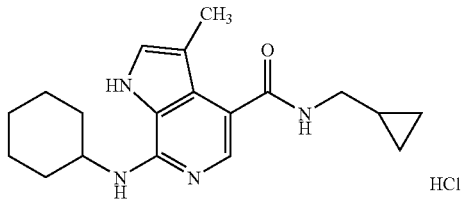

(a) 7-Chloro-4-(cyclopropylmethyl-carbamoyl)-3-methyl-pyrrolo[2,3-c]pyridine-1-carboxylic acid tert-butyl ester

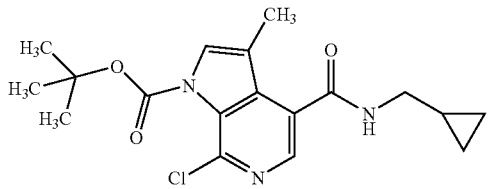

Prepared in a similar manner to Example 11 (b) from 7-chloro-3-methyl-pyrrolo[2,3-c]pyridine-1,4-dicarboxylic acid 1-tert-butyl ester using cyclopropylmethylamine (167 μl) instead of morpholine to give the title compound as a pale brown foam (389 mg).

NMR (d⁶-DMSO) δ 0.25 (2H, m), 0.45 (2H, m), 0.98 (1H, m), 1.61 (9H, s), 2.19 (3H, s), 3.17 (2H, t), 7.84 (1H, s), 8.14 (1H, s), 8.79 (1H, t).

LC/MS t=3.2 min, [MH⁺] 364 consistent with molecular formula $C_{18}H_{22}{}^{35}ClN_3O_3$ (b) 7-Cyclohexylamino-3-methyl-1H-pyrrolo[2,3-c]pyridine-4-carboxylic acid cyclopropylmethyl-amide hydrochloride salt Prepared in a similar manner to Example 12, except that the methanesulfonic acid was omitted. Cyclohexylamine (1.5 ml) was used and the reaction time was 10 h. The solid mass was dissolved in the minimum of methanol and absorbed onto silica gel. The residue was purified as set out in Example 6 to afford the title compound (58 mg).

NMR (d⁶-DMSO) δ 0.24 (2H, m), 0.45 (2H, m), 1.01 (1H, m), 1.23 (1H, m), 1.42 (4H, m), 1.64 (1H, d), 1.80 (2H, m), 1.99 (2H, m), 2.19 (3H, s), 3.14 (2H, t), 3.19 (1H, brs), 7.39 (1H, d), 7.63 (1H, d), 8.66 (1H, t), 9.11 (1H, d), 12.80 (2H, t).

LC/MS t=2.1 min, [MH⁺] 327 consistent with molecular formula $C_{19}H_{26}N_4O$

EXAMPLE 18

3-Methyl-7-morpholin-4-yl-1H-pyrrolo[2,3-c]pyridine-4-carboxylic acid cyclopropylmethyl-amide hydrochloride salt

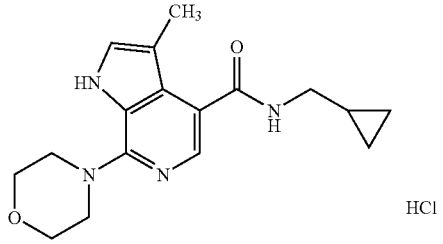

Prepared in a similar manner to Example 11 (c) from 7-chloro-4-(cyclopropylmethyl-carbamoyl)-3-methyl-pyrrolo[2,3-c]pyridine-1-carboxylic acid tert-butyl ester. The solid mass was dissolved in the minimum of methanol and absorbed onto silica gel. The residue was purified by Biotage chromatography as described in Example 6 afford the title compound (14 mg).

NMR (d$^6$-DMSO) δ 0.25 (2H, m), 0.43 (2H,m), 1.05 (1H, m), 2.21 (3H, s), 3.16 (2H, t), 3.74 (4H, brs), 3.84 (4H, m), 7.60 (1H, s), 7.76 (1H, s), 8.76 (1H, t), 12.50 (1H, s), 13.75 (1H, brs).

LC/MS t=1.7 min, [MH$^+$] 315 consistent with molecular formula $C_{17}H_{22}N_4O_2$

EXAMPLE 19

7-(3-Chloro-phenylamino)-1H-pyrrolo[2,3-c]pyridine-4-carboxylic acid (tetrahydro-pyran-4-ylmethyl)-amide

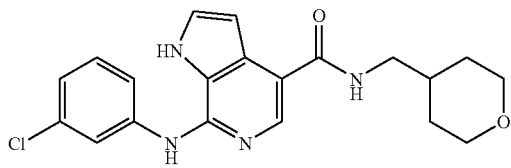

(a) 5-Bromo-2-chloro-3-nitro-pyridine

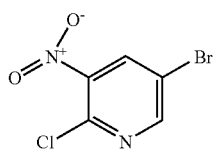

A suspension of 5-bromo-2-hydroxy-3-nitro-pyridine (19.2 g; ex. Maybridge) in phenyl dichlorophosphate (40 ml) was heated at 180° C. for 30 minutes to give a red oil. The reaction mixture was then purified as described in Example 1 Method 1(a) to give the title compound as a pale yellow solid (20.4 g).

NMR (CDCl$_3$) δ 8.36 (1H, d), 8.69 (1H, d).

LC/MS t=2.6 min, [MH$^+$] 239 consistent with molecular formula $C_5H_2{}^{81}Br^{35}ClN_2O_2$ (b) 4-Bromo-7-chloro-1H-pyrrolo[2,3-c]pyridine

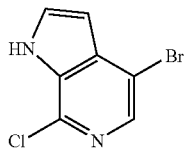

To a solution of 5-bromo-2-chloro-3-nitro-pyridine (7 g) in dry tetrahydrofuran (150 ml) at −70° C. under an atmosphere of nitrogen was added dropwise a solution of vinylmagnesium bromide (1.0M in tetrahydrofuran; 94.5 ml) over 1 h. The solution was stirred at −70° C. for 1 h and then quenched with saturated ammonium chloride (150 ml) and the aqueous was extracted twice with ethyl acetate. The combined organics were dried (MgSO$_4$) and evaporated to give a deep red oil. The residue was triturated with diethyl ether (100 ml) and the solid was then filtered off, sucked dry then dried at 40° C. under vacuum to afford the title compound (1.75 g).

NMR (d$^6$-DMSO) δ 6.61 (1H, d), 7.82 (1H, d), 8.07 (1H, s), 12.50 (1H, s).

LC/MS t=2.9 min, [MH$^+$] 233 consistent with molecular formula $C_7H_4{}^{81}Br^{35}ClN_2$ (c) 4-Bromo-1-(tert-butyl-dimethyl-silanyl)-7-chloro-1H-pyrrolo[2,3-c]pyridine

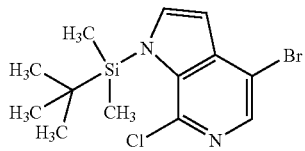

To a solution of 4-bromo-7-chloro-1H-pyrrolo[2,3-c]pyridine (1.64 g) in dry tetrahydrofuran (80 ml) at 0° C. under an atmosphere of nitrogen was added portionwise sodium hydride (60% dispersion in mineral oil, 625 mg). After addition, the solution was stirred at room temperature for 30 minutes. The solution was then recooled to 0° C. and a solution of tert-butyldimethylsilyl trifluoromethanesulphonate (3.75 g) in dry tetrahydrofuran (20 ml) was added dropwise. The solution was partitioned between ethyl acetate (100 ml) and water (100 ml) and washed with water until the pH of the aqueous was neutral. The organic layer was dried (MgSO$_4$) and evaporated to give a brown oil. The residue was purified by Biotage chromatography over silica gel (10 g), eluting with 10% ethyl acetate/isohexane to give the title compound as a red oil. (1.63 g).

NMR (d$^6$-DMSO) δ 0.62 (6H, s), 0.87 (9H, s), 6.64 (1H, d), 7.45 (1H, d), 8.03 (1H, s).

LC/MS t=4.0 min, [MH$^+$] 347 consistent with molecular formula $C_{13}H_{18}{}^{81}Br^{35}ClN_2Si$ (d) 7-Chloro-1H-pyrrolo[2,3-c]pyridine-4-carboxylic acid

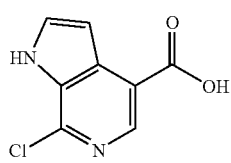

To a solution of 4-bromo-1-(tert-butyl-dimethyl-silanyl)-7-chloro-1H-pyrrolo[2,3-c]pyridine (500 mg) in dry tetrahydrofuran (25 ml) at −78° C. under an atmosphere of nitrogen was added tert-butyllithium (1.7M in pentane, 1.88 ml). After addition, the reaction mixture was stirred for 15 minutes at −78° C. then poured onto crushed pellets of carbon dioxide. The mixture was allowed to warm to room temperature and then evaporated. The residue was dissolved in water and the aqueous washed twice with diethyl ether. The aqueous was then acidified with 2M hydrochloric acid and extracted twice with ethyl acetate. The organic layer was dried (MgSO$_4$) and evaporated to give the title compound as a yellow solid (120 mg).

NMR (d$^6$-DMSO) δ 0.62 (6H, s), 0.87 (9H, s), 6.64 (1H, d), 7.45 (1H, d), 8.03 (1H, s).

LC/MS t=1.8 min, [MH$^+$] 197 consistent with molecular formula $C_8H_5{}^{35}ClN_2O_2$ (e) 7-Chloro-1H-pyrrolo[2,3-c]pyridine-4-carboxylic acid (tetrahydro-pyran-4-ylmethyl)-amide

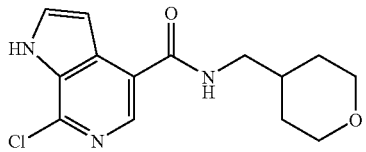

To a solution of 7-chloro-1H-pyrrolo[2,3-c]pyridine-4-carboxylic acid (110 mg) in dimethylformamide (4 ml) was added 4-ethylmorpholine (187 μl), tetrahydro-pyran-4-ylmethylamine (97 mg), 1-hydroxybenzotriazole hydrate (118 mg) and 1-(3-dimethylaminopropyl)-3-ethylcarbodiimide hydrochloride (129 mg) and the solution stirred at room temperature overnight. The dimethylformamide was evaporated and the residue dissolved in ethyl acetate (10 ml). The organic layer was then washed with 5% sodium hydrogen carbonate solution (4 ml) and brine (4 ml). The organic layer was dried (MgSO$_4$) and evaporated to give a pale orange solid. The solid was triturated with diethyl ether and then filtered off, sucked dry then dried at 40° C. under vacuum to afford the title compound (93 mg).

NMR (d$^6$-DMSO) δ 1.21 (2H, m), 1.63 (2H, d), 1.83 (1H, m), 3.21 (2H, t), 3.27 (2H, t), 3.85 (2H, dd), 6.92 (1H, d), 7.76 (1H, d), 8.29 (1H, s), 8.53 (1H, t), 12.20 (1H, s).

LC/MS t=1.9 min, [MH$^+$] 294 consistent with molecular formula $C_{14}H_{16}^{35}ClN_3O_2$ (f) 7-(3-Chloro-phenylamino)-1H-pyrrolo[2,3-c]pyridine-4-carboxylic acid (tetrahydro-pyran-4-ylmethyl)-amide

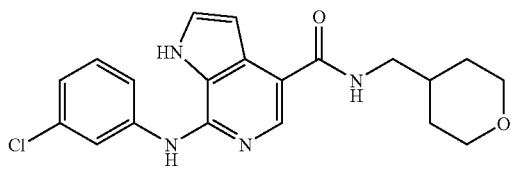

A mixture of 7-chloro-1H-pyrrolo[2,3-c]pyridine-4-carboxylic acid (tetrahydro-pyran-4-ylmethyl)-amide (20 mg), 3-chloroaniline (15 ul), and methanesulfonic acid (9 ul) in 1,4-dioxane (0.5 ml) was heated under microwave conditions at 180° C. for 30 minutes. The solid mass obtained was dissolved in methanol, transferred to a round bottom flask and evaporated. The residue was partitioned between ethyl acetate and 5% sodium hydrogen carbonate solution whereby the title compound remained as a solid at the interface. The solid was filtered off, and washed with 5% sodium hydrogen carbonate solution, water and diethyl ether, then sucked dry and dried at 60° C. under vacuum to afford the title compound (17 mg).

NMR (d$^6$-DMSO) δ 1.21 (2H, m), 1.62 (2H, d), 1.80 (1H, m), 3.19 (2H, t), 3.27 (2H, t), 3.85 (2H, dd), 7.10 (1H, s), 7.32 (1H, s), 7.51 (2H, d), 7.85 (1H, s), 7.91 (1H, s), 7.98 (1H, s), 8.50 (1H, s), 11.85 (1H, brs), 12.45 (1H, brs).

LC/MS t=2.7 min, [MH$^+$] 385 consistent with molecular formula $C_{20}H_{21}^{35}ClN_4O_2$

EXAMPLE 20

7-(3-Chloro-phenylamino)-1H-pyrrolo[2,3-c]pyridine-4-carboxylic acid cyclobutylmethyl-amide

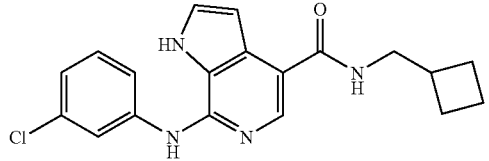

(a) 7-Chloro-1H-pyrrolo[2,3-c]pyridine-4-carboxylic acid cyclobutylmethyl-amide

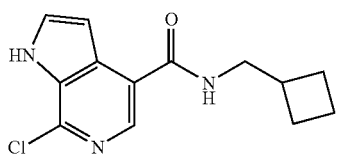

Prepared in a similar manner to Example 19 (e) from 7-chloro-1H-pyrrolo[2,3-c]pyridine-4-carboxylic acid using cyclobutylmethylamine hydrochloride (46 mg) instead of tetrahydro-pyran-4-ylmethylamine to give the title compound (39 mg).

NMR (d$^6$-DMSO) δ 1.72-1.88 (4H, m), 1.99 (2H, m), 2.56 (1H, m), 3.33 (2H, t), 6.91 (1H, s), 7.76 (1H, t), 8.27 (1H, s), 8.48 (1H, t), 12.25 (1H, s).

LC/MS t=2.4 min, [MH$^+$] 264 consistent with molecular formula $C_{13}H_{14}^{35}ClN_3O$ (b) 7-(3-Chloro-phenylamino)-1H-pyrrolo[2,3-c]pyridine-4-carboxylic acid cyclobutylmethyl-amide Prepared in a similar manner to Example 19 (f) except that the title compound was isolated by trituration with 5% sodium hydrogen carbonate solution followed by washing with water and diethyl ether to give the title compound (29 mg).

NMR (d$^6$-DMSO) δ 1.72-1.86 (4H, m), 2.01 (2H, m), 2.55 (1H, m), 3.30 (2H, t), 6.90 (1H, s), 7.08 (1H, brs), 7.38 (1H, t), 7.58 (1H, d), 7.68 (1H, s), 8.19 (3H, d), 9.60 (1H, brs), 11.70 (1H, brs).

LC/MS t=3.5 min, [MH$^+$] 355 consistent with molecular formula $C_{19}H_{19}^{35}ClN_4O$

EXAMPLE 21

7-(3-Chloro-phenylamino)-1H-pyrrolo[2,3-c]pyridine-4-carboxylic acid isobutyl-amide

(a) 7-Chloro-1H-pyrrolo[2,3-c]pyridine-4-carboxylic acid isobutyl-amide

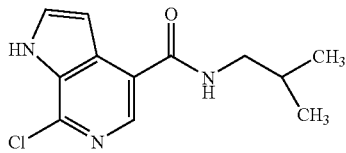

Prepared in a similar manner to Example 19 (e) from 7-chloro-1H-pyrrolo[2,3-c]pyridine-4-carboxylic acid using isobutylamine (28 mg) instead of tetrahydro-pyran-4-ylmethylamine to give the title compound (38 mg).

NMR (d⁶-DMSO) δ 0.92 (6H, d), 1.87 (1H, m), 3.12 (2H, t), 6.91 (1H, d), 7.76 (1H, t), 8.29 (1H, s), 8.50 (1H, t), 12.25 (1H, s).

LC/MS t=2.3 min. [MH⁺] 252 consistent with molecular formula $C_{12}H_{14}{}^{35}ClN_3O$

(b) 7-(3-Chloro-phenylamino)-1H-pyrrolo[2,3-c]pyridine-4-carboxylic acid isobutyl-amide Prepared in a similar manner to Example 19 (f) except that the title compound was isolated by trituration with 5% sodium hydrogen carbonate solution followed by washing with water and diethyl ether to give the title compound (34 mg).

NMR (d⁶-DMSO) δ 0.91 (6H, m), 1.85 (1H, m), 3.11 (2H, t), 7.00 (1H, s), 7.30 (1H, brs), 7.51 (2H, s), 7.88 (2H, s), 8.00 (1H, s), 8.45 (1H, s), 12.20 (1H, brs).

LC/MS t=3.3 min, [MH⁺] 343 consistent with molecular formula $C_{18}H_{19}ClN_4O$

EXAMPLE 22

3-Methyl-7-morpholin-4-yl-1H-pyrrolo[2,3-c]pyridine-4-carboxylic acid (tetrahydro-pyran-4-yl)-amide hydrochloride salt

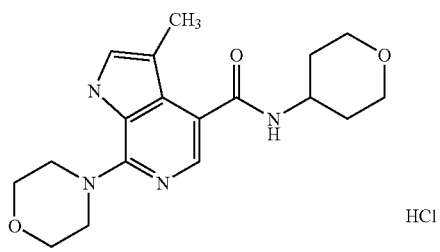

Prepared in a similar manner to Example 11 (c) from 7-chloro-3-methyl-4-(tetrahydro-pyran-4-ylcarbamoyl)-pyrrolo[2,3-c]pyridine-1-carboxylic acid tert-butyl ester and morpholine (71 mg) except that the hydrochloride salt was formed using methanol instead of dichloromethane as solvent to give the title compound (40 mg).

NMR (d⁶-DMSO) 1.48-1.57 (2H, m), 1.81 (2H, d), 2.20 (3H, s), 3.40-3.51 (6H, m), 3.81-3.88 (6H, m), 4.00 (1H, m), 7.55 (1H, s), 7.67 (1H, s), 8.45 (1H, s), 11.80 (1H, brs), 13.40 (1H, brs).

LC/MS t=1.5 min, [MH⁺] 345 consistent with molecular formula $C_{12}H_{24}N_4O_3$

EXAMPLE 23

3-Methyl-7-morpholin-4-yl-1H-pyrrolo[2,3-c]pyridine-4-carboxylic acid (tetrahydro-pyran-4-ylmethyl)-amide hydrochloride salt

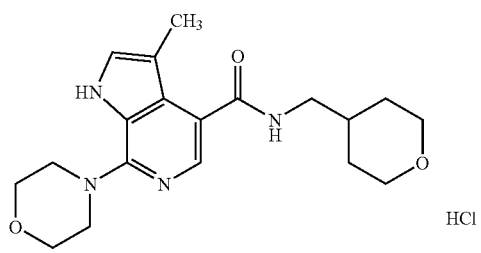

Prepared in a similar manner to Example 11 (c) from 7-chloro-3-methyl-4-[(tetrahydro-pyran-4-ylmethyl)-carbamoyl)]-pyrrolo[2,3-c]pyridine-1-carboxylic acid tert-butyl ester and morphine (68 mg) to give the title compound (33 mg).

NMR (d⁶-DMSO) δ 1.23 (2H, m), 1.62 (2H, d), 1.79 (1H, m), 2.19 (3H, s), 3.17 (2H, t), 3.27 (2H, t), 3.66 (4H, brs), 3.82-3.87 (6H, m), 7.63 (1H, s), 7.71 (1H, brs), 8.64 (1H, brs), 12.30 (1H, brs), 13.50 (1H, brs).

LC/MS t=1.6 min, [MH⁺] 359 consistent with molecular formula $C_{19}H_{26}N_4O_3$

EXAMPLE 24

1-[4-(3-Chloro-phenylamino)-1-methyl-1H-pyrrolo[3,2-c]pyridin-7-yl]-1-morpholin-4-yl-methanone hydrochloride

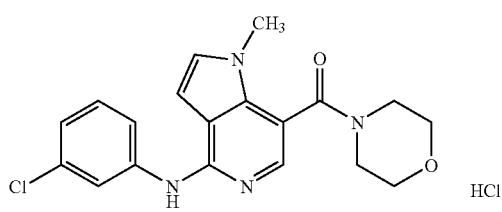

a) 4,7-Dibromo-1H-pyrrolo[3,2-c]pyridine

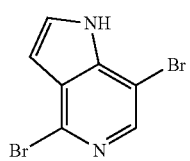

Vinyl magnesium bromide (44 ml, 1M in THF) was added to dry THF (40 ml) and the solution was cooled to 0° C. under an atmosphere of nitrogen. A solution of 2,5-dibromo-4-nitropyridine (prepared by the method of: Lee, Bang-Lin; Yamamoto, Takakazu, *Macromolecules* (1999), 32(5) 1375-1382.) (3.53 g) in THF (80 ml) was added dropwise over 40 mins at 0° C. The mixture was stirred at room temperature for 1 hr then cooled to 0° C. and a saturated solution of ammonium chloride (60 ml) was added. The mixture was stirred at room temperature for 15 min then added to a mixture of ethyl acetate (200 ml) and water (200 ml). The organic layer washed with water and evaporated. The residue was dissolved in a mixture of methanol (20 ml) and conc hydrochloric acid (0.5 ml). After standing at room temp for 30 mins the solution was evaporated and the residue added to ethyl acetate (50 ml) and water (50 ml) and made basic with sodium hydroxide. The organic layer washed with water (2×50 ml) then brine, dried (MgSO$_4$) and evaporated. The residue was triturated with ether (20 ml) to give a solid which was filtered off. The filtrate was evaporated and triturated with ether to afford a second crop which on combination with the above gave the title compound (0.97 g). The filtrate was evaporated and dissolved in DCM and purified with Biotage chromatography eluting with DCM/Et$_2$O 20:1 and evaporated to give white solid (0.38 g)

NMR (DMSO-d$_6$) δ 6.60 (1H, d), 7.66 (1H, d), 8.13 (1H, s), 12.3 (1H, s).

b) 4,7-Dibromo-1-methyl-1H-pyrrolo[3,2-c]pyridine

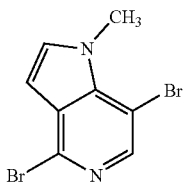

A mixture of 4,7-dibromo-1H-pyrrolo[3,2-c]pyridine (1.35 g), iodomethane (609 ul) and anhydrous potassium carbonate (1.35 g) in dry acetone (90 ml) was refluxed overnight. The mixture was evaporated and the residue added to ethyl acetate (60 ml) and water (60 ml). The organic layer was washed with water then brine, dried (MgSO$_4$) and evaporated. Purification of the residue by chromatography on silica gel, eluting with dichloromethane, gave the title compound (0.99 g)

NMR (DMSO-d$_6$) δ 4.13 (3H, s), 6.54 (1H, d), 7.64 (1H, d), 8.10 (1H, s).

c) (7-Bromo-1-methyl-1H-pyrrolo[3,2-c]pyridin-4-yl)-(3-chloro-phenyl)-amine

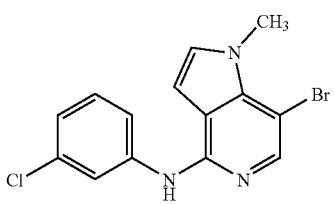

A mixture of 4,7-dibromo-1-methyl-1H-pyrrolo[3,2-c]pyridine (290 mg), 3-chloroaniline (153 mg), cesium carbonate (652 mg), tris(dibenzylidineacetone)dipalladium(0) (10 mg) and 4,5-bis(diphenylphosphino)-9,9-dimethylxanthene (6 mg) in dioxan (5 ml) was heated at reflux under nitrogen overnight. A further addition of tris(dibenzylidineacetone)dipalladium(0) (10 mg) and 4,5-bis(diphenylphosphino)-9,9-dimethylxanthene (6 mg) was made and the mixture refluxed for 4 hrs, then a repeat addition made and reflux continued for 2 hrs. The mixture was diluted with ethyl acetate (5 ml), filtered through Celite using ethylacetate and evaporate. The residue was dissolved in ethyl acetate and passed through silica gel eluting with ethyl acetate and evaporated. Purification of the residue by chromatography on Biotage, eluting with isohexane/dichloromethane 1:1, and evaporation gave the title compound (199 mg)

NMR (DMSO-d$_6$) δ 4.08 (3H, s), 6.94 (1H, d of d), 6.98 (1H, d), 7.30 (1H, t), 7.34 (1H, d), 7.77 (1H, d of d), 7.89 (1H, s), 8.13 (1H, t), 8.99 (1H, s).

d) 4-(3-Chloro-phenylamino)-1-methyl-1H-pyrrolo[3,2-c]pyridin-7-carboxylic acid

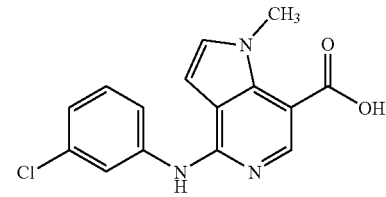

(7-Bromo-1-methyl-1H-pyrrolo[3,2-c]pyridin-4-yl)-(3-chloro-phenyl)-amine (96 mg) was dissolved in dry THF (5 ml) and the solution was cooled to ca −70° C. in a dry ice/acetone bath under an atmosphere of nitrogen. n-Butyl-lithium (450 µl, 1.6 Molar in hexanes) was added over 1 min and then carbon dioxide was bubbled through the mixture for 5 mins. The mixture was stirred at ca −70° C. for 10 mins, then allowed to warm to room temperature over 1 hr. The solvent was evaporated and the residue was added to ethyl acetate (10 ml) and water (10 ml) and the layers were separated. The aqueous layer was washed with ethyl acetate, (10 ml) then acidified to ca pH5.5 with hydrochloric acid. It was extracted with ethyl acetate (2×10 ml), the extracts were dried over MgSO$_4$ and evaporated to give the title compound as a gum (23 mg).

NMR (DMSO-d$_6$) δ 3.94 (3H, s), 7.01 (2H, m), 7.30 (2H, m), 7.83 (1H, m), 8.17 (1H, s), 8.34 (1H, s), 9.20 (1H, s), 12.6 (1H, br s).

e) 1-[4-(3-Chloro-phenylamino)-1-methyl-1H-pyrrolo[3,2-c]pyridin-7-yl]-1-morpholin-4-yl-methanone hydrochloride A mixture of 4-(3-chloro-phenylamino)-1H-methyl-1H-pyrrolo[3,2-c]pyridin-7-carboxylic acid (29 mg), morpholine (36 ul), 1-(3-dimethylamino-propyl)-3-ethylcarbodiimide hydrochloride (76 mg), 1-hydroxybenzotriazole hydrate (54 mg) and N,N-diisopropylethylamine (140 ul) in dimethylformamide (2 ml) was stirred overnight then added to a mixture of ethyl acetate (20 ml) water (20 ml) and saturated sodium bicarbonate (10 ml). The layers were separated and the organic layer washed with water 3 times, brine, dried (MgSO$_4$) and evaporated to give a gum. Purified on MDAP and the product split into two fractions. The first fraction was evaporated, dissolved in ethyl acetate and washed as above, dried and evaporate to give a solid. This was triturated with ether and purified by MDAP and chromatography on silica gel, eluting with dichloromethane/methanol, 20:1, to give the free base which was taken up in DCM treated with ethereal HCl, evaporated and triturated with ether to give the title compound as a solid (11 mg)

NMR (DMSO-d$_6$) δ 3.4-3.9 (1H, m), 7.21 (1H, d), 7.38 (1H, br s), 7.5-7.6 (3H, m), 7.64 (1H, s), 7.75 (1H, br s), 7.89 (1H, s), 10.9 (1H, br s), 13.0 (1H, br s).

LC/MS t=2.14 min, Molecular ion observed (MH+)=371 consistent with the molecular formula C$_{19}$H$_{19}$$^{35}$ClN$_4$O$_2$ Route 2: 1-[4-(3-Chloro-phenylamino)-1-methyl-1H-pyrrolo[3,2-c]pyridin-7-yl]-1-morpholin-4-yl-methanone hydrochloride a)
2-(Carboxymethyl)-1-methyl-1H-pyrrole-3-carboxylic acid

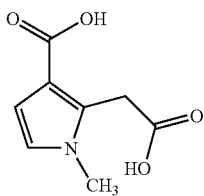

A solution of methylamine (40% wt in water, 496 ml) in water (200 ml) was cooled to 10° C. and 1,3-acetone dicarboxylic acid (90 g) was added portion-wise maintaining the temperature below 15° C. After complete addition the reaction was cooled to 10° C. before the drop-wise addition of chloroacetaldehyde (50% in water, 135 ml), maintaining the reaction temperature below 18° C. The reaction was then allowed to warm to room temperature and stirred for 17 hours. The solution was cooled and acidified with 5N hydrochloric acid (500 ml), followed by concentrated hydrochloric acid until the solution reached pH1. The suspension was filtered. The solid was then heated to reflux in glacial acetic acid (400 ml), stirred for ten minutes and allowed to cool to room temperature, before the suspension was filtered and the solid washed with a minimum of acetic acid. The solid was dried in vacuo to yield the crude title compound (63.7 g).

$^1$H-NMR (400 MHz, DMSO) δ 3.53 (3H, s), 4.02 (2H, s), 6.32 (1H, d), 6.70 (1H, d), 12.03 (2H, s, broad).

The filtrate was reduced in vacuo by about ½ and re-filtered. The solid collected was dried in vacuo to yield the crude title compound (7.55 g).

b) Methyl 1-methyl-2-[2-(methyloxy)-2-oxoethyl]-1H-pyrrole-3-carboxylate

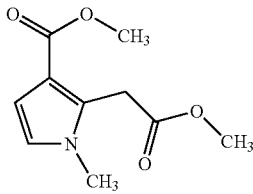

A solution of 2-(carboxymethyl)-1-methyl-1H-pyrrole-3-carboxylic acid (63.7 g), and p-toluenesulfonic acid (33.09 g) in anhydrous methanol (600 ml) was heated at reflux for 44 hours. After cooling the solvent was removed in vacuo. The residue was dissolved in ethyl acetate (600 ml) and washed with saturated sodium bicarbonate (2×250 ml). The aqueous layers were combined and extracted with ethyl acetate (250 ml). The organic layers were combined, dried (MgSO$_4$) and the solvent removed to yield the title compound as a light brown solid (65.6 g).

LC/MS [MH$^+$] 212 consistent with molecular formula C$_{10}$H$_{13}$NO$_4$.

A further 5.84 g of title compound was prepared as above (refluxing for 35 hours) using 7.55 g of starting material A further batch of title compound (40.4 g starting material) was prepared as above refluxing for 2 days. After cooling the mixture was evaporated in vacuo, treated with aqueous sodium bicarbonate (400 ml) and extracted with ethyl acetate (5×200 ml). The combined dried (Na$_2$SO$_4$) organics were extracted to give white crystals. 2.4 g of this was used further. The 2-(carboxymethyl)-1-methyl-1H-pyrrole-3-carboxylic acid starting material was prepared as for (a) however the initial addition of 1,3-acetone dicarboxylic acid was carried out under argon at 10 to 15° C. The chloroacetaldehyde was added whilst the temperature was kept below 10° C. and stirring was continued for 15 hours. When the precipitate was filtered off it was dried in vacuo at 60° C. for 2 hours. The reflux with hot acetic acid took place for 20 mins then cooled. The solid was filtered off.

c) Methyl 2-{2-hydroxy-1-[(methyloxy)carbonyl]ethenyl}-1-methyl-1H-pyrrole-3-carboxylate

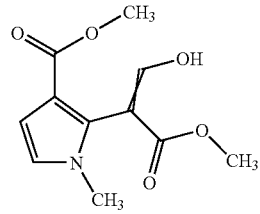

The starting material for this reaction step (37.9 g and 35.5 g) was obtained from three preparations of methyl 1-methyl-2-[2-(methyloxy)-2-oxoethyl]-1H-pyrrole-3-carboxylate.

To a suspension of methyl 1-methyl-2-[2-(methyloxy)-2-oxoethyl]-1H-pyrrole-3-carboxylate (37.9 g) in THF (anhydrous, 300 ml), under argon, was added sodium hydride (60% dispersion in mineral oil, 37.9 g) portion-wise. After complete addition the reaction was stirred at 22° C. for 15 minutes before the drop-wise addition of methyl formate (16.6 ml). The reaction was stirred at 118° C. for 50 minutes. During this period the temperature increased to around 21.5° C. before a rapid rise in temperature with gas evolution. Cooling (solid carbon dioxide) was applied to the outside of the flask. The temperature reached a maximum of 30° C. before dropping to 20° C. The coolant was removed and the reaction stirred for a further 17 hours. The reaction mixture was cooled by an ice/water bath before the cautious addition of methanol (100 ml). The reaction mixture was then combined with the product of another second mixture prepared in a similar manner (starting weight of methyl 1-methyl-2-[2-(methyloxy)-2-oxoethyl]-1H-pyrrole-3-carboxylate was 35.5 g). The solution was concentrated in vacuo. The residue was treated with saturated ammonium chloride solution (600 ml) then acidified to pH1 by the cautious addition concentrated hydrochloric acid. Ice was added to cool the solution and it was then extracted with ethyl acetate (3×400 ml). The combined organics were dried (MgSO$_4$) and the solvent removed to yield a black oily solid. Oil was decanted and the residue triturated with hexane (2×200 ml), diethyl ether (200 ml) and hexane (200 ml). This yielded the title compound as a brown solid (65.2 g).

LC/MS [MH⁻] 1238 consistent with molecular formula C₁₁H₁₃NO₅.

d) Methyl 2-{(Z)-2-amino-1-[(methyloxy)carbonyl]ethenyl}-1-methyl-1H-pyrrole-3-carboxylate

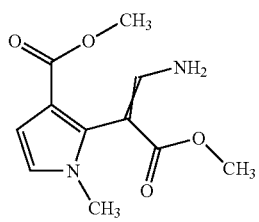

A solution of methyl 2-{2-hydroxy-1-[(methyloxy)carbonyl]ethenyl}-1-methyl-1H-pyrrole-3-carboxylate (65.2 g) and ammonium acetate (105 g) in methanol (800 ml) was heated at reflux for 7 hours. The reaction was cooled and the methanol removed. The residue was partitioned between ethyl acetate and water. Large amounts (>2 L) of ethyl acetate were used to dissolve the residue. The organic solution washed with water, dried (MgSO₄) and the solvent removed to yield the title compound as a brown solid (58.4 g).

LC/MS [MH⁺] 239 consistent molecular formula C₁₁H₁₄N₂O₄.

e) Methyl 1-methyl-4-oxo-4,5-dihydro-1H-pyrrolo[3,2-c]pyridine-7-carboxylate

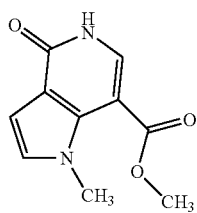

A mixture of methyl 2-{2-amino-1-[(methyloxy)carbonyl]ethenyl}-1-methyl-1H-pyrrole-3-carboxylate (2 g) and sodium t-butoxide (160 mg) in dimethylformamide (18 ml) was irradiated within a microwave reactor at 160° C. for 20 minutes. The reaction was repeated 28 times. The reaction mixtures were combined (56.4 g) and after cooling a precipitate formed which was filtered, washed with water and dried in vacuo to yield the title compound (17.1 g).

¹H-NMR (400 MHz, DMSO) δ 3.82 (3H, s), 3.86 (3H, s), 6.57 (1H, d), 7.12 (1H d), 7.68 (1H, d), 11.41 (1H, s, broad).

The filtrate was reduced in vacuo and the residue triturated with water (100 ml) and 2N HCL (150 ml). The solid was filtered, washed with water and diethyl ether to yield a brown solid (18.38 g). This was stirred in diethyl ether (100 ml) for 15 minutes and re-filtered and dried in vacuo to yield the title compound (16.29 g). Total yield 33.39 g.

Further batches were prepared in a similar way and used in the next step.

f) Methyl 4-chloro-1-methyl-1H-pyrrolo[3,2-c]pyridine-7-carboxylate

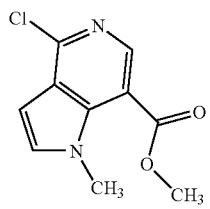

A suspension of methyl 1-methyl-4-oxo-4,5-dihydro-1H-pyrrolo[3,2-c]pyridine-7-carboxylate (47.4 g) in phosphorus oxychloride (64.4 ml) was heated to reflux and stirred for 50 minutes then allowed to cool. The phosphorus oxychloride was removed in vacuo and the residue partitioned between dichloromethane (600 ml) and saturated sodium carbonate (600 ml). The aqueous layer was separated and further extracted with dichloromethane (600 ml). The organic layers were combined, dried (MgSO₄) and the solvent removed. The residue was purified by column chromatography on a Biotage silica column (800 g) eluting with dichloromethane to yield the title compound as a white solid (42.7 g).

¹H-NMR (400 MHz, DMSO) δ 3.91 (3H, s), 3.93 (3H, s), 6.72 (1H, d), 7.65 (1H, d), 8.39 (1H, s).

g) 4-[(3-Chlorophenyl)amino]-1-methyl-1H-pyrrolo[3,2-c]pyridine-7-carboxylic acid

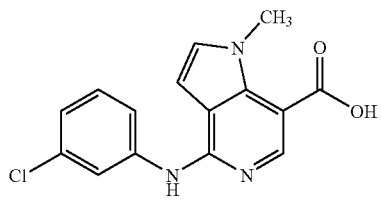

To a suspension of methyl 4-chloro-1-methyl-1H-pyrrolo[3,2-c]pyridine-7-carboxylate (23.1 g) in 1,4-dioxane (300 ml) was added 3-chloroaniline (27 ml). The reaction was heated at 110° C. for 17 hours during which time a solution was rapidly formed upon heating followed by the precipitation of a solid. The reaction was allowed to cool and then partitioned between dichloromethane (700 ml) and saturated sodium carbonate (500 ml). The aqueous layer was separated and further extracted with dichloromethane (300 ml). The organic extracts were combined and dried (MgSO₄). This was then combined with another dichloromethane extract of a reaction conducted as above (weight of methyl 4-chloro-1-methyl-1H-pyrrolo[3,2-c]pyridine-7-carboxylate is 22.9 g). The solvent was removed to yield an orange/brown solid. This was heated in methanol (650 ml) and 2N sodium hydroxide (350 ml) to 80° C. and stirred for 3 hours. The reaction was cooled and then reduced in vacuo. The residue was stirred with diethyl ether (400 ml) for 15 minutes. The orange liquid was decanted and the solid residue triturated with diethyl ether (400 ml). The solid was filtered then added to water (400 ml). The solution was altered in pH to around 7 with 5N hydrochloric acid. The precipitate was filtered, however was in the form of a sticky gum. All material was transferred into a flask with methanol (>1 L in total). The solution was reduced in vacuo. A precipitate formed after the majority of the methanol had been removed. This was filtered and dried in vacuo to yield the title compound (60.23 g).

$^1$H-NMR (400 MHz, DMSO) δ 3.97 (3H, s), 7.02-7.09 (2H, m), 7.32-7.40 (2H, m), 7.80 (1H, d), 8.11 (1H, s), 8.31 (1H, s), 9.42 (1H, s, broad), 12.79 (1H, s, broad).

h) N-(3-Chlorophenyl)-1-methyl-7-(4-morpholinyl-carbonyl)-1H-pyrrolo[3,2-c]pyridin-4-amine

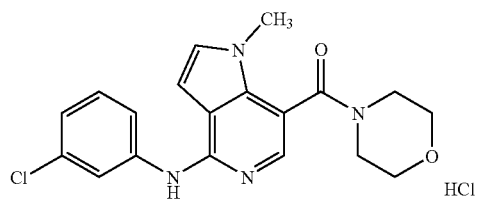

A solution of 4-[(3-chlorophenyl)amino]-1-methyl-1H-pyrrolo[3,2-c]pyridine-7-carboxylic acid (25.0 g) in dry dimethylformamide (300 ml), was treated with 1-hydroxybenzotriazole (14.00 g), N-ethylmorpholine (42 ml), 1-ethyl-3-(3-dimethylaminopropyl)carbodiimide hydrochloride (19.03 g) and morpholine (14.4 ml) at 23° C. under argon with stirring. After 24 h, the solution was evaporated in vacuo and treated with aqueous saturated sodium carbonate (200 ml) and water (300 ml). The mixture was extracted with ethyl acetate (5×200 ml), and the combined, dried (Na$_2$SO$_4$) organic extracts were evaporated in vacuo. The residue was purified by column chromatography on a Biotage silica column (800 g) eluting with ethyl acetate-hexane (1:1 to 7:3) to give the free base of the title compound (26.9 g). A portion of the free base (21.9 g) in methanol (250 ml) was treated with 1.0M hydrochloric acid in diethyl ether to pH1 and then evaporated in vacuo. Trituration of the residue with ether followed by filtration yielded the title compound (22.75 g).

LC/MS [MH$^+$] 371 consistent with molecular formula $C_{19}H_{19}{}^{35}ClN_4O_2$.

$^1$H-NMR (400 MHz, MeOD) δ 3.49-3.59 (2H, m), 3.59-3.74 (2H, m), 3.73-3.92 (7H, m), 7.1 (1H, d), 7.40-7.60 (6H, m).

Conditions, Hardware and Software Used for Mass Directed Auto-Purification Systems Used in Examples 24 Route 2, 25 to 246

Hardware
Waters 2525 Binary Gradient Module, Waters 515 Makeup Pump, Waters Pump Control Module Waters 2767 Inject Collect, Waters Column Fluidics Manager, Waters 2996 Photodiode Array Detector, Waters ZQ Mass Spectrometer, Gilson 202 fraction collector, Gilson Aspec waste collector Software
Waters Masslynx version 4

Column
The columns used are Waters Atlantis, the dimensions of which are 19 mm×100 mm (small scale) and 30 mm×100 mm (large scale). The stationary phase particle size is 5 μm.

Solvents
A: Aqueous solvent=Water+0.1% Formic Acid
B: Organic solvent=Acetonitrile+0.1% Formic Acid
Make up solvent=Methanol:Water 80:20
Needle rinse solvent=Methanol Methods
There are four methods used depending on the analytical retention time of the compound of interest. They all have a 13.5-minute runtime, which comprises of a 10-minute gradient followed by a 13.5 minute column flush and re-equilibration step.
Large/Small Scale 1.0-1.6=0-20% B
Large/Small Scale 1.5-2.1=15-55% B
Large/Small Scale 2.0-2.7=30-85% B
Large/Small Scale 2.6-4.0=50-99% B Flow Rate
All of the above methods have a flow rate of either 20 mls/min (Small Scale) or 40 mls/min (Large Scale)

LCMS for Examples 24 Route 2, 25 to 246 were run on one of the following systems, MS3-2, MS3-1, MS2-2, MS2-1, MS1-3, MS1-2 or MS1-1.

Hardware

MS3-2
Agilent 1100 Gradient Pump, Agilent 1100 Autosampler, Agilent 1100 DAD Detector, Agilent 1100 Degasser, Agilent 1100 Oven, Agilent 1100 Controller, Agilent 1100 ALSTherm, Waters ZQ Mass Spectrometer, Sedere Sedex 85

MS3-1
Waters Alliance 2795, Waters 2996 Photodiode Array Detector, Waters ZQ Mass Spectrometer Sedere Sedex 75

MS2-2
Agilent 1100 Gradient Pump, Agilent 1100 DAD Detector, Agilent 1100 Degasser, Agilent 1100 Oven, Agilent 1100 Controller, Waters ZQ Mass Spectrometer, Waters 2777 Sample Manager Sedere Sedex 75

MS2-1
Agilent 1100 Gradient Pump, Agilent 1100 DAD Detector, Agilent 1100 Degasser, Agilent 1100 Oven, Agilent 1100 Controller, Waters ZMD Mass Spectrometer, Gilson 402 Syringe Pump, Gilson 233XL Sample Rack, Sedere Sedex 75

MS1-3
Waters Alliance 2795, Waters 996 Photodiode Array Detector, Waters ZQ Mass Spectrometer Sedere Sedex 75

MS1-2
Agilent 1100 Gradient Pump, Agilent 1100 DAD Detector, Agilent 1100 Degasser, Agilent 1100 Oven, Agilent 1100 Controller, Waters ZMD Mass Spectrometer, Gilson 402 Syringe Pump Gilson 233XL Sample Rack, Sedere Sedex 75

MS1-1
Waters Alliance 2795, Waters 996 Photodiode Array Detector, Waters ZQ Mass Spectrometer Sedere Sedex 75

The software, column and solvent system used on the above systems were the same and was recorded below.

Software
Waters Masslynx versions 4.0

Column
The column used is a Waters Atlantis, the dimensions of which are 4.6 mm×50 mm. The stationary phase particle size is 3 μm.

Solvents
A: Aqueous solvent=Water+0.05% Formic Acid
B: Organic solvent=Acetonitrile+0.05% Formic Acid Method
The generic method used has a 4 minute runtime, which comprises of a 3-minute gradient (0-100% B) followed by a 1 minute column flush.

Flow Rate
The above method has a flow rate of 1.5 ml/mins

EXAMPLE 25a AND 25b

1-[7-(3-Chloro-phenylamino)-3-methyl-1H-pyrrolo[2,3-c]pyridin-4-yl]-1-piperidin-1-yl-methanone and its hydrochloride salt

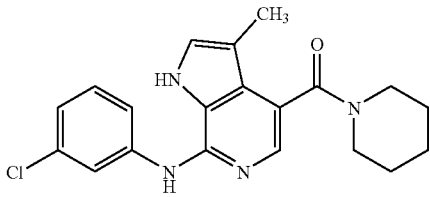

i) 7-Chloro-3-methyl-4-(1-piperidin-1-yl-methanoyl)-pyrrolo[2,3-c]pyridine-1-carboxylic acid tert-butyl ester

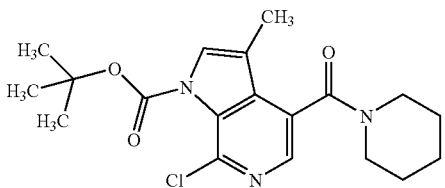

Prepared in a similar manner to Example 11 (b) from Example 11 (a) using piperidine (19 ul) instead of morpholine to give the title compound as a white foam (366 mg).

NMR (d$^6$-DMSO) δ 1.36-1.45 (6H, m), 1.61 (9H, s), 2.12 (3H, s), 3.15 (2H, m), 3.56 (1H, m), 3.75 (1H, m), 7.84 (1H, s), 8.08 (1H, s).

LC/MS [MH$^+$] 378 consistent with molecular formula $C_{19}H_{24}{}^{35}ClN_3O_3$ (a) 1-[7-(3-Chloro-phenylamino)-3-methyl-1H-pyrrolo[2,3-c]pyridin-4-yl]-1-piperidin-1-yl-methanone Prepared in a similar manner to Example 4(d) from 7-chloro-3-methyl-4-(1-piperidin-1-yl-methanoyl)-pyrrolo[2,3-c]pyridine-1-carboxylic acid tert-butyl ester (90 mg) and using 3-chloroaniline (50 ul) instead of 3-bromoaniline and heating for 15 rather than 30 minutes. Isolated by MDAP rather than trituration with diethyl ether to give the title compound (67 mg).

NMR (d$^6$-DMSO) δ 1.38 (2H, brs), 1.60 (4H, brs), 2.13 (3H, s), 3.22 (1H,brs), 3.67 (2H, brd), 4.05 (1H, brs), 6.95 (1H, m), 7.34 (2H, m), 7.60 (2H, m), 8.20 (1H, m) 8.97 (1H, s), 11.1 (1H, s).

LC/MS [MH$^+$] 369 consistent with molecular formula $C_{20}H_{21}{}^{35}ClN_4O$ b) 1-[7-(3-Chloro-phenylamino)-3-methyl-1H-pyrrolo[2,3-c]pyridin-4-yl]-1-piperidin-1-yl-methanone hydrochloride salt 1-[7-(3-Chloro-phenylamino)-3-methyl-1H-pyrrolo[2,3-c]pyridin-4-yl]-1-piperidin-1-yl-methanone (60 mg) was suspended in warm ethyl acetate (10 ml) and treated with a solution of 1M hydrochloric acid in diethyl ether (10 drops). The mixture was evaporated and dried at 40° C. under vacuum to afford the title compound (56 mg).

NMR (d$^6$-DMSO) δ 1.41 (2H, brs), 1.61 (4H, brs), 2.15 (3H, s), 3.26 (2H,brs), 3.67 (2H, brs), 7.36 (1H, d), 7.40 (1H, s), 7.52 (2H, m), 7.73 (2H, d), 11.1 (1H, s), 12.68 (1H, s).

LC/MS [MH$^+$] 369 consistent with molecular formula $C_{20}H_{21}{}^{35}ClN_4O$

EXAMPLE 26

1-[7-(3-Fluoro-phenylamino)-3-methyl-1H-pyrrolo[2,3-c]pyridin-4-yl]-1-piperidin-1-yl-methanone hydrochloride salt

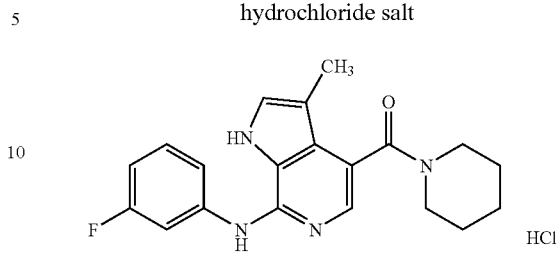

Prepared in a similar manner to Example 4(d) from 7-chloro-3-methyl-4-(1-piperidin-1-yl-methanoyl)-pyrrolo[2,3-c]pyridine-1-carboxylic acid tert-butyl ester (90 mg) and using 3-fluoroaniline (46 ul) instead of 3-bromoaniline and heating for 15 rather than 30 minutes. Isolated by MDAP rather than trituration with diethyl ether and then dissolved in diethyl ether (10 ml) and treated with a solution of 1M hydrochloric acid in diethyl ether (10 drops). The mixture was evaporated and dried at 40° C. under vacuum to afford the title compound (17 mg).

NMR (d$^6$-DMSO) δ 1.39 (2H, brs), 1.60 (4H, brs), 2.14 (3H, s), 3.24 (2H,brs), 3.66 (2H, brd), 6.95 (1H, s), 7.41 (2H, m), 7.50 (1H, s), 7.55 (1H, s), 7.82 (1H, brs), 10.0 (1H, brs), 11.85 (1H, brs).

LC/MS [MH$^+$] 353 consistent with molecular formula $C_{20}H_{21}FN_4O$

EXAMPLE 27a AND 27b

1-[7-(3-Methoxy-phenylamino)-3-methyl-1H-pyrrolo[2,3-c]pyridin-4-yl]-1-piperidin-1-yl-methanone and its hydrochloride salt

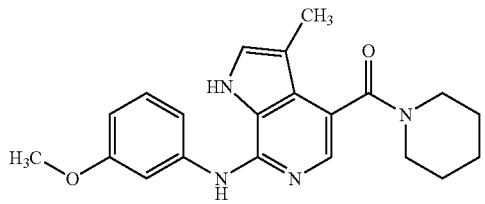

a) Prepared in a similar manner to Example 4(d) from 7-chloro-3-methyl-4-(1-piperidin-1-yl-methanoyl)-pyrrolo[2,3-c]pyridine-1-carboxylic acid tert-butyl ester (90 mg) and using 3-methoxyaniline (54 ul) instead of 3-bromoaniline and heating for 15 rather than 30 minutes. Isolated by MDAP rather than trituration with diethyl ether to give 1-[7-(3-methoxy-phenylamino)-3-methyl-1H-pyrrolo[2,3-c]pyridin-4-yl]-1-piperidin-1-yl-methanone (65 mg).

NMR (d$^6$-DMSO) δ 1.37 (2H, brs), 1.60 (4H, brs), 2.12 (3H, s), 3.23 (2H,brs), 3.61 (2H, brd), 3.76 (3H, s), 6.52 (1H, dd), 7.20 (1H, t), 7.36 (2H, d), 7.55 (1H, s), 7.62 (1H, t), 8.72 (1H, s), 11.1 (1H, s).

LC/MS [MH$^+$] 365 consistent with molecular formula $C_{21}H_{24}N_4O_2$ b) 1-[7-(3-Methoxy-phenylamino)-3-methyl-1H-pyrrolo[2,3-c]pyridin-4-yl]-1-piperidin-1-yl-methanone hydrochloride salt 1-[7-(3-Methoxy-phenylamino)-3-methyl-1H-pyrrolo[2,3-c]pyridin-4-yl]-1-piperidin-1-yl-methanone (50 mg) was suspended in warm ethyl acetate (10 ml) and treated with a solution of 1M hydrochloric acid in diethyl ether (10 drops). The mixture was evaporated and dried at 40° C. under vacuum to afford the title compound (47 mg).

NMR (d⁶-DMSO) δ 1.39 (2H, brs), 1.61 (4H, brs), 2.15 (3H, s), 3.26 (2H,brs), 3.66 (2H, brs), 3.76 (3H, s), 6.87 (1H, d), 7.12 (1H, d), 7.22 (1H, s), 7.35 (1H, s), 7.39 (1H,t), 7.69 (1H, s), 10.75 (1H, s), 12.50 (1H, s).

LC/MS [MH$^+$] 365 consistent with molecular formula $C_{21}H_{24}N_4O_2$

EXAMPLE 28

1-[7-(3-Cyano-phenylamino)-3-methyl-1H-pyrrolo[2,3-c]pyridin-4-yl]-1-piperidin-1-yl-methanone hydrochloride salt

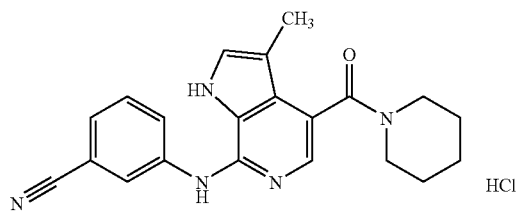

Prepared in a similar manner to Example 4(d) from 7-chloro-3-methyl-4-(1-piperidin-1-yl-methanoyl)-pyrrolo[2,3-c]pyridine-1-carboxylic acid tert-butyl ester (90 mg) and using 3-cyanoaniline (56 mg) instead of 3-bromoaniline and heating for 15 rather than 30 minutes. Isolated by MDAP rather than trituration with diethyl ether and then suspended in ethyl acetate (10 ml) and treated with a solution of 1M hydrochloric acid in diethyl ether (10 drops). The mixture was evaporated and dried at 40° C. under vacuum to afford the title compound (25 mg).

NMR (d⁶-DMSO) δ 1.39 (2H, brs), 1.60 (4H, brs), 2.15 (3H, s), 3.24 (2H,brs), 3.66 (2H, brd), 7.53-7.62 (4H, m), 7.91 (1H, d), 8.33 (1H, s), 10.0 (1H, brs), 11.90 (1H, brs).

LC/MS [MH$^+$] 359 consistent with molecular formula $C_{21}H_{21}N_5O$

EXAMPLE 29a AND 29b

1-[7-(3-Chloro-phenylamino)-3-methyl-1H-pyrrolo[2,3-c]pyridin-4-yl]-1-(1,1-dioxo-1l⁶-thiomorpholin-4-yl)-methanone and its hydrochloride salt

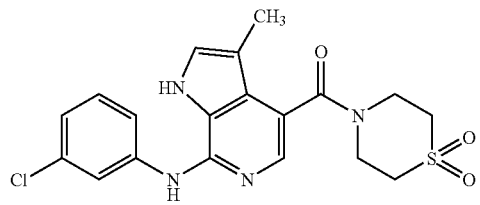

i) 7-(3-Chloro-phenylamino)-3-methyl-1H-pyrrolo[2,3-c]pyridine-4-carboxylic acid

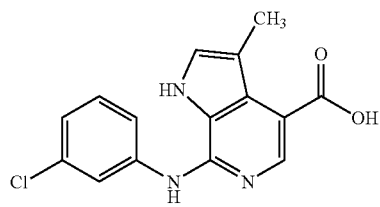

A mixture of 7-chloro-3-methyl-pyrrolo[2,3-c]pyridine-1,4-dicarboxylic acid 1-tert-butyl ester (200 mg) and 3-chloroaniline (0.68 ml) in 1,4-dioxane (3 ml) was heated at 110° C. for 16 hours. The reaction mixture was diluted with EtOAc and basified with 1M NaOH, the aqueous layer was extracted and acidified to pH1 using 1M HCl to afford a precipitate. The precipitate was filtered off and washed with water until neutral. The solid was then sucked dry and dried over sodium hydroxide at 50° C. under vacuum to afford the title compound (197 mg).

NMR (d⁶-DMSO) δ 2.38 (3H, s), 7.02 (1H, d), 7.37 (1H, t), 7.43 (1H, s), 7.44 (1H, d), 8.19 (1H, s), 8.32 (1H, s), 9.18 (1H, s), 11.30 (1H, brs), 12.33 (1H, brs).

LC/MS [MH$^+$] 1302 consistent with molecular formula $C_{15}H_{12}{}^{35}ClN_3O_2$. (a) 1-[7-(3-Chloro-phenylamino)-3-methyl-1H-pyrrolo[2,3-c]pyridin-4-yl]-1-(1,1-dioxo-1l⁶-thiomorpholin-4-yl)-methanone To a solution of 7-(3-chloro-phenylamino)-3-methyl-1H-pyrrolo[2,3-c]pyridine-4-carboxylic acid (150 mg) in dimethylformamide (4 ml) was added 4-ethylmorpholine (253 μl), thiomorpholine 1,1-dioxide hydrochloride (90.mg), 1-hydroxybenzotriazole hydrate (105 mg) and 1-(3-dimethylaminopropyl)-3-ethylcarbodiimide hydrochloride (115 mg) and the solution stirred at room temperature overnight. The dimethylformamide was evaporated and the residue dissolved in ethyl acetate (40 ml) and washed with 5% sodium hydrogen carbonate solution (25 ml) and water (25 ml). The organic layer was dried (MgSO$_4$) and evaporated to give an orange oil. The residue was triturated with diethyl ether to give a white solid which was then filtered off, sucked dry then dried at 40° C. under vacuum to afford the title compound (75 mg).

NMR (d⁶-DMSO) δ 2.11 (3H, s), 2.49-2.57 (8H, m), 6.94 (1H, d), 7.31 (1H, t), 7.38 (1H, s), 7.73 (1H, d), 7.82 (1H, s), 8.32 (1H, s), 9.45 (1H, s), 11.65 (1H, brs).

LC/MS [MH$^+$] 419 consistent with molecular formula $C_{19}H_{19}{}^{35}ClN_4O_3S$. b) 1-[7-(3-Chloro-phenylamino)-3-methyl-1H-pyrrolo[2,3-c]pyridin-4-yl]-1-(1,1-dioxo-1l⁶-thiomorpholin-4-yl)-methanone hydrochloride salt A sample of the free base (70 mg) was dissolved in warm ethyl acetate (10 ml) and treated with a solution of 1M hydrochloric acid in diethyl ether (10 drops). The resultant solid precipitate was then filtered onto a sinter, sucked dry then dried at 40° C. under vacuum to afford the title compound (52 mg).

NMR (MeOD) δ 2.24 (3H, s), 2.97-3.93 (8H, m), 7.42-7.71 (6H, m).

LC/MS [MH$^+$] 419 consistent with molecular formula $C_{19}H_{19}{}^{35}ClN_4O_3S$.

EXAMPLE 30a AND 30b 7-(3-Chloro-phenylamino)-3-methyl-1H-pyrrolo[2,3-c]pyridine--4-carboxylic acid cyclobutylmethyl-amide and its hydrochloride salt

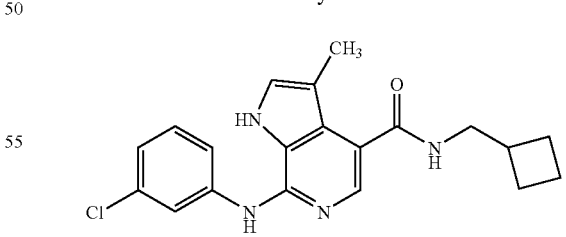

a) Prepared in a similar manner to Example 29 (a) from the compound of Example 29(i) using cyclobutylmethylamine hydrochloride (63.8 mg) instead of thiomorpholine 1,1-dioxide hydrochloride, to afford 7-(3-chloro-phenylamino)-3-methyl-1H-pyrrolo[2,3-c]pyridine-4-carboxylic acid cyclobutylmethyl-amide (69 mg).

NMR (d⁶-DMSO) δ 1.73-1.84 (4H, m), 1.99-2.03 (2H, m), 2.21 (3H, s), 2.50-2.55 (1H, m), 3.29 (2H, t), 6.95 (1H, d), 7.31 (1H, t), 7.34 (1H, s), 7.70 (1H, d), 7.82 (1H, s), 7.85 (1H, t), 8.26 (1H, s), 9.33 (1H, brs), 11.51 (1H, brs).
LC/MS [MH$^+$] 369 consistent with molecular formula $C_{20}H_{21}^{35}ClN_4O$.
b) 7-(3-Chloro-phenylamino)-3-methyl-1H-pyrrolo[2,3-c]pyridine-4-carboxylic acid cyclobutylmethyl-amide hydrochloride salt Prepared in a similar manner to Example 29(b).
NMR (d$^6$-DMSO) δ 1.72-3.54 (12H, m), 7.29-8.51 (9H, m).
LC/MS [MH$^+$] 369 consistent with molecular formula $C_{20}H_{21}^{35}ClN_4O$.

EXAMPLE 31a AND 31b 7-(3-Chloro-phenylamino)-3-methyl-1H-pyrrolo[2,3-c]pyridine-4-carboxylic acid cyclobutylamide and its hydrochloride salt

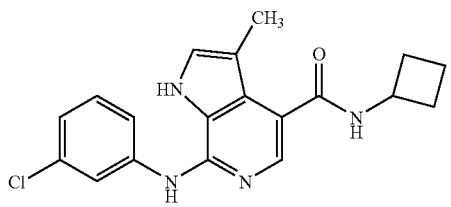

a) Prepared in a similar manner to Example 29(a) from the compound of Example 29(i), using cyclobutylamine (37.3 mg) instead of thiomorpholine 1,1-dioxide hydrochloride and the crude product was purified using Biotage flash 25M with 2% ammonia in methanol:dichloromethane as the elutant, before trituration as example, to afford 7-(3-chloro-phenylamino)-3-methyl-1H-pyrrolo[2,3-c]pyridine-4-carboxylic acid cyclobutylamide (36 mg).
NMR (d$^6$-DMSO) δ 1.66-1.67 (2H, m), 2.01-2.07 (2H, m), 2.21-2.24 (5H, m), 4.42 (1H, m), 6.96 (1H, d), 7.32 (1H, t), 7.37 (1H, s), 7.55 (1H, d), 7.83 (1H, s), 8.24 (1H, s), 8.48 (1H, d), 8.98 (1H, s), 11.11 (1H, s).
LC/MS [MH$^+$] 355 consistent with molecular formula $C_{19}H_{19}^{35}ClN_4O$.

b) 7-(3-Chloro-phenylamino)-3-methyl-1H-pyrrolo[2,3-c]pyridine-4-carboxylic acid cyclobutylamide hydrochloride salt Prepared in a similar manner to Example 29(b).
NMR (d$^6$-DMSO) δ 1.68-2.22 (9H, m), 4.42 (1H, m), 7.47-7.72 (7H, m), 8.79 (1H, s), 12.40 (1H, brs).
LC/MS [MH$^+$] 355 consistent with molecular formula $C_{19}H_{19}^{35}ClN_4O$.

EXAMPLE 32a AND 32b 7-(3-Chloro-phenylamino)-3-methyl-1H-pyrrolo[2,3-c]pyridine-4-carboxylic acid (4-fluoro-phenyl)-amide and its hydrochloride salt

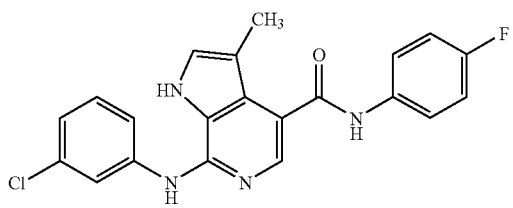

a) Prepared in a similar manner to Example 29(a) using 4-fluoroaniline (58.3 mg) instead of thiomorpholine 1,1-dioxide hydrochloride, to afford the title compound (32 mg).

NMR (MeOH) δ 2.31 (3H, s), 7.01 (1H, d), 7.13 (2H, t), 7.28 (2H, t), 7.49 (1H, d), 7.70-7.72 (2H, m), 7.94 (1H, s), 8.02 (1H, s).
LC/MS [MH$^+$] 395 consistent with molecular formula $C_{21}H_{16}^{35}ClFN_4O$.

b) 7-(3-Chloro-phenylamino)-3-methyl-1H-pyrrolo[2,3-c]pyridine-4-carboxylic acid (4-fluoro-phenyl)-amide hydrochloride salt Prepared in a similar manner to Example 29(b).
NMR (MeOH) δ 2.34 (3H, s), 7.11-7.73 (10H, m).
LC/MS [MH$^+$] 395 consistent with molecular formula $C_{21}H_{16}^{35}ClFN_4O$.

EXAMPLE 33

7-(3-Chloro-phenylamino)-3-methyl-1H-pyrrolo[2,3-c]pyridine-4-carboxylic acid isobutyl-methyl-amide hydrochloride salt

Prepared in a similar manner to Example 1 Method 2(f) from the compound of Example 2(e) using N-methylisobutylamine (45.7 mg) instead of morpholine, to afford the title compound (16 mg).
NMR (d$^6$-DMSO) δ 0.71-3.62 (15H, m), 7.29-7.83 (6H, m), 10.72 (1H, brs), 12.28 (1H, brs).
LC/MS [MH$^+$] 371 consistent with molecular formula $C_{20}H_{23}^{35}ClN_4O$.

EXAMPLE 34

1-Azepan-1-yl-1-[7-(3-chloro-phenylamino)-3-methyl-H-pyrrolo[2,3-c]pyridin-4-yl]-methanone hydrochloride salt

Prepared in a similar manner to Example 1 Method 2(f) using homopiperidine (52 mg) instead of morpholine except that the reaction time was extended by 24 h. An extra 52 mg of homopiperidine was added after the initial 16 h stirring and the mixture was heated at 110° C. to afford the title compound (18 mg).
NMR (d$^6$-DMSO) δ 1.52-3.61 (15H, m), 7.33-7.73 (6H, m), 11.28 (1H, brs), 12.78 (1H, brs).
LC/MS [MH$^+$] 383 consistent with molecular formula $C_{21}H_{23}^{35}ClN_4O$.

EXAMPLE 35

7-(3-Bromo-phenylamino)-3-methyl-1H-pyrrolo[2,3-c]pyridine-4-carboxylic acid methyl-(tetrahydro-pyran-4-ylmethyl)-amide hydrochloride salt

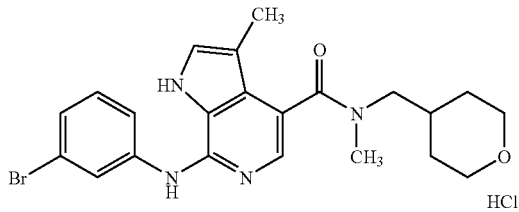

(a) 7-Chloro-3-methyl-4-[methyl-(tetrahydro-pyran-4-ylmethyl)-carbamoyl]-pyrrolo[2,3-c]pyridine-1-carboxylic acid dimethyl-ethyl ester

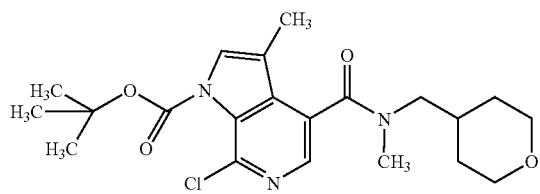

Prepared in a similar manner to Example 11 (b) using methyl-(tetrahydro-pyran-4-ylmethyl)-amine hydrochloride (280 mg) instead of morpholine to give the title compound as a yellow oil (540 mg).

LC/MS [MH$^+$] 422 consistent with molecular formula $C_{21}H_{28}{}^{35}ClN_3O_4$ (b) 7-(3-Bromo-phenylamino)-3-methyl-1H-pyrrolo[2,3-c]pyridine-4-carboxylic acid methyl-(tetrahydro-pyran-4-ylmethyl)-amide hydrochloride salt Prepared in a similar manner to Example 4(d) from 7-chloro-3-methyl-4-[methyl-(tetrahydro-pyran-4-ylmethyl)-carbamoyl]-pyrrolo[2,3-c]pyridine-1-carboxylic acid dimethyl-ethyl ester (120 mg) and 3-bromoaniline. Purified by Biotage chromatography over silica gel eluting with ethyl acetate rather than trituration with diethyl ether. The salt formation was as Example 4 (d) to afford the title compound (66 mg).

NMR (d$^6$-DMSO) δ 0.94 (1H, m), 1.30 (1H, m), 1.42 (1H, brs), 1.62 (1H, d), 1.85-2.04 (1H,m), 2.11 (3H, d), 2.87-3.04 (3H, d), 3.20 (2H, t), 3.34 (2H, t), 3.73-3.90 (2H, m), 7.38-7.57 (4H, m), 7.74-7.85 (2H, d), 11.15 (1H, brs), 12.65 (1H, brs).

LC/MS [MH$^+$] 459 consistent with molecular formula $C_{22}H_{25}{}^{81}BrN_4O_2$

EXAMPLE 36

7-(3-Chloro-phenylamino)-3-methyl-1H-pyrrolo[2,3-c]pyridine-4-carboxylic acid methyl-(tetrahydro-pyran-4-ylmethyl)-amide hydrochloride salt

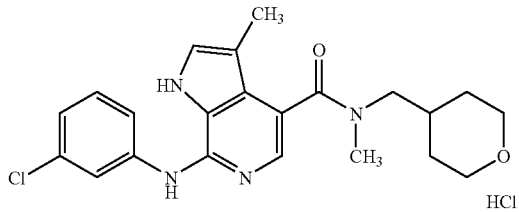

Prepared in a similar manner to Example 4(d) from 7-chloro-3-methyl-4-[methyl-(tetrahydro-pyran-4-ylmethyl)-carbamoyl]-pyrrolo[2,3-c]pyridine-1-carboxylic acid dimethyl-ethyl ester (120 mg) and 3-chloroaniline instead of 3-bromoaniline. Purified by Biotage chromatography over silica gel eluting with ethyl acetate rather than trituration with diethyl ether. The salt formation was as Example 4 (d) to afford the title compound (70 mg).

NMR (d$^6$-DMSO) δ 0.92 (1H, m), 1.33 (1H, m), 1.42 (1H, brs), 1.62 (1H, d), 1.85-2.04 (1H,m), 2.11 (3H, d), 2.87-3.04 (3H, d), 3.20 (2H, t), 3.34 (2H, t), 3.73-3.90 (2H, m), 7.28 (1H, brs), 7.42-7.56 (3H, m), 7.67-7.83 (2H, d), 10.80 (1H, brs), 12.40 (1H, brs).

LC/MS [MH$^+$] 413 consistent with molecular formula $C_{22}H_{25}{}^{35}ClN_4O_2$

EXAMPLE 37a) AND 37b)

7-(3-Chloro-phenylamino)-3-methyl-1H-pyrrolo[2,3-c]pyridine-4-carboxylic acid (2-methoxy-ethyl)-methyl-amide and its hydrochloride salt

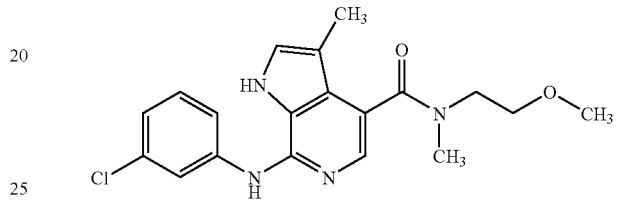

a) Prepared in a similar manner to Example 29(a) using (2-methoxy-ethyl)-methyl-amine (45.7 mg) instead of thiomorpholine 1,1-dioxide hydrochloride, to afford 7-(3-chloro-phenylamino)-3-methyl-1H-pyrrolo[2,3-c]pyridine-4-carboxylic acid (2-methoxy-ethyl)-methyl-amide (36 mg).

NMR (d$^6$-DMSO) δ 1.99-4.11 (13H, m), 6.97 (1H, d), 7.32 (1H, t), 7.38 (1H, s), 7.60 (1H, d), 7.62 (1H, s), 8.19 (1H, d), 8.97 (1H, s), 11.12 (1H, brs).

LC/MS [MH$^+$] 373 consistent with molecular formula $C_{19}H_{21}{}^{35}ClN_4O_2$.

b) 7-(3-Chloro-phenylamino)-3-methyl-1H-pyrrolo[2,3-c]pyridine-4-carboxylic acid (2-methoxy-ethyl)-methyl-amide hydrochloride salt Prepared in a similar manner to Example 29(b).
NMR (MeOH) δ 1.90-4.60 (13H, m), 7.13-8.10 (6H, m).
LC/MS [MH$^+$] 373 consistent with molecular formula $C_{19}H_{21}{}^{35}ClN_4O_2$.

EXAMPLE 38

1-Azetidin-1-yl-1-[7-(3-chloro-phenylamino)-3-methyl-1H-pyrrolo[2,3-c]pyridin-4-yl]-methanone

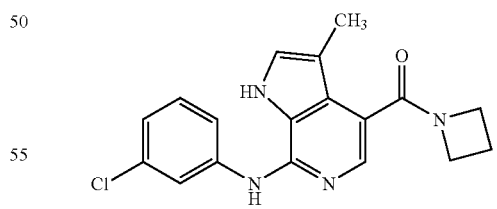

Prepared in a similar manner to Example 29(a) using azetidine (29.9 mg) instead of thiomorpholine 1,1-dioxide hydrochloride except that the reaction time was extended by 24 h. An extra 52 mg of azetidine was added after the initial 16 h stirring and the mixture heated at 110° C. to afford the title compound (20 mg).

NMR (d$^6$-DMSO) δ 1.38 (3H, s), 1.40-1.50 (2H, m), 3.16 (2H, t), 3.32 (2H, t), 6.05 (1H, d), 6.35 (2H, t), 6.56, (1H, d), 6.85, (1H, s), 7.03 (1H, d).

LC/MS [MH⁺] 341 consistent with molecular formula $C_{18}H_{17}{}^{35}ClN_4O$.

EXAMPLE 39a AND 39b 7-(3-Chloro-phenylamino)-3-methyl-1H-pyrrolo[2,3-c]pyridine-4-carboxylic acid 4-fluoro-benzylamide and its hydrochloride salt

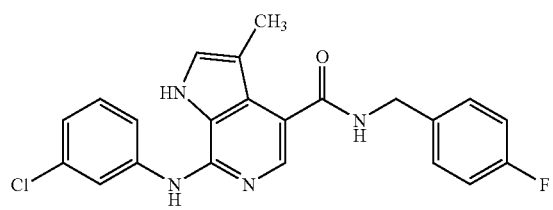

a) Prepared in a similar manner to Example 29(a) using 4-fluoro-benzylamine (65.6 mg) instead of thiomorpholine 1,1-dioxide hydrochloride, to afford 7-(3-chloro-phenylamino)-3-methyl-1H-pyrrolo[2,3-c]pyridine-4-carboxylic acid 4-fluoro-benzylamide (74 mg).

NMR (d⁶-DMSO) δ 2.17 (3H, s), 4.47 (2H, d), 6.96 (1H, d), 7.15-7.32 (6H, m), 7.81 (1H, d), 7.92 (1H, s), 8.36 (1H, s), 8.83 (1H, t), 9.67 (1H, s), 11.88 (1H, s).

LC/MS [MH⁺] 409 consistent with molecular formula $C_{22}H_{18}{}^{35}ClFN_4O$ b) 7-(3-Chloro-phenylamino)-3-methyl-1H-pyrrolo[2,3-c]pyridine-4-carboxylic acid 4-fluoro-benzylamide hydrochloride salt Prepared in a similar manner to Example 29(b).

NMR (MeOH) δ 2.23 (3H, s), 4.57 (2H, s), 7.06-7.69 (10H, m).

LC/MS [MH⁺] 409 consistent with molecular formula $C_{22}H_{18}{}^{35}ClFN_4O$

EXAMPLE 40a AND 40b 7-(3-Chloro-phenylamino)-3-methyl-1H-pyrrolo[2,3-c]pyridine-4-carboxylic acid (2,2-dimethyl-propyl)-amide and its hydrochloride salt

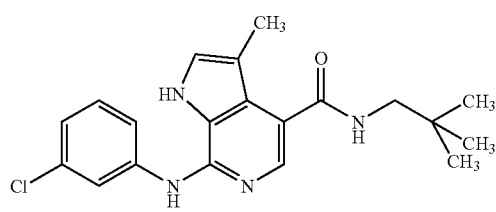

a) Prepared in a similar manner to Example 29(a), using neopentylamine hydrochloride (45.7 mg) instead of thiomorpholine 1,1-dioxide hydrochloride, to afford 7-(3-chloro-phenylamino)-3-methyl-1H-pyrrolo[2,3-c]pyridine-4-carboxylic acid (2,2-dimethyl-propyl)-amide (64 mg).

NMR (d⁶-DMSO) δ 0.94 (9H, s), 2.21 (3H, s), 3.11 (2H, d), 6.93 (1H, d), 7.29 (1H, t), 7.34, 1H, s), 7.69 (1H, d), 7.88 (1H, s), 8.22 (1H, t), 8.33 (1H, s), 9.34 (1H, s), 11.51 (1H, s).

LC/MS [MH⁺] 371 consistent with molecular formula $C_{20}H_{23}{}^{35}ClN_4O$.

b) 7-(3-Chloro-phenylamino)-3-methyl-1H-pyrrolo[2,3-c]pyridine-4-carboxylic acid (2,2-dimethyl-propyl)-amide hydrochloride salt Prepared in a similar manner to Example 29(b).

NMR (MeOH) δ 1.009 (9H, s), 2.32 (3H, s), 3.25 (2H, d), 7.39-7.71 (6H, m), 8.63, (1H, t).

LC/MS [MH⁺] 371 consistent with molecular formula $C_{20}H_{23}{}^{35}ClN_4O$.

EXAMPLE 41

7-(3-Chloro-phenylamino)-3-methyl-1H-pyrrolo[2,3-c]pyridine-4-carboxylic acid tert-butylamide

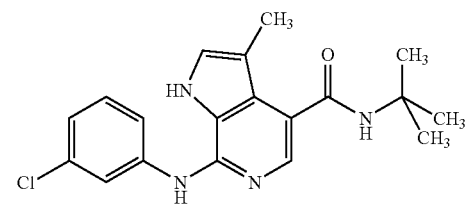

(a) 4-tert-Butylcarbamoyl-7-chloro-3-methyl-pyrrolo[2,3-c]pyridine-1-carboxylic acid tert-butyl ester

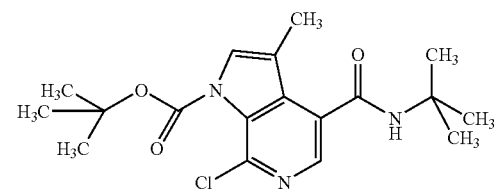

Prepared in a similar manner to Example 11 (b) using ᵗbutylamine (203 ul) instead of morpholine. Purified by Biotage chromatography over silica gel loading with dichloromethane and eluting with 10% ethyl acetate/hexane then 20% ethyl acetate/hexane to give the title compound as a white foam (203 mg).

NMR (d⁶-DMSO) δ 1.39 (9H, s), 1.60 (9H, s), 2.20 (3H, s), 7.81 (1H, d), 8.08 (1H, s), 8.28 (1H, s).

LC/MS [MH⁺] 366 consistent with molecular formula $C_{18}H_{24}{}^{35}ClN_3O_3$ (b) 7-(3-Chloro-phenylamino)-3-methyl-1H-pyrrolo[2,3-c]pyridine-4-carboxylic acid tert-butylamide Prepared in a similar manner to Example 4(d) from 4-tert-butylcarbamoyl-7-chloro-3-methyl-pyrrolo[2,3-c]pyridine-1-carboxylic acid tert-butyl ester (68 mg) and using 3-chloroaniline (39 ul) instead of 3-bromoaniline. Isolated by MDAP rather than trituration with diethyl ether to give the title compound (34 mg).

NMR (d⁶-DMSO) δ 1.39 (9H, s), 2.23 (3H, s), 6.95 (1H, dd), 7.32 (2H, m), 7.57 (1H, d), 7.78 (2H, d), 8.25 (1H, s), 8.98 (1H, s), 11.05 (1H, s).

LC/MS [MH⁺] 357 consistent with molecular formula $C_{19}H_{21}{}^{35}ClN_4O$

EXAMPLE 42

7-(2,4-Difluoro-phenylamino)-3-methyl-1H-pyrrolo[2,3-c]pyridine-4-carboxylic acid tert-butylamide

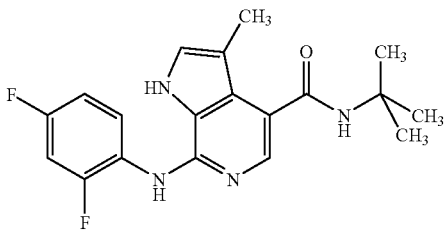

Prepared in a similar manner to Example 4(d) from 4-tert-butylcarbamoyl-7-chloro-3-methyl-pyrrolo[2,3-c]pyridine-1-carboxylic acid tert-butyl ester (68 mg) and using 2,4-difluoroaniline (38 ul) instead of 3-bromoaniline. Isolated by trituration with methanol rather than trituration with diethyl ether to give the title compound (28 mg).

NMR (d$^6$-DMSO) δ 1.38 (9H, s), 2.23 (3H, s), 7.05 (1H, t), 7.32 (2H, m), 7.65 (1H, s), 7.76 (1H, s), 8.25 (1H, m), 8.35 (1H, s), 11.30 (1H, s).

LC/MS [MH$^+$] 359 consistent with molecular formula $C_{19}H_{20}F_2N_4O$

EXAMPLE 43

7-(3,5-Difluoro-phenylamino)-3-methyl-1H-pyrrolo[2,3-c]pyridine-4-carboxylic acid tert-butylamide

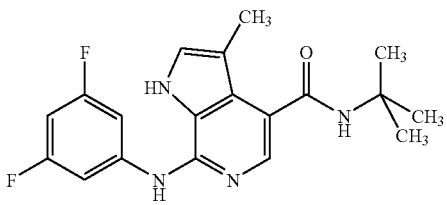

Prepared in a similar manner to Example 4(d) from 4-tert-butylcarbamoyl-7-chloro-3-methyl-pyrrolo[2,3-c]pyridine-1-carboxylic acid ter-butyl ester (68 mg) and using 3,5-difluoroaniline (38 ul) instead of 3-bromoaniline. Isolated by MDAP rather than trituration with diethyl ether to give the title compound (28 mg).

NMR (d$^6$-DMSO) δ 1.39 (9H, s), 2.23 (3H, s), 6.70 (1H, t), 7.37 (1H, s), 7.59 (2H, d), 7.78 (1H, s), 7.83 (1H, s), 9.25 (1H, s), 11.10 (1H, s).

LC/MS [MH$^+$] 359 consistent with molecular formula $C_{19}H_{20}F_2N_4O$

EXAMPLE 44d AND 44e

1-[7-(3-Chloro-phenylamino)-1,3-dimethyl-1H-pyrrolo[2,3-c]pyridin-4-yl]-1-morpholin-4-yl-methanone and its hydrochloride salt

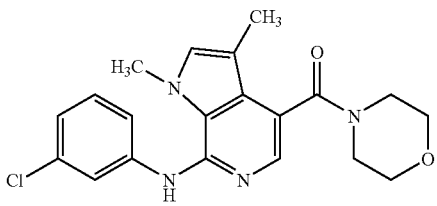

(a) 7-Chloro-4-iodo-1,3-dimethyl-1H-pyrrolo[2,3-c]pyridine

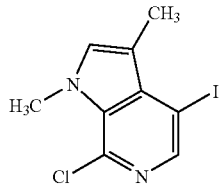

To a solution of 7-chloro-4-iodo-3-methyl-1H-pyrrolo[2,3-c]pyridine (2 g) in dry tetrahydrofuran (100 ml) at 0° C. under argon was added portionwise sodium hydride (60% dispersed in mineral oil 603 mg). After addition the ice-bath was removed and the solution stirred at room temperature for 30 minutes. The solution was re-cooled to 0° C. and a solution of methyl iodide (3.41 ml) in dry tetrahydrofuran (40 ml) was added dropwise. The solution was allowed to warm to room temperature and stirred overnight. The solution was evaporated and the residue partitioned between ethyl acetate (200 ml) and water (100 ml). Washed with water (2×100 ml, pH7) then dried (MgSO$_4$), filtered and evaporated to an orange/yellow solid. The solid was stirred in hexane for 2 h then filtered off and dried to give the title compound (1.19 g).

NMR (d$^6$-DMSO) δ 2.43 (3H, s), 4.05 (3H, s), 7.54 (1H, d), 8.11 (1H, s).

LC/MS [MH$^+$] 307 consistent with molecular formula $C_9H_8^{35}ClIN_2$ (b) 7-Chloro-1,3-dimethyl-1H-pyrrolo[2,3-c]pyridine-4-carboxylic acid

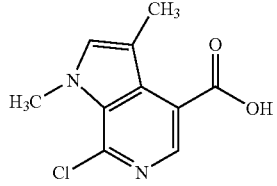

To a solution of 7-chloro-4-iodo-1,3-dimethyl-1H-pyrrolo[2,3-c]pyridine (1.19 g) in dry tetrahydrofuran (30 ml) at room temperature under an atmosphere of argon, was added 4 A molecular sieves. Stirred for 15 minutes then cooled to −40° C. (internal temperature). Then added dropwise was a solution of isopropylmagnesium chloride (2M in tetrahydrofuran, 4.1 ml) and the solution stirred at −40° C. for 5 minutes. The solution was saturated with a stream of carbon dioxide gas (passed through Drierite) and then diluted with ethyl acetate (50 ml). The organic was extracted 1N sodium hydroxide solution (2×100 ml). The combined aqueous was then acidified to pH1 with concentrated hydrochloric acid and extracted with ethyl acetate (2×100 ml). The combined extracts were washed with brine (2×100 ml) then dried (MgSO$_4$), filtered and evaporated to afford the title compound as an off-white solid (738 mg).

NMR (d$^6$-DMSO) δ 2.30 (3H, s), 4.09 (3H, s), 7.57 (1H, d), 8.23 (1H, s), 13.2 (1H, brs).

LC/MS [MH$^+$] 225 consistent with molecular formula $C_{10}H_9^{35}ClN_2O_2$ (c) 1-(7-Chloro-1,3-dimethyl-1H-pyrrolo[2,3-c]pyridine-4-yl)-1-morpholin-4-yl-methanone

Prepared in a similar manner to Example 11 (b) using 7-chloro-1,3-dimethyl-1H-pyrrolo[2,3-c]pyridine-4-carboxylic acid (730 mg) except that the title compound was purified by trituration with diethyl ether to give the title compound as a white solid (463 mg).

NMR (d⁶-DMSO) δ 2.12 (3H, s), 3.10 (2H, brd), 3.45 (2H, brd), 3.67 (3H, brs), 3.75 (1H, db), 4.08 (3H, s), 7.50 (1H, d), 7.78 (1H, s).

LC/MS [MH⁺] 294 consistent with molecular formula $C_{14}H_{16}{}^{35}ClN_3O_2$ (d) 1-[7-(3-Chloro-phenylamino)-1,3-dimethyl-1H-pyrrolo[2,3-c]pyridin-4-yl]-1-morpholin-4-yl-methanone Prepared in a similar manner to Example 4(d) from 1-(7-chloro-1,3-dimethyl-1H-pyrrolo[2,3-c]pyridine-4-yl)-1-morpholin-4-yl-methanone (100 mg) and using 3-chloroaniline (72 ul) instead of 3-bromoaniline. Isolated by MDAP rather than trituration with diethyl ether to give 1-[7-(3-chloro-phenylamino)-1,3-dimethyl-1H-pyrrolo[2,3-c]pyridin-4-yl]-1-morpholin-4-yl-methanone (69 mg).

NMR (d⁶-DMSO) δ 2.15 (3H, s), 3.16-3.67 (8H, bq), 4.02 (3H, s), 6.88 (1H, dd), 7.26 (3H, m), 7.47 (1H, s), 7.62 (1H, s), 8.49 (1H, s).

LC/MS [MH⁺] 385 consistent with molecular formula $C_{20}H_{21}{}^{35}ClN_4O_2$ e) 1-[7-(3-Chloro-phenylamino)-1,3-dimethyl-1H-pyrrolo[2,3-c]pyridin-4-yl]-1-morpholin-4-yl-methanone hydrochloride salt 1-[7-(3-Chloro-phenylamino)-1,3-dimethyl-1H-pyrrolo[2,3-c]pyridin-4-yl]-1-morpholin-4-yl-methanone (55 mg) was dissolved in warm ethanol (1 ml) and treated with a solution of 1M hydrochloric acid in diethyl ether (10 drops). The mixture was evaporated, triturated with diethyl ether and filtered off then dried at 40° C. under vacuum to afford the title compound (54 mg).

NMR (d⁶-DMSO) δ 2.15 (3H, s), 3.25-3.67 (8H, bq), 4.14 (3H, s), 7.19 (1H, dd), 7.34 (1H,dd), 7.42 (1H, t), 7.50 (1H, t), 7.61 (1H, s), 7.72 (1H, s), 9.80 (1H, brs).

LC/MS [MH⁺] 385 consistent with molecular formula $C_{20}H_{21}{}^{35}ClN_4O_2$

EXAMPLE 45a AND 45b

1-[7-(3-Fluoro-phenylamino)-1,3-dimethyl-1H-pyrrolo[2,3-c]pyridin-4-yl]-1-morpholin-4-yl-methanone and its hydrochloride salt

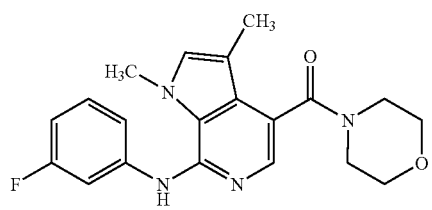

a) Prepared in a similar manner to Example 4(d) from 1-(7-chloro-1,3-dimethyl-1H-pyrrolo[2,3-c]pyridine-4-yl)-1-morpholin-4-yl-methanone (100 mg) and using 3-fluoroaniline (130 ul) instead of 3-bromoaniline and heating for 15 rather than 30 minutes to give 1-[7-(3-fluoro-phenylamino)-1,3-dimethyl-1H-pyrrolo[2,3-c]pyridin-4-yl]-1-morpholin-4-yl-methanone (89 mg).

NMR (d⁶-DMSO) δ 2.10 (3H, s), 3.22 (2H, brs), 3.50 (2H,brs), 3.67 (4H, brs), 4.02 (3H, s), 6.65 (1H, dt), 7.13 (1H, dd), 7.24 (3H, m), 7.62 (1H, s), 8.52 (1H, s).

LC/MS [MH⁺] 369 consistent with molecular formula $C_{20}H_{21}FN_4O_2$ b) 1-[7-(3-Fluoro-phenylamino)-1,3-dimethyl-1H-pyrrolo[2,3-c]pyridin-4-yl]-1-morpholin-4-yl-methanone hydrochloride salt 1-[7-(3-Fluoro-phenylamino)-1,3-dimethyl-1H-pyrrolo[2,3-c]pyridin-4-yl]-1-morpholin-4-yl-methanone (73 mg) was dissolved in warm ethanol (12 ml) and treated with a solution of 1M hydrochloric acid in diethyl ether (10 drops) The mixture was evaporated, triturated with diethyl ether and filtered off then dried at 40° C. under vacuum to afford the title compound (65 mg).

NMR (d⁶-DMSO) δ 2.15 (3H, s), 3.25-3.70 (8H, brt), 4.14 (3H, s), 6.96 (1H, t), 7.24 (1H,dd), 7.29 (1H, dt), 7.45 (1H, q), 7.62 (1H, s), 7.75 (1H, s), 9.90 (1H, brs).

LC/MS [MH⁺] 369 consistent with molecular formula $C_{20}H_{21}FN_4O_2$

EXAMPLE 46a AND 46b

1-[7-(3-Bromo-phenylamino)-1,3-dimethyl-1H-pyrrolo[2,3-c]pyridin-4-yl]-1-morpholin-4-yl-methanone and its hydrochloride salt

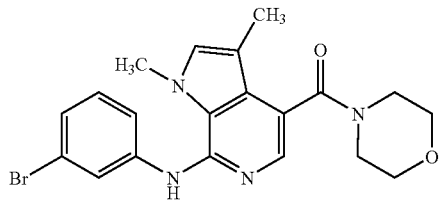

a) Prepared in a similar manner to Example 4(d) from 1-(7-chloro-1,3-dimethyl-1H-pyrrolo[2,3-c]pyridine-4-yl)-1-morpholin-4-yl-methanone (100 mg) and 3-bromoaniline (74 ul) to give 1-[7-(3-bromo-phenylamino)-1,3-dimethyl-1H-pyrrolo[2,3-c]pyridin-4-yl]-1-morpholin-4-yl-methanone (93 mg).

NMR (d⁶-DMSO) δ 2.10 (3H, s), 3.25 (2H, brs), 3.50 (2H,brs), 3.67 (4H, brs), 4.02 (3H, s), 7.03 (1H, d), 7.18 (1H, t), 7.27 (1H, t), 7.33 (1H, d), 7.61 (2H, t), 8.47 (1H, s).

LC/MS [MH⁺] 429 consistent with molecular formula $C_{20}H_{21}{}^{79}BrN_4O_2$ b) 1-[7-(3-Bromo-phenylamino)-1,3-dimethyl-1H-pyrrolo[2,3-c]pyridin-4-yl]-1-morpholin-4-yl-methanone hydrochloride salt 1-[7-(3-Bromo-phenylamino)-1,3-dimethyl-1H-pyrrolo[2,3-c]pyridin-4-yl]-1-morpholin-4-yl-methanone (78 mg) was dissolved in warm ethanol (12 ml) and treated with a solution of 1M hydrochloric acid in diethyl ether (10 drops) The mixture was evaporated, triturated with diethyl ether and filtered off then dried at 40° C. under vacuum to afford the title compound (65 mg).

NMR (d⁶-DMSO) δ 2.15 (3H, s), 7.40 (3H, m), 7.61 (1H, s), 7.65 (1H, s), 7.74 (1H, s), 9.90 (1H, brs).

LC/MS [MH⁺] 369 consistent with molecular formula $C_{20}H_{21}{}^{79}BrN_4O_2$

EXAMPLE 47a AND 47b

1-[7-(3,5-Difluoro-phenylamino)-1,3-dimethyl-1H-pyrrolo[2,3-c]pyridin-4-yl]-1-morpholin-4-yl-methanone and its hydrochloride salt

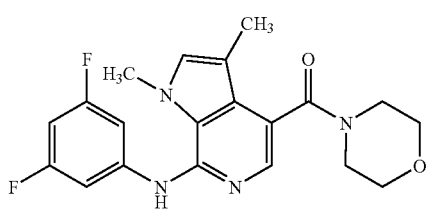

a) Prepared in a similar manner to Example 4(d) from 1-(7-chloro-1,3-dimethyl-1H-pyrrolo[2,3-c]pyridine-4-yl)-1-morpholin-4-yl-methanone (100 mg) and using 3,5-difluoroaniline (88 mg) instead of 3-bromoaniline and heating for 15 rather than 30 minutes to give 1-[7-(3,5-difluoro-phenylamino)-1,3-dimethyl-1H-pyrrolo[2,3-c]pyridin-4-yl]-1-morpholin-4-yl-methanone (33 mg).

NMR (d$^6$-DMSO) δ 2.10 (3H, s), 3.25 (2H, brs), 3.50 (2H,brs), 3.67 (4H, brs), 4.01 (3H, s), 6.62 (1H, m), 7.05 (2H, dd), 7.30 (1H, d), 7.67 (1H, s), 8.76 (1H, s).

LC/MS [MH$^+$] 387 consistent with molecular formula $C_{20}H_{20}F_2N_4O_2$ b) 1-[7-(3,5-Difluoro-phenylamino)-1,3-dimethyl-1H-pyrrolo[2,3-c]pyridin-4-yl]-1-morpholin-4-yl-methanone hydrochloride salt 1-[7-(3,5-Difluoro-phenylamino)-1,3-dimethyl-1H-pyrrolo[2,3-c]pyridin-4-yl]-1-morpholin-4-yl-methanone (24 mg) was dissolved in warm ethanol (5 ml) and treated with a solution of 1M hydrochloric acid in diethyl ether (10 drops) The mixture was evaporated, triturated with diethyl ether and filtered off then dried at 40° C. under vacuum to afford the title compound (20 mg).

NMR (d$^6$-DMSO) δ 2.15 (3H, s), 3.25-3.70 (8H, brt), 4.11 (3H, s), 6.87 (1H, t), 7.10 (2H, t), 7.75 (2H, d), 10.00 (1H, brs).

LC/MS [MH$^+$] 387 consistent with molecular formula $C_{20}H_{20}F_2N_4O_2$

EXAMPLE 48

7-(3-Chloro-phenylamino)-3-methyl-1H-pyrrolo[2,3-c]pyridine-4-carboxylic acid [4,4,4-trifluoro-2-(2,2,2-trifluoro-ethyl)-butyl]-amide

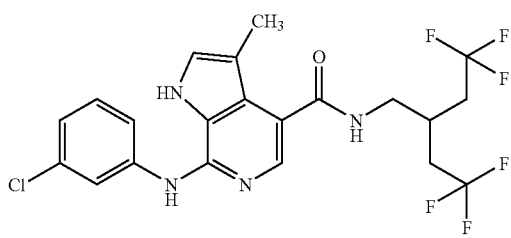

Prepared in a similar manner to Example 29(a) using bis(2,2,2-trifluoroethyl)amine (110 mg) instead of thiomorpholine 1,1-dioxide hydrochloride, to afford the title compound (5 mg).

NMR (d$^6$-DMSO) δ 2.38 (3H, s), 3.32 (7H, s), 7.10 (1H, d), 7.40 (1H, t), 7.53 (1H, d), 7.58 (1H, s), 7.68 (1H,t), 7.93 (1H, d), 8.19 (1H, d), 8.38 (1H, s), 8.91 (1H, s).

EXAMPLE 49

7-(3-Chloro-phenylamino)-3-methyl-1H-pyrrolo[2,3-c]pyridine-4-carboxylic acid [(R)-1-(tetrahydro-furan-2-yl)methyl]-amide hydrochloride salt

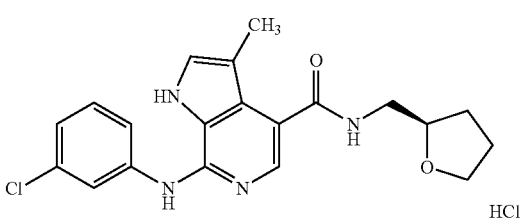

Prepared in a similar manner to Example 1 Method 2(f) using (R)-1-(tetrahydro-furan-2-yl)methylamine (53.0 mg) instead of morpholine, to afford the title compound (18 mg).

NMR (d$^6$-DMSO) δ 1.62-1.93 (4H, m), 2.23 (3H, s), 3.32-4.01 (5H, m), 7.00-8.54 (9H, m).

LC/MS [MH$^+$] 385 consistent with molecular formula $C_{20}H_{21}^{35}ClN_4O_2$

EXAMPLE 50

7-(3-Chloro-phenylamino)-3-methyl-1H-pyrrolo[2,3-c]pyridine-4-carboxylic acid methyl-(tetrahydro-pyran-4-ylmethyl)-amide hydrochloride salt

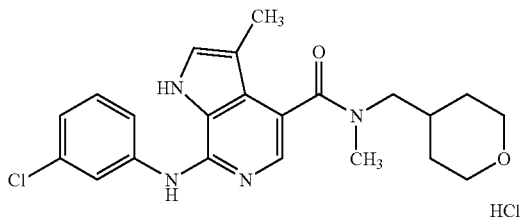

A solution of 7-chloro-3-methyl-4-[(tetrahydro-pyran-4-ylmethyl)-carbamoyl)]-pyrrolo[2,3-c]pyridine-1-carboxylic acid tert-butyl ester (100 mg) in NMP (1 ml) and 3-chloro-N-methyl aniline (0.5 ml) was heated under microwave conditions at 180° C. for 10 h. Purified by Biotage chromatography over silica gel loading the reaction mixture directly onto the column and eluting with hexane then 2-5% methanol/dichloromethane. Further purified by Biotage chromatography over silica gel eluting with 3% methanol/dichloromethane. The hydrochloride salt was formed by dissolving in dichloromethane followed by treatment with a solution of 1M hydrochloric acid in diethyl ether (10) drops. Evaporated to give the title compound as an off-white solid (31 mg).

NMR (d$^6$-DMSO) δ 1.25 (2H, m), 1.65 (2H, dd), 1.81 (1H,m), 2.21 (3H, s), 3.20 (2H, t), 3.28 (2H, t), 3.61 (3H, s), 3.87 (2H, dd), 7.00 (1H, d), 7.23 (2H, t), 7.38 (1H, t), 7.61 (1H, s), 7.84 (1H, s), 8.69 (1H, t), 111.35 (1H, s).

LC/MS [MH+] 413 consistent with molecular formula $C_{22}H_{25}{}^{35}ClN_4O_2$

EXAMPLE 51h AND 51i 4-(3-Chloro-phenylamino)-1-methyl-H-pyrrolo[3,2-c]pyridine-7-carboxylic acid isobutyl-amide and its hydrochloride salt

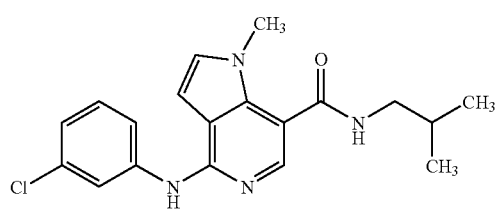

a) 2-Methoxycarbonylmethyl-1-methyl-1H-pyrrole-3-carboxylic acid methyl ester

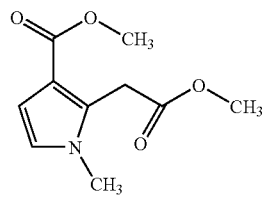

2-Carboxymethyl-1-methyl-1H-pyrrole-3-carboxylic acid (17.67 g) prepared as described by Bottaccio, Giorgio; Campolmi, Stefano; Carletti, Vittorio; Marchi, Marcello. EP105664, para-toluenesulfonic acid (9.17 g) and methanol (250 ml) were refluxed under argon for 48 hours. The solvent was evaporated and the residue washed with ethanol to yield the title compound as a white solid (15.75 g)

NMR (d$^6$-DMSO) δ 3.55 (3H, s), 3.65 (3H, s), 3.68 (3H, s), 4.11 (2H, s), 6.37 (1H, d), 6.77 (1H, d).

b) 2-(2-Hydroxy-1-methoxycarbonyl-vinyl)-1-methyl-1H-pyrrole-3-carboxylic acid methyl ester

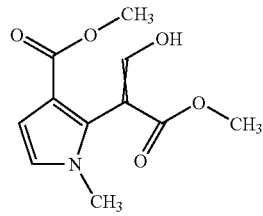

2-Methoxycarbonylmethyl-1-methyl-1H-pyrrole-3-carboxylic acid methyl ester (5.7 g) in dry tetrahydrofuran (100 ml) was stirred at room temperature under argon. Sodium hydride (60% dispersion in mineral oil, 7.13 g) was added portionwise followed by methyl formate (2.5 ml) and the mixture was left to stir overnight. The reaction was cooled in ice and quenched by the addition of the minimum amount of methanol. The solution was again cooled and acidified to pH1 with aqueous 5N hydrochloric acid. The reaction was diluted with ethyl acetate and water, the aqueous separated and extracted three times with ethyl acetate. The combined organic layers were then washed with brine, dried (MgSO$_4$) and filtered. The solvent was evaporated to yield an oil consisting of two layers. The top layer was discarded and the lower layer solidified on standing to give the crude title compound as a brown solid (8.62 g).

LC/MS [M+Na] 262 consistent with isomers of molecular formula $C_{11}H_{13}NO_5$.

c) 2-(2-Amino-1-methoxycarbonyl-vinyl)-1-methyl-1H-pyrrole-3-carboxylic acid methyl ester

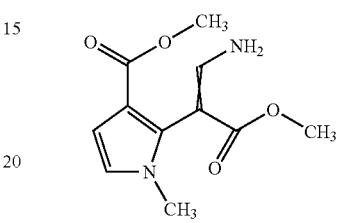

2-(2-Hydroxy-1-methoxycarbonyl-vinyl)-1-methyl-1H-pyrrole-3-carboxylic acid methyl ester (12.46 g), ammonium acetate (20.09 g) and methanol (200 ml) were refluxed under argon for 5 hours. After cooling the solvent was evaporated and the residue dissolved in ethyl acetate and washed with water, the aqueous was separated and extracted three times with ethyl acetate. The combined organics were washed with saturated brine solution and the organic layer was dried (MgSO$_4$), filtered and evaporated. The residue was then taken up in the minimum amount of ethyl acetate and a precipitate formed which was filtered off to yield the title compound as an off-white solid (3.3 g). The filtrate was evaporated to yield the title compound as a brown solid (6.36 g). Both were taken through without further purification.

LC/MS [M+Na] 261 consistent with isomers of molecular formula $C_{11}H_{14}N_2O_4$.

d) 1-Methyl-4-oxo-4,5-dihydro-1H-pyrrolo[3,2-c]pyridine-7-carboxylic acid methyl ester

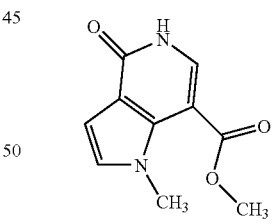

A mixture of 2-(2-amino-1-methoxycarbonyl-vinyl)-1-methyl-1H-pyrrole-3-carboxylic acid methyl ester (3.3 g), sodium tert-butoxide (0.267 g) and dimethylformamide (22 ml) was split equally between 2×20 ml sealed vessels and irradiated with microwaves at 160° C. for 5 minutes. The cooled solutions were combined and added slowly to ice water and stirred for 10 minutes. A precipitate formed which was filtered off and dried to yield the title compound as a white solid (1.12 g). The aqueous filtrate was extracted three times with ethyl acetate and the combined organics were washed with saturated brine solution. The dried (Na$_2$SO$_4$) organic layer was evaporated to yield a yellow oil which was triturated with warm isopropyl alcohol to yield the title compound as a white solid (0.66 g). Total product weight (1.78 g).

LC/MS [MH+] 207 consistent with molecular formula $C_{10}H_{10}N_2O_3$.

e) 4-Chloro-1-methyl-1H-pyrrolo[3,2-c]pyridine-7-carboxylic acid methyl ester

1-Methyl-4-oxo-4,5-dihydro-1H-pyrrolo[3,2-c]pyridine-7-carboxylic acid methyl ester (1.25 g) and phenyl dichlorophosphate (12 ml) were heated at 180° C. under argon for 30 minutes. The reaction was allowed to cool at which point a precipitate formed. This was filtered off and washed with diethyl ether to yield the title compound as a grey solid (1.2 g).

LC/MS [MH+] 225 consistent with molecular formula $C_{10}H_9{}^{35}ClN_2O_2$.

f) 4-(3-Chloro-phenylamino)-1-methyl-1H-pyrrolo[3,2-c]pyridine-7-carboxylic acid methyl ester

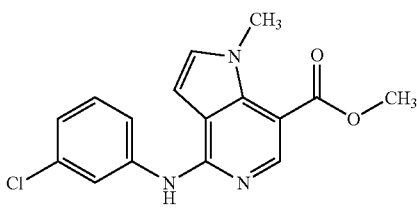

4-Chloro-1-methyl-1H-pyrrolo[3,2-c]pyridine-7-carboxylic acid methyl ester (1.04 g), 3-chloroaniline (0.97 ml) and methanesulfonic acid (0.60 ml) in 1,4-dioxan (10 ml) were irradiated at 180° C. for 30 minutes with microwaves. The solid mass obtained was dissolved in methanol and the solvent evaporated. The residue was dissolved in ethyl acetate and washed with water followed by saturated brine solution then dried (MgSO4)), filtered and evaporated to yield a brown oil (1.6 g). The brown oil was purified by column chromatography on a Biotage® 40M column eluting in 20% ethyl acetate/iso-hexane, to give the title compound as an off-white solid (0.62 g).

LC/MS [MH+] 316 consistent with molecular formula $C_{16}H_{14}{}^{35}ClN_3O_2$.

g) 4-(3-Chloro-phenylamino)-1-methyl-1H-pyrrolo[3,2-c]pyridine-7-carboxylic acid

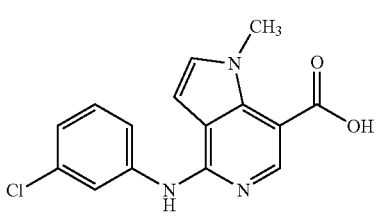

4-(3-Chloro-phenylamino)-1-methyl-1H-pyrrolo[3,2-c]pyridine-7-carboxylic acid methyl ester (0.6 g) and 2N sodium hydroxide (2 ml) in methanol were irradiated at 120° C. for 3 minutes with microwaves. The solvent was evaporated and the residue partitioned between ethyl acetate and water. The organic layer washed with dilute citric acid solution and saturated brine solution then dried (MgSO4), filtered and evaporated to yield the title compound as an off-white solid (0.48 g).

LC/MS [MH+] 302 consistent with molecular formula $C_{15}H_{12}{}^{35}ClN_3O_2$.

h) 4-(3-Chloro-phenylamino)-1-methyl-H-pyrrolo[3,2-c]pyridine-7-carboxylic acid isobutyl-amide 4-(3-Chloro-phenylamino)-1-methyl-1H-pyrrolo[3,2-c]pyridine-7-carboxylic acid (100 mg), 1-ethyl-3-(3-dimethylaminopropyl)carbodiimide hydrochloride (127 mg), 1-hydroxybenzotriazole hydrate (89 mg), iso-butylamine (67 ul) and N-ethylmorpholine (85 ul) in dimethylformamide (2 ml) were stirred under argon over 72 hours. The reaction was diluted with ethyl acetate and washed three times with water and once with saturated brine solution then dried (MgSO4) and evaporated to yield a brown solid (140 mg). This was purified on MDAP to yield the title compound as a white solid (86 mg).

LC/MS [MH+] 357 consistent with molecular formula $C_{19}H_{21}{}^{35}ClN_4O$.

i) 4-(3-Chloro-phenylamino)-1-methyl-H-pyrrolo[3,2-c]pyridine-7-carboxylic acid isobutyl-amide hydrochloride 4-(3-Chloro-phenylamino)-1-methyl-H-pyrrolo[3,2-c]pyridine-7-carboxylic acid isobutyl-amide (60 mg) was dissolved in ethylacetate and a few drops of 11.0M hydrochloric in diethyl ether added and the solvent evaporated to yield the title compound as a white solid (60 mg).

$^1$H-NMR (MeOD) δ 1.00 (6H, d), 1.92-2.00 (1H, m), 3.23 (2H, d), 3.86 (3H, s), 6.92 (1H, d), 7.13 (1H, d), 7.26 (1H, d), 7.35 (1H, t), 7.50 (1H, d), 7.76 (2H, d).

LC/MS [MH+] 357 consistent with molecular formula $C_{19}H_{21}{}^{35}ClN_4O$.

EXAMPLE 52a AND 52b 4-(3-Chloro-phenylamino)-1-methyl-1H-pyrrolo[3,2-c]pyridine-7-carboxylic acid cyclobutylmethyl-amide and its hydrochloride salt

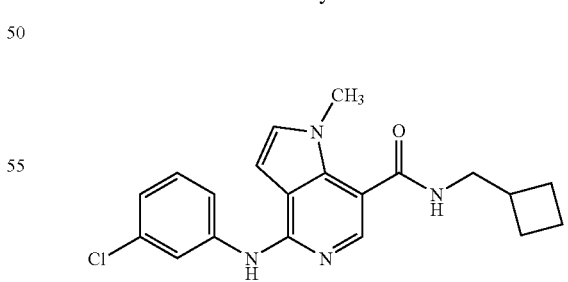

a) Prepared in a similar manner to Example 51(h), using cyclobutylmethylamine hydrochloride to yield 4-(3-chloro-phenylamino)-1-methyl-1H-pyrrolo[3,2-c]pyridine-7-carboxylic acid cyclobutylmethyl-amide as a white solid (79 mg).

LC/MS [MH+] 369 consistent with molecular formula $C_{20}H_{21}{}^{35}ClN_4O$.

b) 4-(3-Chloro-phenylamino)-1-methyl-1H-pyrrolo[3,2-c]pyridine-7-carboxylic acid cyclobutylmethyl-amide hydrochloride Prepared in a similar manner to Example 51(i) to yield the title compound as a white solid (60 mg).
$^1$H-NMR (MeOD) 1.80-1.87 (2H, m), 1.90-1.95 (2H, m), 2.11-2.16 (2H, m), 2.63-2.67 (1H, m), 3.43 (2H, d), 3.90 (3H, s), 7.03 (1H, d), 7.35-7.52 (4H, m), 7.60-7.62 (2H, m).
LC/MS [MH$^+$] 369 consistent with molecular formula $C_{20}H_{21}{}^{35}ClN_4O$.

EXAMPLE 53a AND 53b 4-(3-Chloro-phenylamino)-1-methyl-1H-pyrrolo[3,2-c]pyridine-7-carboxylic acid cyclopropylmethyl amide and its hydrochloride salt

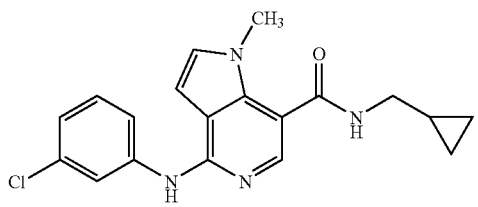

a) Prepared in a similar manner to Example 51(h), using aminomethylcyclopropane to yield 4-(3-chloro-phenylamino)-1-methyl-1H-pyrrolo[3,2-c]pyridine-7-carboxylic acid cyclopropylmethyl amide as a white solid (70 mg).
LC/MS [MH$^+$] 355 consistent with molecular formula $C_{19}H_{19}{}^{35}ClN_4O$.

b) 4-(3-Chloro-phenylamino)-1-methyl-1H-pyrrolo[3,2-c]pyridine-7-carboxylic acid cyclopropylmethyl amide hydrochloride Prepared in a similar manner to Example 51(i), to yield the title compound as a white solid (44 mg).
$^1$H-NMR (DMSO) δ 0.25-0.28 (2H, m), 0.45-0.48 (2H, m), 1.04-1.08 (1H, m), 3.16 (2H, d), 3.84 (3H, s), 7.19-7.26 (2H, m), 7.44-7.48 (2H, m), 7.60 (1H, t), 7.72-7.73 (1H, m), 7.87-7.91 (1H, m), 8.88 (1H, brs).
LC/MS [MH$^+$] 355 consistent with molecular formula $C_{19}H_{19}{}^{35}ClN_4O$.

EXAMPLE 54a AND 54b 4-(3-Chloro-phenylamino)-1-methyl-1H-pyrrolo[3,2-c]pyridine-7-carboxylic acid (tetrahydro-pyran-4-ylmethyl)-amide and its hydrochloride salt

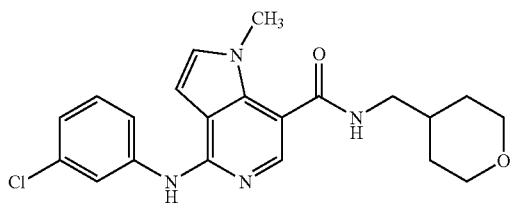

a) Prepared in a similar manner to Example 51(h), using 4-aminomethyltetrahydropyran hydrochloride and purified by trituration with dichloromethane to yield 4-(3-chloro-phenylamino)-1-methyl-1H-pyrrolo[3,2-c]pyridine-7-carboxylic acid (tetrahydro-pyran-4-ylmethyl)-amide as a white solid (56 mg).
LC/MS [H] 397 consistent with molecular formula $C_{21}H_{23}{}^{35}ClN_4O_2$.

b) 4-(3-Chloro-phenylamino)-1-methyl-1H-pyrrolo[3,2-c]pyridine-7-carboxylic acid (tetrahydro-pyran-4-ylmethyl)-amide hydrochloride Prepared in a similar manner to Example 51(i) except that the solvent used was methanol to yield the title compound as a white solid (61 mg).
$^1$H-NMR (MeOD) δ 1.29-1.42 (2H, m), 1.71-1.74 (2H, m), 1.89-1.95 (1H, m), 3.3-3.34 (2H, m), 3.40-3.45 (2H, t), 3.93-3.98 (5H, m), 7.09 (1H, d), 7.40 (1H, d), 7.47-7.49 (2H, m), 7.54-7.59 (3H, m).
LC/MS [MH$^-$] 397 consistent with molecular formula $C_{21}H_{23}{}^{35}ClN_4O_2$.

EXAMPLE 55a AND 55 b 4-(3-Chloro-phenylamino)-1-methyl-1H-pyrrolo[3,2-c]pyridine-7-carboxylic acid cyclopentylamide and its hydrochloride salt

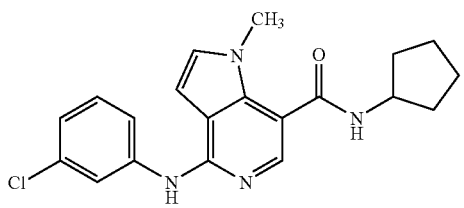

a) Prepared in a similar manner to Example 51(h), using cyclopentylamine and purified by column chromatography on Flashmaster II eluting with a 20%-70% gradient of ethyl acetate/n-hexane over 20 minutes to yield 4-(3-chloro-phenylamino)-1-methyl-1H-pyrrolo[3,2-c]pyridine-7-carboxylic acid cyclopentylamide as a pale orange solid (90 mg).
LC/MS [MH$^+$] 369 consistent with molecular formula $C_{20}H_{21}{}^{35}ClN_4O$.

b) 4-(3-Chloro-phenylamino)-1-methyl-1H-pyrrolo[3,2-c]pyridine-7-carboxylic acid cyclopentylamide hydrochloride Prepared in a similar manner to Example 51(i), to yield the title compound as a white solid (95 mg).
$^1$H-NMR (MeOD) δ 1.59-1.67 (4H, m), 1.69-1.79 (2H, m), 2.02-2.09 (2H, m), 3.90 (3H, s), 4.32-4.35 (1H, m), 7.01-7.02 (1H, d), 7.32-7.34 (1H, m), 7.38 (1H, d), 7.42-7.50 (2H, m), 7.60-7.62 (2H, m).
LC/MS [MH$^+$] 369 consistent with molecular formula $C_{20}H_{21}{}^{35}ClN_4O$.

EXAMPLE 56a AND 56b 4-(3-Chloro-phenylamino)-1-methyl-1H-pyrrolo[3,2-c]pyridine-7-carboxylic acid cyclobutylamide

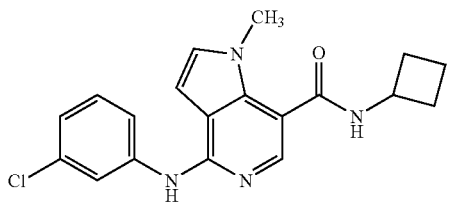

a) Prepared in a similar manner to Example 51(h), using cyclobutylamine and purified by column chromatography on Flashmaster II eluting with a 20%-70% gradient of ethyl acetate/n-hexane over 20 minutes to yield 4-(3-chloro-phenylamino)-1-methyl-1H-pyrrolo[3,2-c]pyridine-7-carboxylic acid cyclobutylamide as a off-white solid (73 mg).

LC/MS [MH+] 355 consistent with molecular formula $C_{19}H_{19}{}^{35}ClN_4O$.

b) 4-(3-Chloro-phenylamino)-1-methyl-1H-pyrrolo[3,2-c]pyridine-7-carboxylic acid cyclobutylamide hydrochloride Prepared in a similar manner to Example 51(i) to yield the title compound as a white solid (89 mg).

$^1$H-NMR (MeOD) δ 1.78-1.86 (2H, m), 2.06-2.16 (2H, m), 2.36-2.44 (2H, m), 3.91 (3H, s), 4.48-4.52 (1H, m), 7.07 (1H, d), 7.40-7.42 (1H, m), 7.48 (2H, m), 7.49-7.59 (3H, m).

LC/MS [MH+] 355 consistent with molecular formula $C_{19}H_{19}{}^{35}ClN_4O$.

EXAMPLE 57a AND 57b 4-(3-Chloro-phenylamino)-1-methyl-1H-pyrrolo[3,2-c]pyridine-7-carboxylic acid cyclohexylamide and its hydrochloride salt

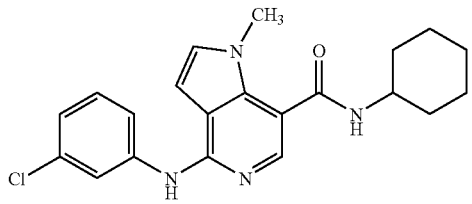

a) Prepared in a similar manner to Example 51(h), using cyclohexyl amine to yield the title compound as a white solid (73 mg)

LC/MS [MH+] 383 consistent with molecular formula $C_{21}H_{23}{}^{35}ClN_4O$.

b) 4-(3-Chloro-phenylamino)-1-methyl-1H-pyrrolo[3,2-c]pyridine-7-carboxylic acid cyclohexylamide hydrochloride Prepared in a similar manner to Example 51(i) except that the solvent used was methanol to yield the title compound as a white solid (90 mg).

$^1$H-NMR (MeOD) δ 1.19-1.45 (5H, m), 1.68-1.71 (1H, m), 1.81-1.84 (2H, m), 2.01-2.04 (2H, m), 3.85-3.91 (1H, m), 3.93 (3H, s), 7.07 (1H, d), 7.40-7.42 (1H, m), 7.47-7.57 (5H, m).

LC/MS [MH+] 381 consistent with molecular formula $C_{21}H_{23}{}^{35}ClN_4O$.

EXAMPLE 58a AND 58b 4-(3-Chloro-phenylamino)-1-methyl-1H-pyrrolo[3,2-c]pyridine-7-carboxylic acid cyclohexylmethylamine and its hydrochloride salt

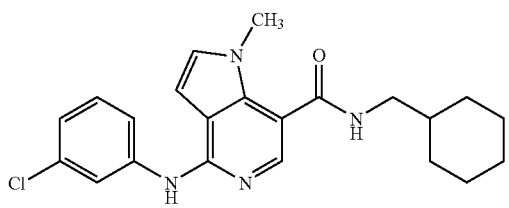

Prepared in a similar manner Example 51(h), using cyclohexylmethylamine and purified by column chromatography on Flashmaster II eluting with a 0% to 50% gradient of ethyl acetate/n-hexane over mins to yield the title compound as a white solid (84 mg)

LC/MS [MH−] 395 consistent with molecular formula $C_{22}H_{25}{}^{35}ClN_4O$.

b) 4-(3-Chloro-phenylamino)-1-methyl-1H-pyrrolo[3,2-c]pyridine-7-carboxylic acid cyclohexylmethylamine hydrochloride Prepared in a similar manner to Example 51(i), to yield the title compound as a white solid (93 mg).

$^1$H-NMR (MeOD) δ 1.02-1.08 (2H, m), 1.22-1.32 (3H, m), 1.63-1.85 (6H, m), 3.25 (2H, d), 3.90 (3H, s), 7.01 (1H, d), 7.33-7.35 (1H, m), 7.39 (1H, d), 7.43-7.50 (2H, m), 7.63 (2H, s).

LC/MS [MH+] 397 consistent with molecular formula $C_{22}H_{25}{}^{35}ClN_4O$.

EXAMPLE 59a AND 59b

1-[4-(3-Chloro-phenylamino)-1-methyl-1H-pyrrolo[3,2-c]pyridin-7-yl]-1-pyrrolidin-1-yl-methanone and it hydrochloride salt

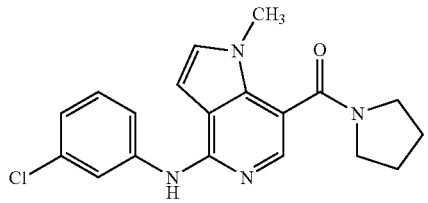

a) Prepared in a similar manner to Example 51(h), using pyrrolidine and purified by column chromatography on Flashmaster II eluting with a 30%-80% gradient of ethyl acetate/n-hexane over 20 minutes to yield 1-[4-(3-chlorophenylamino)-1-methyl-1H-pyrrolo[3,2-c]pyridin-7-yl]-1-pyrrolidin-1-yl-methanone as a white solid (89 mg).

LC/MS [MH+] 355 consistent with molecular formula $C_{19}H_{19}{}^{35}ClN_4O$.

b): 1-[4-(3-Chloro-phenylamino)-1-methyl-1H-pyrrolo[3,2-c]pyridin-7-yl]-1-pyrrolidin-1-yl-methanone hydrochloride Prepared in a similar manner to Example 51l except that the solvent used was methanol to yield the title compound as a white solid (78 mg).

$^1$H-NMR (400 MHz, MeOD) δ 1.96-2.06 (4H, m), 3.42 (2H, t), 3.67 (2H, t), 3.85 (3H, s), 7.08 (1H, d), 7.42-7.44 (1H, m), 7.48-7.50 (2H, m), 7.56-7.59 (3H, m).

LC/MS [MH−] 353 consistent with molecular formula $C_{19}H_{19}{}^{35}ClN_4O$.

EXAMPLE 60a AND 60b

1-[4-(3-Chloro-phenylamino)-1-methyl-1H-pyrrolo[3,2-c]pyridin-7-yl]-1-piperidin-1-yl-methanone and its hydrochloride salt

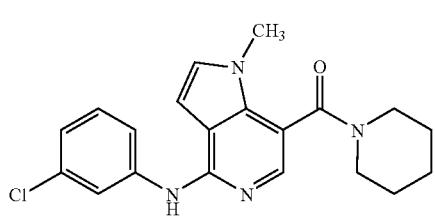

a) Prepared in a similar manner to Example 51(h) using piperidine and purified by column chromatography on Flashmaster II eluting with a 50%-100% gradient of ethyl acetate/n-hexane over 20 minutes to yield 1-[4-(3-chloro-phenylamino)-1-methyl-1H-pyrrolo[3,2-c]pyridin-7-yl]-1-piperidin-1-yl-methanone as a white solid (89 mg).

LC/MS [MH+] 369 consistent with molecular formula $C_{20}H_{21}{}^{35}ClN_4O$.

b) 1-[4-(3-Chloro-phenylamino)-1-methyl-1H-pyrrolo[3,2-c]pyridin-7-yl-]1-piperidin-1-yl-methanone hydrochloride Prepared in a similar manner to Example 51(i), except that the solvent used was methanol to yield the title compound as a white solid (92 mg).

$^1$H-NMR (MeOD) δ 1.56-1.59 (2H, m), 1.72-1.78 (4H, m), 3.44-3.48 (2H, m), 3.72-3.76 (1H, m), 3.86 (3H, s), 3.87-3.91 (1H, m), 7.08 (1H, d), 7.42-7.44 (1H, m), 7.47 (1H, s), 7.48-7.50 (2H, m), 7.55-7.59 (2H, m).

LC/MS [MH$^-$] 1367 consistent with molecular formula $C_{20}H_{21}{}^{35}ClN_4O$.

EXAMPLE 61a AND 61b

1-[4-(3-Chloro-phenylamino)-1-methyl-1H-pyrrolo[3,2-c]pyridin-7-yl]-1-(1,1-dioxo-1l$^6$-thiomorpholin-4-yl)-methanone

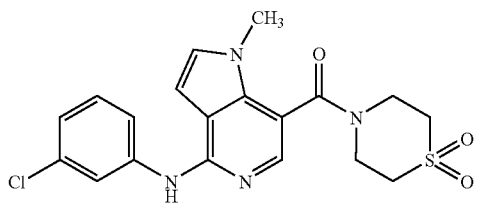

a) Prepared in a similar manner to Example 51(h) and purified by column chromatography on Flashmaster II eluting with a 30%-80% gradient of ethyl acetate/n-hexane over 20 minutes to yield 1-[4-(3-chloro-phenylamino)-1-methyl-1H-pyrrolo[3,2-c]pyridin-7-yl]-1-(1,1-dioxo-1l$^6$-thiomorpholin-4-yl)-methanone as a white solid (78 mg).

LC/MS [MH$^-$] 417 consistent with molecular formula $C_{19}H_{19}{}^{35}ClN_4O_3S$.

b) 1-[4-(3-Chloro-phenylamino)-1-methyl-1H-pyrrolo[3,2-c]pyridin-7-yl]-1-(1,1-dioxo-1l$^6$-thiomorpholin-4-yl)-methanone hydrochloride Prepared in a similar manner to Example 51(i) except that the solvent used was methanol to yield the title compound as a white solid (65 mg).

$^1$H-NMR (MeOD) δ 3.05-3.08 (1H, m), 3.30-3.32 (2H+MeOH, m), 3.41-3.44 (1H, m), 3.85 (3H, s), 3.90-3.95 (2H, m), 4.01-4.03 (1H, m), 4.67-4.70 (1H, m), 7.09 (1H, d), 7.42-7.44 (1H, m), 7.47-7.51 (2H, m), 7.55-7.59 (2H, m), 7.73 (1H, s).

LC/MS [MH$^-$] 417 consistent with molecular formula $C_{19}H_{19}{}^{35}ClN_4O_3S$.

EXAMPLE 62a AND 62b 4-(3-Chloro-phenylamino)-1-methyl-1H-pyrrolo[3,2-c]pyridine-7-carboxylic acid (2-methoxy-ethyl)-amide and its hydrochloride salt

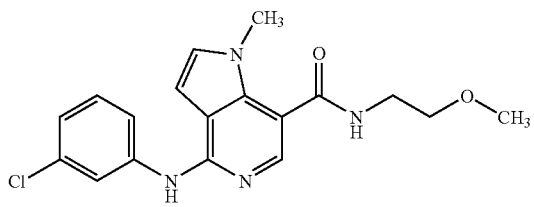

a) Prepared in a similar manner to Example 51(h) using 2-methoxyethylamine and attempted purification by column chromatography on Flashmaster II eluting with a gradient of 30%-80% ethyl acetate/n-hexane over 20 mins followed by 80%-100% over a further 5 mins however this failed to purify the compound. Purification on MDAP however yielded the title compound as a colourless gum (138 mg).

LC/MS [MH$^+$] 359 consistent with molecular formula $C_{18}H_{19}{}^{35}ClN_4O_2$.

b) 4-(3-Chloro-phenylamino)-1-methyl-1H-pyrrolo[3,2-c]pyridine-7-carboxylic acid (2-methoxy-ethyl)-amide hydrochloride Prepared in a similar manner to Example 51(i) except that the solvent used was methanol to yield the title compound as a white solid (66 mg).

$^1$H-NMR (DMSO) δ 3.29 (3H, s), 3.35-3.60 (4H+MeOH, m), 3.85 (3H, s), 7.27 (1H, d, J=4 Hz), 7.41-7.65 (6H, m), 8.96 (1H, broad s), 11.11 (1H, broad s).

LC/MS [MH$^+$] 359 consistent with molecular formula $C_{18}H_{19}{}^{35}ClN_4O_2$.

EXAMPLE 63a AND 63b 4-(3-Chloro-phenylamino)-1-methyl-1H-pyrrolo[3,2-c]pyridine-7-carboxylic acid-4-fluoro-benzylamide and its hydrochloride salt

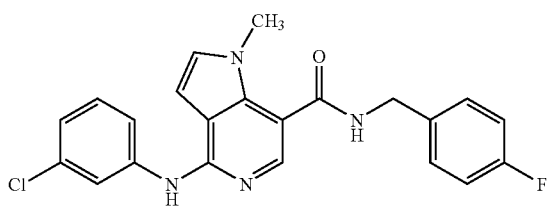

a) Prepared in a similar manner to Example 51(h) and purified on MDAP to yield the title compound as a white solid (33 mg).

LC/MS [MH$^+$] 409 consistent with molecular formula $C_{22}H_{18}{}^{35}ClFN_4O$.

b) 4-(3-Chloro-phenylamino)-1-methyl-1H-pyrrolo[3,2-c]pyridine-7-carboxylic acid-4-fluoro-benzylamide hydrochloride Prepared in a similar manner to Example 51(i) except that the solvent used was 1:1 dichloromethane/methanol to yield the title compound as a white solid (28 mg).

1H-NMR (DMSO) δ 3.77 (3H, s), 4.48 (2H, d, J=6 Hz), 7.17-7.21 (2H, m), 7.28 (1H, s), 7.38-7.50 (4H, m), 7.53-7.72 (4H, m), 9.49 (1H, broad s), 11.21 (1H, broad s).

LC/MS [MH$^+$] 409 consistent with molecular formula $C_{22}H_{11}{}^{35}ClFN_4O$

EXAMPLE 64

4-{[(3-Chloro-phenyl)-methyl-amino]-1-methyl-1H-pyrrolo[3,2-c]pyridin-7-yl}-morpholin-4-yl-methanone hydrochloride

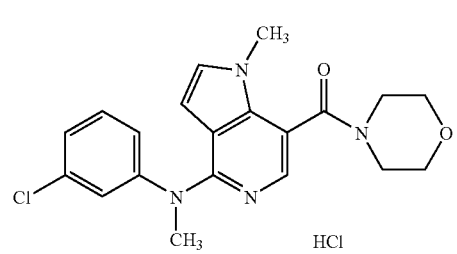

a) 4-[(3-Chloro-phenyl)-methyl-amino]-1-methyl-1H-pyrrolo[3,2-c]pyridine-7-carboxylic acid methyl ester

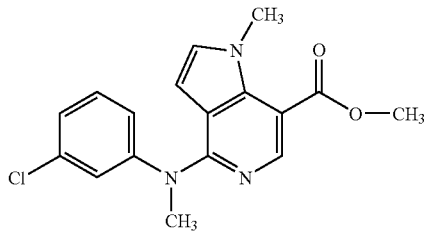

To a solution of 4-chloro-1-methyl-1H-pyrrolo[3,2-c]pyridine-7-carboxylic acid methyl ester (0.5 g) in 1,4-dioxane (5 ml) was added 3-chloro-N-methyl aniline (0.629 g) and methanesulfonic acid (0.289 ml). The mixture was irradiated under microwave conditions at 180° C. for 30 min. 1,4-dioxane was removed in vacuo and the residue purified by MDAP to give the title compound (350 mg).

LC/MS [MH$^+$] 330 consistent with molecular formula $C_{17}H_{16}{}^{35}ClN_3O_2$ b) 4-[(3-Chloro-phenyl)-methyl-amino]-1-methyl-1H-pyrrolo[3,2-pyrrolo[3,2-c]pyridine-7-carboxylic acid

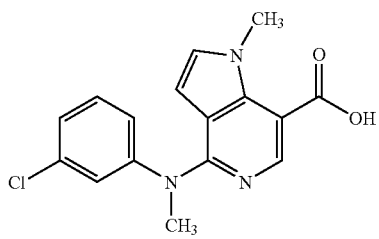

To a solution of 4-[(3-chloro-phenyl)-methyl-amino]-1-methyl-1H-pyrrolo[3,2-c]pyridine-7-carboxylic acid methyl ester (350 mg) in methanol (20 ml), was added aqueous 2M sodium hydroxide solution (2 ml) and the mixture was heated to reflux for 4 hours. The methanol was removed under vacuo and the residue was taken up into water (50 ml) and acidified to pH1 using aqueous 2M hydrochloric acid. Solid sodium chloride was added to saturate the aqueous phase, the solution was extracted with tetrahydrofuran (2×50 ml). The tetrahydrofuran layers were combined and evaporated under vacuo to give the title compound (332 mg)

LC/MS [MH$^+$] 316 consistent with molecular formula $C_{16}H_{14}{}^{35}ClN_3O_2$ NMR (d$^6$-DMSO) δ 3.64 (3H, s), 3.87 (3H, s), 5.11 (1H, d), 7.21 (1H, d), 7.37-7.40 (1H, m), 7.43-7.60 (3H, m), 8.27 (1H, s), 13.00-13.80 (1H, acid proton broad peak)

c) 4-{[(3-Chloro-phenyl)-methyl-amino]-1-methyl-1-pyrrolo[3,2-c]pyridin-7-yl}-morpholin-4-yl-methanone hydrochloride

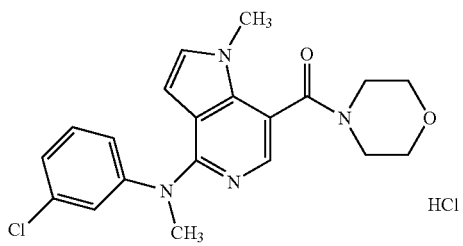

To a solution of 4-[(3-chloro-phenyl)-methyl-amino]-1-methyl-1H-pyrrolo[3,2-c]pyridine-7-carboxylic acid (50 mg), in dimethylformamide (1 ml) was added 1[3-(dimethylamino)propyl]-3-ethylcarbodiimide (35 mg), 1-hydroxybenzotriazole (26 mg), N-ethylmorpholine (250 μl), and morpholine (30 μl). The mixture was stirred at room temperature overnight. The dimethylformamide was evaporated and the residue was purified by MDAP to give the title compound. This was treated with 4M HCl in dioxane and then freeze dried to give the hydrochloride (23 mg).

LC/MS [MH$^+$] 385 consistent with molecular formula $C_{20}H_{21}N_4{}^{35}ClO_2$ NMR (MeOD) δ 3.49-3.88 (14H, m), 5.37 (1H, d), 6.93 (1H, d), 7.10-7.31 (3H, m), 7.34(1H, t), 7.81 (1H, s).

EXAMPLE 65

4-{[(3-Chloro-phenyl)-methyl-amino]-1-methyl-1H-pyrrolo[3,2-c]pyridin-7-yl}-piperidin-1-yl-methanone hydrochloride

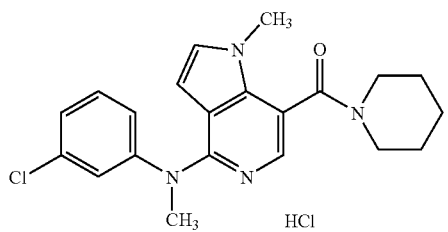

Prepared in a similar manner to Example 64 (c) using 4-[(3-chloro-phenyl)-methyl-amino]-1-methyl-1H-pyrrolo[3,2-pyrrolo[3,2-c]pyridine-7-carboxylic acid (50 mg) and piperidine (32 ul) to give the title compound (31 mg).

LC/MS [MH$^+$] 383 consistent with molecular formula $C_{21}H_{23}{}^{35}ClN_4O$ NMR (MeOD) δ 1.56-1.58 (2H, m), 1.72-1.78 (4H, m), 3.41-3.48 (2H, m) 3.56 (3H, s), 3.70 (4H, m), 3.76-3.91(1H, m), 5.39-5.40 (1H, d), 6.97-6.98(1H, d), 7.13-7.23 (3H, m), 7.33-7.35 (1H, t), 7.77(1H, s).

EXAMPLE 66

4-[(3-Chloro-phenyl)-methyl-amino]-1-methyl-1H-pyrrolo[3,2-c]pyridine-7-carboxylic acid cyclobutylamide hydrochloride

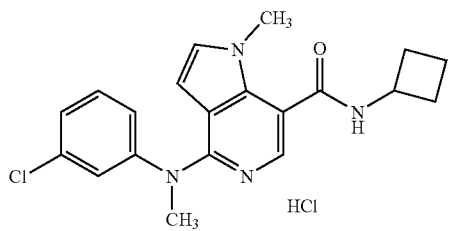

Prepared in a similar manner to Example 64 (c) using 4-[(3-chloro-phenyl)-methyl-amino]-1-methyl-1H-pyrrolo[3,2-pyrrolo[3,2-c]pyridine-7-carboxylic acid (50 mg) and cyclobutylamine (27 ul) to give the title compound (38 mg).

LC/MS [MH$^+$] 369 consistent with molecular formula $C_{20}H_{21}{}^{35}ClN_4O$ NMR (MeOD) δ 1.80-1.83 (2H, m), 2.08-2.14 (2H, m), 2.38-2.41 (2H, m), 3.56(3H, s), 3.75 (3H, s), 4.50-4.54 (1H, m) 5.41-5.42 (1H, d), 6.96-6.97 (1H, d), 7.12-7.23 (3H, m), 7.33-7.37 (1H, t), 7.92(1H, s).

EXAMPLE 67

4-[(3-Chloro-phenyl)-methyl-amino]-1-methyl-1H-pyrrolo[3,2-c]pyridine-7-carboxylic acid cyclobutyl-methyl amide hydrochloride

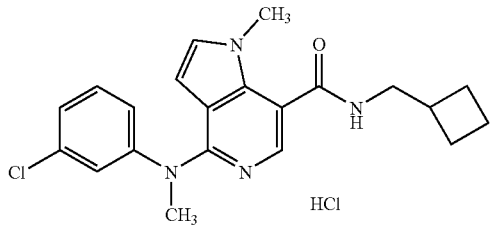

Prepared in a similar manner to Example 64 (c) using 4-[(3-chloro-phenyl)-methyl-amino]-1-methyl-1H-pyrrolo[3,2-pyrrolo[3,2-c]pyridine-7-carboxylic acid (50 mg) and cyclobutylmethyl amine (27 ul) to give the title compound (38 mg).

LC/MS [MH$^+$] 383 consistent with molecular formula $C_{21}H_{23}{}^{35}ClN_4O$ NMR (MeOD) δ 1.81-1.95(4H, m), 2.11-2.15 (2H, m), 3.64-2.68 (1H, m), 3.43-3.45(2H, d), 3.54 (3H, s), 3.76 (3H, s), 5.41-5.42 (1H, d), 6.94-6.95 (1H, d), 7.08-7.19 (3H, m), 7.31-7.33 (1H, t), 7.94 (1H, s).

EXAMPLE 68

4-[(3-Chloro-phenyl)-methyl-amino]-1-methyl-1H-pyrrolo[3,2-c]pyridine-7-carboxylic acid (tetrahydropyran-4-ylmethyl)-amide hydrochloride

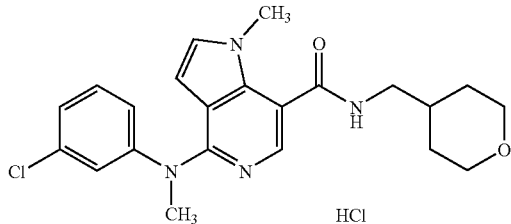

Prepared in a similar manner to Example 64 (c) using 4-[(3-chloro-phenyl)-methyl-amino]-1-methyl-1H-pyrrolo[3,2-pyrrolo[3,2-c]pyridine-7-carboxylic acid (50 mg) and tetrahydro-pyran-4-yl-methylamine (37 mg) to give the title compound (39 mg).

LC/MS [MH$^+$] 413 consistent with molecular formula $C_{22}H_{25}{}^{35}ClN_4O_2$ NMR (MeOD) δ 1.33-1.43 (2H, m), 1.72-1.76 (2H, m), 1.92-1.94 (1H, m), 3.29-3.33 (2H, m+MeOH), 3.40-3.46 (2H, m), 3.56 (3H, s), 3.77 (3H, s), 3.96-3.99 (2H, m), 5.41-5.42 (1H, d), 6.96-6.97 (1H, d), 7.12-7.16 (3H, m), 7.33-7.37 (1H, m), 7.95 (1H, s)

EXAMPLE 69

4-[(3-Chloro-phenyl)-methyl-amino]-1-methyl-1H-pyrrolo[3,2-c]pyridin-7-yl}-(dioxo-1l$^6$-thiomorpholin-4-yl)-methanone hydrochloride

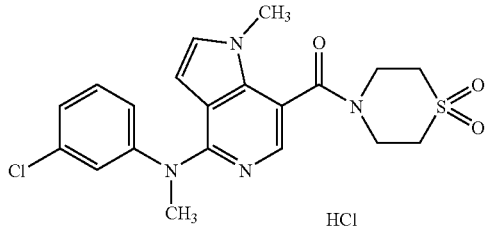

Prepared in a similar manner to Example 64 (c) using 4-[(3-chloro-phenyl)-methyl-amino]-1-methyl-1H-pyrrolo[3,2-pyrrolo[3,2-c]pyridine-7-carboxylic acid (50 mg) and thiomorpholine 1,1-dioxide (43 mg) to give the title compound (24 mg).

LC/MS [MH$^+$] 433 consistent with molecular formula $C_{20}H_{21}{}^{35}ClN_4O_3S$ NMR ($\square^6$-DMSO) δ 3.65-3.67 (6H, m), 3.75-4.25 (4H, m), 3.00-3.50 (4H, m), 5.12 (1H, d), 7.31 (1H, d), 7.46-7.64 (4H, m), 8.07 (1H, s)

EXAMPLE 70

7-[(3-Chloro-phenyl)(methyl)amino]-3-methyl-1H-pyrrolo[2,3-c]pyridine-4-carboxylic acid (tetrahydro-pyran-4-ylmethyl)-amide hydrochloride salt

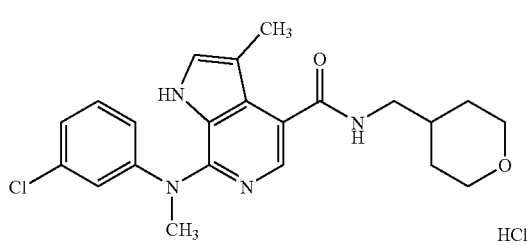

A mixture of 7-chloro-3-methyl-4-[(tetrahydro-pyran-4-ylmethyl)-carbamoyl)]-pyrrolo[2,3-c]pyridine-1-carboxylic acid tert-butyl ester (100 mg) and 3-chloro-N-methylaniline (0.5 ml) in 1,4-dioxane (1 ml) was heated under microwave conditions at 180° C. for 10 hours. The reaction mixture was purified by Biotage chromatography over silica gel (40 g), eluting with hexane followed by 2% methanol/dichloromethane followed by 5% methanol/dichloromethane. The residue was purified further by Biotage chromatography over silica gel (50 g), eluting with 3% methanol/dichloromethane. The residue was dissolved in dichloromethane and treated with a solution of 1M hydrochloric acid in diethyl ether (10 drops). The solution was evaporated to afford the title compound as an off-white solid (31 mg).

LC/MS [MH$^+$] 413 consistent with molecular formula $C_{22}H_{25}{}^{35}ClN_4O_2$

EXAMPLE 71

1-[{7-(3-Chloro-phenyl)(methyl)amino}-3-methyl-1H-pyrrolo[2,3-c]pyridin-4-yl]-1-morpholin-4-yl-methanone hydrochloride salt

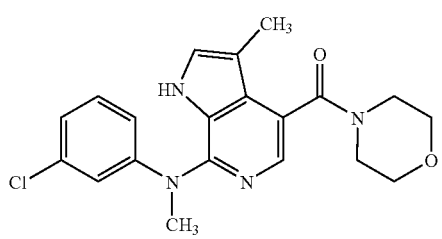

To a solution of 3-chloro-N-methylaniline (187 mg) in 1,4-dioxane (1 ml) was added portionwise sodium hydride (60% dispersed in mineral oil, 53 mg). When effervescence had ceased, a solution of 7-chloro-3-methyl-4-(1-morpholin-4-yl-methanoyl)-pyrrolo[2,3-c]pyridine-1-carboxylic acid tert-butyl ester in 1,4-dioxane (1 ml) was added and the solution was heated under microwave conditions at 180° C. for 1 hour. The 1,4-dioxane was evaporated and the residue dissolved in ethyl acetate (40 ml). The organic layer was then washed with 5% sodium hydrogen carbonate solution (25 ml) and water (2×25 ml). The organic layer was dried (MgSO$_4$) and evaporated. The residue was purified by Biotage chromatography over silica gel (50 g), eluting with hexane followed by 50% ethyl acetate/hexane followed by ethyl acetate. The residue was dissolved in ethyl acetate (10 ml) and treated with a solution of 1M hydrochloric acid in diethyl ether (10 drops). The solution was evaporated to afford the title compound as a pale orange solid (9 mg).

LC/MS [M-H] 383 consistent with molecular formula $C_{20}H_{21}^{35}ClN_4O_2$

EXAMPLE 72

1-[7-(2-Methoxy-phenylamino)-3-methyl-1H-pyrrolo[2,3-c]pyridin-4-yl]-1-morpholin-4-yl-methanone hydrochloride salt

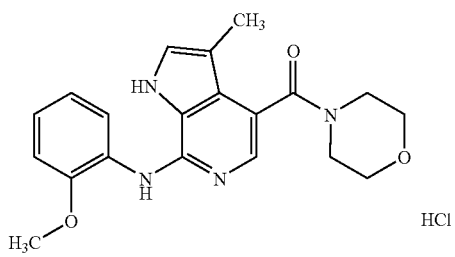

A mixture of 7-chloro-3-methyl-4-(1-morpholin-4-yl-methanoyl)-pyrrolo[2,3-c]pyridine-1-carboxylic acid tert-butyl ester (120 mg), o-anisidine (71 ul), and methanesulfonic acid (41 μl) in 1,4-dioxane (2 ml) was heated under microwave conditions at 180° C. for 30 minutes. The solid mass obtained was dissolved in methanol, transferred to a round bottom flask and evaporated. The residue was dissolved in dichloromethane (40 ml) and washed with 5% sodium hydrogen carbonate solution (2×10 ml) and water (2×10 ml). The organic layer was dried (MgSO$_4$) and evaporated to give a brown oil. The residue was purified by Biotage chromatography over silica gel (9 g), eluting with hexane followed by 25% ethyl acetate/hexane followed by 50% ethyl acetate/hexane. The residue was dissolved in ethyl acetate (10 ml) and treated with a solution of 1M hydrochloric acid in diethyl ether (10 drops). The resultant solid precipitate was then filtered off, sucked dry then dried at 40° C. under vacuum to afford the title compound (56 mg).

LC/MS [MH$^+$] 367 consistent with molecular formula $C_{20}H_{22}N_4O_3$

EXAMPLE 73

1-[7-(2-Chloro-phenylamino)-3-methyl-1H-pyrrolo[2,3-c]pyridin-4-yl]-1-morpholin-4-yl-methanone hydrochloride salt

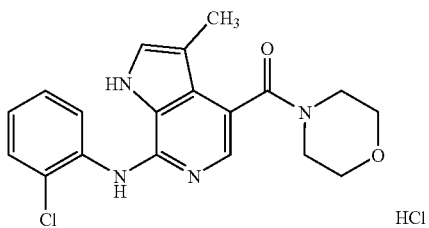

Prepared in a similar manner to Example 72 using 2-chloroaniline heating for 1 hour. Purified by Biotage chromatography over silica gel (9 g), eluting with 50% ethyl acetate/hexane.

LC/MS [MH$^+$] 371 consistent with molecular formula $C_{19}H_{19}^{35}ClN_4O_2$

EXAMPLE 74

1-[7-(5-Chloro-2-methoxy-phenylamino)-3-methyl-1H-pyrrolo[2,3-c]pyridin-4-yl]-1-morpholin-4-yl-methanone hydrochloride salt

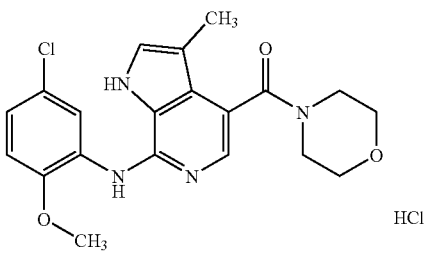

Prepared in a similar manner to Example 72 using 5-chloro-2-methoxyaniline except that purification was by trituration with diethyl ether and the hydrochloride salt was formed by dissolving in methanol and treating with a solution of 1M hydrochloric acid in diethyl ether (10 drops). The mixture was evaporated, triturated with diethyl ether and filtered off then dried at 40° C. under vacuum.

LC/MS [MH$^+$] 401 consistent with molecular formula $C_{20}H_{21}^{35}ClN_4O_3$

EXAMPLE 75

1-[7-(3-Isopropyl-phenylamino)-3-methyl-1H-pyrrolo[2,3-c]pyridin-4-yl]-1-morpholin-4-yl-methanone hydrochloride salt

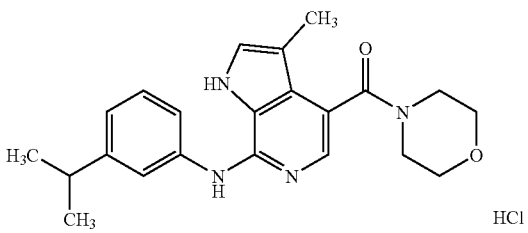

Prepared in a similar manner to Example 72 using 3-isopropylaniline. Purified by Biotage chromatography over silica gel (9 g), eluting with ethyl acetate.

LC/MS [MH$^+$] 379 consistent with molecular formula $C_{22}H_{26}N_4O_2$

EXAMPLE 76

1-[7-(3-Methoxy-phenylamino)-3-methyl-1H-pyrrolo[2,3-c]pyridin-4-yl]-1-morpholin-4-yl-methanone hydrochloride salt

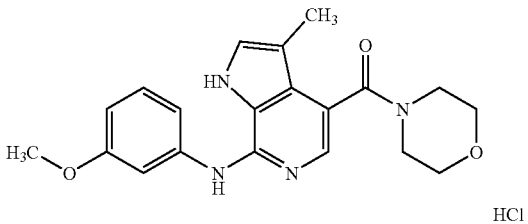

Prepared in a similar manner to Example 72 using m-anisidine heating for 1 hour. Purified by Biotage chromatography over silica gel (9 g), eluting with 80% ethyl acetate/hexane.

LC/MS [MH+] 367 consistent with molecular formula $C_{20}H_{22}N_4O_3$

EXAMPLE 77

1-[7-(3-Cyano-phenylamino)-3-methyl-1H-pyrrolo[2,3-c]pyridin-4-yl]-1-morpholin-4-yl-methanone hydrochloride salt

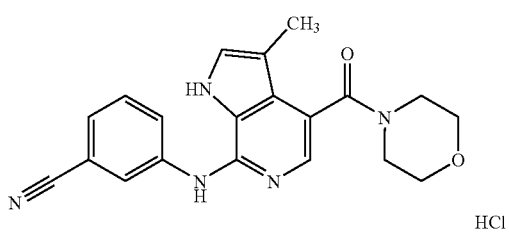

Prepared in a similar manner to Example 72 using 3-cyanoaniline heating for 1 hour. Purified by Biotage chromatography over silica gel (9 g), eluting with 80% ethyl acetate/hexane.

LC/MS [MH+] 362 consistent with molecular formula $C_{20}H_{19}N_5O_2$

EXAMPLE 78

1-[7-(3-Trifluoromethyl-phenylamino)-3-methyl-1H-pyrrolo[2,3-c]pyridin-4-yl]-1-morpholin-4-yl-methanone hydrochloride salt

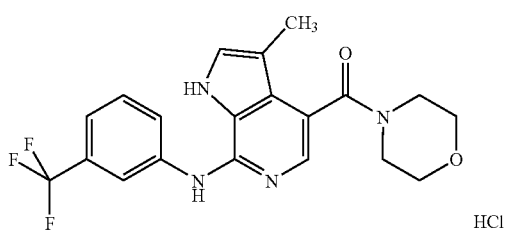

Prepared in a similar manner to Example 72 using 3-trifluoromethylaniline. Purified by Biotage chromatography over silica gel (9 g), eluting with 70% ethyl acetate/hexane.

LC/MS [MH+] 405 consistent with molecular formula $C_{20}H_{19}F_3N_4O_2$

EXAMPLE 79

1-[7-(2-Methoxy-5-trifluoromethyl-phenylamino)-3-methyl-1H-pyrrolo[2,3-c]pyridin-4-yl]-1-morpholin-4-yl-methanone hydrochloride salt

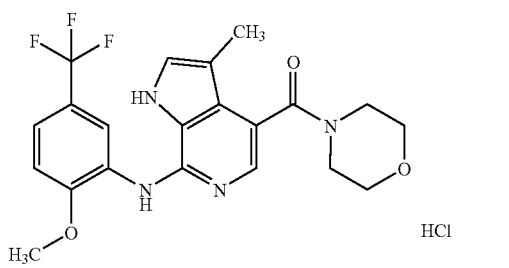

Prepared in a similar manner to Example 72 using 2-methoxy-5-trifluoromethylaniline. Purified by Biotage chromatography over silica gel (9 g), eluting with 75% ethyl acetate/hexane. Salt formation similar to Example 74.

LC/MS [MH+] 435 consistent with molecular formula $C_{21}H_{21}F_3N_4O_3$

EXAMPLE 80

1-[7-(5-Fluoro-2-methoxy-phenylamino)-3-methyl-1H-pyrrolo[2,3-c]pyridin-4-yl]-1-morpholin-4-yl-methanone hydrochloride salt

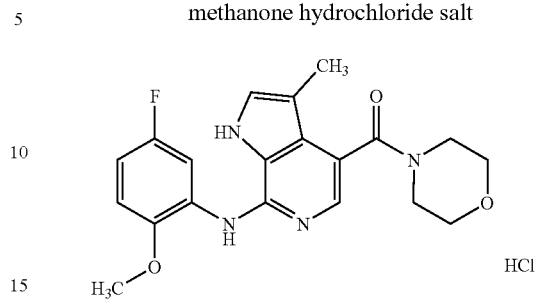

Prepared in a similar manner to Example 72 using 5-fluoro-2-methoxyaniline. Purification and salt formation similar to Example 74.

LC/MS [MH+] 385 consistent with molecular formula $C_{20}H_{21}FN_4O_3$

EXAMPLE 81

1-[7-(3-Chloro-phenylamino)-2,3-dimethyl-1H-pyrrolo[2,3-c]pyridin-4-yl]-1-morpholin-4-yl-methanone hydrochloride salt

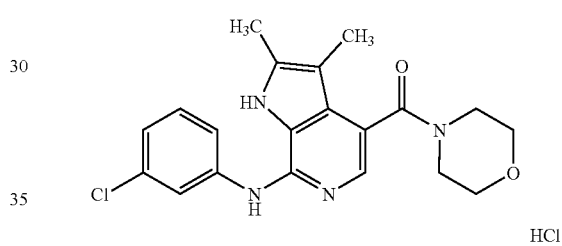

(a) 7-Chloro-4-iodo-2,3-dimethyl-1H-pyrrolo[2,3-c]pyridine

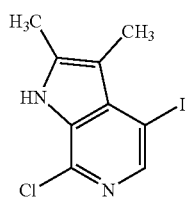

Prepared in a similar manner to Example 1 Method 2(c) using 1-methyl-1-propenylmagnesium bromide (0.5M solution in tetrahydrofuran) (142 ml) and purified by Biotage chromatography eluting with 10% ethyl acetate/hexane.

LC/MS [MH+] 307 consistent with molecular formula $C_9H_8{}^{35}ClIN_2$ (b) 7-Chloro-2,3-dimethyl-1H-pyrrolo[2,3-c]pyridine-4-carboxylic acid

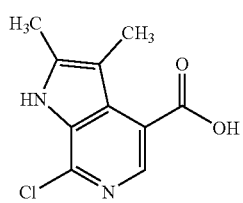

Prepared in a similar manner to Example 4(b) using three equivalents of isopropyl magnesium chloride and performing the reaction at 0° C.

LC/MS [MH⁺] 225 consistent with molecular formula $C_{10}H_9{}^{35}ClN_2O_2$

(c) 7-Chloro-2,3-dimethyl-4-(1-morpholin-4-yl-methanoyl)-pyrrolo[2,3-c]pyridine

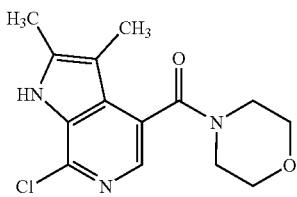

Prepared in a similar manner to Example 4(c).

LC/MS [MH⁺] 294 consistent with molecular formula $C_{14}H_{16}{}^{35}ClN_3O_2$

(d) 1-[7-(3-Chloro-phenylamino)-2,3-dimethyl-1H-pyrrolo[2,3-c]pyridin-4-yl]-1-morpholin-4-yl-methanone hydrochloride salt

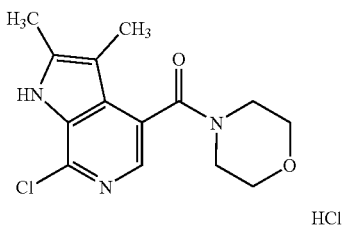

Prepared in a similar manner to Example 4(d) using 3-chloroaniline. Methanol was used instead of ethyl acetate when forming the salt.

LC/MS [MH⁺] 385 consistent with molecular formula $C_{20}H_{21}{}^{35}ClN_4O_2$

EXAMPLE 82

7-Chloro-2,3-dimethyl-1H-pyrrolo[2,3-c]pyridine-4-carboxylic acid cyclobutylmethyl-amide hydrochloride salt

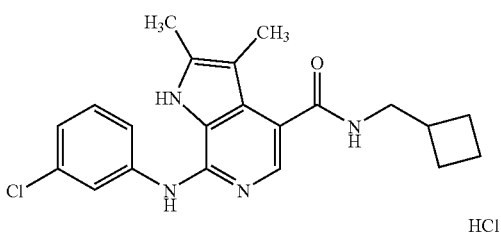

(a) 7-(3-Chloro-phenylamino)-2,3-dimethyl-1H-pyrrolo[2,3-c]pyridine-4-carboxylic acid cyclobutyl-methyl-amide

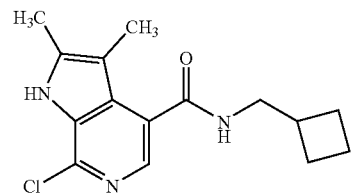

Prepared in a similar manner to Example 4(c) from 7-chloro-2,3-dimethyl-1H-pyrrolo[2,3-c]pyridine-4-carboxylic acid and 1-cyclobutylmethanamine.

LC/MS [MH⁺] 292 consistent with molecular formula $C_{15}H_{18}{}^{35}ClN_3O$

(b) 7-Chloro-2,3-dimethyl-1H-pyrrolo[2,3-c]pyridine-4-carboxylic acid cyclobutylmethyl-amide hydrochloride salt

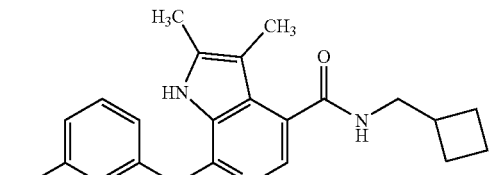

Prepared in a similar manner to Example 4(d) using 3-chloroaniline. Methanol was used instead of ethyl acetate when forming the salt.

LC/MS [MH⁺] 383 consistent with molecular formula $C_{21}H_{23}{}^{35}ClN_4O$

The following examples were prepared in a manner similar to Example 51(h) using 4-(3-chloro-phenylamino)-1-methyl-1H-pyrrolo[3,2-c]pyridine-7-carboxylic acid and the appropriate amine except that the ethyl acetate mixture washed first with 5% sodium bicarbonate then three times with water and once with saturated brine solution then dried (MgSO₄) and evaporated. Salt formation was carried out in a manner similar to Example 51i except that the salt was formed by dissolving in methanol prior to treatment with 1.0M hydrochloric acid in diethyl ether.

Example 84 was too insoluble for MDAP and was purified by trituration with diethyl ether and suspended in methanol to form the hydrochloride salt.

Example 89 precipitated out during the work up and was filtered off and washed with water and ethyl acetate.

| Example No | Structure | Compound Name | Data |
|---|---|---|---|
| 83 | 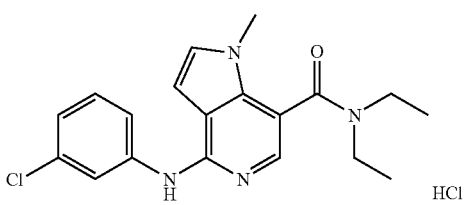 | 4-[(3-Chlorophenyl)amino]-N,N-diethyl-1-methyl-1H-pyrrolo[3,2-c]pyridine-7-carboxamide hydrochloride | LCMS [MH$^+$] 357 C$_{19}$H$_{21}$$^{35}$ClN$_4$O |
| 84 | 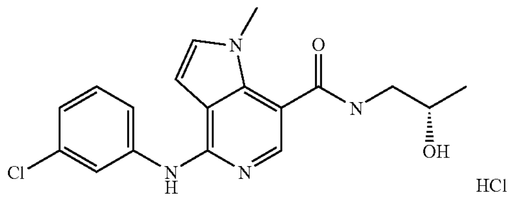 | 4-[(3-Chlorophenyl)amino]-N-[(2S)-2-hydroxypropyl]-1-methyl-1H-pyrrolo[3,2-c]pyridine-7-carboxamide hydrochloride | LCMS [MH$^+$] 359 C$_{18}$H$_{19}$$^{35}$ClN$_4$O$_2$ |
| 85 | 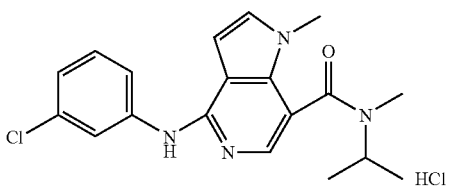 | 4-[(3-Chlorophenyl)amino]-N,1-dimethyl-N-(1-methylethyl)-1H-pyrrolo[3,2-c]pyridine-7-carboxamide hydrochloride | LCMS [MH$^+$] 357 C$_{19}$H$_{21}$$^{35}$ClN$_4$O |
| 86 | 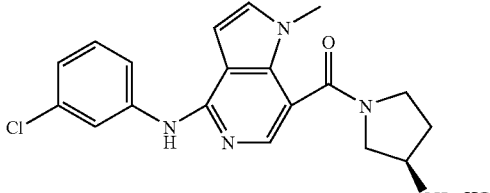 | (3R)-1-({4-[(3-Chlorophenyl)amino]-1-methyl-1H-pyrrolo[3,2-c]pyridin-7-yl}carbonyl)-3-pyrrolidinol hydrochloride | LCMS [MH$^+$] 371 C$_{19}$H$_{19}$$^{35}$ClN$_4$O$_2$ |
| 87 | 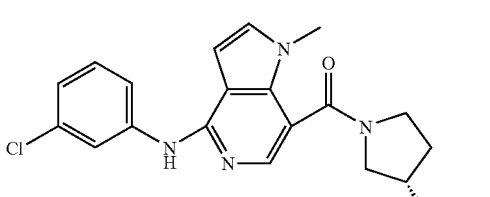 | (3S)-1-({4-[(3-Chlorophenyl)amino]-1-methyl-1H-pyrrolo[3,2-c]pyridin-7-yl}carbonyl)-3-pyrrolidinol hydrochloride | LCMS [MH$^+$] 371 C$_{19}$H$_{19}$$^{35}$ClN$_4$O$_2$ |
| 88 | 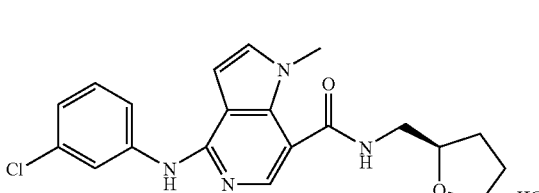 | 4-[(3-Chlorophenyl)amino]-1-methyl-N-[(2R)-tetrahydro-2-furanylmethyl]-1H-pyrrolo[3,2-c]pyridine-7-carboxamide hydrochloride | LCMS [MH$^+$] 385 C$_{20}$H$_{21}$$^{35}$ClN$_4$O$_2$ |
| 89 | 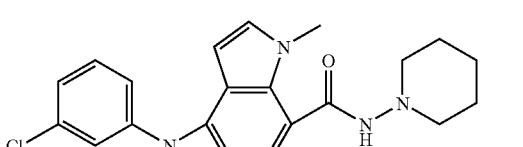 | 4-[(3-Chlorophenyl)amino]-1-methyl-N-1-piperidinyl-1H-pyrrolo[3,2-c]pyridine-7-carboxamide hydrochloride | LCMS [MH$^+$] 384 C$_{20}$H$_{22}$$^{35}$ClN$_5$O |

| Example No | Structure | Compound Name | Data |
|---|---|---|---|
| 90 | 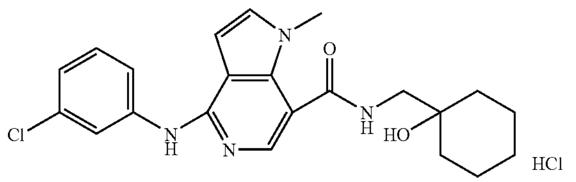 | 4-[(3-Chlorophenyl)amino]-N-[(1-hydroxycyclohexyl)methyl]-1-methyl-1H-pyrrolo[3,2-c]pyridine-7-carboxamide hydrochloride | LCMS [MH$^+$] 413 C$_{22}$H$_{25}$$^{35}$ClN$_4$O$_2$ |
| 91 | 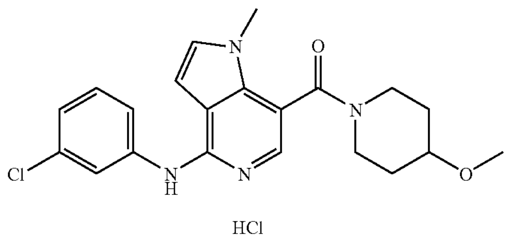 | N-(3-Chlorophenyl)-1-methyl-7-{[4-(methyloxy)-1-piperidinyl]carbonyl}-1H-pyrrolo[3,2-c]pyridin-4-amine hydrochloride | LCMS [MH$^+$] 399 C$_{21}$H$_{23}$$^{35}$ClN$_4$O$_2$ |
| 92 | 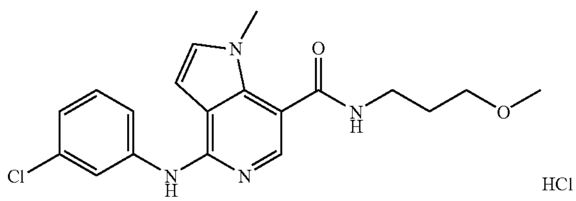 | 4-[(3-Chlorophenyl)amino]-1-methyl-N-[3-(methyloxy)propyl]-1H-pyrrolo[3,2-c]pyridine-7-carboxamide hydrochloride | LCMS [MH$^+$] 373 C$_{19}$H$_{21}$$^{35}$ClN$_4$O$_2$ |
| 93 | 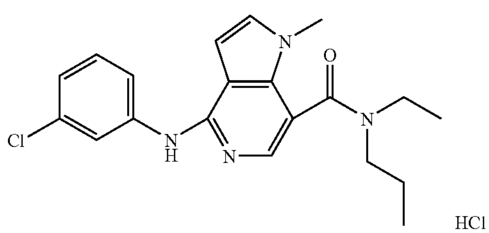 | 4-[(3-Chlorophenyl)amino]-N-ethyl-1-methyl-N-propyl-1H-pyrrolo[3,2-c]pyridine-7-carboxamide hydrochloride | LCMS [MH$^+$] 371 C$_{20}$H$_{23}$$^{35}$ClN$_4$O |
| 94 | 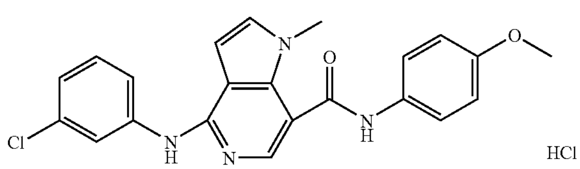 | 4-[(3-Chlorophenyl)amino]-1-methyl-N-[4-(methyloxy)phenyl]-1H-pyrrolo[3,2-c]pyridine-7-carboxamide hydrochloride | LCMS [MH$^+$] 407 C$_{22}$H$_{19}$$^{35}$ClN$_4$O$_2$ |
| 95 | 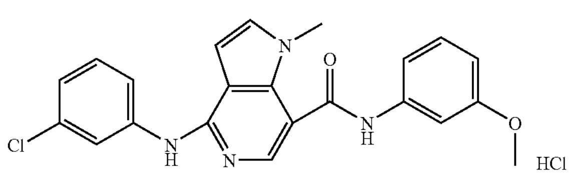 | 4-[(3-Chlorophenyl)amino]-1-methyl-N-[3-(methyloxy)phenyl]-1H-pyrrolo[3,2-c]pyridine-7-carboxamide hydrochloride | LCMS [MH$^+$] 407 C$_{22}$H$_{19}$$^{35}$ClN$_4$O$_2$ |
| 96 | 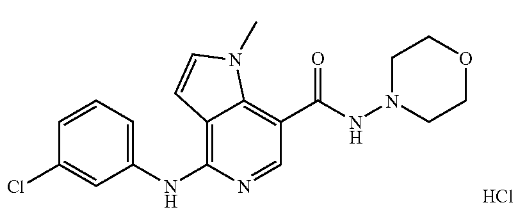 | 4-[(3-Chlorophenyl)amino]-1-methyl-N-4-morpholinyl-1H-pyrrolo[3,2-c]pyridine-7-carboxamide hydrochloride | LCMS [MH$^+$] 386 C$_{19}$H$_{20}$$^{35}$ClN$_5$O$_2$ |

-continued

| Example No | Structure | Compound Name | Data |
|---|---|---|---|
| 97 | 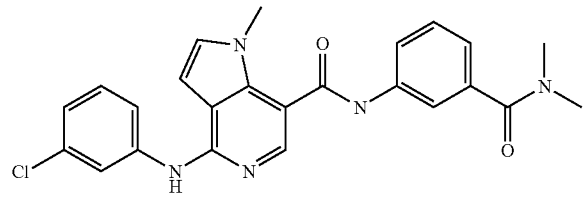 | 4-[(3-Chlorophenyl)amino]-N-{3-(dimethylamino)carbonyl]phenyl}-1-methyl-1H-pyrrolo[3,2-c]pyridine-7-carboxamide hydrochloride | LCMS [MH+] 448 $C_{24}H_{22}{}^{35}ClN_5O_2$ |
| 98 | 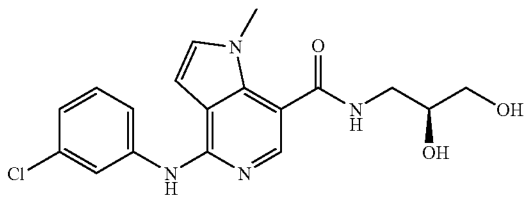 | 4-[(3-chlorophenyl)amino]-N-[(2S)-2,3-dihydroxypropyl]-1-methyl-1H-pyrrolo[3,2-c]pyridine-7-carboxamide hydrochloride | LCMS [MH+] 375 $C_{18}H_{19}{}^{35}ClN_4O_3$ |
| 99 | 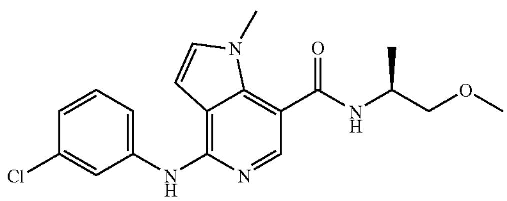 | 4-[(3-chlorophenyl)amino]-1-methyl-N-[(1S)-1-methyl-2-(methyloxy)ethyl]-1H-pyrrolo[3,2-c]pyridine-7-carboxamide hydrochloride | LCMS [MH+] 373 $C_{19}H_{21}{}^{35}ClN_4O_2$ |
| 100 | 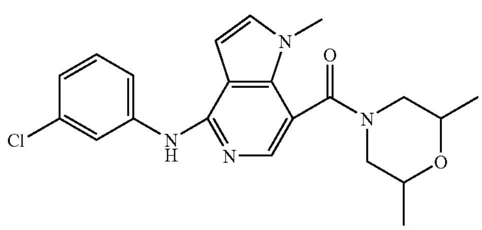 | N-(3-Chlorophenyl)-7-[(2,6-dimethyl-4-morpholinyl)carbonyl]-1-methyl-1H-pyrrolo[3,2-c]pyridin-4-amine hydrochloride | LCMS [MH+] 399 $C_{21}H_{23}{}^{35}ClN_4O_2$ |

EXAMPLE 101

N-{3-Chloro-4-[(trifluoromethyl)oxy]phenyl}-1-methyl-7-(4-morpholinylcarbonyl)-1H-pyrrolo[3,2-c]pyridin-4-amine hydrochloride

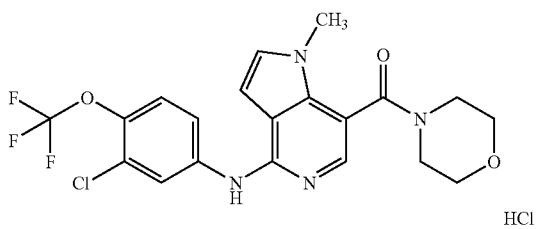

(a) 4-Chloro-1-methyl-1H-pyrrolo[3,2-c]pyridine-7-carboxylic acid

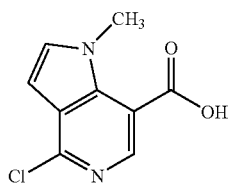

To a solution of 4-chloro-1-methyl-1H-pyrrolo[3,2-c]pyridine-7-carboxylic acid methyl ester (0.5 g), in methanol (20 ml) was added aqueous 2M sodium hydroxide solution (2 ml) and the mixture was heated to reflux for 4 hours. The methanol was evaporated and the residue was dissolved in water (50 ml) and acidified to pH 1 using aqueous 2M hydrochloric acid. Solid sodium chloride was added to saturated the aqueous phase, the solution was extracted with tetrahydrofuran (2×50 ml). The tetrahydrofuran layers were combined and evaporated to afford the title compound (460 mg).

NMR (MeOD) δ 3.95 (3H, s), 6.69 (1H, d), 7.62 (1H, d), 8.37 (1H, s), 13.60 (1H, bs).

(b) 4-Chloro-1-methyl-7-(4-morpholinylcarbonyl)-1H-pyrrolo[3,2-c]pyridine

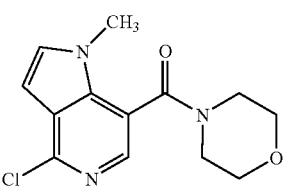

To a solution of 4-chloro-1-methyl-1H-pyrrolo[3,2-c]pyridine-7-carboxylic acid (660 mg) in dimethylformamide (10 ml) was added 1-[3-(dimethylamino)propyl]-3-ethylcarbodiimide (1.21 g), 1-hydroxybenzotriazole (0.86 g), N-ethylmorpholine (0.8 ml) and morpholine (0.55 ml). The solution was stirred at room temperature overnight. The reaction was diluted with water and extracted three times with ethyl acetate. The ethyl acetate layers were combined, washed with saturated sodium chloride solution and dried (MgSO$_4$) then evaporated to afford the title compound as an off-white solid (783 mg). This was carried through without further purification.

LC/MS [MH$^+$] 280 consistent with molecular formula $C_{13}H_{14}{}^{35}ClN_3O_2$.

(c) N-{3-Chloro-4-[(trifluoromethyl)oxy]phenyl}-1-methyl-7-(4-morpholinylcarbonyl)-1H-pyrrolo[3,2-c]pyridin-4-amine hydrochloride

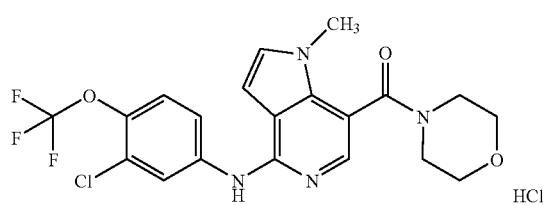

A mixture of 4-chloro-1-methyl-7-(4-morpholinylcarbonyl)-1H-pyrrolo[3,2-c]pyridine (100 mg), 3-chloro-4-(trifluoromethoxy)aniline (152 mg) and methane sulfonic acid (47 µl) in 1,4-dioxan (1.5 ml) was heated under microwave conditions at 180° C. for 30 minutes. The solvent was evaporated and the residue dissolved in dichloromethane, washed with water, dried (Na$_2$SO$_4$) and evaporated. The residue was purified by MDAP to afford the free base as a white solid (97 mg). This was dissolved in methanol and a solution of 1.0M hydrochloric acid in diethyl ether (0.3 ml) and after evaporation afforded the title compound as a white solid (100 mg).

LC/MS [MH$^+$] 455 consistent with molecular formula $C_{20}H_{18}{}^{35}ClF_3N_4O_3$.

Examples in the following table were prepared in a manner similar to Example 101 (c) from 4-chloro-1-methyl-7-(4-morpholinylcarbonyl)-1H-pyrrolo[3,2-c]pyridine and the appropriate commercially available aniline. Microwave reaction times were either 30 or 60 min. Dichloromethane or ethylacetate could be used in the aqueous work up which could be washed with saturated sodium bicarbonate prior to washing with brine and/or water and before drying with a drying agent. Examples could be purified by MDAP without the aqueous work-up and prior to treatment with 1.0M hydrochloric acid in diethyl ether, compounds could be dissolved in methanol, ethanol, ethyl acetate, methanol/dichloromethane or dichloromethane. Example 162 was purified by reverse phase column chromatography on Flashmaster II eluting with a 5%-55% gradient of acetonitrile/water.

| Example No. | Structure | Compound Name | Data |
|---|---|---|---|
| 102 | 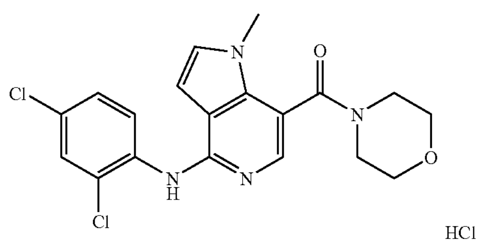 | N-(2,4-Dichlorophenyl)-1-methyl-7-(4-morpholinylcarbonyl)-1H-pyrrolo[3,2-c]pyridin-4-amine hydrochloride | LCMS [MH$^+$] 405 $C_{19}H_{18}{}^{35}Cl_2N_4O_2$ |
| 103 | 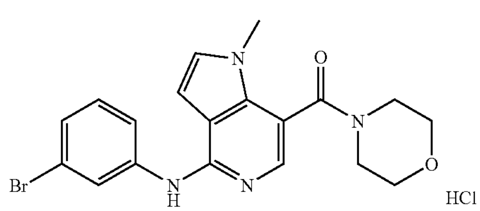 | N-(3-Bromophenyl)-1-methyl-7-(4-morpholinylcarbonyl)-1H-pyrrolo[3,2-c]pyridine-4-amine hydrochloride | LCMS [MH$^+$] 415 $C_{19}H_{19}{}^{79}BrN_4O_2$ |
| 104 | 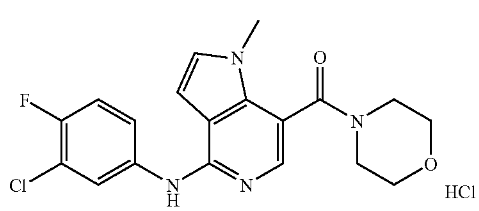 | N-(3-Chloro-4-fluorophenyl)-1-methyl-7-(4-morpholinylcarbonyl)-1H-pyrrolo[3,2-c]pyridin-4-amine hydrochloride | LCMS [MH$^+$] 389 $C_{19}H_{18}{}^{35}ClFN_4O_2$ |

-continued

| Example No. | Structure | Compound Name | Data |
|---|---|---|---|
| 105 | 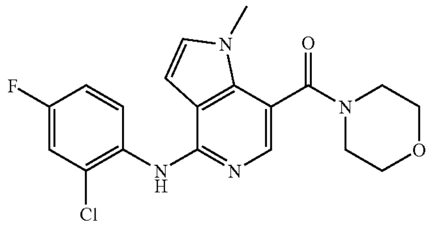 | N-(2-Chloro-4-fluorophenyl)-1-methyl-7-(4-morpholinylcarbonyl)-1H-pyrrolo[3,2-c]pyridin-4-amine hydrochloride | LCMS [MH$^+$] 389 $C_{19}H_{18}{}^{35}ClFN_4O_2$ |
| 106 | 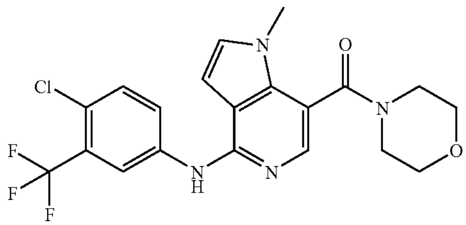 | N-[4-Chloro-3-(trifluoromethyl)phenyl]-1-methyl-7-(4-morpholinylcarbonyl)-1H-pyrrolo[3,2-c]pyridin-4-amine hydrochloride | LCMS [MH$^+$] 439 $C_{20}H_{18}{}^{35}ClF_3N_4O_2$ |
| 107 | 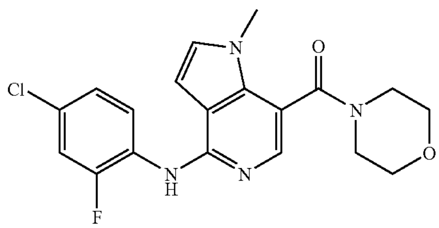 | N-(4-Chloro-2-fluorophenyl)-1-methyl-7-(4-morpholinylcarbonyl)-1H-pyrrolo[3,2-c]pyridin-4-amine hydrochloride | LCMS [MH$^+$] 389 $C_{19}H_{18}{}^{35}ClFN_4O_2$ |
| 108 | 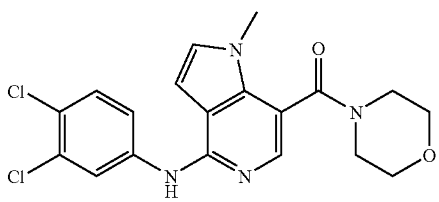 | N-(3,4-Dichlorophenyl)-1-methyl-7-(4-morpholinylcarbonyl)-1H-pyrrolo[3,2-c]pyridin-4-amine hydrochloride | LCMS [MH$^+$] 405 $C_{19}H_{18}{}^{35}Cl_2N_4O_2$ |
| 109 | 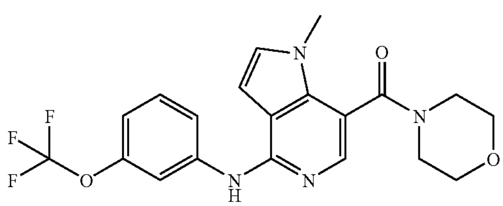 | 1-Methyl-7-(4-morpholinylcarbonyl)-N-{3-[(trifluoromethyl)oxy]phenyl}-1H-pyrrolo[3,2-c]pyridin-4-amine hydrochloride | LCMS [MH$^+$] 421 $C_{20}H_{19}F_3N_4O_3$ |
| 110 | 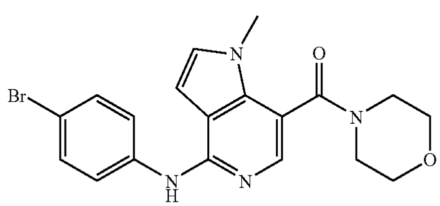 | N-(4-Bromophenyl)-1-methyl-7-(4-morpholinylcarbonyl)-1H-pyrrolo[3,2-c]pyridin-4-amine hydrochloride | LCMS [MH$^+$] 415 $C_{19}H_{19}{}^{79}BrN_4O_2$ |
| 111 | 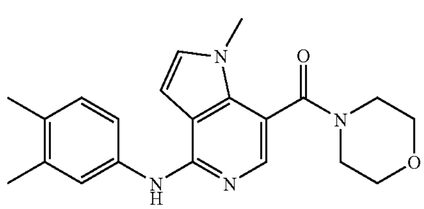 | N-(3,4-Dimethylphenyl)-1-methyl-7-(4-morpholinylcarbonyl)-1H-pyrrolo[3,2-c]pyridin-4-amine hydrochloride | LCMS [MH$^+$] 365 $C_{21}H_{24}N_4O_2$ |

| Example No. | Structure | Compound Name | Data |
|---|---|---|---|
| 112 | 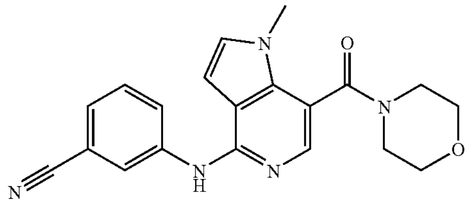 | 3-{[1-Methyl-7-(4-morpholinylcarbonyl)-1H-pyrrolo[3,2-c]pyridin-4-yl]amino}benzonitrile hydrochloride | LCMS [MH⁺] 362 $C_{20}H_{19}N_5O_2$ |
| 113 | 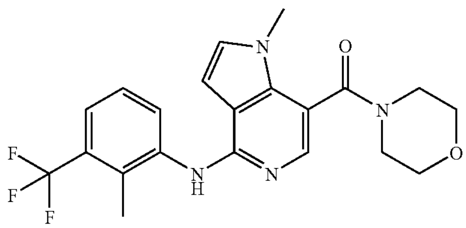 | 1-Methyl-N-[2-methyl-3-(trifluoromethyl)phenyl]-7-(4-morpholinylcarbonyl)-1H-pyrrolo[3,2-c]pyridin-4-amine hydrochloride | LCMS [MH⁺] 419 $C_{21}H_{21}F_3N_4O_2$ |
| 114 | 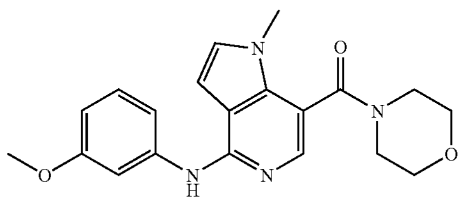 | 1-Methyl-N-[3-(methyloxy)phenyl]-7-(4-morpholinylcarbonyl)-1H-pyrrolo[3,2-c]pyridin-4-amine hydrochloride | LCMS [MH⁺] 367 $C_{20}H_{22}N_4O_3$ |
| 115 | 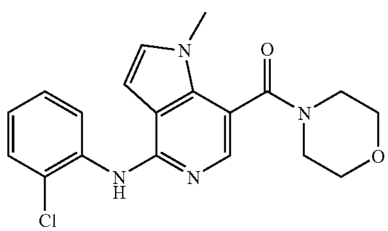 | N-(2-Chlorophenyl)-1-methyl-7-(4-morpholinylcarbonyl)-1H-pyrrolo[3,2-c]pyridin-4-amine hydrochloride | LCMS [MH⁺] 371 $C_{19}H_{19}{}^{35}ClN_4O_2$ |
| 116 | 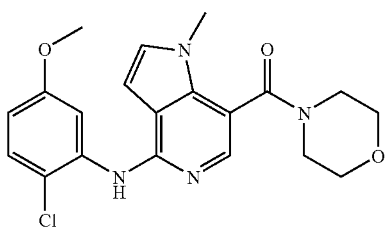 | N-[2-Chloro-5-(methyloxy)phenyl]-1-methyl-7-(4-morpholinylcarbonyl)-1H-pyrrolo[3,2-c]pyridin-4-amine hydrochloride | LCMS [MH⁺] 401 $C_{20}H_{21}{}^{35}ClN_4O_3$ |
| 117 | 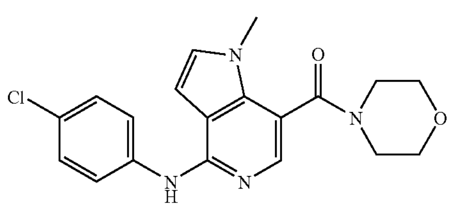 | N-(4-Chlorophenyl)-1-methyl-7-(4-morpholinylcarbonyl)-1H-pyrrolo[3,2-c]pyridin-4-amine hydrochloride | LCMS [MH⁺] 371 $C_{19}H_{19}{}^{35}ClN_4O_2$ |
| 118 | 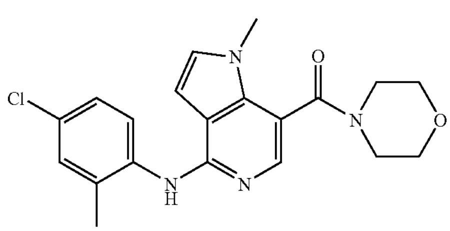 | N-(4-Chloro-2-methylphenyl)-1-methyl-7-(4-morpholinylcarbonyl)-1H-pyrrolo[3,2-c]pyridin-4-amine hydrochloride | LCMS [MH⁺] 385 $C_{20}H_{21}{}^{35}ClN_4O_2$ |

-continued

| Example No. | Structure | Compound Name | Data |
|---|---|---|---|
| 119 | 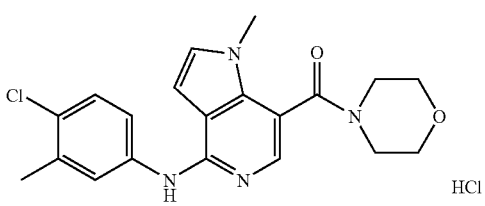 | N-(4-Chloro-3-methylphenyl)-1-methyl-7-(4-morpholinylcarbonyl)-1H-pyrrolo[3,2-c]pyridin-4-amine hydrochloride | LCMS [MH$^+$] 385 $C_{20}H_{21}{}^{35}ClN_4O_2$ |
| 120 | 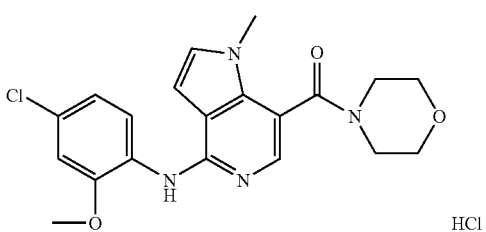 | N-[4-Chloro-2-(methyloxy)phenyl]-1-methyl-7-(4-morpholinylcarbonyl)-1H-pyrrolo[3,2-c]pyridin-4-amine hydrochloride | LCMS [MH$^+$] 401 $C_{20}H_{21}{}^{35}ClN_4O_3$ |
| 121 | 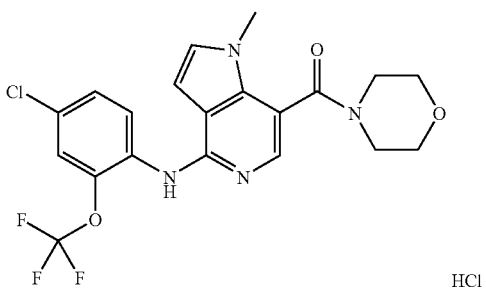 | N-{4-Chloro-2-[(trifluoromethyl)oxy]phenyl}-1-methyl-7-(4-morpholinylcarbonyl)-1H-pyrrolo[3,2-c]pyridin-4-amine hydrochloride | LCMS [MH$^+$] 455 $C_{20}H_{18}{}^{35}ClF_3N_4O_3$ |
| 122 | 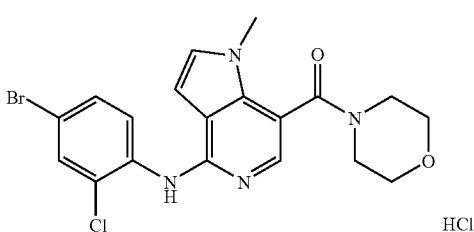 | N-(4-Bromo-2-chlorophenyl)-1-methyl-7-(4-morpholinylcarbonyl)-1H-pyrrolo[3,2-c]pyridin-4-amine hydrochloride | LCMS [MH$^+$] 451 $C_{19}H_{18}{}^{81}Br{}^{35}ClN_4O_2$ |
| 123 | 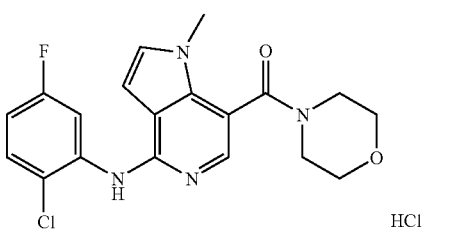 | N-(2-Chloro-5-fluorophenyl)-1-methyl-7-(4-morpholinylcarbonyl)-1H-pyrrolo[3,2-c]pyridin-4-amine hydrochloride | LCMS [MH$^+$] 389 $C_{19}H_{18}{}^{35}ClFN_4O_2$ |
| 124 | 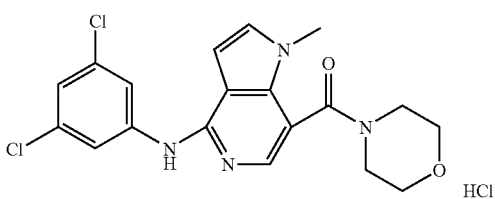 | N-(3,5-Dichlorophenyl)-1-methyl-7-(4-morpholinylcarbonyl)-1H-pyrrolo[3,2-c]pyridin-4-amine hydrochloride | LCMS [MH$^+$] 405 $C_{19}H_{18}{}^{35}Cl_2N_4O_2$ |

-continued

| Example No. | Structure | Compound Name | Data |
|---|---|---|---|
| 125 | 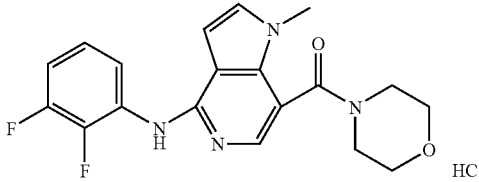 | N-(2,3-Difluorophenyl)-1-methyl-7-(4-morpholinylcarbonyl)-1H-pyrrolo[3,2-c]pyridin-4-amine hydrochloride | LCMS [MH$^+$] 373 $C_{19}H_{18}F_2N_4O_2$ |
| 126 | 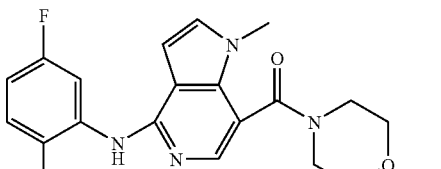 | N-(2,5-Difluorophenyl)-1-methyl-7-(4-morpholinylcarbonyl)-1H-pyrrolo[3,2-c]pyridin-4-amine hydrochloride | LCMS [MH$^+$] 373 $C_{19}H_{18}F_2N_4O_2$ |
| 127 | 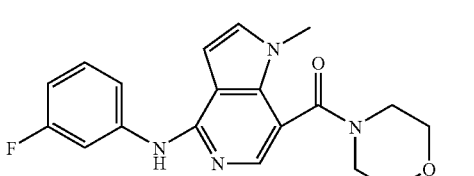 | N-(3-Fluorophenyl)-1-methyl-7-(4-morpholinylcarbonyl)-1H-pyrrolo[3,2-c]pyridin-4-amine hydrochloride | LCMS [MH$^+$] 355 $C_{19}H_{19}FN_4O_2$ |
| 128 | 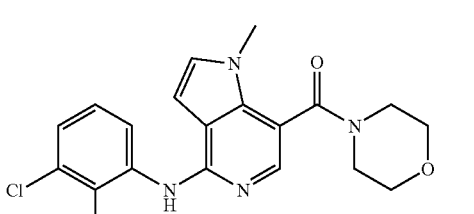 | N-(3-Chloro-2-methylphenyl)-1-methyl-7-(4-morpholinylcarbonyl)-1H-pyrrolo[3,2-c]pyridin-4-amine hydrochloride | LCMS [MH$^+$] 385 $C_{20}H_{21}{}^{35}ClN_4O_2$ |
| 129 | 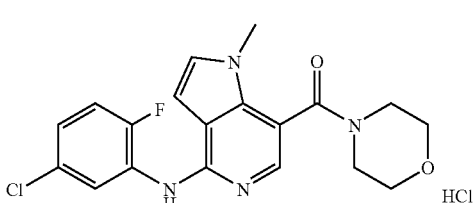 | N-(5-Chloro-2-fluorophenyl)-1-methyl-7-(4-morpholinylcarbonyl)-1H-pyrrolo[3,2-c]pyridin-4-amine hydrochloride | LCMS [MH$^+$] 389 $C_{19}H_{18}{}^{35}ClFN_4O_2$ |
| 130 | 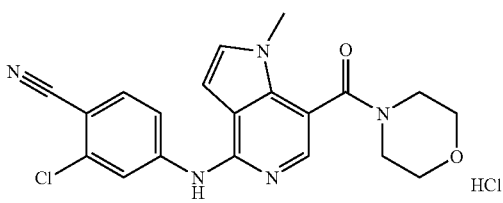 | 2-Chloro-4-{[1-methyl-7-(4-morpholinylcarbonyl)-1H-pyrrolo[3,2-c]pyridin-4-yl]amino}benzonitrile hydrochloride | LCMS [MH$^+$] 396 $C_{20}H_{18}{}^{35}ClN_5O_2$ |
| 131 | 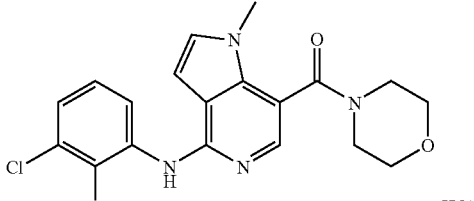 | N-(3-Chloro-2-fluorophenyl)-1-methyl-7-(4-morpholinylcarbonyl)-1H-pyrrolo[3,2-c]pyridin-4-amine hydrochloride | LCMS [MH$^+$] 389 $C_{19}H_{18}{}^{35}ClFN_4O_2$ |

-continued

| Example No. | Structure | Compound Name | Data |
|---|---|---|---|
| 132 | 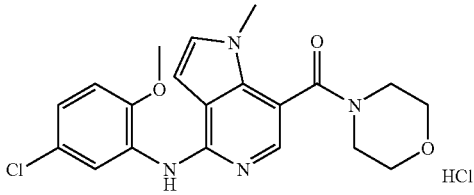 | N-[5-Chloro-2-(methyloxy)phenyl]-1-methyl-7-(4-morpholinylcarbonyl)-1H-pyrrolo[3,2-c]pyridin-4-amine hydrochloride | LCMS [MH$^+$] 401 $C_{20}H_{21}{}^{35}ClN_4O_3$ |
| 133 | 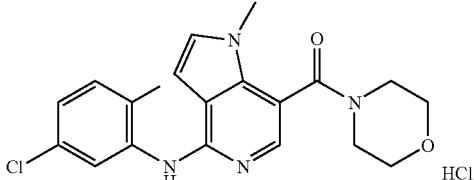 | N-(5-Chloro-2-methylphenyl)-1-methyl-7-(4-morpholinylcarbonyl)-1H-pyrrolo[3,2-c]pyridin-4-amine hydrochloride | LCMS [MH$^+$] 385 $C_{20}H_{21}{}^{35}ClN_4O_2$ |
| 134 | 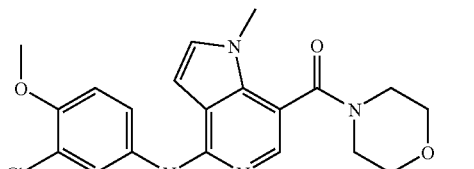 | N-[3-Chloro-4-(methyloxy)phenyl]-1-methyl-7-(4-morpholinylcarbonyl)-1H-pyrrolo[3,2-c]pyridin-4-amine hydrochloride | LCMS [MH$^+$] 401 $C_{20}H_{21}{}^{35}ClN_4O_3$ |
| 135 | 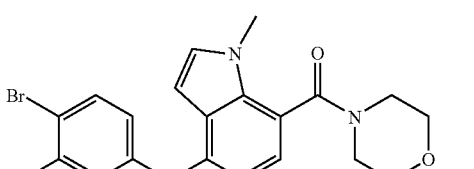 | N-(4-Bromo-3-chlorophenyl)-1-methyl-7-(4-morpholinylcarbonyl)-1H-pyrrolo[3,2-c]pyridin-4-amine hydrochloride | LCMS [MH$^+$] 451 $C_{19}H_{18}{}^{81}Br{}^{35}ClN_4O_2$ |
| 136 | 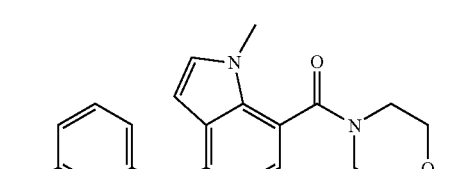 | N-[3-Chloro-2-(methyloxy)phenyl]-1-methyl-7-(4-morpholinylcarbonyl)-1H-pyrrolo[3,2-c]pyridin-4-amine hydrochloride | LCMS [MH$^+$] 401 $C_{20}H_{21}{}^{35}ClN_4O_3$ |
| 137 | 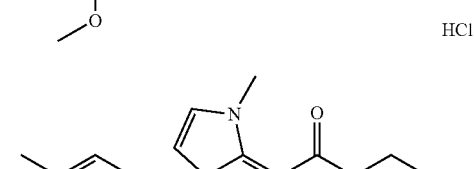 | N-(3-Chloro-4-methylphenyl)-1-methyl-7-(4-morpholinylcarbonyl)-1H-pyrrolo[3,2-c]pyridin-4-amine hydrochloride | LCMS [MH$^+$] 385 $C_{20}H_{21}{}^{35}ClN_4O_2$ |
| 138 | 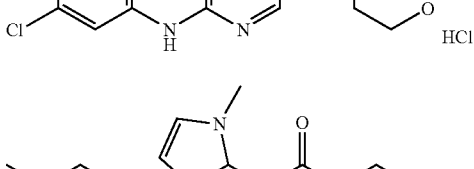 | N-(2-Chloro-4-methylphenyl)-1-methyl-7-(4-morpholinylcarbonyl)-1H-pyrrolo[3,2-c]pyridin-4-amine hydrochloride | LCMS [MH$^+$] 385 $C_{20}H_{21}{}^{35}ClN_4O_2$ |

-continued

| Example No. | Structure | Compound Name | Data |
|---|---|---|---|
| 139 | 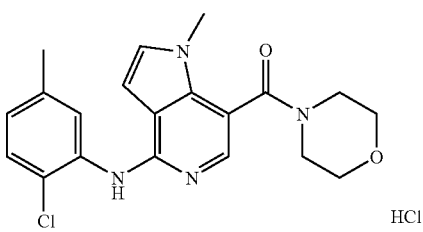 | N-(2-Chloro-5-methylphenyl)-1-methyl-7-(4-morpholinylcarbonyl)-1H-pyrrolo[3,2-c]pyridin-4-amine hydrochloride | LCMS RT = 1.66 min [MH$^+$] 385 C$_{20}$H$_{21}$$^{35}$ClN$_4$O$_2$ |
| 140 | 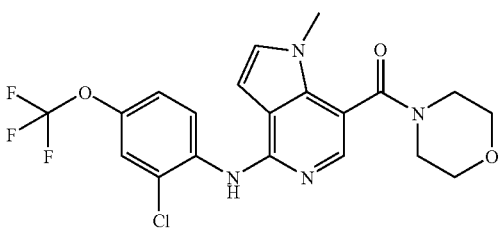 | N-{2-Chloro-4-[(trifluoromethyl)oxy]phenyl}-1-methyl-7-(4-morpholinylcarbonyl)-1H-pyrrolo[3,2-c]pyridin-4-amine hydrochloride | LCMS [MH$^+$] 455 C$_{20}$H$_{18}$$^{35}$ClF$_3$N$_4$O$_3$ |
| 141 | 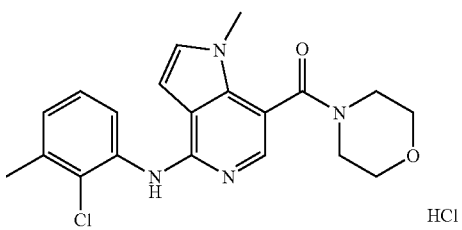 | N-(2-Chloro-3-methylphenyl)-1-methyl-7-(4-morpholinylcarbonyl)-1H-pyrrolo[3,2-c]pyridin-4-amine hydrochloride | LCMS [MH$^+$] 385 C$_{20}$H$_{21}$$^{35}$ClN$_4$O$_2$ |
| 142 | 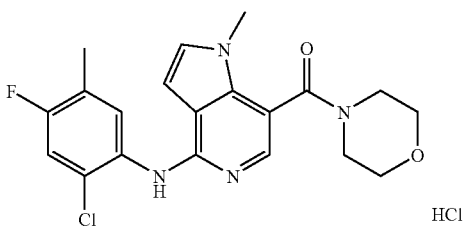 | N-(2-Chloro-4-fluoro-5-methylphenyl)-1-methyl-7-(4-morpholinylcarbonyl)-1H-pyrrolo[3,2-c]pyridin-4-amine hydrochloride | LCMS [MH$^+$] 403 C$_{20}$H$_{20}$$^{35}$ClFN$_4$O$_2$ |
| 143 | 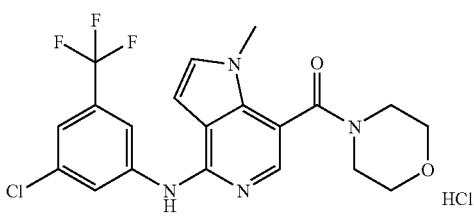 | N-[3-Chloro-5-(trifluoromethyl)phenyl]-1-methyl-7-(4-morpholinylcarbonyl)-1H-pyrrolo[3,2-c]pyridin-4-amine hydrochloride | LCMS [MH$^+$] 439 C$_{20}$H$_{18}$$^{35}$ClF$_3$N$_4$O$_2$ |
| 144 | 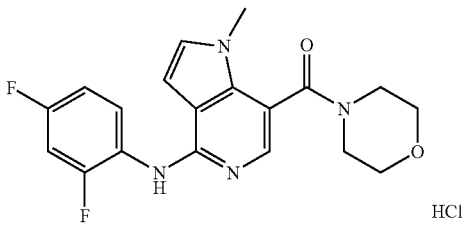 | N-(2,4-Difluorophenyl)-1-methyl-7-(4-morpholinylcarbonyl)-1H-pyrrolo[3,2-c]pyridin-4-amine hydrochloride | LCMS [MH$^+$] 373 C$_{19}$H$_{18}$F$_2$N$_4$O$_2$ |

| Example No. | Structure | Compound Name | Data |
|---|---|---|---|
| 145 | 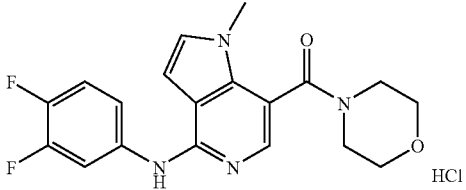 | N-(3,4-Difluorophenyl)-1-methyl-7-(4-morpholinylcarbonyl)-1H-pyrrolo[3,2-c]pyridin-4-amine hydrochloride | LCMS [MH$^+$] 373 $C_{19}H_{18}F_2N_4O_2$ |
| 146 | 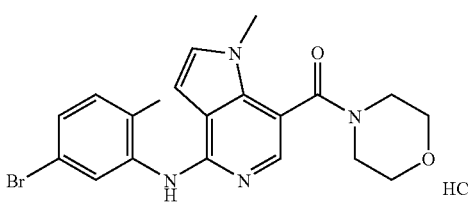 | N-(5-Bromo-2-methylphenyl)-1-methyl-7-(4-morpholinylcarbonyl)-1H-pyrrolo[3,2-c]pyridin-4-amine hydrochloride | LCMS [MH$^+$] 429 $C_{20}H_{21}{}^{79}BrN_4O_2$ |
| 147 | 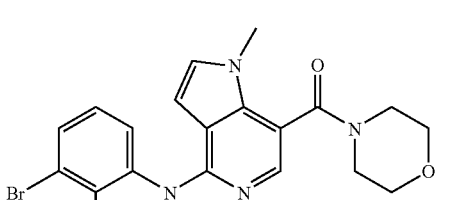 | N-(3-Bromo-2-methylphenyl)-1-methyl-7-(4-morpholinylcarbonyl)-1H-pyrrolo[3,2-c]pyridin-4-amine hydrochloride | LCMS [MH$^+$] 429 $C_{20}H_{21}{}^{79}BrN_4O_2$ |
| 148 | 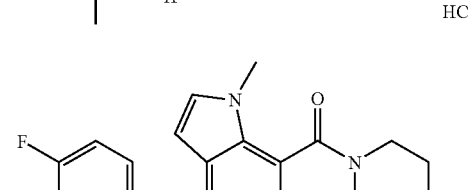 | N-(3-Bromo-4-fluorophenyl)-1-methyl-7-(4-morpholinylcarbonyl)-1H-pyrrolo[3,2-c]pyridin-4-amine hydrochloride | LCMS [MH$^+$] 433 $C_{19}H_{18}{}^{79}BrFN_4O_2$ |
| 149 | 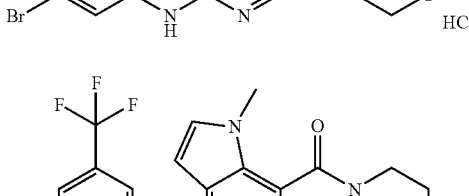 | N-[3-Bromo-5-(trifluoromethyl)phenyl]-1-methyl-7-(4-morpholinylcarbonyl)-1H-pyrrolo[3,2-c]pyridin-4-amine hydrochloride | LCMS [MH$^+$] 483 $C_{20}H_{18}{}^{79}BrF_3N_4O_2$ |
| 150 | 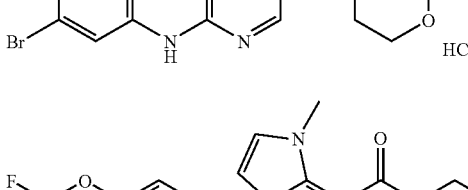 | N-{3-Bromo-4-[(trifluoromethyl)oxy]phenyl}-1-methyl-7-(4-morpholinylcarbonyl)-1H-pyrrolo[3,2-c]pyridin-4-amine hydrochloride | LCMS [MH$^+$] 499 $C_{20}H_{18}{}^{79}BrF_3N_4O_3$ |
| 151 | 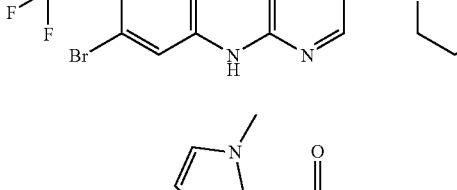 | N-(3-Bromo-4-methylphenyl)-1-methyl-7-(4-morpholinylcarbonyl)-1H-pyrrolo[3,2-c]pyridin-4-amine hydrochloride | LCMS [MH$^+$] 429 $C_{20}H_{21}{}^{79}BrN_4O_2$ |

| Example No. | Structure | Compound Name | Data |
|---|---|---|---|
| 152 | 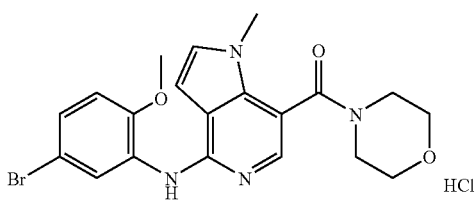 | N-[5-Bromo-2-(methyloxy)phenyl]-1-methyl-7-(4-morpholinylcarbonyl)-1H-pyrrolo[3,2-c]pyridin-4-amine hydrochloride | LCMS [MH$^+$] 445 $C_{20}H_{21}{}^{79}BrN_4O_3$ |
| 153 | 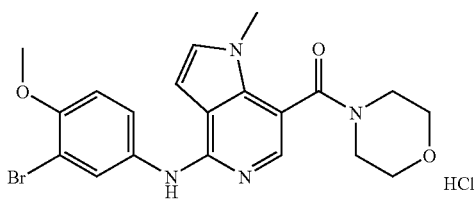 | N-[3-Bromo-4-(methyloxy)phenyl]-1-methyl-7-(4-morpholinylcarbonyl)-1H-pyrrolo[3,2-c]pyridin-4-amine hydrochloride | LCMS [MH$^+$] 445 $C_{20}H_{21}{}^{79}BrN_4O_3$ |
| 154 | 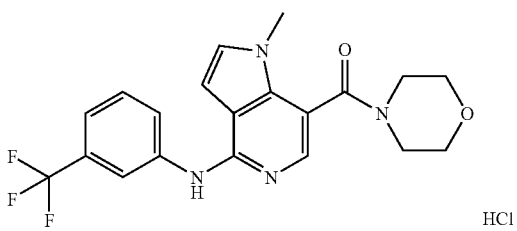 | 1-Methyl-7-(4-morpholinylcarbonyl)-N-[3-(trifluoromethyl)phenyl]-1H-pyrrolo[3,2-c]pyridin-4-amine hydrochloride | LCMS [MH$^+$] 405 $C_{20}H_{19}F_3N_4O_2$ |
| 155 | 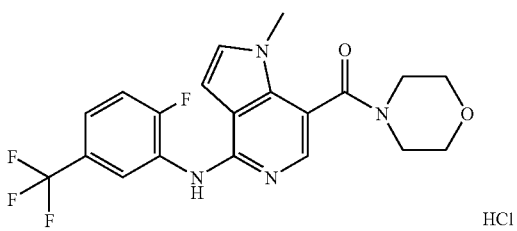 | N-[2-Fluoro-5-(trifluoromethyl)phenyl]-1-methyl-7-(4-morpholinylcarbonyl)-1H-pyrrolo[3,2-c]pyridin-4-amine hydrochloride | LCMS [MH$^+$] 423 $C_{20}H_{18}F_4N_4O_2$ |
| 156 | 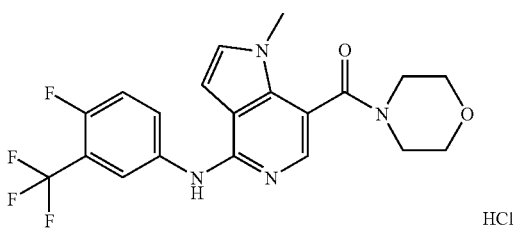 | N-[4-Fluoro-3-(trifluoromethyl)phenyl]-1-methyl-7-(4-morpholinylcarbonyl)-1H-pyrrolo[3,2-c]pyridin-4-amine hydrochloride | LCMS [MH$^+$] 423 $C_{20}H_{18}F_4N_4O_2$ |
| 157 | 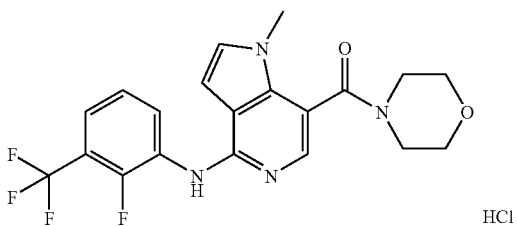 | N-[2-Fluoro-3-(trifluoromethyl)phenyl]-1-methyl-7-(4-morpholinylcarbonyl)-1H-pyrrolo[3,2-c]pyridin-4-amine hydrochloride | LCMS [MH$^+$] 423 $C_{20}H_{18}F_4N_4O_2$ |

| Example No. | Structure | Compound Name | Data |
|---|---|---|---|
| 158 | 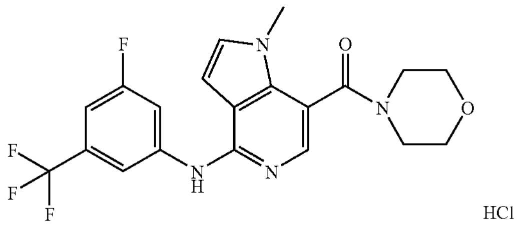 | N-[3-Fluoro-5-(trifluoromethyl)phenyl]-1-methyl-7-(4-morpholinylcarbonyl)-1H-pyrrolo[3,2-c]pyridin-4-amine hydrochloride | LCMS [MH$^+$] 423 $C_{20}H_{18}F_4N_4O_2$ |
| 159 | 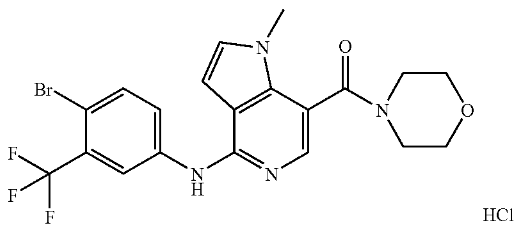 | N-[4-Bromo-3-(trifluoromethyl)phenyl]-1-methyl-7-(4-morpholinylcarbonyl)-1H-pyrrolo[3,2-c]pyridin-4-amine hydrochloride | LCMS [MH$^+$] 485 $C_{20}H_{18}{}^{81}BrF_3N_4O_2$ |
| 160 | 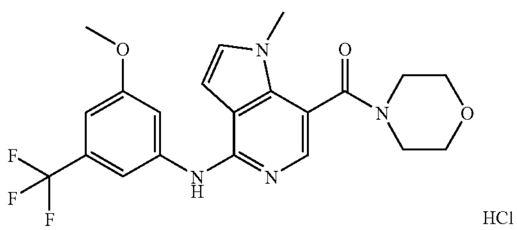 | 1-Methyl-N-[3-(methyloxy)-5-(trifluoromethyl)phenyl]-7-(4-morpholinylcarbonyl)-1H-pyrrolo[3,2-c]pyridin-4-amine hydrochloride | LCMS [MH$^+$] 435 $C_{21}H_{21}F_3N_4O_3$ |
| 161 | 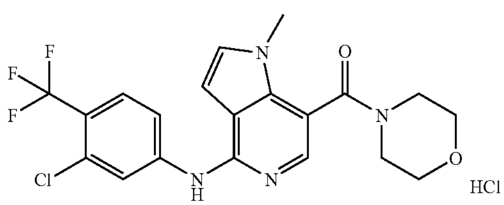 | N-[3-Chloro-4-(trifluoromethyl)phenyl]-1-methyl-7-(4-morpholinylcarbonyl)-1H-pyrrolo[3,2-c]pyridin-4-amine hydrochloride | LCMS [MH$^+$] 439 $C_{20}H_{18}{}^{35}ClF_3N_4O_2$ |
| 162 | 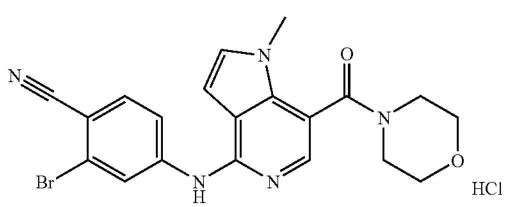 | 2-Bromo-4-{[1-methyl-7-(4-morpholinylcarbonyl)-1H-pyrrolo[3,2-c]pyridin-4-yl]amino}benzonitrile hydrochloride | LCMS [MH$^+$] 440 $C_{20}H_{18}{}^{79}BrN_5O_2$ |
| 163 | 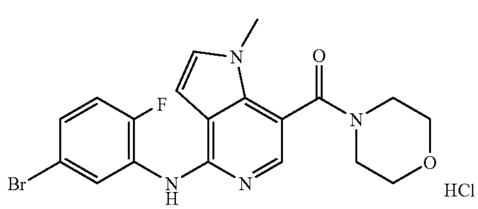 | N-(5-Bromo-2-fluorophenyl)-1-methyl-7-(4-morpholinylcarbonyl)-1H-pyrrolo[3,2-c]pyridin-4-amine hydrochloride | LCMS [MH$^+$] 433 $C_{19}H_{18}{}^{79}BrFN_4O_2$ |
| 164 | 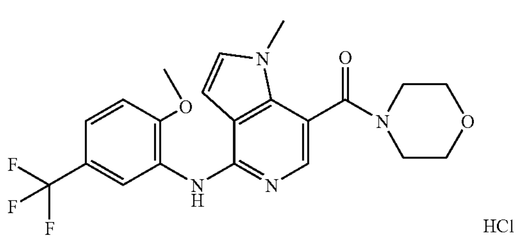 | 1-Methyl-N-[2-(methyloxy)-5-(trifluoromethyl)phenyl]-7-(4-morpholinylcarbonyl)-1H-pyrrolo[3,2-c]pyridin-4-amine hydrochloride | LCMS [MH$^+$] 435 $C_{21}H_{21}F_3N_4O_3$ |

-continued

| Example No. | Structure | Compound Name | Data |
|---|---|---|---|
| 165 | 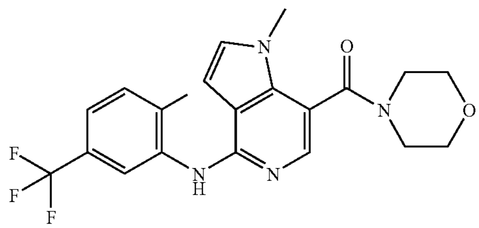 | 1-Methyl-N-[2-methyl-5-(trifluoromethyl)phenyl]-7-(4-morpholinylcarbonyl)-1H-pyrrolo[3,2-c]pyridin-4-amine hydrochloride | LCMS [MH$^+$] 419 $C_{21}H_{21}F_3N_4O_2$ |
| 166 | 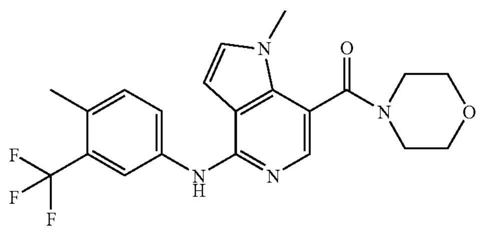 | 1-Methyl-N-[4-methyl-3-(trifluoromethyl)phenyl]-7-(4-morpholinylcarbonyl)-1H-pyrrolo[3,2-c]pyridin-4-amine hydrochloride | LCMS [MH$^+$] 419 $C_{21}H_{21}F_3N_4O_2$ |
| 167 | 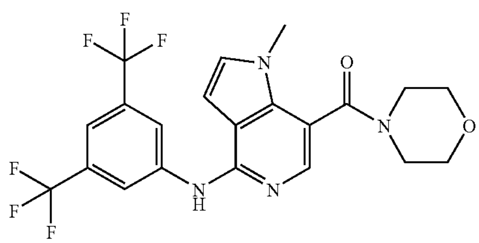 | N-[3,5-Bis(trifluoromethyl)phenyl]-1-methyl-7-(4-morpholinylcarbonyl)-1H-pyrrolo[3,2-c]pyridin-4-amine hydrochloride | LCMS [MH$^+$] 473 $C_{21}H_{18}F_6N_4O_2$ |
| 168 | 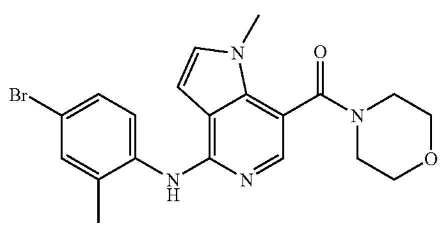 | N-(4-Bromo-2-methylphenyl)-1-methyl-7-(4-morpholinylcarbonyl)-1H-pyrrolo[3,2-c]pyridin-4-amine hydrochloride | LCMS [MH$^+$] 429 $C_{20}H_{21}^{79}BrN_4O_2$ |
| 169 | 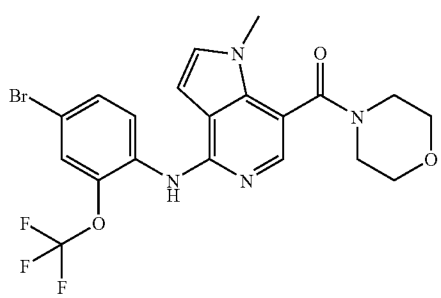 | N-{4-Bromo-2-[(trifluoromethyl)oxy]phenyl}-1-methyl-7-(4-morpholinylcarbonyl)-1H-pyrrolo[3,2-c]pyridin-4-amine hydrochloride | LCMS [MH$^+$] 499 $C_{20}H_{18}^{79}BrF_3N_4O_3$ |
| 170 | 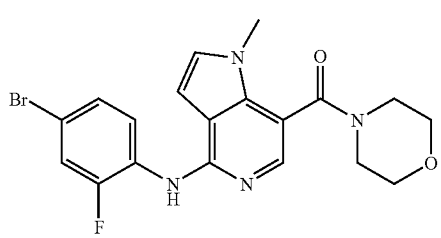 | N-(4-Bromo-2-fluorophenyl)-1-methyl-7-(4-morpholinylcarbonyl)-1H-pyrrolo[3,2-c]pyridin-4-amine hydrochloride | LCMS [MH$^+$] 433 $C_{19}H_{18}^{79}BrFN_4O_2$ |

-continued

| Example No. | Structure | Compound Name | Data |
|---|---|---|---|
| 171 | 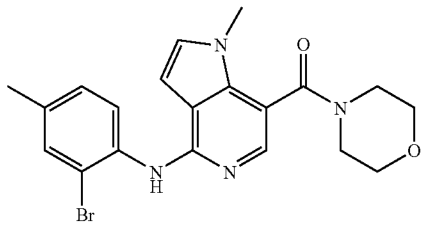 | N-(2-Bromo-4-methylphenyl)-1-methyl-7-(4-morpholinylcarbonyl)-1H-pyrrolo[3,2-c]pyridin-4-amine hydrochloride | LCMS [MH$^+$] 429 $C_{20}H_{21}{}^{79}BrN_4O_2$ |
| 172 | 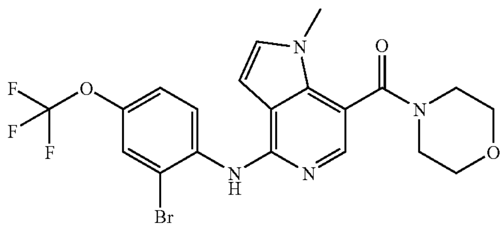 | N-{2-Bromo-4-[(trifluoromethyl)oxy]phenyl}-1-methyl-7-(4-morpholinylcarbonyl)-1H-pyrrolo[3,2-c]pyridin-4-amine hydrochloride | LCMS [MH$^+$] 499 $C_{20}H_{18}{}^{79}BrF_3N_4O_3$ |
| 173 | 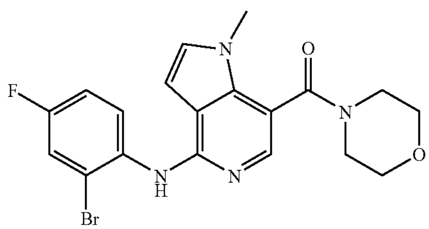 | N-(2-Bromo-4-fluorophenyl)-1-methyl-7-(4-morpholinylcarbonyl)-1H-pyrrolo[3,2-c]pyridin-4-amine hydrochloride | LCMS [MH$^+$] 433 $C_{19}H_{18}{}^{79}BrFN_4O_2$ |
| 174 | 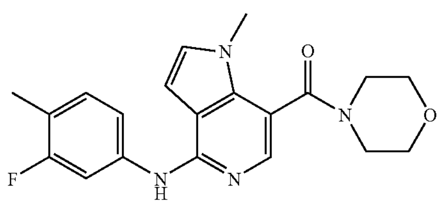 | N-(3-Fluoro-4-methylphenyl)-1-methyl-7-(4-morpholinylcarbonyl)-1H-pyrrolo[3,2-c]pyridin-4-amine hydrochloride | LCMS [MH$^+$] 369 $C_{20}H_{21}FN_4O_2$ |
| 175 | 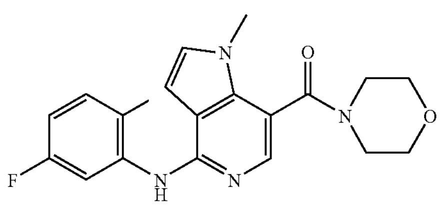 | N-(5-Fluoro-2-methylphenyl)-1-methyl-7-(4-morpholinylcarbonyl)-1H-pyrrolo[3,2-c]pyridin-4-amine hydrochloride | LCMS [MH$^+$] 369 $C_{20}H_{21}FN_4O_2$ |
| 176 | 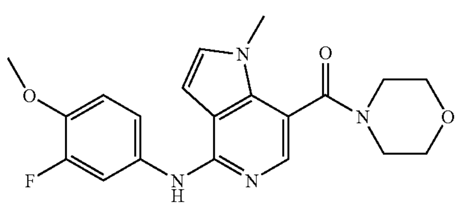 | N-[3-Fluoro-4-(methyloxy)phenyl]-1-methyl-7-(4-morpholinylcarbonyl)-1H-pyrrolo[3,2-c]pyridin-4-amine hydrochloride | LCMS [MH$^+$] 385 $C_{20}H_{21}FN_4O_3$ |
| 177 | 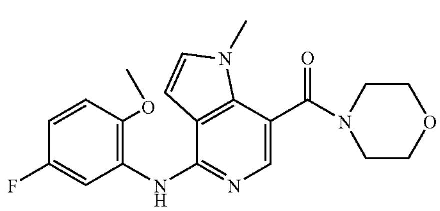 | N-[5-Fluoro-2-(methyloxy)phenyl]-1-methyl-7-(4-morpholinylcarbonyl)-1H-pyrrolo[3,2-c]pyridin-4-amine hydrochloride | LCMS [MH$^+$] 385 $C_{20}H_{21}FN_4O_3$ |

-continued

| Example No. | Structure | Compound Name | Data |
|---|---|---|---|
| 178 | 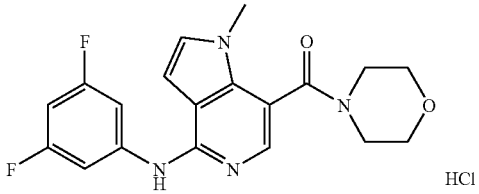 | N-(3,5-Difluorophenyl)-1-methyl-7-(4-morpholinylcarbonyl)-1H-pyrrolo[3,2-c]pyridin-4-amine hydrochloride | LCMS [MH$^+$] 373 $C_{19}H_{18}F_2N_4O_2$ |
| 179 | 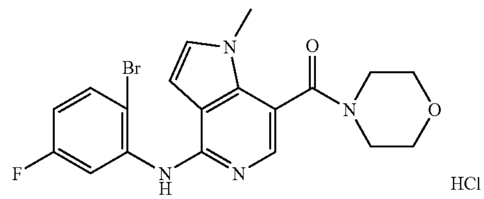 | N-(2-Bromo-5-fluorophenyl)-1-methyl-7-(4-morpholinylcarbonyl)-1H-pyrrolo[3,2-c]pyridin-4-amine hydrochloride | LCMS [MH$^+$] 435 $C_{19}H_{18}{}^{81}BrFN_4O_2$ |
| 180 | 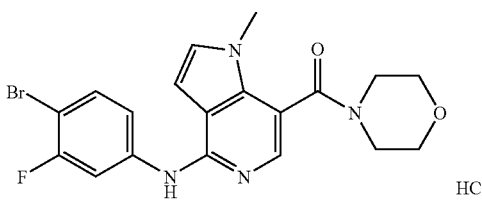 | N-(4-Bromo-3-fluorophenyl)-1-methyl-7-(4-morpholinylcarbonyl)-1H-pyrrolo[3,2-c]pyridin-4-amine hydrochloride | LCMS [MH$^+$] 435 $C_{19}H_{18}{}^{81}BrFN_4O_2$ |
| 181 | 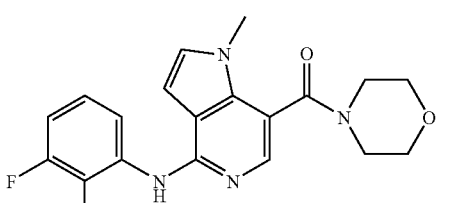 | N-(3-Fluoro-2-methylphenyl)-1-methyl-7-(4-morpholinylcarbonyl)-1H-pyrrolo[3,2-c]pyridin-4-amine hydrochloride | LCMS [MH$^+$] 369 $C_{20}H_{21}FN_4O_2$ |
| 182 | 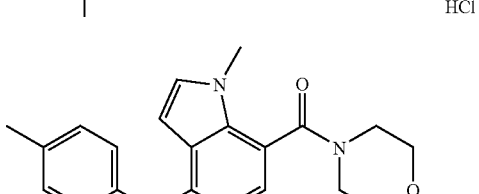 | N-(2-Fluoro-4-methylphenyl)-1-methyl-7-(4-morpholinylcarbonyl)-1H-pyrrolo[3,2-c]pyridin-4-amine hydrochloride | LCMS [MH$^+$] 369 $C_{20}H_{21}FN_4O_2$ |
| 183 | 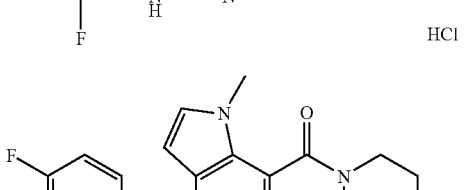 | N-(4-Fluoro-2-methylphenyl)-1-methyl-7-(4-morpholinylcarbonyl)-1H-pyrrolo[3,2-c]pyridin-4-amine hydrochloride | LCMS [MH$^+$] 369 $C_{20}H_{21}FN_4O_2$ |
| 184 | 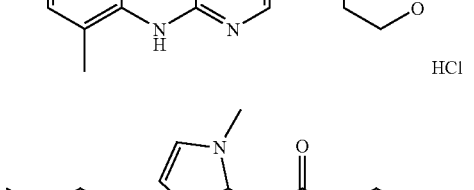 | N-(2,4-Dimethylphenyl)-1-methyl-7-(4-morpholinylcarbonyl)-1H-pyrrolo[3,2-c]pyridin-4-amine hydrochloride | LCMS [MH$^+$] 365 $C_{21}H_{24}N_4O_2$ |

-continued

| Example No. | Structure | Compound Name | Data |
|---|---|---|---|
| 185 | 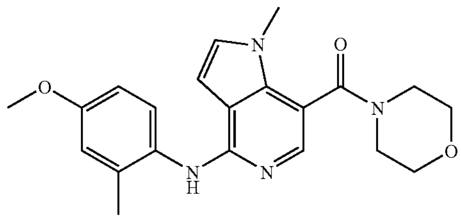 | 1-Methyl-N-[2-methyl-4-(methyloxy)phenyl]-7-(4-morpholinylcarbonyl)-1H-pyrrolo[3,2-c]pyridin-4-amine hydrochloride | LCMS [MH$^+$] 381 $C_{21}H_{24}N_4O_3$ |
| 186 | 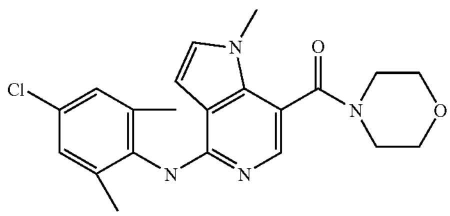 | N-(4-Chloro-2,6-dimethylphenyl)-1-methyl-7-(4-morpholinylcarbonyl)-1H-pyrrolo[3,2-c]pyridin-4-amine hydrochloride | LCMS [MH$^+$] 399 $C_{21}H_{23}{}^{35}ClN_4O_2$ |
| 187 | 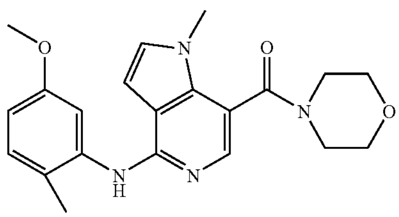 | 1-Methyl-N-[2-methyl-5-(methyloxy)phenyl]-7-(4-morpholinylcarbonyl)-1H-pyrrolo[3,2-c]pyridin-4-amine hydrochloride | LCMS [MH$^+$] 381 $C_{21}H_{24}N_4O_3$ |

Description 1: 4-Chloro-1-methyl-7-(1-piperidinylcarbonyl)-1H-pyrrolo[3,2-c]pyridine

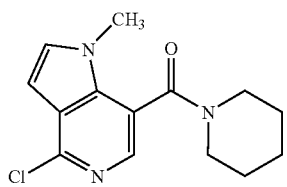

A solution of oxalylchloride (3.43 ml) in DCM (40 ml) was cooled to 0° C. and 4-chloro-1-methyl-1H-pyrrolo[3,2-c]pyridine-7-carboxylic acid (3.75 g) was added portionwise followed by the addition of DMF (4 drops). The reaction mixture was stirred at 0° C. for 90 min, DCM (5 ml) was added and stirring continued for a further 30 min. The reaction mixture was evaporated and the residue dissolved in dichloromethane (20 ml) and dimethylformamide (10 ml). N-ethylmorpholine (9.09 ml) followed by piperidine (3.53 ml) were added and the mixture stirred at 0° C. for 45 min. The reaction mixture was evaporated and the residue dissolved in EtOAc (150 ml). The organic layer washed with water (100 ml), sodium bicarbonate (3×100 ml) and brine (30 ml) then dried (MgSO$_4$) and evaporated to a yellow oil. The oil was triturated with diethyl ether, and the solid filtered and dried at 60° C. under vacuum, to afford the title compound (3.95 g).

LC/MS [MH$^+$] 278 consistent with molecular formula $C_{14}H_{16}{}^{35}ClN_3O$.

Description 2: 4-Chloro-7-[(1,1-dioxido-4-thiomorpholinyl)carbonyl]-1-methyl-1H-pyrrolo[3,2-c]pyridine

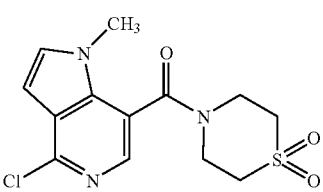

To a solution of 4-chloro-1-methyl-1H-pyrrolo[3,2-c]pyridine-7-carboxylic acid (726 mg) in dimethylformamide (12 ml) was added 1-[3-(dimethylamino)propyl]-3-ethylcarbodiimide (0.73 g), 1-hydroxybenzotriazole (0.52 g), N-ethylmorpholine (0.48 ml) and thiomorpholine 1,1-dioxide hydrochloride (0.66 g). The solution was stirred at room temperature overnight. The reaction was diluted with water and extracted three times with ethyl acetate. The ethyl acetate layers were combined, washed with saturated sodium chloride solution and dried (MgSO$_4$) then evaporated. The residue was triturated with diethyl ether/n-hexane and filtered to afford the title compound as an off-white solid (0.907 g).

LC/MS [MH$^+$] 328 consistent with molecular formula $C_{13}H_{14}{}^{35}ClN_3O_3S$.

Description 3: 4-Chloro-1-methyl-7-(1-pyrrolidinyl-carbonyl)-1H-pyrrolo[3,2-c]pyridine

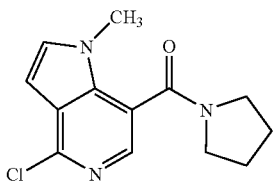

To a solution of 4-chloro-1-methyl-1H-pyrrolo[3,2-c]pyridine-7-carboxylic acid (0.84 mg) in dimethylformamide (20 ml) was added 1-[3-(dimethylamino)propyl]-3-ethylcarbodiimide (0.92 g), 1-hydroxybenzotriazole (0.65 g), N-ethylmorpholine (0.61 ml) and pyrrolidine (0.4 ml). The solution was stirred at room temperature overnight. The reaction was diluted with water and extracted three times with ethyl acetate. The ethyl acetate layers were combined, washed with saturated sodium chloride solution and dried (MgSO$_4$) then evaporated. The residue was purified by column chromatography on a Biotage 25M silica column eluting with 97:3:0.3 dichloromethane/ethanol/ammonia to afford the title compound as a pale yellow oil (0.72 g).

LC/MS [MH$^+$] 264 consistent with molecular formula $C_{13}H_{14}{}^{35}ClN_3O$.

Examples in the following table were prepared in a manner similar to Example 101 from 4-chloro-1-methyl-7-(1-piperidinylcarbonyl)-1H-pyrrolo[3,2-c]pyridine or 4-chloro-7-[(1,1-dioxido-4-thiomorpholinyl)carbonyl]-1-methyl-1H-pyrrolo[3,2-c]pyridine or 4-chloro-1-methyl-7-(1-pyrrolidinylcarbonyl)-1H-pyrrolo[3,2-c]pyridine and the appropriate commercially available aniline. Microwave reaction times were either 30 or 60 min. Dichloromethane or ethylacetate could be used in the aqueous work up. Prior to treatment with 1.0M hydrochloric acid in diethyl ether, compounds could be dissolved in methanol, ethyl acetate, methanol/dichloromethane, dichloromethane or ethyl acetate/ethanol. Example 195 was further purified by column chromatography on Flashmaster II eluting with a 50%-100% gradient of ethyl acetate/n-hexane.

| Example No. | Structure | Compound Name | Data |
|---|---|---|---|
| 188 | 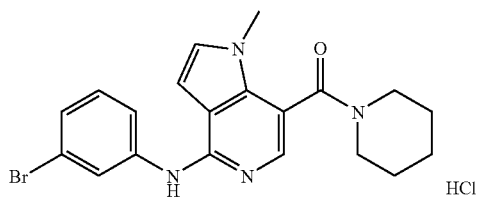 | N-(3-Bromophenyl)-1-methyl-7-(1-piperidinylcarbonyl)-1H-pyrrolo[3,2-c]pyridin-4-amine hydrochloride | LCMS [MH$^+$] 413/415 $C_{20}H_{21}BrN_4O$ |
| 189 | 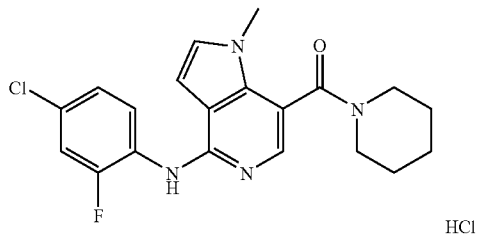 | N-(4-Chloro-2-fluorophenyl)-1-methyl-7-(1-piperidinylcarbonyl)-1H-pyrrolo[3,2-c]pyridin-4-amine hydrochloride | LCMS [MH$^+$] 387 $C_{20}H_{20}{}^{35}ClFN_4O$ |
| 190 | 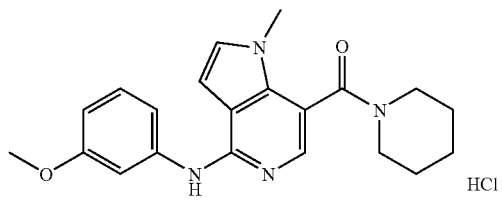 | 1-Methyl-N-[3-(methyloxy)phenyl]-7-(1-piperidinylcarbonyl)-1H-pyrrolo[3,2-c]pyridin-4-amine hydrochloride | LCMS [MH$^+$] 365 $C_{21}H_{24}N_4O_2$ |
| 191 | 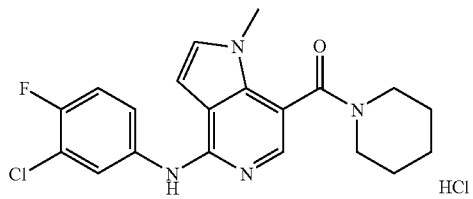 | N-(3-Chloro-4-fluorophenyl)-1-methyl-7-(1-piperidinylcarbonyl)-1H-pyrrolo[3,2-c]pyridin-4-amine hydrochloride | LCMS [MH$^+$] 387 $C_{20}H_{20}{}^{35}ClFN_4O$ |

-continued

| Example No. | Structure | Compound Name | Data |
|---|---|---|---|
| 192 | 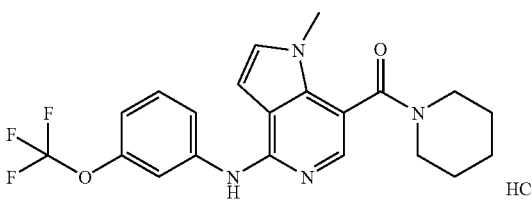 | 1-Methyl-7-(1-piperidinylcarbonyl)-N-{3-[(trifluoromethyl)oxy]phenyl}-1H-pyrrolo[3,2-c]pyridin-4-amine hydrochloride | LCMS [MH$^+$] 419 C$_{21}$H$_{21}$F$_3$N$_4$O$_2$ |
| 193 | 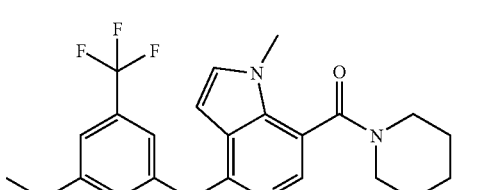 | 1-Methyl-N-[3-(methyloxy)-5-(trifluoromethyl)phenyl]-7-(1-piperidinylcarbonyl)-1H-pyrrolo[3,2-c]pyridin-4-amine hydrochloride | LCMS [MH$^+$] 433 C$_{22}$H$_{23}$F$_3$N$_4$O$_2$ |
| 194 | 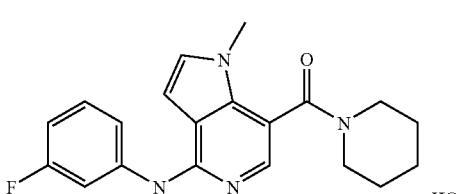 | N-(3-Fluorophenyl)-1-methyl-7-(1-piperidinylcarbonyl)-1H-pyrrolo[3,2-c]pyridin-4-amine hydrochloride | LCMS [MH$^+$] 353 C$_{20}$H$_{21}$FN$_4$O |
| 195 | 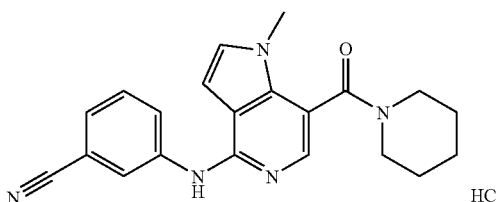 | 3-{[1-Methyl-7-(1-piperidinylcarbonyl)-1H-pyrrolo[3,2-c]pyridin-4-yl]amino}benzonitrile hydrochloride | LCMS [MH$^+$] 360 C$_{21}$H$_{21}$N$_5$O |
| 196 | 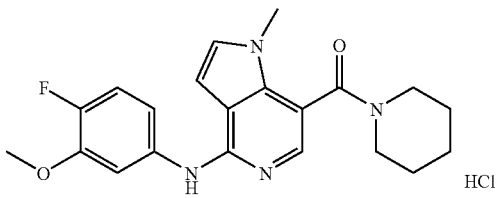 | N-[4-Fluoro-3-(methyloxy)phenyl]-1-methyl-7-(1-piperidinylcarbonyl)-1H-pyrrolo[3,2-c]pyridin-4-amine hydrochloride | LCMS [MH$^+$] 383 C$_{21}$H$_{23}$FN$_4$O$_2$ |
| 197 | 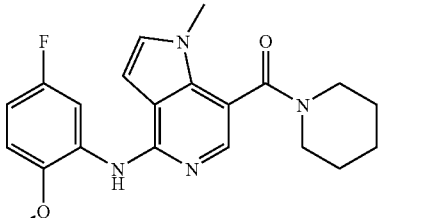 | N-[5-Fluoro-2-(methyloxy)phenyl]-1-methyl-7-(1-piperidinylcarbonyl)-1H-pyrrolo[3,2-c]pyridin-4-amine hydrochloride | LCMS [MH$^+$] 383 C$_{21}$H$_{23}$FN$_4$O$_2$ |
| 198 | 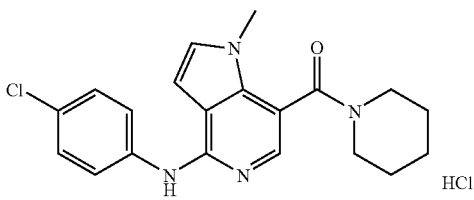 | N-(4-Chlorophenyl)-1-methyl-7-(1-piperidinylcarbonyl)-1H-pyrrolo[3,2-c]pyridin-4-amine hydrochloride | LCMS [MH$^+$] 369 C$_{20}$H$_{21}$$^{35}$ClN$_4$O |

-continued

| Example No. | Structure | Compound Name | Data |
|---|---|---|---|
| 199 | 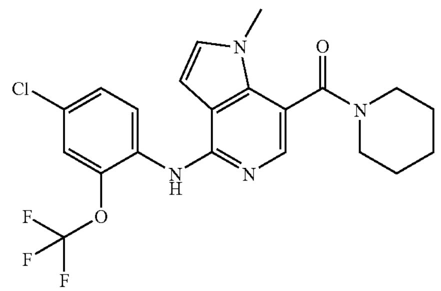 | N-{4-Chloro-2-[(trifluoromethyl)oxy]phenyl}-1-methyl-7-(1-piperidinylcarbonyl)-1H-pyrrolo[3,2-c]pyridin-4-amine hydrochloride | LCMS [MH$^+$] 453 C$_{21}$H$_{20}$$^{35}$ClF$_3$N$_4$O$_2$ |
| 200 | 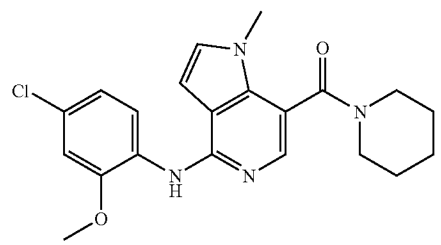 | N-[4-Chloro-2-(methyloxy)phenyl]-1-methyl-7-(1-piperidinylcarbonyl)-1H-pyrrolo[3,2-c]pyridin-4-amine hydrochloride | LCMS [MH$^+$] 399 C$_{21}$H$_{23}$$^{35}$ClN$_4$O$_2$ |
| 201 | 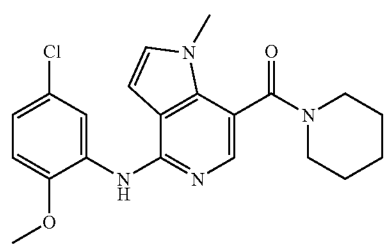 | N-[5-Chloro-2-(methyloxy)phenyl]-1-methyl-7-(1-piperidinylcarbonyl)-1H-pyrrolo[3,2-c]pyridin-4-amine hydrochloride | LCMS [MH$^+$] 399 C$_{21}$H$_{23}$$^{35}$ClN$_4$O$_2$ |
| 202 | 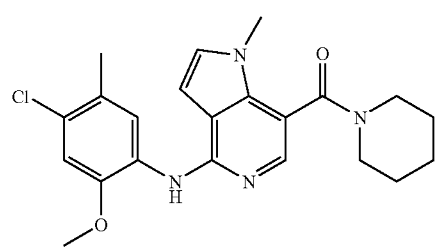 | N-[4-Chloro-5-methyl-2-(methyloxy)phenyl]-1-methyl-7-(1-piperidinylcarbonyl)-1H-pyrrolo[3,2-c]pyridin-4-amine hydrochloride | LCMS [MH$^+$] 413 C$_{22}$H$_{25}$$^{35}$ClN$_4$O$_2$ |
| 203 | 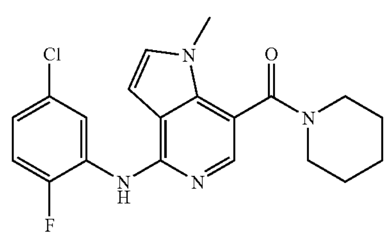 | N-(5-Chloro-2-fluorophenyl)-1-methyl-7-(1-piperidinylcarbonyl)-1H-pyrrolo[3,2-c]pyridin-4-amine hydrochloride | LCMS [MH$^+$] 387 C$_{20}$H$_{20}$$^{35}$ClFN$_4$O |
| 204 | 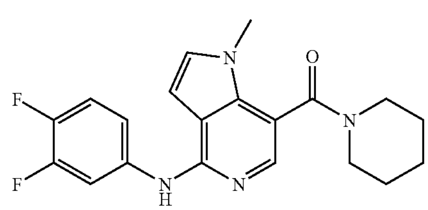 | N-(3,4-Difluorophenyl)-1-methyl-7-(1-piperidinylcarbonyl)-1H-pyrrolo[3,2-c]pyridin-4-amine hydrochloride | LCMS [MH$^+$] 371 C$_{20}$H$_{20}$F$_2$N$_4$O |

-continued

| Example No. | Structure | Compound Name | Data |
|---|---|---|---|
| 205 | 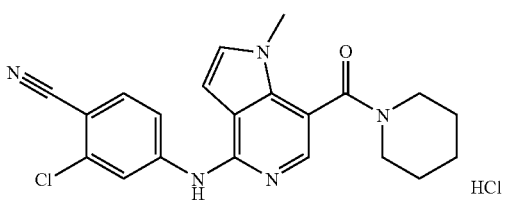 | 2-Chloro-4-{[1-methyl-7-(1-piperidinylcarbonyl)-1H-pyrrolo[3,2-c]pyridin-4-yl]amino}benzonitrile hydrochloride | LCMS [MH$^+$] 394 $C_{21}H_{20}{}^{35}ClN_5O$ |
| 206 | 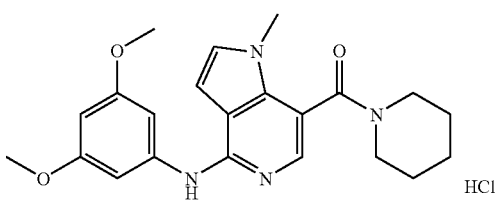 | N-[3,5-Bis(methyloxy)phenyl]-1-methyl-7-(1-piperidinylcarbonyl)-1H-pyrrolo[3,2-c]pyridin-4-amine hydrochloride | LCMS [MH$^+$] 395 $C_{22}H_{26}N_4O_3$ |
| 207 | 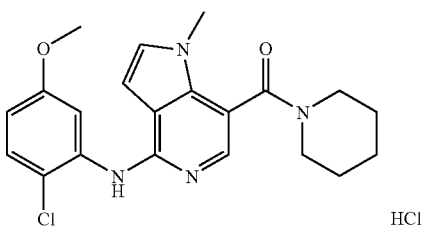 | N-[2-Chloro-5-(methyloxy)phenyl]-1-methyl-7-(1-piperidinylcarbonyl)-1H-pyrrolo[3,2-c]pyridin-4-amine hydrochloride | LCMS [MH$^+$] 399 $C_{21}H_{23}{}^{35}ClN_4O_2$ |
| 208 | 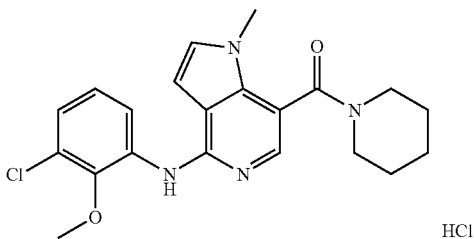 | N-[3-Chloro-2-(methyloxy)phenyl]-1-methyl-7-(1-piperidinylcarbonyl)-1H-pyrrolo[3,2-c]pyridin-4-amine hydrochloride | LCMS [MH$^+$] 399 $C_{21}H_{23}{}^{35}ClN_4O_2$ |
| 209 | 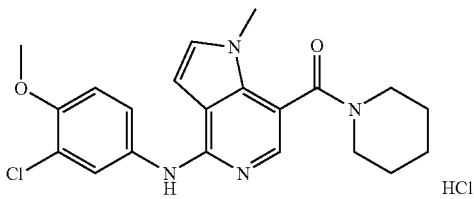 | N-[3-Chloro-4-(methyloxy)phenyl]-1-methyl-7-(1-piperidinylcarbonyl)-1H-pyrrolo[3,2-c]pyridin-4-amine hydrochloride | LCMS [MH$^+$] 399 $C_{21}H_{23}{}^{35}ClN_4O_2$ |
| 210 | 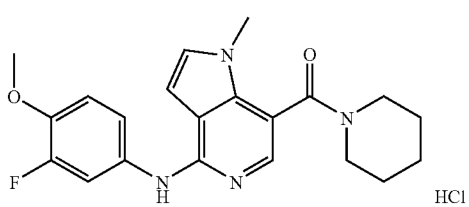 | N-[3-Fluoro-4-(methyloxy)phenyl]-1-methyl-7-(1-piperidinylcarbonyl)-1H-pyrrolo[3,2-c]pyridin-4-amine hydrochloride | LCMS [MH$^+$] 383 $C_{21}H_{23}FN_4O_2$ |

| Example No. | Structure | Compound Name | Data |
|---|---|---|---|
| 211 | 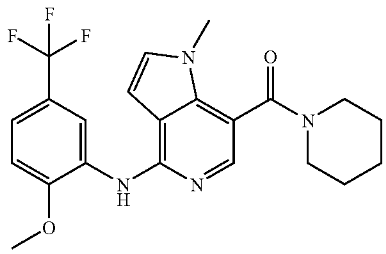 | 1-Methyl-N-[2-(methyloxy)-5-(trifluoromethyl)phenyl]-7-(1-piperidinylcarbonyl)-1H-pyrrolo[3,2-c]pyridin-4-amine hydrochloride | LCMS [MH$^+$] 433 C$_{22}$H$_{23}$F$_3$N$_4$O$_2$ |
| 212 | 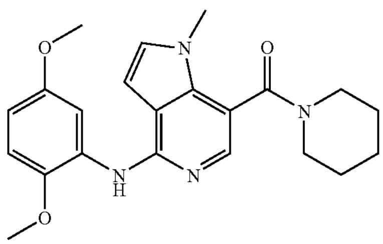 | N-[2,5-Bis(methyloxy)phenyl]-1-methyl-7-(1-piperidinylcarbonyl)-1H-pyrrolo[3,2-c]pyridin-4-amine hydrochloride | LCMS [MH$^+$] 395 C$_{22}$H$_{26}$N$_4$O$_3$ |
| 213 | 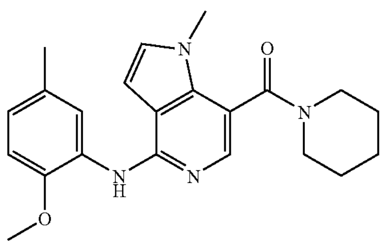 | 1-Methyl-N-[5-methyl-2-(methyloxy)phenyl]-7-(1-piperidinylcarbonyl)-1H-pyrrolo[3,2-c]pyridin-4-amine hydrochloride | LCMS [MH$^+$] 379 C$_{22}$H$_{26}$N$_4$O$_2$ |
| 214 | 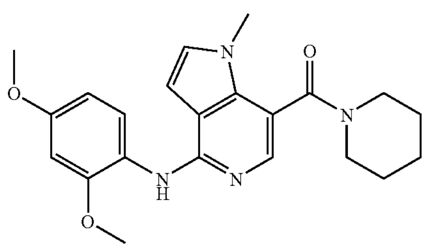 | N-[2,4-Bis(methyloxy)phenyl]-1-methyl-7-(1-piperidinylcarbonyl)-1H-pyrrolo[3,2-c]pyridin-4-amine hydrochloride | LCMS [MH$^+$] 395 C$_{22}$H$_{26}$N$_4$O$_3$ |
| 215 | 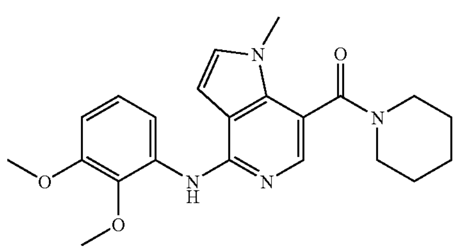 | N-[2,3-Bis(methyloxy)phenyl]-1-methyl-7-(1-piperidinylcarbonyl)-1H-pyrrolo[3,2-c]pyridin-4-amine hydrochloride | LCMS [MH$^+$] 395 C$_{22}$H$_{26}$N$_4$O$_3$ |
| 216 | 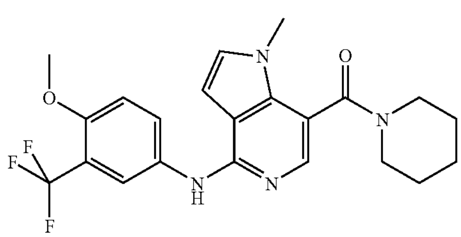 | 1-Methyl-N-[4-(methyloxy)-3-(trifluoromethyl)phenyl]-7-(1-piperidinylcarbonyl)-1H-pyrrolo[3,2-c]pyridin-4-amine hydrochloride | LCMS [MH$^+$] 433 C$_{22}$H$_{23}$F$_3$N$_4$O$_2$ |

-continued

| Example No. | Structure | Compound Name | Data |
|---|---|---|---|
| 217 | 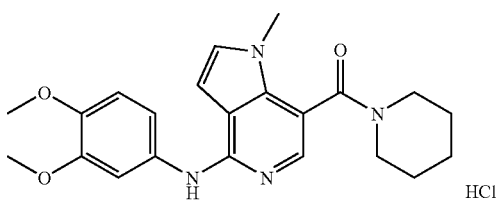 | N-[3,4-Bis(methyloxy)phenyl]-1-methyl-7-(1-piperidinylcarbonyl)-1H-pyrrolo[3,2-c]pyridin-4-amine hydrochloride | LCMS [MH$^+$] 395 $C_{22}H_{26}N_4O_3$ |
| 218 | 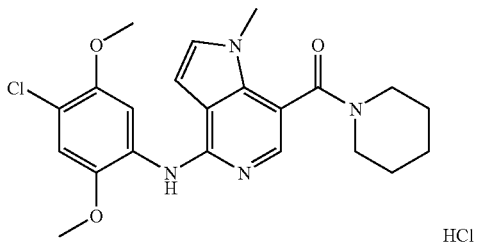 | N-[4-Chloro-2,5-bis(methyloxy)phenyl]-1-methyl-7-(1-piperidinylcarbonyl)-1H-pyrrolo[3,2-c]pyridin-4-amine hydrochloride | LCMS [MH$^+$] 429 $C_{22}H_{25}{}^{35}ClN_4O_3$ |
| 219 | 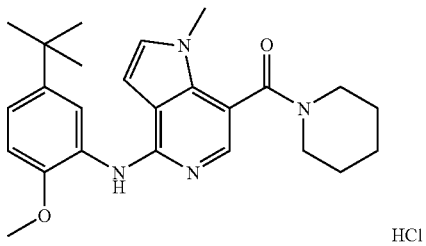 | N-[5-(1,1-Dimethylethyl)-2-(methyloxy)phenyl]-1-methyl-7-(1-piperidinylcarbonyl)-1H-pyrrolo[3,2-c]pyridin-4-amine hydrochloride | LCMS [MH$^+$] 421 $C_{25}H_{32}N_4O_2$ |
| 220 | 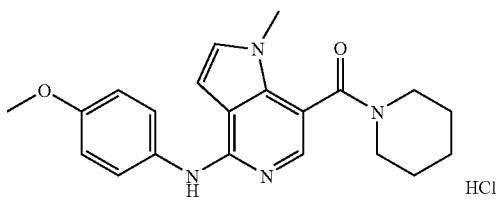 | 1-Methyl-N-[4-(methyloxy)phenyl]-7-(1-piperidinylcarbonyl)-1H-pyrrolo[3,2-c]pyridin-4-amine hydrochloride | LCMS [MH$^+$] 365 $C_{21}H_{24}N_4O_2$ |
| 221 | 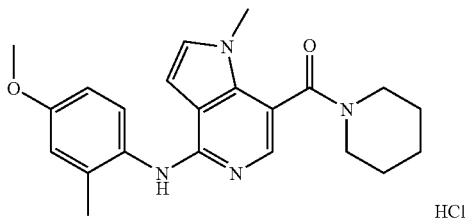 | 1-Methyl-N-[2-methyl-4-(methyloxy)phenyl]-7-(1-piperidinylcarbonyl)-1H-pyrrolo[3,2-c]pyridin-4-amine hydrochloride | LCMS [MH$^+$] 379 $C_{22}H_{26}N_4O_2$ |
| 222 | 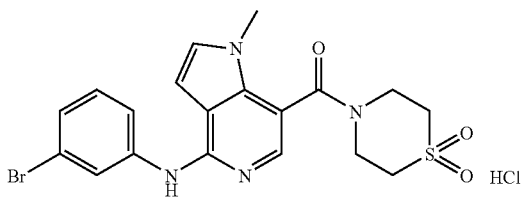 | N-(3-Bromophenyl)-7-[(1,1-dioxido-4-thiomorpholinyl)carbonyl]-1-methyl-1H-pyrrolo[3,2-c]pyridin-4-amine hydrochloride | LCMS [MH$^+$] 463 $C_{19}H_{19}{}^{79}BrN_4O_3S$ |

-continued

| Example No. | Structure | Compound Name | Data |
|---|---|---|---|
| 223 | 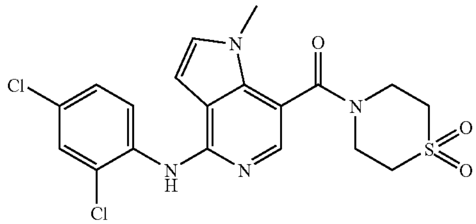 | N-(2,4-Dichlorophenyl)-7-[(1,1-dioxido-4-thiomorpholinyl)carbonyl]-1-methyl-1H-pyrrolo[3,2-c]pyridin-4-amine hydrochloride | LCMS [MH$^+$] 453 C$_{19}$H$_{18}$$^{35}$Cl$_2$N$_4$O$_3$S |
| 224 | 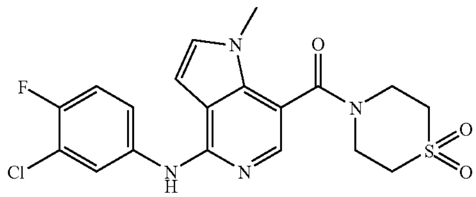 | N-(3-Chloro-4-fluorophenyl)-7-[(1,1-dioxido-4-thiomorpholinyl)carbonyl]-1-methyl-1H-pyrrolo[3,2-c]pyridin-4-amine hydrochloride | LCMS [MH$^+$] 437 C$_{19}$H$_{18}$$^{35}$ClFN$_4$O$_3$S |
| 225 | 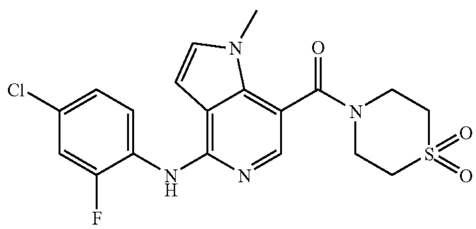 | N-(4-Chloro-2-fluorophenyl)-7-[(1,1-dioxido-4-thiomorpholinyl)carbonyl]-1-methyl-1H-pyrrolo[3,2-c]pyridin-4-amine hydrochloride | LCMS [MH$^+$] 437 C$_{19}$H$_{18}$$^{35}$ClFN$_4$O$_3$S |
| 226 | 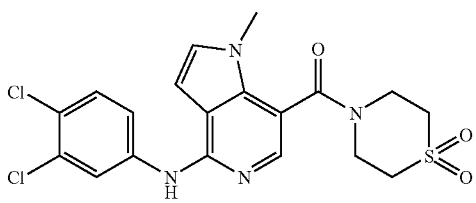 | N-(3,4-Dichlorophenyl)-7-[(1,1-dioxido-4-thiomorpholinyl)carbonyl]-1-methyl-1H-pyrrolo[3,2-c]pyridin-4-amine hydrochloride | LCMS [MH$^+$] 453 C$_{19}$H$_{18}$$^{35}$Cl$_2$N$_4$O$_3$S |
| 227 | 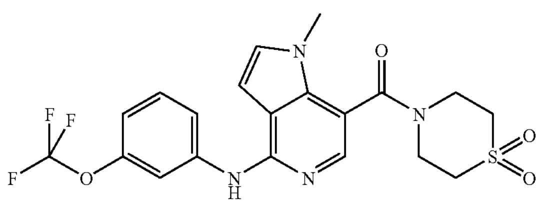 | 7-[(1,1-Dioxido-4-thiomorpholinyl)carbonyl]-1-methyl-N-{3-[(trifluoromethyl)oxy]phenyl}-1H-pyrrolo[3,2-c]pyridin-4-amine hydrochloride | LCMS [MH$^+$] 469 C$_{20}$H$_{19}$F$_3$N$_4$O$_4$S |
| 228 | 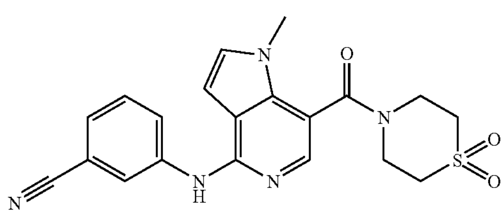 | 3-({7-[(1,1-Dioxido-4-thiomorpholinyl)carbonyl]-1-methyl-1H-pyrrolo[3,2-c]pyridin-4-yl}amino)benzonitrile hydrochloride | LCMS [MH$^+$] 410 C$_{20}$H$_{19}$N$_5$O$_3$S |
| 229 | 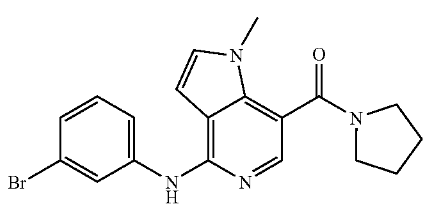 | N-(3-Bromophenyl)-1-methyl-7-(1-pyrrolidinylcarbonyl)-1H-pyrrolo[3,2-c]pyridin-4-amine hydrochloride | LCMS [MH$^+$] 399 C$_{19}$H$_{19}$$^{79}$BrN$_4$O |

-continued

| Example No. | Structure | Compound Name | Data |
|---|---|---|---|
| 230 | 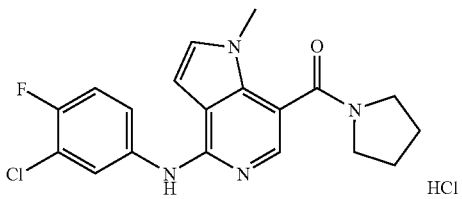 | N-(3-Chloro-4-fluorophenyl)-1-methyl-7-(1-pyrrolidinylcarbonyl)-1H-pyrrolo[3,2-c]pyridin-4-amine hydrochloride | LCMS [MH$^+$] 373 C$_{19}$H$_{18}$$^{35}$ClFN$_4$O |
| 231 | 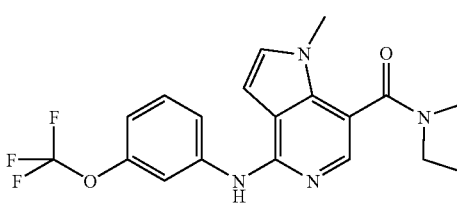 | 1-Methyl-7-(1-pyrrolidinylcarbonyl)-N-{3-[(trifluoromethyl)oxy]phenyl}-1H-pyrrolo[3,2-c]pyridin-4-amine hydrochloride | LCMS [MH$^+$] 405 C$_{20}$H$_{19}$F$_3$N$_4$O$_2$ |
| 232 | 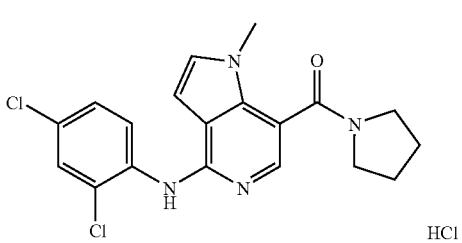 | N-(2,4-Dichlorophenyl)-1-methyl-7-(1-pyrrolidinylcarbonyl)-1H-pyrrolo[3,2-c]pyridin-4-amine hydrochloride | LCMS [MH$^+$] 389 C$_{19}$H$_{18}$$^{35}$Cl$_2$N$_4$O |
| 233 | 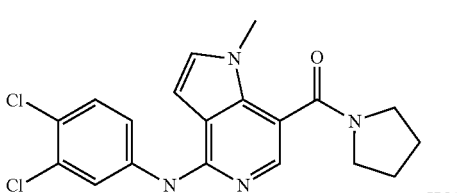 | N-(3,4-Dichlorophenyl)-1-methyl-7-(1-pyrrolidinylcarbonyl)-1H-pyrrolo[3,2-c]pyridin-4-amine hydrochloride | LCMS [MH$^+$] 389 C$_{19}$H$_{18}$$^{35}$Cl$_2$N$_4$O |
| 234 | 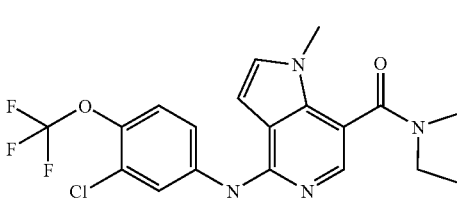 | N-{3-Chloro-4-[(trifluoromethyl)oxy]phenyl}-1-methyl-7-(1-pyrrolidinylcarbonyl)-1H-pyrrolo[3,2-c]pyridin-4-amine hydrochloride | LCMS [MH$^+$] 439 C$_{20}$H$_{18}$$^{35}$ClF$_3$N$_4$O$_2$ |
| 235 | 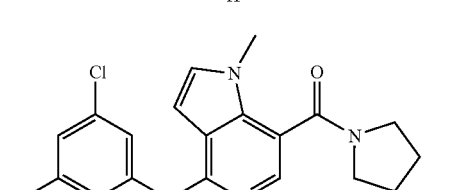 | N-(3,5-Dichlorophenyl)-1-methyl-7-(1-pyrrolidinylcarbonyl)-1H-pyrrolo[3,2-c]pyridin-4-amine hydrochloride | LCMS [MH$^+$] 389 C$_{19}$H$_{18}$$^{35}$Cl$_2$N$_4$O |
| 236 | 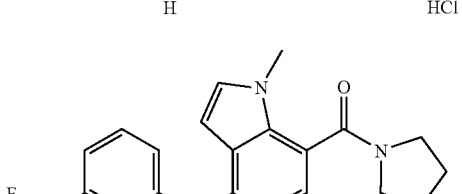 | N-[2-Fluoro-3-(trifluoromethyl)phenyl]-1-methyl-7-(1-pyrrolidinylcarbonyl)-1H-pyrrolo[3,2-c]pyridin-4-amine hydrochloride | LCMS [MH$^+$] 407 C$_{20}$H$_{18}$F$_4$N$_4$O |

EXAMPLE 237

N-(3-Chlorophenyl)-1-methyl-7-(4-thiomorpholinyl-carbonyl)-1H-pyrrolo[3,2-c]pyridin-4-amine

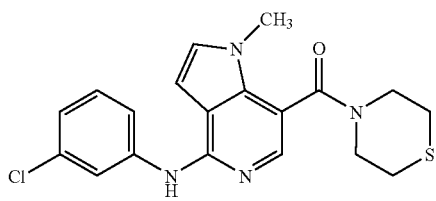

To a solution of 4-[(3-chlorophenyl)amino]-1-methyl-1H-pyrrolo[3,2-c]pyridine-7-carboxylic acid (0.2 g) in dimethylformamide (5 ml) was added 1-[3-(dimethylamino)propyl]-3-ethylcarbodiimide (0.15 g), 1-hydroxybenzotriazole (0.14 g), N-ethylmorpholine (0.34 ml) and thiomorpholine (0.13 ml). The solution was stirred at room temperature overnight. The reaction was diluted with water and extracted three times with ethyl acetate. The ethyl acetate layers were combined, washed with saturated sodium bicarbonate solution followed by saturated sodium chloride solution then dried (MgSO$_4$) and evaporated. The residue was purified by MDAP to afford the title compound as a white solid (236 mg).

LC/MS [MH$^+$] 387 consistent with molecular formula $C_{19}H_{19}{}^{35}ClN_4OS$.

EXAMPLE 238

N-(3-Chlorophenyl)-1-methyl-7-[(1-oxido-4-thiomorpholinyl)carbonyl]-1H-pyrrolo[3,2-c]pyridin-4-amine hydrochloride

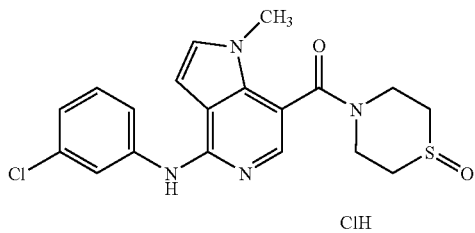

A solution of N-(3-chlorophenyl)-1-methyl-7-(4-thiomorpholinylcarbonyl)-1H-pyrrolo[3,2-c]pyridin-4-amine (100 mg) in DCM (3 ml) was cooled to −78 C and meta-chloroperoxybenzoic acid (58 mg) was added and the reaction stirred under argon for 30 minutes. The reaction was partitioned between dichloromethane and water and the organic layer separated. The organic layer was then washed three times with water, aqueous sodium sulfite solution, dried (Na$_2$SO$_4$) and evaporated. The residue was purified by MDAP to afford the free base as a white solid (84 mg). This was dissolved in methanol and a solution of 11.0M hydrochloric acid in diethyl ether (0.5 ml) and after evaporation afforded the title compound as a white solid (85 mg).

LC/MS [MH$^+$] 403 consistent with molecular formula $C_{19}H_{19}{}^{35}ClN_4O_2S$.

EXAMPLE 239

1-Methyl-N-[2-methyl-4-(trifluoromethyl)phenyl]-7-(4-morpholinylcarbonyl)-1H-pyrrolo[3,2-c]pyridin-4-amine

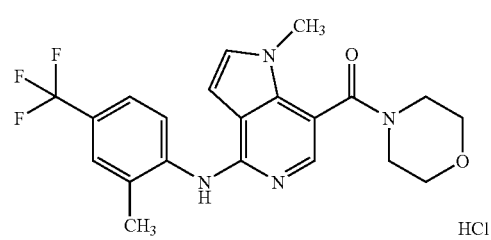

A mixture of 4-chloro-1-methyl-7-(4-morpholinylcarbonyl)-1H-pyrrolo[3,2-c]pyridine (100 mg), 2-methyl-4-trifluoromethylaniline (60 µl), cesium carbonate (163 mg), tris (dibenzylideneacetone)dipalladium (0) (7 mg) and 4,5-bis (diphenylphosphino)-9,9-dimethylxanthene (5 mg) in 1,4-dioxan (2 ml) was heated to 100° C. under argon overnight. The reaction mixture was diluted with dichloromethane and washed with water followed by saturated sodium chloride solution, then dried (MgSO$_4$), filtered and evaporated. Purification and salt formation was as described in Example 101 to afford the title compound as a white solid (52 mg).

LC/MS [MH$^+$] 419 consistent with molecular formula $C_{21}H_{21}F_3N_4O_2$.

EXAMPLE 240

3-Methyl-4-{[1-methyl-7-(4-morpholinylcarbonyl)-1H-pyrrolo[3,2-c]pyridin-4-yl]amino}benzonitrile

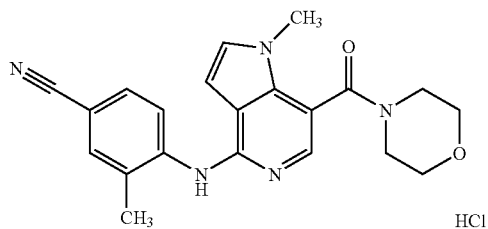

A mixture of 4-chloro-1-methyl-7-(4-morpholinylcarbonyl)-1H-pyrrolo[3,2-c]pyridine (100 mg), 4-amino-3-methylbenzonitrile (57 mg), cesium carbonate (163 mg), tris (dibenzylideneacetone)dipalladium (0) (7 mg) and 4,5-bis (diphenylphosphino)-9,9-dimethylxanthene (5 mg) in 1,4-dioxan (2 ml) was heated to 100° C. under argon overnight. The reaction mixture was diluted with dichloromethane and washed with water, followed by saturated sodium chloride solution, then dried (MgSO$_4$), filtered and evaporated. The residue was triturated with 2:1:1 methanol/dimethylsulfoxide/diethyl ether to yield an off white solid. This was dissolved in 1:1 methanol/dichloromethane and a solution of 1.0M hydrochloric acid in diethyl ether (1.4 ml) and the solvent evaporated to afford the title compound as an off white solid (36 mg).

LC/MS [MH+] 376 consistent with molecular formula $C_{21}H_{21}N_5O_2$.

EXAMPLE 241

N-[2-Chloro-4-(trifluoromethyl)phenyl]-1-methyl-7-(4-morpholinylcarbonyl)-1H-pyrrolo[3,2-c]pyridin-4-amine hydrochloride

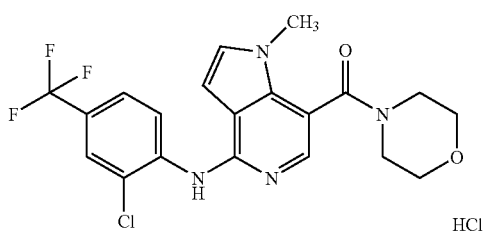

A mixture of 4-chloro-1-methyl-7-(4-morpholinylcarbonyl)-1H-pyrrolo[3,2-c]pyridine (100 mg), 2-chloro-4-trifluoromethylaniline (80 mg), cesium carbonate (168 mg), tris(dibenzylideneacetone)dipalladium (0) (3.4 mg) and 4,5-bis(diphenylphosphino)-9,9-dimethylxanthene (2.3 mg) in 1,4-dioxan (2 ml) was heated to 100° C. under nitrogen for 2 h. Added tris(dibenzylideneacetone)dipalladium (0) (10 mg) and 4,5-bis(diphenylphosphino)-9,9-dimethylxanthene (7 mg) and continued heating at 100° C. under nitrogen overnight. The reaction mixture was diluted with dichloromethane and washed with water then dried (MgSO$_4$), filtered and evaporated. Purification and salt formation was as described in Example 101 to afford the title compound as a white solid (64 mg).

LC/MS t=2.14 min, [MH+] 439 consistent with molecular formula $C_{20}H_{18}{}^{35}ClF_3N_4O_2$.

EXAMPLE 242

3-Chloro-4-{[1-methyl-7-(4-morpholinylcarbonyl)-1H-pyrrolo[3,2-c]pyridin-4-yl]amino}benzonitrile hydrochloride

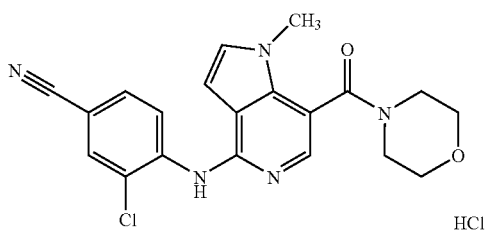

A mixture of 4-chloro-1-methyl-7-(4-morpholinylcarbonyl)-1H-pyrrolo[3,2-c]pyridine (100 mg), 2-chloro-4-cyanoaniline (60 mg), cesium carbonate (168 mg), tris(dibenzylideneacetone)dipalladium (0) (15 mg) and 4,5-bis(diphenylphosphino)-9,9-dimethylxanthene (10 mg) in 1,4-dioxan (2 ml) was heated to 100° C. under nitrogen for 2 h. Added tris(dibenzylideneacetone)dipalladium (0) (15 mg) and 4,5-bis(diphenylphosphino)-9,9-dimethylxanthene (10 mg) and continued heating at 100° C. under nitrogen overnight. Added tris(dibenzylideneacetone)dipalladium (0) (15 mg) and 4,5-bis(diphenylphosphino)-9,9-dimethylxanthene (10 mg) and continued heating at 100° C. under nitrogen overnight. The reaction mixture was diluted with dichloromethane and washed with water then dried (MgSO$_4$), filtered and evaporated. Purified by trituration with 1:1 methanol:DMSO washing the filtered solid with methanol. Salt formation was as described in Example 101 to afford the title compound as a pale yellow solid (27 mg).

LC/MS t=1.89 min, [MH+] 396 consistent with molecular formula $C_{20}H_{18}{}^{35}ClN_5O_2$.

EXAMPLE 243

N-(3-Chlorophenyl)-7-(4-morpholinylcarbonyl)-1H-pyrrolo[3,2-c]pyridin-4-amine formate

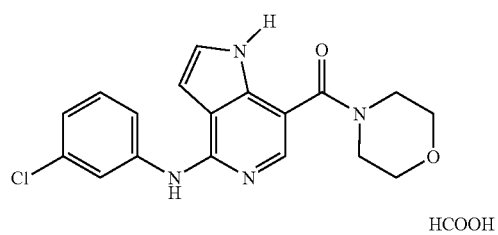

a) Ethyl 2-[2-(ethyloxy)-2-oxoethyl]-1-{[4-(methyloxy)phenyl]methyl}-1H-pyrrole-3-carboxylate

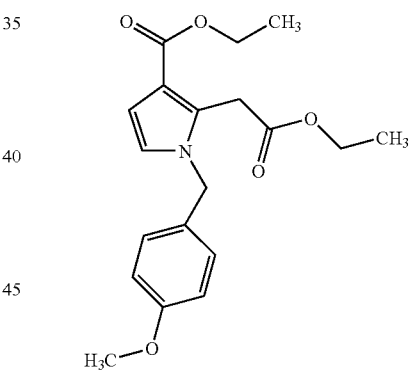

A solution of diethyl 1,3 acetone dicarboxylic acid (27.0 ml) in 1,4 dioxan (60 ml) was added to 4-methoxybenzylamine (104.1 ml) at −10° C. and the reaction mixture allowed to warm to 5° C. Cold chloroacetaldehyde (32.1 ml) was then added dropwise over 1.5 h maintaining the temperature at 15-17° C. The reaction mixture was allowed to warm to room temperature and stirred overnight. The reaction mixture was evaporated and the residue partitioned between ethyl acetate and aqueous 2M hydrochloric acid solution. The aqueous layer was removed and extracted twice with ethyl acetate and then the combined organic layers were washed with brine and dried (MgSO$_4$). The solution was evaporated and the residue purified using Biotage Flash 75L eluting with 20% ethyl acetate/n-hexane to afford the title compound as white needles (9.44 g).

LCMS [MH+] 346 consistent with isomers of molecular formula $C_{19}H_{23}NO_5$ b) Ethyl 2-{1-[(ethyloxy)carbonyl]-2-hydroxyethenyl}-1-{[4-(methyloxy)phenyl]methyl}-1H-pyrrole-3-carboxylate

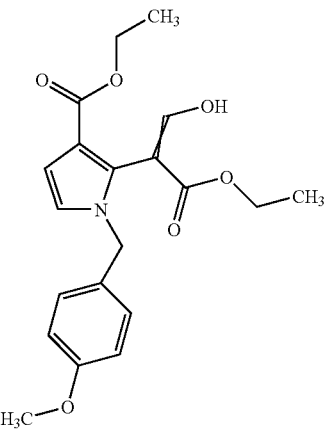

Ethyl 2-[2-(ethyloxy)-2-oxoethyl]-1-{[4-(methyloxy)phenyl]methyl}-1H-pyrrole-3-carboxylate (6.1 g) in dry tetrahydrofuran (100 ml) was stirred at room temperature under argon. Sodium hydride (60% dispersion in mineral oil, 23.0 g) was added portionwise and stirring continued for 20 minutes after complete addition. Ethyl formate (3 ml) was added to the reaction mixture and stirred for 45 minutes after which time an exotherm was observed and controlled by cooling the reaction mixture to room temperature with an ice bath. The reaction mixture was stirred for a further 90 minutes then ethyl formate (3 ml) was added and the mixture stirred overnight. The reaction mixture was cooled in an ice bath and quenched by addition of the minimum amount of ethanol then evaporated. The residue was partitioned between ethyl acetate and saturated ammonium chloride, the aqueous layer was removed and acidified to pH 1 with a 2M solution of aqueous hydrochloric acid. The aqueous layer was extracted three times with ethyl acetate and the combined organic layers were washed with brine and dried (MgSO$_4$). The solvent was evaporated to afford an oil consisting of two layers. The top layer was discarded and the lower layer isolated to afford the title compound as a brown oil (6.59 g).

LC/MS [MH$^+$] 374 consistent with isomers of molecular formula C$_{20}$H$_{23}$NO$_6$ c) Ethyl 2-{2-amino-1-[(ethyloxy)carbonyl]ethenyl}-1-{[4-(methyloxy)phenyl]methyl}-1H-pyrrole-3-carboxylate

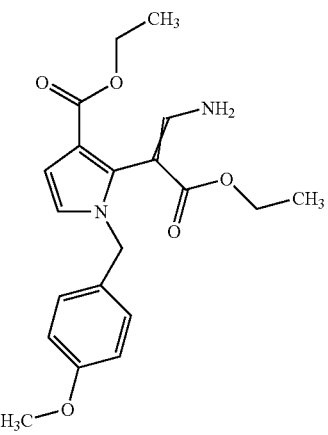

A mixture of ethyl 2-{1-[(ethyloxy)carbonyl]-2-hydroxyethenyl}-1-{[4-(methyloxy)phenyl]methyl}-1H-pyrrole-3-carboxylate (6.59 g), ammonium acetate (6.47 g) and ethanol (80 ml) was stirred at 60° C. under argon for 4 h, at room temperature over night then heated at 60° C. for a further hour. After cooling the solvent was evaporated and the residue partitioned between ethyl acetate and water, extracting the separated aqueous layer three times with ethyl acetate. The combined organic layers were washed with brine then dried (MgSO$_4$), filtered and evaporated. The residue was stirred in n-hexane for 1 h and then the mixture was allowed to settle. The n-hexane was decanted off and the oil dried to afford the title compound as a brown oil (4.99 g).

LC/MS [MH$^+$] 373 consistent with isomers of molecular formula C$_{20}$H$_{24}$N$_2$O$_5$ d) Ethyl 1-{[4-(methyloxy)phenyl]methyl}-4-oxo-4,5-dihydro-1H-pyrrolo[3,2-c]pyridine-7-carboxylate

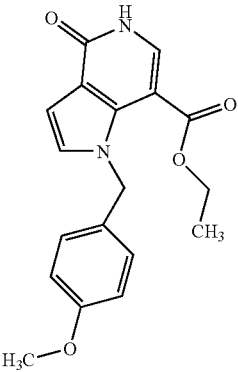

A mixture of ethyl 2-{2-amino-1-[(ethyloxy)carbonyl]ethenyl}-1-{[4-(methyloxy)phenyl]methyl}-1H-pyrrole-3-carboxylate (0.2 g), sodium tert-butoxide (26 mg) and dimethylformamide (2 ml) was irradiated with microwaves at 160° C. for 8 minutes. The procedure was repeated on a 2 g and 3 g scale, the cooled solutions combined, added slowly to iced water then stirred for 25 minutes. A precipitate formed which was dissolved in ethyl acetate and washed with water. The aqueous layer was separated and extracted three times with ethyl acetate. The combined organic layers were washed with brine, dried (MgSO$_4$), filtered and evaporated to afford the title compound as a white solid (3.00 g).

LC/MS [MH$^+$] 327 consistent with molecular formula C$_{18}$H$_{18}$N$_2$O$_4$ e) Ethyl 4-chloro-1-{[4-(methyloxy)phenyl]methyl}-1H-pyrrolo[3,2-c]pyridine-7-carboxylate

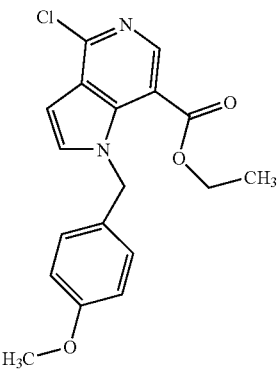

Ethyl 1-{[4-(methyloxy)phenyl]methyl}-4-oxo-4,5-dihydro-1H-pyrrolo[3,2-c]pyridine-7-carboxylate (2.90 g) and phenyl dichlorophosphate (18 ml) were heated at 180° C. under argon for 30 minutes. The reaction mixture was allowed to cool, poured onto iced water, and neutralised to pH7 using solid sodium bicarbonate. To the reaction mixture was added ethyl acetate and the insoluble material was filtered off. The aqueous was separated and extracted three times with ethyl acetate. The combined organic layers were washed with brine, dried (MgSO$_4$), filtered and evaporated to afford the title compound as a clear oil (2.0 g).

LC/MS [MH$^+$] 345 consistent with molecular formula C$_{18}$H$_{17}$$^{35}$ClN$_2$O$_3$ f) Ethyl 4-chloro-1H-pyrrolo[3,2-c]pyridine-7-carboxylate

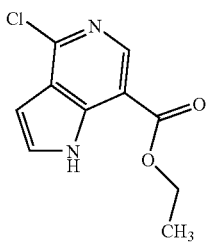

A solution of ethyl 4-chloro-1-{[4-(methyloxy)phenyl]methyl}-1H-pyrrolo[3,2-c]pyridine-7-carboxylate (2.00 g) in TFA (30 ml), anisole (1.84 ml), and sulphuric acid (15 ml) was stirred at room temperature for 30 minutes. The solution was added to an aqueous saturated sodium bicarbonate solution at 0° C. and extracted with ethyl acetate. The aqueous layer was separated and extracted three times with ethyl acetate. The combined organic layers were washed with brine, dried (MgSO$_4$), filtered and evaporated to afford the title compound as a brown solid (0.49 g).

LC/MS [MH$^+$] 225 consistent with molecular formula C$_{10}$H$_9$$^{35}$ClN$_2$O$_2$ g) Ethyl 4-[(3-chlorophenyl)amino]-1H-pyrrolo[3,2-c]pyridine-7-carboxylate

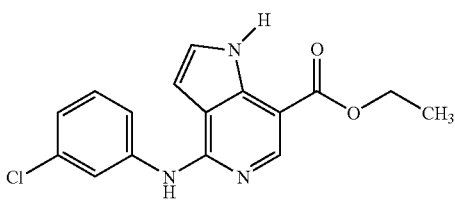

A mixture of ethyl 4-chloro-1H-pyrrolo[3,2-c]pyridine-7-carboxylate (0.49 g), 3-chloroaniline (0.46 ml) and methanesulfonic acid (0.28 ml) in 1,4-dioxan (10 ml) was irradiated at 180° C. for 30 minutes with microwaves. The residue was partitioned between ethyl acetate and water, the aqueous layer was separated, basified with an aqueous 2M sodium bicarbonate solution and extracted three times with ethyl acetate. The combined organic layers were washed with brine, dried (MgSO$_4$), filtered and evaporated to afford the title compound as a brown solid (0.91 g).

LC/MS [MH$^+$] 316 consistent with molecular formula C$_{16}$H$_{14}$$^{35}$ClN$_3$O$_2$ h) 4-[(3-chlorophenyl)amino]-1H-pyrrolo[3,2-c]pyridine-7-carboxylic acid

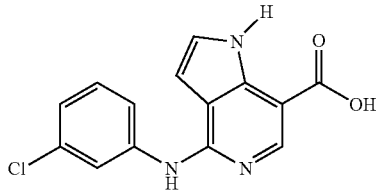

A mixture of ethyl 4-chloro-1H-pyrrolo[3,2-c]pyridine-7-carboxylate (0.34 g) and 2M sodium hydroxide (1 ml) in methanol (3 ml) was irradiated at 120° C. for 3 minutes with microwaves. The solvent was evaporated, the residue dissolved in an aqueous 2M sodium hydroxide solution and washed three times with diethyl ether. The aqueous layer was separated and acidified with an aqueous 2M hydrochloric acid solution. The aqueous layer was extracted with diethyl ether then the aqueous and organic layers were combined and evaporated to afford the title compound as a brown solid (0.175 g).

LC/MS [MH$^+$] 288 consistent with molecular formula C$_{14}$H$_{10}$$^{35}$ClN$_3$O$_2$ i) N-(3-chlorophenyl)-7-(4-morpholinylcarbonyl)-1H-pyrrolo[3,2-c]pyridin-4-amine formate

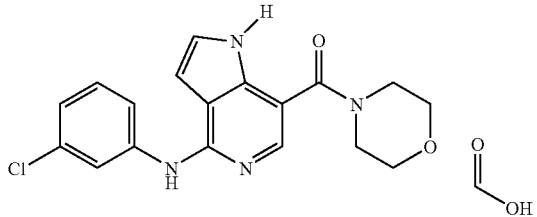

A solution of 4-[(3-chlorophenyl)amino]-1H-pyrrolo[3,2-c]pyridine-7-carboxylic acid (175 mg), 1-ethyl-3-(3-dimethylaminopropyl)carbodiimide hydrochloride (140 mg), 1-hydroxybenzotriazole hydrate (108 mg), morpholine (106 ul) and N-ethylmorpholine (309 ul) in dimethylformamide (3 ml) was stirred under argon over night. The reaction mixture was diluted with diethyl ether and washed with water. The aqueous layer was acidified with an aqueous 2M hydrochloric acid solution and then extracted three times with diethyl ether. The combined organic layers were washed with brine, dried (MgSO$_4$) and evaporated to afford a brown oil. Purification by MDAP afforded the title compound as a clear oil (86 mg).

LC/MS [MH$^+$] 357 consistent with molecular formula C$_{18}$H$_{17}$$^{35}$ClN$_4$O$_2$

EXAMPLE 244

N-(3-chlorophenyl)-1-ethyl-7-(4-morpholinylcarbonyl)-1H-pyrrolo[3,2-c]pyridin-4-amine hydrochloride

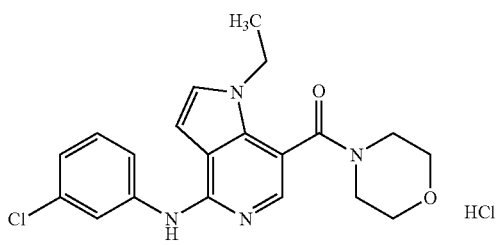

a) Methyl 2-{1-[(ethyloxy)carbonyl]-2-hydroxyethenyl}-1-{[4-(methyloxy)phenyl]methyl}-1H-pyrrole-3-carboxylate

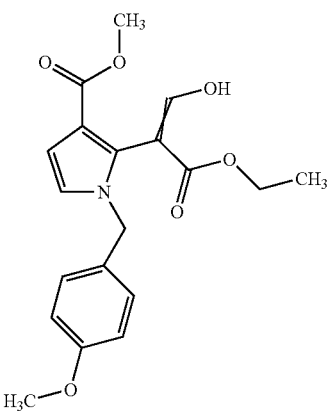

Ethyl 2-[2-(ethyloxy)-2-oxoethyl]-1-{[4-(methyloxy)phenyl]methyl}-1H-pyrrole-3-carboxylate (18.51 g) in dry tetrahydrofuran (300 ml) was stirred at room temperature under argon. Sodium hydride (60% dispersion in mineral oil, 70.0 g) was added portionwise and stirring continued for 15 minutes after complete addition. Ethyl formate (9.12 ml) was added to the reaction mixture and stirred for 30 minutes after which time an exotherm was observed and controlled by cooling the reaction mixture to room temperature with an ice bath. The reaction mixture was stirred for a further 3.5 h. The reaction mixture was cooled in an ice bath and quenched by addition of the minimum amount of methanol then evaporated. The residue was partitioned between ethyl acetate and saturated ammonium chloride, the aqueous layer was removed and acidified to pH 1 with a 2M solution of aqueous hydrochloric acid. The aqueous layer was extracted three times with ethyl acetate and the combined organic layers were washed with brine and dried (MgSO$_4$). The solvent was evaporated to afford an oil consisting of two layers. The top layer was discarded and the lower layer isolated to afford the title compound as a brown oil (17.6 g).

LC/MS [MH$^+$] 374 consistent with isomers of molecular formula C$_{19}$H$_{21}$NO$_6$ b) Methyl 2-{2-amino-1-[(ethyloxy)carbonyl]ethenyl}-1-{[4-(methyloxy)phenyl]methyl}-1H-pyrrole-3-carboxylate

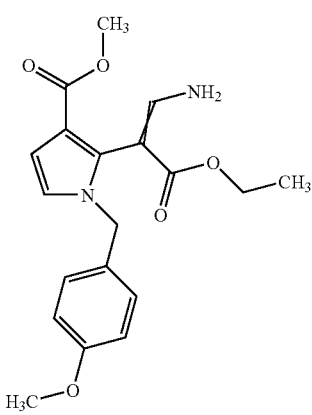

A mixture of methyl 2-{1-[(ethyloxy)carbonyl]-2-hydroxyethenyl}-1-{[4-(methyloxy)phenyl]methyl}-11H-pyrrole-3-carboxylate (17.6 g), ammonium acetate (17.2 g) and ethanol (200 ml) was stirred at 60° C. under argon for 5 h, then stirred at room temperature over night.

The solvent was evaporated and the residue partitioned between ethyl acetate and water, extracting the separated aqueous layer three times with ethyl acetate. The combined organic layers were washed with brine then dried (MgSO$_4$), filtered and evaporated to afford the title compound as a brown oil (17.7 g).

LC/MS [MH$^+$] 359 consistent with isomers of molecular formula C$_{19}$H$_{22}$N$_2$O$_5$ c) Ethyl 1-{[4-(methyloxy)phenyl]methyl}-4-oxo-4,5-dihydro-1H-pyrrolo[3,2-c]pyridine-7-carboxylate

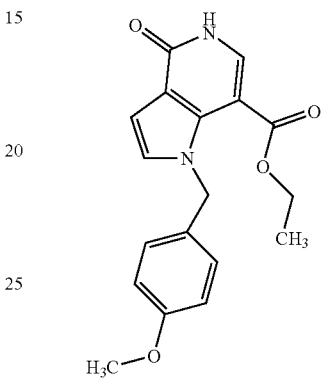

A mixture of methyl 2-{2-amino-1-[(ethyloxy)carbonyl]ethenyl}-1-{[4-(methyloxy)phenyl]methyl}-1H-pyrrole-3-carboxylate (2.95 g), sodium tert-butoxide (0.38 g) and dimethylformamide (20 ml) was irradiated with microwaves at 180° C. for 2.5 h. The procedure was repeated five times, the cooled solutions combined, added slowly to iced water then stirred for 25 minutes. A precipitate formed which was dissolved in ethyl acetate and washed with water. The aqueous layer was separated and extracted three times with ethyl acetate. The combined organic layers were washed with brine, dried (MgSO$_4$), filtered and evaporated to afford the title compound as a brown solid (14.45 g).

LC/MS [MH$^+$] 327 consistent with molecular formula C$_{18}$H$_{18}$N$_2$O$_4$ d) Ethyl 4-chloro-1-{[4-(methyloxy)phenyl]methyl}-1H-pyrrolo[3,2-c]pyridine-7-carboxylate

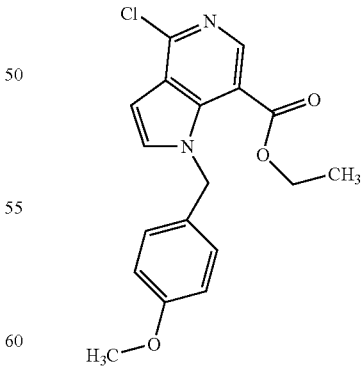

Prepared in a similar manner to Example 243(e) using ethyl 1-{[4-(methyloxy)phenyl]methyl}-4-oxo-4,5-dihydro-1H-pyrrolo[3,2-c]pyridine-7-carboxylate (14.45 g) and phenyl dichlorophosphate (100 ml) to afford the title compound as a yellow oil (7.2 g).

LC/MS [MH$^+$] 345 consistent with molecular formula C$_{18}$H$_{17}$$^{35}$ClN$_2$O$_3$ e) Ethyl 4-chloro-1H-pyrrolo[3,2-c]pyridine-7-carboxylate

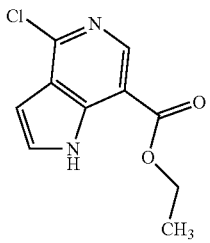

A solution of ethyl 4-chloro-1-{[4-(methyloxy)phenyl]methyl}-1H-pyrrolo[3,2-c]pyridine-7-carboxylate (1.00 g) in TFA (5 ml) and anisole (0.92 ml) was stirred at room temperature for 2.5 h. Sulphuric acid (5 drops) was added to the reaction mixture and stirring continued for 2 h then sulphuric acid (2 ml) was added and the reaction mixture stirred for 24 h at room temperature. The solution was added to saturated sodium bicarbonate at 0° C. and extracted with ethyl acetate. The aqueous layer was separated and extracted three times with ethyl acetate. The combined organic layers were washed with brine, dried (MgSO$_4$), filtered and evaporated to afford the title compound as a brown solid (0.50 g).

LC/MS [MH$^+$] 225 consistent with molecular formula C$_{10}$H$_9$$^{35}$ClN$_2$O$_2$ f) Ethyl 4-chloro-1-ethyl-1H-pyrrolo[3,2-c]pyridine-7-carboxylate

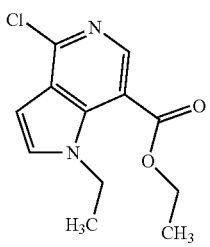

Ethyl 4-chloro-1H-pyrrolo[3,2-c]pyridine-7-carboxylate (0.10 g) was dissolved in dimethylformamide (2 ml), cooled to 0° C. and sodium hydride (60% dispersion in oil) (0.027 g) added. The reaction mixture was stirred for 45 minutes at 0° C., allowed to warm to room temperature and stirred for a further 45 minutes. The reaction mixture was cooled to 0° C., ethyl iodide (0.039 ml) added, the reaction mixture allowed to warm to room temperature, and stirred for 1 hour. The reaction mixture was partitioned between ethyl acetate and water, the aqueous was separated and extracted three times with ethyl acetate. The combined organic layers were washed with brine, dried (MgSO$_4$), filtered and evaporated to afford the title compound as a yellow oil (0.095 g).

LC/MS [MH$^+$] 253 consistent with molecular formula C$_{12}$H$_{13}$$^{35}$ClN$_2$O$_2$ g) Ethyl 4-[(3-chlorophenyl)amino]-1-ethyl-1H-pyrrolo[3,2-c]pyridine-7-carboxylate

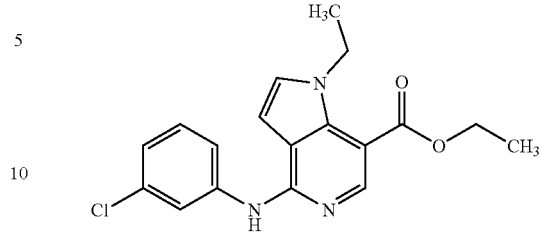

A mixture of ethyl 4-chloro-1-ethyl-1H-pyrrolo[3,2-c]pyridine-7-carboxylate (0.095 g), 3-chloroaniline (0.079 ml) and methanesulfonic acid (0.049 ml) in 1,4-dioxan (2.5 ml) was irradiated at 180° C. for 30 minutes with microwaves. The residue was partitioned between ethyl acetate and water, the aqueous was separated, basified with an aqueous 2M sodium bicarbonate solution and extracted three times with ethyl acetate. The combined organic layers were washed with brine, dried (MgSO$_4$), filtered and evaporated to afford the title compound as a brown oil (0.160 g).

LC/MS [MH$^+$] 344 consistent with molecular formula C$_{18}$H$_{18}$$^{35}$ClN$_3$O$_2$ h) 4-[(3-Chlorophenyl)amino]-1-ethyl-1H-pyrrolo[3,2-c]pyridine-7-carboxylic acid

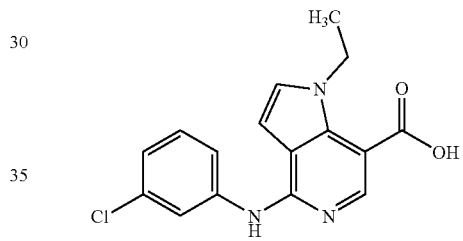

A mixture of ethyl 4-[(3-chlorophenyl)amino]-1-ethyl-1H-pyrrolo[3,2-c]pyridine-7-carboxylate (0.160 g) and 2M sodium hydroxide (0.5 ml) in methanol (1.5 ml) was irradiated at 120° C. for 3 minutes with microwaves. The solvent was evaporated and the residue partitioned between ethyl acetate and water. The aqueous layer was removed, acidified to pH1 and extracted with ethyl acetate three times. The combined organic layers were washed with brine, dried (MgSO$_4$), filtered and evaporated to afford the title compound as a white oil (0.020 g).

LC/MS [MH$^+$] 316 consistent with molecular formula C$_{16}$H$_{14}$$^{35}$ClN$_3$O$_2$ i) N-(3-Chlorophenyl)-1-ethyl-7-(4-morpholinylcarbonyl)-1H-pyrrolo[3,2-c]pyridin-4-amine

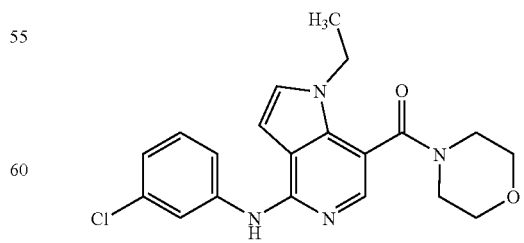

A solution of 4-[(3-chlorophenyl)amino]-1-ethyl-1H-pyrrolo[3,2-c]pyridine-7-carboxylic acid (20 mg), 1-ethyl-3-(3-dimethylaminopropyl)carbodiimide hydrochloride (15 mg), 1-hydroxybenzotriazole hydrate (11 mg), morpholine (11 ul)

and N-ethylmorpholine (32 ul) in dimethylformamide (2 ml) was stirred under argon over night. The reaction mixture was diluted with diethyl ether and washed with water. The aqueous layer was acidified with an aqueous 2M hydrochloric acid solution and then extracted three times with diethyl ether. The combined organic layers were washed with brine, dried (MgSO₄) and evaporated to afford the title compound as a yellow oil (14 mg).

LC/MS [MH⁺] 385 consistent with molecular formula $C_{20}H_{21}{}^{35}ClN_4O_2$ j) N-(3-Chlorophenyl)-1-ethyl-7-(4-morpholinylcarbonyl)-1H-pyrrolo[3,2-c]pyridin-4-amine hydrochloride

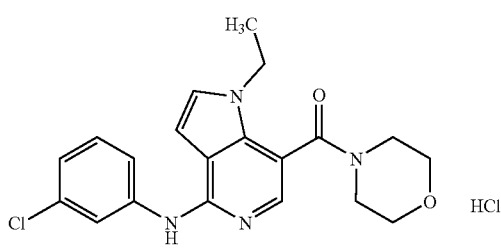

N-(3-Chlorophenyl)-1-ethyl-7-(4-morpholinylcarbonyl)-1H-pyrrolo[3,2-c]pyridin-4-amine (14 mg) was dissolved in diethyl ether (2 ml) and 2M hydrochloric acid solution in diethyl ether added to give a solid precipitate. The diethyl ether was decanted off and the solid dried by evaporation to afford the title compound as a white powder (9 mg).

LC/MS [MH⁺] 385 consistent with molecular formula $C_{20}H_{21}{}^{35}ClN_4O_2$

EXAMPLE 245

N-(3-chlorophenyl)-7-(4-morpholinylcarbonyl)-1-propyl-1H-pyrrolo[3,2-c]pyridin-4-amine hydrochloride

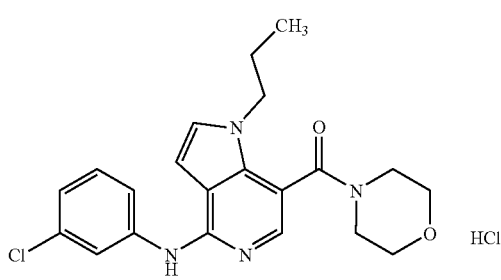

(a) Propyl 4-chloro-1-propyl-1H-pyrrolo[3,2-c]pyridine-7-carboxylate

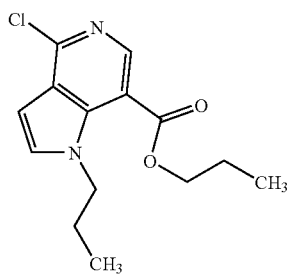

Prepared in a similar manner to Example 244(f) using ethyl 4-chloro-1H-pyrrolo[3,2-c]pyridine-7-carboxylate (500 mg) and 1-iodopropane (0.48 ml). Purification was by column chromatography on Flashmaster II eluting with a 30%-70% gradient of ethyl acetate/n-hexane to afford the title compound as a yellow oil (110 mg).

LC/MS [MH⁺] 281 consistent with molecular formula $C_{14}H_{17}{}^{35}ClN_2O_2$ (b) Propyl 4-[(3-chlorophenyl)amino]-1-propyl-1H-pyrrolo[3,2-c]pyridine-7-carboxylate

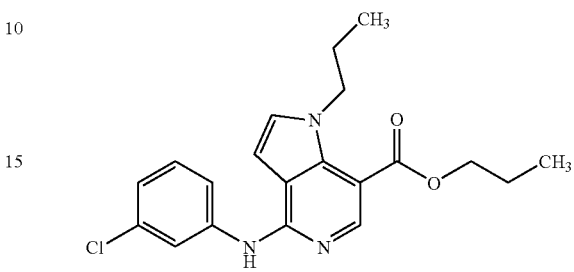

Prepared in a similar manner to Example 244(g) using propyl 4-chloro-1-propyl-1H-pyrrolo[3,2-c]pyridine-7-carboxylate (110 mg) to afford the title compound as a yellow oil (200 mg).

LC/MS [MH⁺] 372 consistent with molecular formula $C_{20}H_{22}{}^{35}ClN_3O_2$ (c) 4-[(3-Chlorophenyl)amino]-1-propyl-1H-pyrrolo[3,2-c]pyridine-7-carboxylic acid

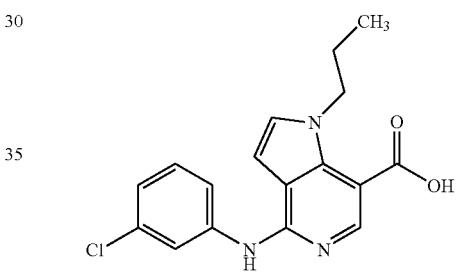

Prepared in a similar manner to Example 244(h) using propyl 4-[(3-chlorophenyl)amino]-1-propyl-1H-pyrrolo[3,2-c]pyridine-7-carboxylate (200 mg). Purification was by MDAP to afford the title compound as a white solid (16 mg).

LC/MS [MH⁺] 330 consistent with molecular formula $C_{17}H_{16}{}^{35}ClN_3O_2$ (d) N-(3-Chlorophenyl)-7-(4-morpholinylcarbonyl)-1-propyl-1H-pyrrolo[3,2-c]pyridin-4-amine

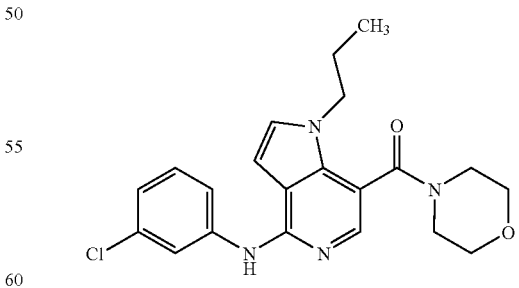

Prepared in a similar manner to Example 244(i) using 4-[(3-chlorophenyl)amino]-1-propyl-1H-pyrrolo[3,2-c]pyridine-7-carboxylic acid (16 mg) stirring over the weekend rather than overnight to afford the title compound as a white solid (11 mg).

LC/MS [MH⁺] 399 consistent with molecular formula $C_{21}H_{23}{}^{35}ClN_4O_2$ (e) N-(3-Chlorophenyl)-7-(4-morpholinylcarbonyl)-1-propyl-1H-pyrrolo[3,2-c]pyridin-4-amine hydrochloride

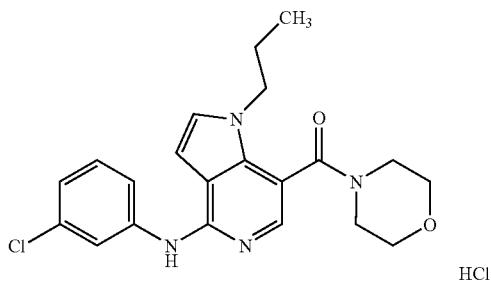

Prepared in a similar manner to Example 244(j) using N-(3-chlorophenyl)-7-(4-morpholinylcarbonyl)-1-propyl-1H-pyrrolo[3,2-c]pyridin-4-amine (11 mg) to afford the title compound as a white solid (11 mg).
LC/MS 399 consistent with molecular formula $C_{21}H_{23}{}^{35}ClN_4O_2$

EXAMPLE 246

N-(3-Chlorophenyl)-1,2-dimethyl-7-(4-morpholinylcarbonyl)-1H-pyrrolo[3,2-c]pyridin-4-amine hydrochloride

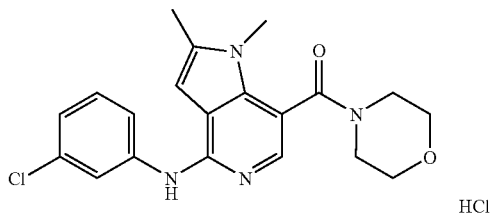

(a) 2-(Carboxymethyl)-1,5-dimethyl-1H-pyrrole-3-carboxylic acid

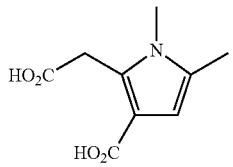

A mixture of 2-chloro-1,1-bis(methyloxy)propane (31 ml), 1,4-dioxan (20 ml), water (20 ml) and concentrated hydrochloric acid (7.2 ml) was heated under reflux for 30 minutes. After cooling in an ice bath, sodium bicarbonate (7.2 g) was added portionwise. The mixture which contained 2-chloropropionaldehyde was stirred for stirred for a further thirty minutes. In the meantime methylamine (40% in water, 110 ml) and water (20 ml) were cooled in an ice bath and 1,3-acetonedicarboxylic acid (20 g) was added portionwise whilst keeping the temperature below 20° C. After cooling to 110° C., the solution containing the 2-chloropropionaldehyde was added slowly whilst keeping the temperature below 15° C. The reaction mixture was stirred at 15° C. for one hour, then at room temperature for sixteen hours. The reaction mixture was cooled, acidified to pH 1 by the addition of 5N hydrochloric acid, and the resulting solid collected by filtration. The solid was washed with cold water, then diethyl ether. After drying, the solid washed with diethyl ether, and then dried, to afford the title compound as a buff solid 11.85 g.

$^1$H NMR (DMSO-$d_6$) δ 2.15 (s, 3H), 3.36 (s, 3H), 4.04 (s, 2H), 6.09 (s, 1H), 11.98 (br s, 2H).

(b) Methyl 1,5-dimethyl-2-[2-(methyloxy)-2-oxoethyl]-1H-pyrrole-3-carboxylate

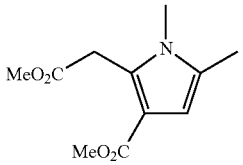

A mixture of 2-(carboxymethyl)-1,5-dimethyl-1H-pyrrole-3-carboxylic acid (11.85 g), p-toluenesulphonic acid hydrate (5.7 g) and methanol (200 ml) was heated under reflux for thirty hours, then evaporated. The residue was dissolved in ethyl acetate and washed twice with saturated sodium bicarbonate. The aqueous layers were combined and extracted with ethyl acetate. The combined organic layers were washed with water, then brine, dried (MgSO$_4$) and evaporated. The crude product was crystallised from methyl tert-butyl ether to afford the title compound as a buff solid 2.63 g. The mother liquors were evaporated and purified by chromatography on silica gel (ethyl acetate/hexane) to afford a further 3.38 g of the title compound.

$^1$H NMR (MeOD-$d_4$) δ 2.19 (s, 3H), 3.44 (s, 3H), 3.69 (s, 3H), 3.72 (s, 3H), 4.12 (s, 2H), 6.21 (s, 1H).

(c) Methyl 2-[1-formyl-2-(methyloxy)-2-oxoethyl]-1,5-dimethyl-1H-pyrrole-3-carboxylate

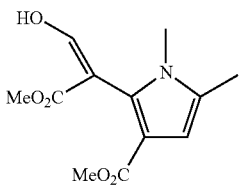

Sodium hydride (2.29 g, 60% dispersion in mineral oil) was added portionwise to a stirred solution of methyl 1,5-dimethyl-2-[2-(methyloxy)-2-oxoethyl]-1H-pyrrole-3-carboxylate (2.37 g) in tetrahydrofuran (30 ml) at 20° C. After fifteen minutes the reaction mixture was cooled to 10° C. and methyl formate (1.0 ml) added. After ten minutes a mixture of methanol (0.05 ml) and tetrahydrofuran (1 ml) was added. The reaction mixture was stirred at room temperature for sixteen hours. After cooling to 10° C., methanol (0.1 ml) was added, the mixture was stirred at room temperature for two hours. After cooling in an ice bath, methanol (8.4 ml) was added dropwise, the mixture was stirred for a further fifteen minutes, then evaporated. The residue was partitioned between ethyl acetate and aqueous ammonium chloride, and then acidified by addition of 5N hydrochloric acid. The aqueous phase was extracted with a second portion of ethyl acetate. The combined organic extracts were washed with water, then brine, dried (MgSO$_4$) and evaporated. The solid residue washed with hexane and then dried to give the title compound 2.59 g as a tautomeric mixture.

$^1$H NMR (MeOD-$d_4$) δ 2.21, 2.22 (s+s, 3H), 3.31, 3.34 (s+s, 3H), 3.65 (s, 3H), 3.67, 3.71 (s+s, 3H), 6.26, 6.28 (s+s, 1H), 7.22, 7.92 (s+s, 1H).

(d) Methyl 2-{2-amino-1-[(methyloxy)carbonyl]ethenyl}-1,5-dimethyl-1H-pyrrole-3-carboxylate

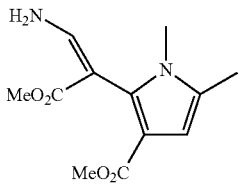

A mixture of methyl 2-[1-formyl-2-(methyloxy)-2-oxoethyl]-1,5-dimethyl-1H-pyrrole-3-carboxylate (2.59 g), ammonium acetate (4.0 g) and methanol (50 ml) was heated under reflux for 4 hours. After cooling the solvent was evaporated and the residue was partitioned between ethyl acetate and water. The aqueous phase was extracted with 2 further portions of ethyl acetate. The combined organic layers were washed with brine, dried (MgSO$_4$) and evaporated to afford the title compound 2.5 g, as a tautomeric mixture.

$^1$H NMR (MeOD-d$_4$) δ 2.18, 2.22 (s+s, 3H), 3.31 (s, 3H), 3.61 (s, 3H), 3.66, (s, 3H), 6.21, 6.31 (s+s, 1H), 6.87, 7.78 (s+s, 1H).

(e) Methyl 1,2-dimethyl-4-oxo-4,5-dihydro-1H-pyrrolo[3,2-c]pyridine-7-carboxylate

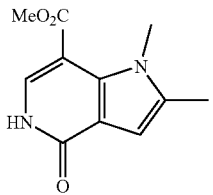

A mixture of methyl 2-{2-amino-1-[(methyloxy)carbonyl]ethenyl}-1,5-dimethyl-1H-pyrrole-3-carboxylate (1.42 g), potassium tert-butoxide (0.13 g) and dimethylformamide (10 ml) was heated under microwave conditions at 160° C. for twenty minutes. The solvent was evaporated and then the residue was suspended in water (20 ml). 2N hydrochloric acid (0.5 ml), then saturated aqueous sodium bicarbonate (1 ml) were added and the mixture stirred for one hour. The solid was collected by filtration, washed with water, then diethyl ether, and dried to afford the title compound 0.789 g.

$^1$H NMR (DMSO-d$_6$) δ 2.32 (s, 3H), 3.67 (s, 3H), 3.81 (s, 3H), 6.38 (s, 1H), 7.59 (d, 1H), 11.33 (s, 1H).

(f) Methyl 4-chloro-1,2-dimethyl-1H-pyrrolo[3,2-c]pyridine-7-carboxylate

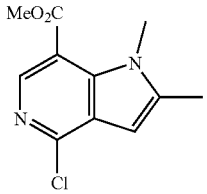

A solution of methyl 1,2-dimethyl-4-oxo-4,5-dihydro-1H-pyrrolo[3,2-c]pyridine-7-carboxylate (1.311 g) in phosphorus oxychloride (7 ml) was heated under reflux for four hours, then evaporated under reduced pressure. The residual liquid was added to a mixture of ethyl acetate and saturated aqueous sodium bicarbonate. The aqueous layer was extracted with a further portion of ethyl acetate. The combined organic extracts were washed with saturated aqueous sodium bicarbonate and then water. After filtering the water and ethyl acetate mixture, the organic phase washed with brine, dried (MgSO$_4$) and evaporated. Purification by chromatography on silica gel (ethyl acetate/toluene) afforded the title compound as a pale cream solid 1.027 g.

LC/MS [MH$^+$] 239 consistent with molecular formula C$_{11}$H$_{11}$$^{35}$ClN$_2$O$_2$ (g) 4-Chloro-1,2-dimethyl-1H-pyrrolo[3,2-c]pyridine-7-carboxylic acid hydrochloride

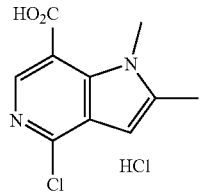

A solution of methyl 4-chloro-1,2-dimethyl-1H-pyrrolo[3,2-c]pyridine-7-carboxylate (1.027 g) in 5N hydrochloric acid was heated under microwave conditions at 120° C. for one and a half hours, then evaporated to dryness to afford the title compound as a white solid 1.087 g.

LC/MS [MH$^+$]$^+$ 225 consistent with molecular formula C$_{10}$H$_9$$^{35}$ClN$_2$O$_2$ (h) 4-Chloro-1,2-dimethyl-7-(4-morpholinylcarbonyl)-1H-pyrrolo[3,2-c]pyridine

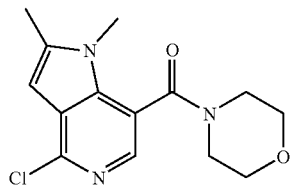

To a mixture of 4-chloro-1,2-dimethyl-1H-pyrrolo[3,2-c]pyridine-7-carboxylic acid hydrochloride (60 mg), N,N-diisopropylethylamine (0.2 ml) and morpholine (0.04 ml) in dry dimethylformamide (2 ml) was added O-benzotriazol-1-yl-N,N,N,N'-tetramethyluronium hexafluorophosphate (131 mg). The reaction mixture was stirred at room temperature for one hour. The reaction mixture was diluted with ethyl acetate, washed twice with saturated sodium bicarbonate and water, dried (MgSO$_4$), filtered and evaporated to afford the title compound as a white foam 68 mg.

LC/MS [MH$^+$] 294 consistent with molecular formula C$_{14}$H$_{16}$$^{35}$ClN$_3$O$_2$ (i) N-(3-Chlorophenyl)-1,2-dimethyl-7-(4-morpholinylcarbonyl)-1H-pyrrolo[3,2-c]pyridin-4-amine hydrochloride

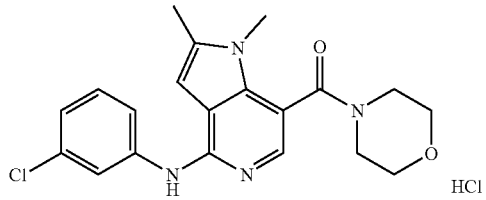

A mixture of 4-chloro-1,2-dimethyl-7-(4-morpholinylcarbonyl)-1H-pyrrolo[3,2-c]pyridine (68 mg), 3-chloroaniline (0.05 ml) and methanesulfonic acid (0.03 ml) in dry 1,4-dioxan was heated under microwave conditions at 180° C. for fifteen minutes. The reaction mixture was transferred to a round bottom flask and evaporated. The residue was partitioned between ethyl acetate (10 ml) and saturated sodium bicarbonate solution and washed with saturated sodium bicarbonate solution and water. The organic layer was dried (MgSO$_4$) and evaporated to afford a brown oil. The oil was purified by Biotage chromatography on silica gel loading the column using dichloromethane and eluting with 5% ethyl acetate/hexane (200 ml) increasing the percentage of ethyl acetate to 20%, 50% and 100% to afford a white foam. The foam was dissolved in warm ethyl acetate and treated with 1M hydrochloric acid in diethyl ether. The mixture was evaporated, the residue triturated with diethyl ether to afford a white solid which was filtered off, washed with diethyl ether and dried to afford the title compound (59 mg).

LC/MS [MH$^+$]$^+$ 385 consistent with molecular formula C$_{20}$H$_{21}$$^{35}$ClN$_4$O$_2$ Formulations for pharmaceutical use incorporating compounds of the present invention can be prepared in various forms and with numerous excipients. Examples of such formulations are given below.

EXAMPLE 247

Inhalant Formulation

A compound of formula (I) or a pharmaceutically acceptable derivative thereof, (1 mg to 100 mg) is aerosolized from a metered dose inhaler to deliver the desired amount of drug per use.

EXAMPLE 248

Tablet Formulation

| Tablets/Ingredients | Per Tablet |
|---|---|
| 1. Active ingredient (Compound of formula (I) or pharmaceutically acceptable derivative) | 40 mg |
| 2. Corn Starch | 20 mg |
| 3. Alginic acid | 20 mg |
| 4. Sodium Alginate | 20 mg |
| 5. Mg stearate | 1.3 mg |

Procedure for Tablet Formulation:

Ingredients 1, 2, 3 and 4 are blended in a suitable mixer/blender. Sufficient water is added portion-wise to the blend with careful mixing after each addition until the mass is of a consistency to permit its conversion to wet granules. The wet mass is converted to granules by passing it through an oscillating granulator using a No. 8 mesh (2.38 mm) screen. The wet granules are then dried in an oven at 140° F. (60° C.) until dry. The dry granules are lubricated with ingredient No. 5, and the lubricated granules are compressed on a suitable tablet press.

EXAMPLE 249

Parenteral Formulation

A pharmaceutical composition for parenteral administration is prepared by dissolving an appropriate amount of a compound of formula (I) in polyethylene glycol with heating. This solution is then diluted with water for injections Ph Eur. (to 100 ml). The solution is then rendered sterile by filtration through a 0.22 micron membrane filter and sealed in sterile containers.

What is claimed is:

1. A compound of formula (I)

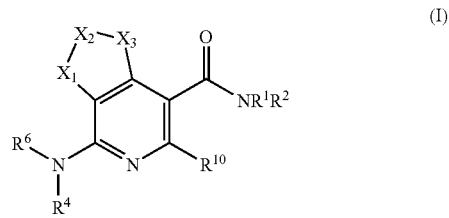

wherein:
X$_1$ is NR$^{12}$ and X$_2$ and X$_3$ together form a —CR$^{13}$═CR$^{11}$- group or X$_3$ is NR$^{12}$ and X$_2$ and X$_1$ together form a —CR$^{13}$═CR$^{11}$- group;

R$^1$ is selected from hydrogen, C$_{1-6}$ alkyl, C$_{3-6}$cycloalkyl and halosubstitutedC$_{1-6}$ alkyl;

R$^2$ is hydrogen or (CH$_2$)$_m$R$^3$ where m is 0 or 1;

or R$^1$ and R$^2$ together with N to which they are attached form an optionally substituted 4- to 8- membered non-aromatic heterocyclyl ring;

R$^3$ is a 4- to 8- membered non-aromatic heterocyclyl group, a C$_{3-8}$ cycloalkyl group, a straight or branched C$_{1-10}$ alkyl, a C$_{2-10}$alkenyl, a C$_{3-8}$cycloalkenyl, a C$_{2-10}$alkynyl, a C$_{3-8}$cycloalkynyl or phenyl group, any of which can be unsubstituted or substituted, or R$^5$;

R$^4$ is selected from hydrogen, C$_{1-6}$ alkyl, C$_{3-6}$ cycloalkyl, halosubstitutedC$_{1-6}$ alkyl, COCH$_3$ and SO$_2$Me;

R$^5$ is

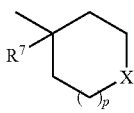

wherein p is 0, 1 or 2, and X is CH$_2$, O, S, or SO$_2$;

R$^6$ is unsubstituted or substituted phenyl, unsubstituted or substituted C$_{3-6}$cycloalkyl or an unsubstituted or substituted 4- to 8- membered non-aromatic heterocyclyl ring;

or R$^4$ and R$^6$ together with N to which they are attached form an optionally substituted 4- to 8- membered non-aromatic heterocyclyl ring;

R$^7$ is OH, C$_{1-6}$alkoxy, NR$^{8a}$R$^{8b}$, NHCOR$^9$, NHSO$_2$R$^9$ or SOqR$^9$;

R$^{8a}$ is H or C$_{1-6}$alkyl;

R$^{8b}$ is H or C$_{1-6}$alkyl;

R$^9$ is C$_{1-6}$alkyl;

R$^{10}$ is hydrogen, substituted or unsubstituted (C$_{1-6}$)alkyl or chloro;

R$^{11}$ is hydrogen or C$_{1-6}$alkyl;

R$^{12}$ is hydrogen or C$_{1-6}$alkyl;

R10 is hydrogen;

q is 0, 1 or 2;

or a pharmaceutically acceptable salt thereof wherein the compound is not 3-methyl-7-morpholin-4-yl-1H-pyrrolo[2,3-c]pyridine-4-carboxylic acid (tetrahydro-pyran-4-yl)-amide or 3-methyl-7-morpholin-4-yl-1H-pyrrolo[2,3-c]pyridine-4-carboxylic acid (tetrahydro-pyran-4-ylmethyl)-amide.

2. A compound as claimed in claim 1 wherein the compound is of formula (Ia) or (Ib):

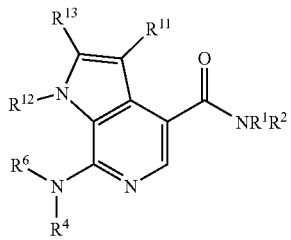

(Ia)

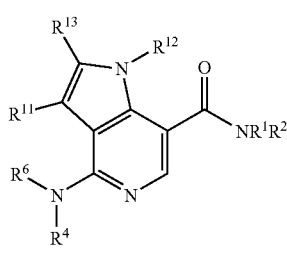

(Ib)

wherein $R^1$, $R^2$, $R^4$, $R^6$, $R^{11}$, $R^{12}$ and $R^{13}$ are as defined for compounds of formula (I).

3. A compound as claimed in claim 1 wherein $R^1$ is hydrogen.

4. A compound as claimed in claim 1 wherein $R^{13}$ is hydrogen.

5. A compound as claimed in claim 1 wherein $R^3$ is an unsubstituted or substituted 4- to 8- membered non-aromatic heterocyclyl group, or an unsubstituted or substituted $C_{3-8}$ cycloalkyl group.

6. A compound as claimed in claim 1 wherein $R^4$ is methyl or hydrogen.

7. A compound as claimed in claim 1 wherein $R^1$ and $R^2$ together with the nitrogen to which they are attached form a morpholinyl, pyrrolidinyl, piperidinyl, azetidinyl, azapine, or thiomorpholinyl-s,s-dioxide ring.

8. A compound as claimed in claim 1 wherein $R^6$ is a substituted phenyl, cyclohexyl or tetrahydrofuranyl.

9. A compound as claimed in claim 1 wherein $R^{11}$ is methyl or hydrogen.

10. A compound of formula (Ic) or (Id):

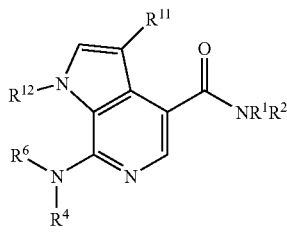

(Ic)

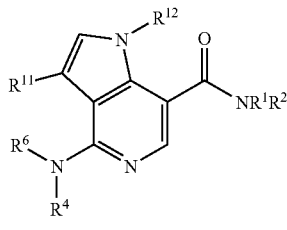

(Id)

wherein $R^1$ is selected from hydrogen;

$R^2$ is $(CH_2)_m R^3$ where m is 0 or 1;

or $R^1$ and $R^2$ together with N to which they are attached form a morpholinyl, pyrrolidinyl, piperidinyl, thiomorpholine-s,s-dioxide, azetidinyl or azapine ring any of which may be unsubstituted or substituted;

$R^3$ is a selected from tetrahydropyranyl, tetrahydrofuranyl, a $C_{3-6}$ cycloalkyl group, a straight or branched $C_{1-6}$ alkyl, or phenyl group, any of which can be unsubstituted or substituted;

$R^4$ is hydrogen or methyl, $R^6$ is phenyl, $C_{3-6}$cycloalkyl, tetrahydropyran, any of which can be unsubstituted or substituted $R^{11}$ is hydrogen or methyl;

$R^{12}$ is hydrogen or methyl;

or a pharmaceutically acceptable salt thereof.

11. A compound selected from 1-[7-(3-Chloro-phenylamino)-3-methyl-1H-pyrrolo[2,3-c]pyridin-4-yl]-1-morpholin-4-yl-methanone;

1-[4-(3-Chloro-phenylamino)-1-methyl-1H-pyrrolo[3,2-c]pyridin-7-yl]-1-piperidin-1-yl-methanone;

1-[4-(3-Chloro-phenylamino)-1-methyl-1H-pyrrolo[3,2-c]pyridin-7-yl]-1-morpholin-4-yl-methanone;

1-[4-(3-Chloro-phenylamino)-1-methyl-1H-pyrrolo[3,2-c]pyridin-7-yl]-1-pyrrolidin-1-yl-methanone;

-(3-Bromophenyl)-1-methyl-7-(4-morpholinylcarbonyl)-1H-pyrrolo[3,2-c]pyridine-4-amine hydrochloride N-(3,4-Dichlorophenyl)-1-methyl-7-(4-morpholinylcarbonyl)-1H-pyrrolo[3,2-c]pyridin-4-amine;

1-Methyl-7-(4-morpholinylcarbonyl)-N-{3-[(trifluoromethyl)oxy]phenyl}-1H-pyrrolo [3,2-c]pyridin-4-amine;

N-(3-Fluorophenyl)-1-methyl-7-(4-morpholinylcarbonyl)-1H-pyrrolo[3,2 -c]pyridin-4-amine;

N-(4-Bromo-3-chlorophenyl)-1-methyl-7-(4-morpholinylcarbonyl)-1H-pyrrolo [3,2-c]pyridin-4-amine;

N-(3-Chloro-4-fluorophenyl)-1-methyl-7-(1-piperidinylcarbonyl)-1H-pyrrolo[3,2-c]pyridin-4-amine;

1-Methyl-7-(1-piperidinylcarbonyl)-N-{3-[(trifluoromethyl)oxy]phenyl}-1H-pyrrolo [(3,2-c]pyridin-4-amine;

N-(3-Chlorophenyl)-1-ethyl-7-(4-morpholinylcarbonyl)-1H-pyrrolo[3,2-c]pyridin-4-amine or N-(3,5-Difluorophenyl)-1-methyl-7-(4-morpholinylcarbonyl)-1H-pyrrolo[3,2-c]pyridin-4-amine and pharmaceutically acceptable salt thereof.

12. A pharmaceutical composition comprising a compound as claimed in claim 1 or a pharmaceutically acceptable salt thereof.

13. A pharmaceutical composition as claimed in claim 12 further comprising a pharmaceutical carrier or diluent thereof.

* * * * *